United States Patent
Roubos et al.

(10) Patent No.: US 9,738,890 B2
(45) Date of Patent: Aug. 22, 2017

(54) CLONING METHOD

(71) Applicant: DSM IP ASSETS B.V., Heerlen (NL)

(72) Inventors: Johannes Andries Roubos, Echt (NL); Herman Jan Pel, Echt (NL); Bernard Meijrink, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 14/386,354

(22) PCT Filed: Mar. 27, 2013

(86) PCT No.: PCT/EP2013/056623
§ 371 (c)(1),
(2) Date: Sep. 19, 2014

(87) PCT Pub. No.: WO2013/144257
PCT Pub. Date: Oct. 3, 2013

(65) Prior Publication Data
US 2015/0050696 A1    Feb. 19, 2015

Related U.S. Application Data

(60) Provisional application No. 61/616,254, filed on Mar. 27, 2012.

(51) Int. Cl.
*C12N 15/10* (2006.01)
*C12N 15/66* (2006.01)
*C12N 15/90* (2006.01)

(52) U.S. Cl.
CPC ......... *C12N 15/1024* (2013.01); *C12N 15/66* (2013.01); *C12N 15/90* (2013.01); *C12N 2800/30* (2013.01); *C12N 2800/40* (2013.01); *C12N 2800/50* (2013.01); *C12N 2800/80* (2013.01)

(58) Field of Classification Search
CPC ... C12N 15/90–15/907; C12N 15/1082; C12N 15/1024; C12N 15/66; C12N 2800/80
See application file for complete search history.

(56) References Cited

U.S. PATENT DOCUMENTS 6,936,470 B2 * 8/2005 Liang ............... C12N 15/66
435/320.1
2010/0124768 A1 * 5/2010 Serber ............. C12N 15/1093
435/91.5

FOREIGN PATENT DOCUMENTS

| EP | 2395087 A1 | 12/2011 | |
|---|---|---|---|
| WO | 2008095927 A1 | 8/2008 | |
| WO | 2010059763 A1 | 5/2010 | |
| WO | 2010113031 A2 | 10/2010 | |
| WO | WO 2012012738 A1 * | 1/2012 | ............. C12N 15/85 |

OTHER PUBLICATIONS

Weber et al. A modular cloning system for standardized assembly of multigene constructs. PLoS One, vol. 6, No. 2, e16765, Feb. 18, 2011, printed as pp. 1-11.*
Marx et al. Broad-host-range cre-lox xystem for antibiotic marker recycling in gram-negative bacteria. BioTechniques, vol. 33, pp. 1062-1067, Nov. 2002.*
Shao et al. DNA assembler, an in vivo genetic method for rapid construction of biochemical pathways. Nucleic Acids Research, vol. 37, No. 2, e16, 2009, published online Dec. 12, 2008, and printed as pp. 1/10-10-10.*
Carola Engler et al., "Golden Gate Shuffling: A One-Pot DNA Shuffling Method Based on Type IIs Restriction Enzymes." PLoS ONE, May 2009, vol. 4, No. 5.
Alejandro Sarrion-Perdigones et al., "GoldenBraid: An Iterative Cloning System for Standardized Assembly of Reusable Genetic Modules." PLoS ONE, Jul. 2011, vol. 6, No. 7.
Tianwen Wang et al., "Available methods for assembling expression cassettes for synthetic biology," Appl Microbiol Biotechnol, 2012, vol. 93, 1853-1863.
Laura M. Wingler et al., "Reiterative Recombination for the in vivo assembly of libraries of multigene pathways." PNAS, Sep. 2011, vol. 108, No. 37, 15135-15140.
International Search Report from corresponding PCT/EP2013/056623, mailed Jun. 26, 2013.

\* cited by examiner

*Primary Examiner* — Jennifer Dunston
(74) *Attorney, Agent, or Firm* — McBee Moore Woodward & Vanik IP, LLC

(57) ABSTRACT

The present invention relates to a method based on the use of restriction enzyme digestion and ligation via cleavage sites, thereby to prepare two or more standardized expression cassettes.

19 Claims, 29 Drawing Sheets

Level 2 step a
assemble modular cassettes by *in vitro* cloning and recovery of multi-part DNA cassettes

Level 2 step b
assemble modular cassettes by *in vivo* recombination of multi-part DNA cassettes at a target locus

Level 3 (after 2b)
recover modular cassettes from host for usage in second host

SEQUENCE LISTING

```
<160> NUMBER OF SEQ ID NOS: 153

<210> SEQ ID NO 1
<211> LENGTH: 621
<212> TYPE: DNA
<213> ORGANISM: Saccharomyces cerevisiae

<400> SEQUENCE: 1
ggtctcggtg cccgcggaac cgccagatat tcattacttg acgcaaaagc gtttgaaata      60
atgacgaaaa agaaggaaga aaaaaaaaga aaaataccgc ttctaggcgg gttatctact     120
gatccgagct tccactagga tagcacccaa acacctgcat atttggacga cctttactta     180
caccaccaaa aaccactttc gcctctcccg cccctgataa cgtccactaa ttgagcgatt     240
acctgagcgg tcctcttttg tttgcagcat gagacttgca tactgcaaat cgtaagtagc     300
aacgtgtcaa ggtcaaaact gtatggaaac cttgtcacct cacttaattc tagctagcct     360
accctgcaag tcaagaggtg tccgtgattc ctagccacct caaggtatgc ctctccccgg     420
aaactgtggc cttttctggc acacatgatc tccacgattt caacatataa atagcttttg     480
ataatggcaa tattaatcaa atttatttta cttctttctt gtaacatctc tcttgtaatc     540
ccttattcct tctagctatt tttcataaaa aaccaagcaa ctgcttatca acacacaaac     600
actaaatcaa aatgggagac c                                               621

<210> SEQ ID NO 2
<211> LENGTH: 621
<212> TYPE: DNA
<213> ORGANISM: Saccharomyces cerevisiae

<400> SEQUENCE: 2
ggtctcggtg cttttggtg gttccggctt ccttcccgat tccgcccgct aaacgcatat      60
ttttgttgcc tggtggcatt tgcaaaatgc ataacctatg catttaaaag attatgtatg     120
ctgttctgac ttttcgtgtg atgaggctcg tggaaaaaat gaataattta tgaatttgag     180
aacaattttg tgttgttacg gtattttact atggaataat caatcaattg aggattttat     240
gcaaatatcg tttgaatatt tttccgaccc tttgagtact tttcttcata attgcataat     300
attgtccgct gccccttttt ctgttagacg gtgtcttgat ctacttgcta tcgttcaaca     360
ccaccttatt ttctaactat tttttttta gctcatttga atcagcttat ggtgatggca     420 cattttttgca taaacctagc tgtcctcgtt gaacatagga aaaaaaata tataaacaag     480 gctctttcac tctccttgca atcagatttg ggtttgttcc ctttatttc atatttcttg     540 tcatattcct ttctcaatta ttatttttcta ctcataacct cacgcaaaat aacacagtca     600
aatcaatcaa aatgggagac c                                               621

<210> SEQ ID NO 3
<211> LENGTH: 621
<212> TYPE: DNA
<213> ORGANISM: Saccharomyces cerevisiae

<400> SEQUENCE: 3
```

```
ggtctcggtg cgtgtcgacg ctgcgggtat agaaagggtt ctttactcta tagtacctcc     60
tcgctcagca tctgcttctt cccaaagatg aacgcggcgt tatgtcacta acgacgtgca    120
ccaacttgcg gaaagtggaa tcccgttcca aaactggcat ccactaattg atacatctac    180
acaccgcacg ccttttttct gaagcccact ttcgtggact ttgccatatg caaaattcat    240
gaagtgtgat accaagtcag catacacctc actagggtag tttctttggt tgtattgatc    300
atttggttca tcgtggttca ttaattttt ttctccattg ctttctggct ttgatcttac    360
tatcatttgg attttttgtcg aaggttgtag aattgtatgt gacaagtggc accaagcata    420
tataaaaaaa aaaagcatta tcttcctacc agagttgatt gttaaaaacg tatttatagc    480
aaacgcaatt gtaattaatt cttatttgt atcttttctt cccttgtctc aatctttat    540 ttttattta ttttttctttt cttagtttct ttcataacac caagcaacta atactataac    600
atacaataat aatgggagac c                                              621

<210> SEQ ID NO 4
<211> LENGTH: 621
<212> TYPE: DNA
<213> ORGANISM: Saccharomyces cerevisiae

<400> SEQUENCE: 4
ggtctcggtg cctacttggc ttcacatacg ttgcatacgt cgatatagat aataatgata     60
atgacagcag gattatcgta atacgtaata gttgaaaatc tcaaaaatgt gtgggtcatt    120
acgtaaataa tgataggaat gggattcttc tattttttcct ttttccattc tagcagccgt    180
cgggaaaacg tggcatcctc tctttcgggc tcaattggag tcacgctgcc gtgagcatcc    240
tctctttcca tatctaacaa ctgagcacgt aaccaatgga aaagcatgag cttagcgttg    300
ctccaaaaaa gtattggatg gttaatacca tttgtctgtt ctcttctgac tttgactcct    360
caaaaaaaaa aaatctacaa tcaacagatc gcttcaatta cgccctcaca aaaacttttt    420
tccttcttct tcgcccacgt taaattttat ccctcatgtt gtctaacgga tttctgcact    480
tgatttatta taaaaagaca aagacataat acttctctat caatttcagt tattgttctt    540
ccttgcgtta ttcttctgtt cttctttttc ttttgtcata taaaccata accaagtaat    600 acatattcaa aatgggagac c                                              621

<210> SEQ ID NO 5
<211> LENGTH: 621
<212> TYPE: DNA
<213> ORGANISM: Saccharomyces cerevisiae

<400> SEQUENCE: 5
ggtctcggtg cagagaattt tgccatcgga catgctacct tacgcttata tctctcattg     60
gaatatcgtt ttctgattaa aacacggaag taagaactta attcgttttt cgttgaacta    120
tgttgtgcca gcgtaacatt aaaaaagagt gtacaaggcc acgttctgtc accgtcagaa    180
aaatatgtca atgaggcaag aaccgggatg gtaacaaaaa tcacgatctg gtgtgggtgtg    240 ggtgtattgg attataggaa gccacgcgct caacctggaa ttacaggaag ctggtaattt    300
tttgggtttg caatcatcac catctgcacg ttgtttataat gtcccgtgtc tatatatatc    360
cattgacggt attctatttt tttgctattg aaatgagcgt tttttgttac tacaattggt    420
tttacagacg gaattttccc tatttgtttc gtcccatttt tccttttctc attgttctca    480
tatcttaaaa aggtccttc ttcataatca atgctttctt ttacttaata ttttacttgc    540
```

```
attcagtgaa ttttaataca tattcctcta gtcttgcaaa atcgatttag aatcaagata      600
ccagcctaaa aatgggagac c                                               621

<210> SEQ ID NO 6
<211> LENGTH: 621
<212> TYPE: DNA
<213> ORGANISM: Saccharomyces cerevisiae

<400> SEQUENCE: 6
ggtctcggtg cgggccagaa aaggaagtg tttccctcct tcttgaattg atgttaccct       60
cataaagcac gtggcctctt atcgagaaag aaattaccgt cgctcgtgat ttgtttgcaa     120
aaagaacaaa actgaaaaaa cccagacacg ctcgacttcc tgtcttccta ttgattgcag     180
cttccaattt cgtcacacaa caaggtccta gcgacggctc acaggttttg taacaagcaa     240
tcgaaggttc tggaatggcg ggaaagggtt tagtaccaca tgctatgatg cccactgtga     300
tctccagagc aaagttcgtt cgatcgtact gttactctct ctctttcaaa cagaattgtc     360
cgaatcgtgt gacaacaaca gcctgttctc acacactctt ttcttctaac caaggggggtg    420 gtttagttta gtagaacctc gtgaaactta catttacata tatataaact tgcataaatt     480
ggtcaatgca agaaatacat atttggtctt ttctaattcg tagttttttca agttcttaga    540 tgctttcttt ttctctttttt tacagatcat caaggaagta attatctact ttttacaaca    600
aatataaaac aatgggagac c                                               621

<210> SEQ ID NO 7
<211> LENGTH: 621
<212> TYPE: DNA
<213> ORGANISM: Saccharomyces cerevisiae

<400> SEQUENCE: 7
ggtctcggtg cggacgtgca atgcagacga cagatctaaa tgaccgtgtc ggtgaagtgt      60
tcgccaaact tttcggttaa cacatgcagt gatgcacgcg cgatggtgct aagttacata     120
tatatatata tatatatata tatatatata tagccatagt gatgtctaag taacctttat     180
ggtatatttc ttaatgtgga aagatactag cgcgcgcacc cacacacaag cttcgtcttt     240
tcttgaagaa aagaggaagc tcgctaaatg ggattccact ttccgttccc tgccagctga     300
tggaaaaagg ttagtggaac gatgaagaat aaaagagag atccactgag gtgaaatttc      360
agctgacagc gagtttcatg atcgtgatga acaatggtaa cgagttgtgg ctgttgccag     420
ggagggtggt tctcaacttt taatgtatgg ccaaatcgct acttgggttt gttatataac     480
aaagaagaaa taatgaactg attctcttcc tccttcttgt cctttcttaa ttctgttgta     540
attaccttcc tttgtaattt tttttgtaat tattcttctt aataatccaa acaaacacac     600
atattacaat aatgggagac c                                               621

<210> SEQ ID NO 8
<211> LENGTH: 621
<212> TYPE: DNA
<213> ORGANISM: Saccharomyces cerevisiae

<400> SEQUENCE: 8
ggtctcggtg cccatcatga aaaatctctc gacaccgttt atccattgct tttttgttgt      60 cttttttccct cgttcacaga aagtctgaag aagctatagt agaactatga gctttttttg    120
tttctgtttt ccttttttttt ttttttacct ctgtggaaat tgttactctc acactcttta    180
gttcgtttgt ttgttttgtt tattccaatt atgaccggtg acgaaacgtg gtcgatggtg    240
```

-continued

```
ggtaccgctt atgctcccct ccattagttt cgattatata aaaaggccaa atattgtatt      300
attttcaaat gtcctatcat tatcgtctaa catctaattt ctcttaaatt ttttctcttt      360
ctttcctata acaccaatag tgaaaatctt tttttcttct atatctacaa aaactttttt      420
tttctatcaa cctcgttgat aaattttttc tttaacaatc gttaataatt aattaattgg      480
aaaataacca tttttttctct cttttataca cacattcaaa agaaagaaaa aaaatatacc    540
ccagctagtt aaagaaaatc attgaaaaga ataagaagat aagaaagatt taattatcaa     600
acaatatcaa aatgggagac c                                                621
```

<210> SEQ ID NO 9
<211> LENGTH: 621
<212> TYPE: DNA
<213> ORGANISM: Saccharomyces cerevisiae

<400> SEQUENCE: 9

```
ggtctcggtg cactacaatt tagcggctta gcacaatacg cgttttcaac ttcctacgct      60
agcgatgaca aaatgtctcc aagaggcgga acttgcgacg gatgcatgga aatatcttac    120
gtaatgaact tccgtaatga acttccgtaa ttcaagatct cttagcatct cttgttcaat    180
cttcagactc tactaagtgt tcttaccaac cattggatgc tcattacaaa tgaatgaata   240
tattgcacgg aacggaagcg gcatgctttt tccgtgtcgt gtgcttagta aagcaaaacg    300
gagtagaatc ggtaagaact tcctttttgg gttggaaaat cattgccatt gtttggacac   360
cttttctttt t ccgtattgtt cgagcaccgc gtttctttt gggtacttga tgaggtagca    420
gattcctgga acgtgctttc tctcgaggta acctgccttg ttcctcctgg tgactttcta    480
aaatataaaa ggaaaagcat atctctagtt tcgagttttt tcttcatact ttatttcctt     540
atgttaaacg gtccagatat agaataaatc atcatattaa gctaaatata gacgataata    600
tagtatcgat aatgggagac c                                                621
```

<210> SEQ ID NO 10
<211> LENGTH: 621
<212> TYPE: DNA
<213> ORGANISM: Saccharomyces cerevisiae

<400> SEQUENCE: 10

```
ggtctcggtg ctcatccgac atacatctgt acactaggaa gccctgtttt tctgaagcag     60
cttcaaatat atatatttttt tacatatttta ttatgattca atgaacaatc taattaaatc    120
gaaaacaaga accgaaacgc gaataaataa tttatttaga tggtgacaag tgtataagtc     180
ctcatcggga cagctacgat ttctctttcg gttttggctg agctactggt tgctgtgacg   240
cagcggcatt agcgcggcgt tatgagctac cctcgtggcc tgaaagatgg cgggaataaa    300
gcggaactaa aaattactga ctgagccata ttgaggtcaa tttgtcaact cgtcaagtca    360
cgtttggtgg acgcccctt tccaacgaat cgtatatact aacatgcgcg cgcttcctat     420
atacacatat acatatatat atatatatat atgtgtgcgt gtatgtgtac acctgtatttt   480 aatttcctta ctcgcgggtt tttcttttttt ctcaattctt ggcttcctct ttctcgagta    540 tataatttttt caggtaaaat ttagtacgat agtaaaatac ttctcgaact cgtcacatat   600
acgtgtacat aatgggagac c                                                621
```

<210> SEQ ID NO 11
<211> LENGTH: 621
<212> TYPE: DNA

<213> ORGANISM: Saccharomyces cerevisiae

<400> SEQUENCE: 11

| | | | | | |
|---|---|---|---|---|---|
| ggtctcggtg | ccagcgccag | tagggttgtt | gagcttagta | aaaatgtgcg | caccacaagc | 60 |
| ctacatgact | ccacgtcaca | tgaaaccaca | ccgtggggcc | ttgttgcgct | aggaatagga | 120 |
| tatgcgacga | agacgcttct | gcttagtaac | cacaccacat | tttcaggggg | tcgatctgct | 180 |
| tgcttccttt | actgtcacga | gcggcccata | atcgcgcttt | ttttttaaaa | ggcgcgagac | 240 |
| agcaaacagg | aagctcgggt | ttcaaccttc | ggagtggtcg | cagatctgga | gactggatct | 300 |
| ttacaataca | gtaaggcaag | ccaccatctg | cttcttaggt | gcatgcgacg | gtatccacgt | 360 |
| gcagaacaac | atagtctgaa | gaaggggggg | aggagcatgt | tcattctctg | tagcagtaag | 420 |
| agcttggtga | taatgaccaa | aactggagtc | tcgaaatcat | ataaatagac | aatatatttt | 480 |
| cacacaatga | gatttgtagt | acagttctat | tctctctctt | gcataaataa | gaaattcatc | 540 |
| aagaacttgg | tttgatattt | caccaacaca | cacaaaaaac | agtacttcac | taaatttaca | 600 |
| cacaaaacaa | aatgggagac | c | | | | 621 |

<210> SEQ ID NO 12
<211> LENGTH: 621
<212> TYPE: DNA
<213> ORGANISM: Saccharomyces cerevisiae

<400> SEQUENCE: 12

| | | | | | |
|---|---|---|---|---|---|
| ggtctcggtg | cttagtcaaa | aaattagcct | tttaattctg | ctgtaacccg | tacatgccca | 60 |
| aaatagggg | cgggttacac | agaatatata | acatcgtagg | tgtctgggtg | aacagtttat | 120 |
| tcctggcatc | cactaaatat | aatggagccc | gcttttttaag | ctggcatcca | gaaaaaaaaa | 180 |
| gaatcccagc | accaaaatat | tgttttcttc | accaaccatc | agttcatagg | tccattctct | 240 |
| tagcgcaact | acagagaaca | ggggcacaaa | caggcaaaaa | acgggcacaa | cctcaatgga | 300 |
| gtgatgcaac | ctgcctggag | taatgatgaa | cacaaggcaa | ttgacccacg | catgtatcta | 360 |
| tctcattttc | ttacaccttc | tattaccttc | tgctctctct | gatttggaaa | aagctgaaaa | 420 |
| aaaaggttga | aaccagttcc | ctgaaattat | tcccctactt | gactaataag | tatataaaga | 480 |
| cggtaggtat | tgattgtaat | tctgtaaatc | tatttcttaa | acttcttaaa | ttctactttt | 540 |
| atagttagtc | tttttttttag | ttttaaaaca | ccaagaactt | agtttcgaat | aaacacacat | 600 |
| aaacaaacaa | aatgggagac | c | | | | 621 |

<210> SEQ ID NO 13
<211> LENGTH: 621
<212> TYPE: DNA
<213> ORGANISM: Saccharomyces cerevisiae

<400> SEQUENCE: 13

| | | | | | |
|---|---|---|---|---|---|
| ggtctcggtg | cttggctgat | aatagcgtat | aaacaatgca | tactttgtac | gttcaaaata | 60 |
| caatgcagta | gatatatttta | tgcatattac | atataataca | tatcacatag | gaagcaacag | 120 |
| gcgcgttgga | ctttttaattt | tcgaggaccg | cgaatcctta | catcacaccc | aatcccccac | 180 |
| aagtgatccc | ccacacacca | tagcttcaaa | atgtttctac | tcctttttta | ctcttccaga | 240 |
| ttttctcgga | ctccgcgcat | cgccgtacca | cttcaaaaca | cccaagcaca | gcatactaaa | 300 |
| tttcccctct | ttcttcctct | agggtgtcgt | taattacccg | tactaaaggt | ttggaaaaga | 360 |
| aaaaagacac | cgcctcgttt | cttttttcttc | gtcgaaaaag | gcaataaaaa | ttttttatcac | 420 |
| gtttcttttt | cttgaaaatt | ttttttttttg | atttttttttct | ctttcgatga | cctcccattg | 480 |

```
atatttaagt taataaacgg tcttcaatttt ctcaagtttc agtttcattt ttcttgttct    540
attacaactt ttttactttc ttgctcatta gaaagaaagc atagcaatct aatctaagtt    600
ttaattacaa aatgggagac c                                              621
```

<210> SEQ ID NO 14
<211> LENGTH: 621
<212> TYPE: DNA
<213> ORGANISM: Saccharomyces cerevisiae

<400> SEQUENCE: 14

```
ggtctcggtg cgacacctaa ctacatagtg tttaaagatt acggatattt aacttactta     60
gaataatgcc attttttga gttataataa tcctacgtta gtgtgagcgg gatttaaact    120
gtgaggacct taatacattc agacacttct gcggtatcac cctacttatt cccttcgaga    180
ttatatctag gaacccatca ggttggtgga agattacccg ttctaagact tttcagcttc    240
ctctattgat gttacacctg gacacccctt ttctggcatc cagtttttaa tcttcagtgg    300
catgtgagat tctccgaaat taattaaagc aatcacacaa ttctctcgga taccacctcg    360
gttgaaactg acaggtggtt tgttacgcat gctaatgcaa aggagcctat atacctttgg    420
ctcggctgct gtaacaggga atataaaggg cagcataatt taggagttta gtgaacttgc    480
aacatttact attttcccctt cttacgtaaa tattttctt tttaattcta aatcaatctt    540
tttcaatttt ttgtttgtat tctttttcttg cttaaatcta taactacaaa aaacacatac    600
ataaactaaa aatgggagac c                                              621
```

<210> SEQ ID NO 15
<211> LENGTH: 621
<212> TYPE: DNA
<213> ORGANISM: Saccharomyces cerevisiae

<400> SEQUENCE: 15

```
ggtctcggtg caacatatat acacaattac agtaacaata acaagaggac agatactacc     60
aaaatgtgtg gggaagcggg taagctgcca cagcaattaa tgcacaacat ttaacctaca    120
ttcttcctta tcggatcctc aaaacccttaa aaacatatg cctcacccta acatattttc     180
caattaaccc tcaatatttc tctgtcaccc ggcctctatt ttccatttt ttctttaccc     240 gccacgcgtt ttttctttc aaattttttt cttcttcctt ctttttcttc cacgtcctct     300
tgcataaata aataaaccgt tttgaaacca aactcgcctc tctctctcct ttttgaaata    360
tttttgggtt tgttgatcc tttccttccc aatctctctt gtttaatata tattcattta    420
tatcacgctc tcttttttatc ttccttttt tcctctctct tgtattcttc cttcccctttt    480 ctactcaaac caagaagaaa aagaaaaaggt caatctttgt taaagaatag gatcttctac    540
tacatcagct tttagatttt tcacgcttac tgctttttc ttcccaagat cgaaaattta    600
ctgaattaac aatgggagac c                                              621
```

<210> SEQ ID NO 16
<211> LENGTH: 390
<212> TYPE: DNA
<213> ORGANISM: Ashbya gossypii

<400> SEQUENCE: 16

```
ggtctcggtg cgtccccgcc gggtcacccg gccagcgaca tggaggccca gaatacccctc     60 cttgacagtc ttgacgtgcg cagctcaggg gcatgatgtg actgtcgccc gtacatttag    120
```

```
cccatacatc cccatgtata atcatttgca tccatacatt ttgatggccg cacggcgcga    180
agcaaaaatt acggctcctc gctgcagacc tgcgagcagg gaaacgctcc cctcacagac    240
gcgttgaatt gtccccacgc cgcgcccctg tagagaaata taaaaggtta ggatttgcca    300
ctgaggttct tctttcatat acttcctttt aaaatcttgc taggatacag ttctcacatc    360
acatccgaac ataaacaaca atgggagacc                                    390
```

<210> SEQ ID NO 17
<211> LENGTH: 621
<212> TYPE: DNA
<213> ORGANISM: Saccharomyces cerevisiae

<400> SEQUENCE: 17

```
ggtctcggtg ccaaacatta atttgttctg catactttga acctttcaga aaataaaaaa     60
cattacgcgc atacttaccc tgctcgcgaa gaagagtaac actaacgcat tctatgggca    120
attgaagaca gtattcagta caagacatag tccgtttcct tgagtcaatt cctatagcat    180
tatgaactag ccgcctttaa gagtgccaag ctgttcaaca ccgatcattt ttgatgattt    240 ggcgttttg ttatattgat agatttcttt tgaattttgt cattttcact tttccactcg    300
caacggaatc cggtggcaaa aagggaaaa gcattgaaat gcaatcttta acagtatttt    360
aaacaagttg cgacacggtg tacaattacg ataagaattg ctacttcaaa gtacacacag    420
aaagttaaca tgaatggaat tcaagtggac atcaatcgtt tgaaaagggg cgaagtcagt    480
ttaggtacct caatgtatgt atataagaat ttttcctccc actttattgt ttctaaaagt    540
tcaatgaagt aaagtctcaa ttggccttat tactaactaa taggtatctt ataatcacct    600
aataaaatag aatgggagac c                                             621
```

<210> SEQ ID NO 18
<211> LENGTH: 621
<212> TYPE: DNA
<213> ORGANISM: Saccharomyces cerevisiae

<400> SEQUENCE: 18

```
ggtctcggtg cgatatagcc gctacgactg attagtgatg tgataaagat agaagattta     60
agtcacagag gcgtgcatct acgattttgg cgtttcacat tttttacact taaatttag    120 tgatctagcc gtgaccttgg cagcagtttc caaaatcatt ccatgaccat gtcatgctta    180
agaacgttag acccagaaca gtggacctg tattctaact cttcactctt gggcaaagat    240
aatagtatta tcttttaccc cattttttgt atgttttttc gtttattgag tttggcgttt    300
cctatttaga aatagtacaa tccggtcaat cattcgatag tgaaatatat atatttaact    360
aggaaaatta gtaaacctc atttaaagat cattcacctt gatatatact actattgacc    420
ttttgttaat gaccattttc gtaaaaatga actgcgattc tcttctggaa tttgttaccc    480
taccttattc actaaatcag aaataataat gtgcagcgcc cctttcataa agaaggcaag    540
tatagggcat atagttaaag gtcagaactc tttatcccca actacaagat caattagaaa    600
atcacatcat aatgggagac c                                             621
```

<210> SEQ ID NO 19
<211> LENGTH: 1021
<212> TYPE: DNA
<213> ORGANISM: Kluyveromyces lactis

<400> SEQUENCE: 19

```
ggtctcggtg ccgtatccct atctggatta acatcactgc cacagatcga attgcaagaa     60
```

```
gccacacttc acgtgatcca ctcgttcatc aggtttgtag cttcatggcg caggacttct    120
gatgatgaac tatctggctc atccggatgg atcacaagga tggatacccct cagacagtac    180 gtttccgtat ggagcgatct acaagaaacc aacagttgat cctattactt ttttttttatt   240 ttttgtccct ccgggatggc aagagggaca agaagaatc ttcgttcttc tttcttgttc    300
tcaacttccc agcttccgtg tgattaccct ccgggacaac agaaaaactg gcattcggta    360
tcccgggaat ctgctgagaa ggaagaaaa cgaaaaaaaa attgtacatt tgtgtcacat    420
tatgaattac aggaagtcag aaaacaggca gcacatgtct cgcacatgca tgtccatcag    480
acgagacatt atgagacatg cacgcgtgtg agagacatag caaaagtctc tccagtacac    540
acagaaagac acgttcacaa tccaggcacc ccacagagaa aaaaaaaga agagcccgg     600 aagctggcac gccatcatca accaccgctc ggtttacacg catcccaact gtctttttt    660 tctggaatcc tataataact ggcatctgga atcacgttg tatgttgcac catagtgact    720
ggctgtctga ctagcaaaca ttgattccct gattcccatt tggctcaatt ttgatgagaa    780
acagttgatt gattcttgtc aattttttt tctttggacc accaccaacc aattgacatt    840
gaagtacttt cccatgattt gaggttatat aaaaggacgt tcaaatcact ttcaaggtta    900
attcagtttt gtcaattgat ttaagttcaa ttgttaacaa atttaattta attcgaaaca    960 aaccaaaacca attcatttga attaacaaac caacccacaa aacaaaaaaa aatgggagac   1020
c                                                                      1021

<210> SEQ ID NO 20
<211> LENGTH: 1021
<212> TYPE: DNA
<213> ORGANISM: Kluyveromyces lactis

<400> SEQUENCE: 20
ggtctcggtg cgttcctcat cactagaagc cgaactgttg tcttcagtgg ggattggttc     60
gacattttgc caattgctgt cgatgtaccc tttcaaagcc atgtaccttca atcttcatc   120 cttggcaagt agattcatcg ggtgtgtttg aagtaagaat atttgcttgt ttttatggta    180
tcaaaggtat atgttgtaga agacaatttc cggtaatcca attgtctgtc tgctcagttt    240
agcacatgta tagtacgttg cacatagtct acaatattca gcattcagca ttcagtatac    300
agcatatggc taaatgatca caaatgtgat tgatgatttg acacgactag aaaagagaac    360
gaaaaaggga aattccatgt cacgtgcgtt ggcacgtgac atggaatatc gaagaaagaa    420
aaaaaaaacg atctcgtcct agtggaagcc cagagtctgg tcccccggga gtcttcccaa    480
aacaagaagc tgacacatgt tgacacagaa caccccacag caaatgcacc acgctacgta    540
gatcaggaag cttaactcta gcgacctgtc gctcgcccca cagaacctca cccgagaacc    600
acacattaca cgccgccagc tcccactata ctcatcttgc ttcccttaag cgttctcacg    660
attcgttcgc tgcccttctt caagagtctt ctgattctaa ttctcattcg aaatcctcta    720
cagttaatga attgcttgac atgacattca ttgtctcatg gttttggctt tttggctttt    780
gtcttttaaa gctatatcaa ctttacatat aaatatacgt caaaggggga ttcattaatt    840
agaaaattct cttttttcaat agttgctatt cattatcaat ctattcaact caattggtta    900 ttatttttcat ctttttgtca tcctaaacca tcaacaatat ttaaatatat ctgttgctac    960
attaagagtt acttcagaaa taacaaaaaa atcgatcaag aattaataaa aatgggagac    1020
c                                                                       1021
```

<210> SEQ ID NO 21
<211> LENGTH: 1021
<212> TYPE: DNA
<213> ORGANISM: Kluyveromyces lactis

<400> SEQUENCE: 21

| | | | | | | |
|---|---|---|---|---|---|---|
| ggtctcggtg | cgagcctgtc | caagcaaatg | ccttctcata | aatggtgcca | agacccgca | 60 |
| agcccaaagc | aattacccccc | caaaaagaaa | tgatatagtg | caagatacgt | atatgaccat | 120 |
| gacttgacta | ggtgaaacag | tgcagaaaca | gccgcacaaa | agcagccta | accctcagag | 180 |
| tcgattttac | tctttcaggt | aataaagcct | cgacatcaat | tttagacaga | agccaggctg | 240 |
| gcctcgagat | tatagccata | ggcaagcaag | aggagagaag | gggaggcccc | ccatgggggg | 300 |
| cctccccccc | gctgtcaagg | tttggcagaa | cctagcttca | ttaggccact | agcccagcct | 360 |
| aaaacgtcaa | cgggcaggag | gaacactccc | acaagacggc | gtagtattct | cgattcataa | 420 |
| ccattttctc | aatcgaatta | cacagaacac | accgtacaaa | cctctctatc | ataactactt | 480 |
| aatagtcaca | cacgtactcg | tctaaataca | catcatcgtc | ctacaagttc | atcaaagtgt | 540 |
| tggacagaca | actataccag | catggatctc | ttgtatcggt | tcttttctcc | cgctctctcg | 600 |
| caataacaat | gaacactggg | tcaatcatag | cctacacagg | tgaacagagt | agcgtttata | 660 |
| cagggtttat | acgtgattc | ctacggcaaa | aattttcat | ttctaaaaaa | aaaaagaaaa | 720 |
| attttctttt | ccaacgctag | aaggaaaaga | aaatctaat | taaattgatt | tggtgatttt | 780 |
| ctgagagttc | cctttttcat | atatcgaatt | ttgaatataa | aaggagatcg | aaaaaatttt | 840 |
| tctattcaat | ctgttttctg | gtttatttg | atagttttt | tgtgtattat | tattatggat | 900 |
| tagtactggt | ttatatgggt | ttttctgtat | aacttctttt | tattttagtt | tgtttaatct | 960 |
| tattttgagt | tacattatag | ttccctaact | gcaagagaag | taacattaaa | aatgggagac | 1020 |
| c | | | | | | 1021 |

<210> SEQ ID NO 22
<211> LENGTH: 1021
<212> TYPE: DNA
<213> ORGANISM: Kluyveromyces lactis

<400> SEQUENCE: 22

| | | | | | | |
|---|---|---|---|---|---|---|
| ggtctcggtg | cctccaatgc | aatccatgta | ctcaacagaa | gtgtctacaa | acttgacgag | 60 |
| atctaaggcc | caactcctca | actttgtggt | ttctggtgtt | gcccaatttg | ttaatcaatt | 120 |
| tgctactcca | aaggcaatga | agaatatcaa | atattggttc | tatgtgttct | acgttttctt | 180 |
| cgatattttc | gaatttattg | ttatctactt | cttcttcgtt | gaaactaagg | gtagaagctt | 240 |
| agaagaatta | gaagttgtct | ttgaagctcc | aaacccaaga | aaggcatccg | ttgatcaagc | 300 |
| attcttggct | caagtcaggg | caactttggt | ccaacgaaat | gacgttagag | ttgcaaatgc | 360 |
| tcaaaatttg | aaagagcaag | agcctctaaa | gagcgatgct | gatcatgtcg | aaaagctttc | 420 |
| agaggcagaa | tctgtttaaa | gccatctttt | caatatattt | tgttaggtgc | aagaagtttc | 480 |
| cgtacttcat | aatttgtttt | ttattctgct | tgatcttctc | ctaattgcag | caaaaagtct | 540 |
| tgtggaattc | atcaattaaa | aagccacagg | ctttagactc | ttaatggatt | attctaacag | 600 |
| ttactgttag | acgttagcac | atgggccggt | atgtcattga | agtacgttta | aattgcctga | 660 |
| attgggaaaa | gtattgacct | ttgagccggt | tgcataccgc | cttgcggtat | gcagtttggc | 720 |
| tcggttttcc | cagcacgcat | gtgggcatca | tttccacacg | tgtgaaccct | cggcagttaa | 780 |
| atgtgtgcat | ttaggatcgg | ctaatagttg | tttttagctt | cagcttcagc | tcatcggatt | 840 |

| | |
|---|---|
| ttgtgaaaca tataaatctg gcgtcaattg agtctctcga atggttgaaa ggtcaattca | 900 |
| ggttggaatt ttgtattatg ttagctatat gggattgatc aaaaaaacca gccaaggatt | 960 |
| cagagaatta cagcgcaagc tcaggtagca ctccagtttt aaacataaaa aatgggagac | 1020 |
| c | 1021 |

<210> SEQ ID NO 23
<211> LENGTH: 2596
<212> TYPE: DNA
<213> ORGANISM: Kluyveromyces lactis

<400> SEQUENCE: 23

| | |
|---|---|
| ggtctcggtg cagacctcca attaaccgat tgtccttgtc ataatgagct agagtagcaa | 60 |
| ggtatcaaca acagtatgga catcttattg tcaactttct agtacggagg gaagaatccc | 120 |
| gaatatgtta aatctgacgc gcgggtattg ctaagtcacg ttgcaggccc acgcagaccc | 180 |
| gagtttcttt cttacaaaag cgtgtacaca cgtaaacgcg ctcggtgcac cgaacggcca | 240 |
| gggtcggggt tcattcggta tagagccacg caggtaactt gccaattcca aaaaaaatta | 300 |
| aatgacgata ctagtaacca aggaaagga acagatagat aaaattccga gactgtcaaa | 360 |
| ttaggttttt ttcttttttt tggcgggag tcagtgggcc gaaatatgtt cttggcctag | 420 |
| aacttaatct ggtttgatca tgccaatact tgcctgagtg cccgacttttt tgcccaccct | 480 |
| tttgccttct gtctatcctt caaaacccac ctgttttcca gccgtatctt cgctcgcatc | 540 |
| tacacatact gtgccatatc ttgtgtgtag ccggacgtga ctatgaccaa aaacaaacaa | 600 |
| ggagaactgt tcgccgattt gtaacactcc tgcatccatc caagtgggta tgcgctatgc | 660 |
| aatgttaagc taggtcaggt cagaccaggt ccaaggacag caacttgact gtatgcaacc | 720 |
| tttaccatct ttgcacagaa catacttgta gctagctagt tacacttatg gaccgaaaag | 780 |
| gcaccccacc atgtctgtcc ggctttagag tacggccgca gaccgctgat ttgccttgcc | 840 |
| aagcagtagt cacaatgcat cgcatgagca cacgggcacg ggcacgggca caggaaccat | 900 |
| tggcaaaaat accagataca ctataccgac gtatatcaag cccaagttta aaattcctaa | 960 |
| atttccgcgg ggatcgactc ataaaatagt aaccttctaa tgcgtatcta ttgactacca | 1020 |
| accattagtg tggttgcaga aggcggaatt ctcccttctt cgaattcagc ttgcttttttc | 1080 |
| atttttatt ttccattttt cagttttgt ttgtgtcgaa tttagccagt tgcttctcca | 1140 |
| agatgaaaaa aaccccctgcg cagtttctgt gctgcaagat cctaatcgac ttttccaccc | 1200 |
| cccacaaaag taaatgttct tttgttacat tcgcgtgggt agctagctcc ccgaatcttc | 1260 |
| aaaggactta gggactgcac tacatcagag tgtgttcacc tggtttgctg cctggtttga | 1320 |
| aagaaaagag cagggaactc gcgggttccc ggcgaataat catgcgatag tcctttggcc | 1380 |
| ttccaagtcg catgtagagt agacaacaga cagggagggc aggaaggatc tttcactgag | 1440 |
| atcctgtatc ttgttgggta agtcggatga aaggggaatc gtatgagatt ggagaggatg | 1500 |
| cggaagaggt aacgcctttt gttaacttgt ttaattatta tggggcaggc gagaggggga | 1560 |
| ggaatgtatg tgtgtgaggc gggcgacacg gagccatcca ggccaggtag aaatagagaa | 1620 |
| agccgaatgt tagacaatat ggcagcgtag tagagtaggt aggtaggcaa gtactgctag | 1680 |
| caaagaggag aagggtaagc tcactcttcg cattccacac cgttagtgtg tcagtttgaa | 1740 |
| caaaaaaaca atcatcatac caattgatgg actgtggact ggcttttgga acggcttttc | 1800 |
| ggactgcgat tattcgtgag gaatcaaggt aggaatttgg tcatatttac ggacaacagt | 1860 |

```
gggtgattcc catatggagt aggaaaacga gatcatggta tcctcagata tgttgcggaa    1920
ttctgttcac cgcaaagttc agggtgctct ggtgggtttc ggttggtctt tgctttgctt    1980
ctcccttgtc ttgcatgtta ataatagcct agcctgtgag ccgaaactta gggtaggctt    2040
agtgttggaa cgtacatatg tatcacgttg acttggttta accaggcgac ctggtagcca    2100
gccataccca cacacgtttt tgtatcttc agtatagttg tgaaaagtgt agcggaaatt    2160
tgtggtccga gcaacagcgt cttttttctag tagtgcggtc ggttacttgg ttgacattgg    2220
tatttggact tgttgctac accattcact acttgaagtc gagtgtgaag ggtatgattt    2280
ctagtggtga acacctttag ttacgtaatg ttttcattgc tgttttactt gagatttcga    2340
ttgagaaaaa ggtatttaat agctcgaatc aatgtgttat cattgtgaag atgttcttcc    2400
ctaactcgaa aggtatatga ggcttgtgtt tcttaggaga attattattc ttttgttatg    2460
ttgcgcttgt agttggaaaa ggtgaagaga caaaagcgct taacacttga aatttaggaa    2520
agagcagaat ttggcaaaaa aaataaaaaa aaaataaaca cacatactca tcgagaactg    2580
aaagaaatgg gagacc                                                     2596

<210> SEQ ID NO 24
<211> LENGTH: 1021
<212> TYPE: DNA
<213> ORGANISM: Kluyveromyces lactis

<400> SEQUENCE: 24
ggtctcggtg ccaaagggg ggcagggaca gggatacgac aagggctggg gaaaaaaaaa      60
aagatagata cgattggccg ggtaagcctg gggaaatgta gcaagtgcgg gtaagttaaa    120
aggtaaccac gtgactccgg aagagtcacg tggttacgga cttttttctc tagatctcag    180 cttttttatcg gtcttaccct gccctcctgc ccctgcccc ttcccttgc cccaaaaga     240 aaggaaatct gttggatttc gctcaggcca tccctttcgt taatatcggt tatcgcttta    300
cacactgcac atccttctgt ccaaaaggaa tccagaagtt tagcttttcc ttcctttccc    360
acagacatta gcctaggccc tctctcatca tttgcatgcc tcagccaatg taccaagaat    420
aacgcaacga ggttgggaaa ttttaaccca caatcgatg cagatgtgac aagagattag     480
acacgttcca gataccagat tacacagctt gtgctagcag agtgacatat ggtggtgttg    540
tgtctcgttt agtacctgta atcgagagtg ttcaaatcag tcgatttgaa cacccttact    600
gccactgaat attgattgaa taccgtttat tgaaggtttt atgagtgatc ttctttcggt    660
ccaggacaat tgttgagct ttttctatgt agagttccgt ccctttttttt tttttttttg    720 cttttctcgca cttactagca ctatttttt ttcacacact aaaacacttt attttaatct    780
atatatatat atatatatat atgtaggaat ggaatcacag acatttgata ctcatcctca    840
tccttattaa ttcttgtttt aatttgtttg acttagccaa accaccaatc tcaacccatc    900
gtatttcagg tattgtgtgt ctagtgtgtc tctggtatac ggaaataagt gccgaagta     960 aggaagaaac aaagaacaag tgtctgaata ctactagcct ctcttttcat aatgggagac   1020
c                                                                    1021

<210> SEQ ID NO 25
<211> LENGTH: 1021
<212> TYPE: DNA
<213> ORGANISM: Kluyveromyces lactis

<400> SEQUENCE: 25
ggtctcggtg ctgtattact accgcaactc acgtaagaaa taattatcaa gttttcctat     60
```

```
gggctagtac aacatttgct aaataagcac tcttggactt gttggaggtt catgcaaaac    120
tataatggaa tattctcacc agacatagca caggacgtgt ctcatatcaa gcaggtcgaa    180
tggcattcgc aataaacata gatgacattc gttactcacg attatcttat cgtgactcaa    240
acactgcctg tctctttctt tctctaaagt cagcactgtt aaccggcctc taggataata    300
acacccgcag ggtcgatact tattttttcga gggttatcgc ctccctaata taaaaacaga    360
tgaaaagata aaacagcccc ttaagcgctt gggtccaccc ccttagaatt agtatataag    420
taaagcggca aatcacgaag ttctttcaga tctcctaacc actctttctt gaagtcattt    480
cttctattct tgaatatata tattttgtat tacatgctcc ccctccatcg agaagaactc    540
tctctggata catattacat ttcaaaacgc tactctctat tataaccgcc gagtgtttct    600
cttaagcacc cgctataaaa atcctatcct aaacgtcttt ttgtctagga gttacggaag    660
aaactaactg ctgaattcta tcggaatcat aagcatacac attatttgga taaagctgcg    720
ttaatcctac ttcattttac ttttgaactt ttttttgttt ttcgggagac taaggttctt    780
gttcacccct tcactataaa aagaaaaagt accctttttc aattaggaaa gcaaaaactg    840
aactataaag taaactatac tcagtaatac ttcaatcaac aaagaacttg aaaagctgat    900
acaagcaagt ccttgataca aaaaaaaaaa agacaggtaa gttcatcaga tatcctgtta    960
ctaaaaaaac ttcaaacaaa aacaaaagat aacgcacttt tcattatcaa aatgggagac   1020
c                                                                   1021

<210> SEQ ID NO 26
<211> LENGTH: 1021
<212> TYPE: DNA
<213> ORGANISM: Kluyveromyces lactis

<400> SEQUENCE: 26
ggtctcggtg cgacttccat cttgttcgga tttgataatg tcatctgcat gcaaatgaga     60
tcgcgaaatg tatagaaagg ctgatgataa atgaattgcg tcgtatgatt gatataatta    120
tcataccctc tgaaacttgt catcaattca ccagggtgga atgaactgat ctactattgt    180
tggaagagag agacagtgat gatctgtcga ggagcttttt tcgatctaat tttaacctca    240
gcggaacaat ggggcgagta atggctggtg aaaaagcaag actacttagc accaataaac    300
tcagaaacct tccttgtggt tctttgttga tcgaagatac gaggatgcga cgagcaacga    360
agtcaggccg tattagtgtg ttttcgaagg tacatcattc attacgtata caattgctcc    420
agattagtta atcaaggttt ctcgaaatcg aaaaacaccc ttgctattac ctaatagcaa    480
catacccaat tacaaagaat taggaattta ccacctcatc cttttgactc cgtactttgt    540
gccttgtgtc tttcaccatt tttgctattg gcaatgaggt aatgctattg cttttgctat    600
tattactacc ttaattttgg aaactaagct ttgaaaaaaa aaaacaaagc gagcgcagcg    660
acgttttcac tagatgagat aatggcaagg gaaacgtcag aaatggacat acgaggtatc    720
gtggaggtca ttgcgtatgt gcgtgtcctt tacattcgga aatcattatc tgcgaatgga    780
acctggttgt ccaaacaagg tcaaacccac actaagtttt ttttgctgt aacttgatcc    840 atcgaaaaac cctaaaccaa aaagtatata agcagactct tgattcatct tgctccaaat    900
taattccagt ctccttcttt cctaatataa tatattcatt tgaacctcat aaaccaagcc    960
aaatttaata ggttatccaa tacaaaacac acacaaacac taataataaa aatgggagac   1020
c                                                                   1021
```

<210> SEQ ID NO 27
<211> LENGTH: 1021
<212> TYPE: DNA
<213> ORGANISM: Kluyveromyces lactis

<400> SEQUENCE: 27

| | | | | | |
|---|---|---|---|---|---|
| ggtctcggtg | caaccaaaag | agagatcatg | gaaattacta | atgatgtggt | gtatgggtgc | 60 |
| atgtgtcttt | tttttccatt | ttctccttcg | agagatcccc | aaagggcatc | aaaatagatc | 120 |
| tgacgtgatc | tatgccaact | ttagtaatcg | acatgggacg | gttttcattg | gccggtttta | 180 |
| agagctcttg | aaccttgaat | ccactaactt | ttctattatt | ggaattcaaa | taggaaaaat | 240 |
| ttgtttgttt | tgcttttatt | gttactgcta | ggtttacaga | tatgaattta | acaagctaat | 300 |
| cttgttttttt | acatgtttca | gccgttccaa | cctgtcataa | agtgtcaatg | aaggttctga | 360 |
| ggtggagcaa | tctgtgatcg | gcccacttag | ctccattgta | taagcaacat | atgtccttgt | 420 |
| aggtgttgtt | tgtaaaatag | ccggcttcca | ttttaatatg | gccaaaccga | atgcgggtat | 480 |
| ggaattacgc | agaaacagga | agaaatgact | ggataattag | attttgctta | ttgtttgggc | 540 |
| agagccattt | gagggatgac | ggcttctatt | ttgagggttt | ctgctgtatc | tgcgtacaac | 600 |
| tccatttttt | gtttactatt | ctcgatttta | cttaattgga | ctaaagtgga | tatttgttgt | 660 |
| gacaaagatt | gtttctatta | ttgtcatgtt | catctttttt | ttttggtatg | acagtgctgc | 720 |
| aatggagagg | gaaaaaattg | cgtagatctt | gtgactaaaa | taaattgcca | ggtgaagaaa | 780 |
| gcaaggggat | aagaatagcg | atatgagtgg | gccgactgaa | agtatataa | ggcattggtt | 840 |
| tgtttcaaga | gttttagaat | aatatatccc | ttcttccact | ttttttttcct | gttgaataat | 900 |
| ctgtattgtt | atagctgtaa | catcaggatt | cactattgta | tcttctagat | aagcaagaaa | 960 |
| acttactatc | gctaacacat | cgcgttcatc | aataaagaaa | tactgcaaaa | aatgggagac | 1020 |
| c | | | | | | 1021 |

<210> SEQ ID NO 28
<211> LENGTH: 1021
<212> TYPE: DNA
<213> ORGANISM: Kluyveromyces lactis

<400> SEQUENCE: 28

| | | | | | |
|---|---|---|---|---|---|
| ggtctcggtg | ctaggcaatt | ggcatttttt | cctccataca | agttttttct | aggcttttct | 60 |
| tctgccccac | tgaaaaagat | ccgcagctgc | ctgtcttctt | cacttttctc | cgagtgatat | 120 |
| gcttcatcca | ggctgccact | tttcgtttca | tatcttcttc | aaaatgatag | gaatccagat | 180 |
| actctcttgt | ggggtgcctt | ttacctgtga | tattcgatag | caaaaaatgg | gaagctcaca | 240 |
| gagtcaggct | atttccacgt | tagtggatgt | cgcagccagt | gggtccttct | ttcacttgaa | 300 |
| ggctaccaat | aatagacctt | caatagtcac | tatacggtct | gtatggtctg | tacgggtgta | 360 |
| tatggcacga | tcaatatcgt | accatattct | gtcctgctct | gttctggtag | tctgcgtaaa | 420 |
| ctctgccaat | tatgttcttc | tatatccagt | tctgtcgcat | gtcggctaga | ttatttgtcc | 480 |
| taagtttcga | atggctggct | gttccttggc | ttctaatccc | catatagaat | taatcggtc | 540 |
| aagatggaac | cgagcagttc | cgattgatca | gaccgtatcg | atgcaacaac | aggtgatgtt | 600 |
| gaattctgaa | ttctgtcaaa | gaatcacaat | ctatctcgat | ttcccttctt | tctttttttt | 660 |
| cagcttagtt | tagatatggg | catcgaggtt | cccctaaatt | ttgtttgcca | gctagacata | 720 |
| gcactggatt | cttatactgt | ctaaagctca | ccacgggcct | ggagaaaccg | ttaaaggatg | 780 |
| cccccacaaa | gttataaggt | agaactatga | aagtgatggg | gttaggtttt | tgaaaagaaa | 840 |

```
tgaaattaga acttatataa ggggatggat tttagtatat tttccaattc tcttgttgag    900
atcgtaataa ttgtcgttct tccaatcaca tttagttaca taaatcacca tcagctatca    960
tactgaataa caagcaatca agctaaaaag aatatcaata ttaattaaaa aatgggagac   1020
c                                                                  1021
```

<210> SEQ ID NO 29
<211> LENGTH: 1021
<212> TYPE: DNA
<213> ORGANISM: Kluyveromyces lactis

<400> SEQUENCE: 29

```
ggtctcggtg cttttctttt tttgcggtca cccccatgtg gcggggaggc agaggagtag     60
gtagagcaac gaatcctact atttatccaa attagtctag gaactctttt tctagatttt    120
ttagatttga gggcaagcgc tgttaacgac tcagaaatgt aagcactacg gagtagaacg    180
agaaatccgc cataggtgga aatcctagca aaatcttgct tacccctagct agcctcaggt    240 aagctagcct tagcctgtca aattttttc aaaatttggt aagtttctac tagcaaagca    300
aacacggttc aacaaaccga aaactccact cattatacgt ggaaaccgaa acaaaaaaac    360
aaaaaccaaa atactcgcca atgagaaagt tgctgcgttt ctactttcga ggaagaggaa    420
ctgagaggat tgactacgaa aggggcaaaa acgagtcgta ttctcccatt attgtctgct    480
accacgcggt ctagtagaat aagcaaccag tcaacgctaa gacaggtaat caaaatacca    540
gtctgctggc tacgggctag ttttttacctc ttttagaacc cactgtaaaa gtccgttgta    600
aagcccgttc tcactgttgg cgttttttt tttttggttt agtttcttat ttttcatttt    660
tttctttcat gaccaaaaac aaacaaatct cgcgatttgt actgcggcca ctggggcgtg    720
gccaaaaaaa tgacaaattt agaaaccttaa gtttctgatt tttcctgtta tgaggagata    780
tgataaaaaa tattactgct ttattgtttt tttttatct actgaaatag agaaacttac    840
ccaaggagga ggcaaaaaaa agagtatata tacagcaggt accattcaga ttttaatata    900
ttcttttctc ttcttctaca ctattattat aataatttta ctatattcat ttttagctta    960
aaacctcata gaatattatt cttcagtcac tcgcttaaat acttatcaaa aatgggagac   1020
c                                                                  1021
```

<210> SEQ ID NO 30
<211> LENGTH: 1021
<212> TYPE: DNA
<213> ORGANISM: Kluyveromyces lactis

<400> SEQUENCE: 30

```
ggtctcggtg ccgtaaaaac taaaacgagc ccccaccaaa gaacaaaaaa gaaggtgctg     60
ggcccccact ttcttccctt gcacgtgata ggaagatggc tacagaaaca agaagatgga    120
aatcgaagga aagagggaga ctggaagctg taaaaactga aatgaaaaaa aaaaaaaaa    180 aaaaaaacaa gaagctgaaa atggaagact gaaatttgaa aaatggtaaa aaaaaaaaag    240
aaacacgaag ctaaaaacct ggattccatt ttgagaagaa gcaagaaagg taagtatggt    300
aacgaccgta caggcaagcg cgaaggcaaa tggaaaagct ggagtccgga agataatcat    360
ttcatcttct tttgttagaa cagaacagtg gatgtccctc atctcggtaa cgtattgtcc    420
atgccctaga actctctgtc cctaaaaaga ggacaaaaac ccaatggttt ccccagcttc    480
cagtggagcc accgatccca ctggaaacca ctggacagga agagaaaatc acggacttcc    540
```

```
tctattgaag gataattcaa cactttcacc agatcccaaa tgtcccgccc ctattcccgt    600
gttccatcac gtaccataac ttaccatttc atcacgttct ctatggcaca ctggtactgc    660
ttcgactgct ttgcttcatc ttctctatgg gccaatgagc taatgagcac aatgtgctgc    720
gaaataaagg gatatctaat ttatattatt acattataat atgtactagt gtggttattg    780
gtaattgtac ttaattttga tatataaagg gtggatcttt tcattttga atcagaattg     840 gaattgcaac ttgtctcttg tcactattac ttaatagtaa ttatatttct tattaacctt    900 tttttaagt caaaacacca aggacaagaa ctactcttca aaggtatttc aagttatcat     960
acgtgtcaca cacgcttcac agtttcaagt aaaaaaaaag aatattacac aatgggagac   1020
c                                                                   1021

<210> SEQ ID NO 31
<211> LENGTH: 733
<212> TYPE: DNA
<213> ORGANISM: Aequorea victoria

<400> SEQUENCE: 31
ggtctcgaat gtctaaaggt gaagaattat tcactggtgt tgtcccaatt ttggttgaat     60
tagatggtga tgttaatggt cacaaatttt ctgtctccgg tgaaggtgaa ggtgatgcta    120
cttacggtaa attgacctta aaattgattt gtactactgg taaattgcca gttccatggc    180
caaccttagt cactacttta ggttatggtt tgcaatgttt tgctagatac ccagatcata    240
tgaaacaaca tgactttttc aagtctgcca tgccagaagg ttatgttcaa gaagaactat    300 ttttttcaa agatgacggt aactacaaga ccagagctga agtcaagttt gaaggtgata    360
ccttagttaa tagaatcgaa ttaaaaggta ttgattttaa agaagatggt aacattttag    420
gtcacaaatt ggaatacaac tataactctc acaatgttta catcactgct gacaaacaaa    480
agaatggtat caaagctaac ttcaaaatta gacacaacat tgaagatggt ggtgttcaat    540
tagctgacca ttatcaacaa aatactccaa ttggtgatgg tccagtcttg ttaccagaca    600
accattactt atcctatcaa tctgccttat ccaaagatcc aaacgaaaag agagatcaca    660
tggtcttgtt agaatttgtt actgctgctg gtattaccca tggtatggat gaattgtaca    720
aataaaggag acc                                                      733

<210> SEQ ID NO 32
<211> LENGTH: 727
<212> TYPE: DNA
<213> ORGANISM: Discosoma sp.

<400> SEQUENCE: 32
ggtctcgaat ggtaagtaag ggtgaagaag acaatatggc gatcattaag gaattcatgc     60
gtttcaaagt acacatggag ggaagcgtga acggacatga atttgaaatc gaaggggaag    120
gcgaaggtag accatacgaa ggaacccaga ccgcaaagct taaagttacc aaaggcgggc    180
cactaccatt tgcatgggat atcttgagcc ctcagtttat gtatggcagt aaggcctacg    240
ttaaacaccc agctgatatt cccgactatt tgaaattgtc ttttccagaa ggattcaaat    300
gggaaagagt aatgaatttc gaggacggcg gagttgttac tgttactcaa gattcaagtt    360
tgcaagacgg tgaatttatt tacaaggtca aattaagagg gactaatttc cctagtgatg    420
gtcccgtcat gcaaaagaag actatgggtt gggaagcctc atctgaacgt atgtatccag    480
aagatggcgc gcttaagggg gaaattaaac aaagattgaa gttaaaagac ggtggtcact    540
acgacgcgga agttaagacc acttataaag ctaaaaagcc cgttcagtta cctggtgcat    600
```

-continued

| ataacgtaaa cattaaattg gatatcactt cacataatga agattacact attgtggaac | 660 |
| aatatgaaag agctgaaggt aggcactcaa cgggtggaat ggacgaattg tacaaataaa | 720 |
| ggagacc | 727 |

<210> SEQ ID NO 33
<211> LENGTH: 3091
<212> TYPE: DNA
<213> ORGANISM: Escherichia coli

<400> SEQUENCE: 33

| ggtctcgaat gaccatgatt acggattcac tggccgtcgt tttacaacgt cgtgactggg | 60 |
| aaaaccctgg cgttacccaa cttaatcgcc ttgcagcaca tccccctttc gccagctggc | 120 |
| gtaatagcga agaggcccgc accgatcgcc cttcccaaca gttgcgcagc ctgaatggcg | 180 |
| aatggcgctt tgcctggttt ccggcaccag aagcggtgcc ggaaagctgg ctggagtgcg | 240 |
| atcttcctga ggccgatact gtcgtcgtcc cctcaaactg gcagatgcac ggttacgatg | 300 |
| cgcccatcta caccaacgtg acctatccca ttacggtcaa tccgccgttt gttcccacgg | 360 |
| agaatccgac gggttgttac tcgctcacat ttaatgttga tgaaagctgg ctacaggaag | 420 |
| gccagacgcg aattattttt gatggcgtta actcggcgtt tcatctgtgg tgcaacgggc | 480 |
| gctgggtcgg ttacggccag gacagtcgtt tgccgtctga atttgacctg agcgcatttt | 540 |
| tacgcgccgg agaaaaccgc ctcgcggtga tggtgctgcg ctggagtgac ggcagttatc | 600 |
| tggaagatca ggatatgtgg cggatgagcg gcattttccg tgacgtctcg ttgctgcata | 660 |
| aaccgactac acaaatcagc gatttccatg ttgccactcg ctttaatgat gatttcagcc | 720 |
| gcgctgtact ggaggctgaa gttcagatgt gcggcgagtt gcgtgactac ctacgggtaa | 780 |
| cagtttcttt atggcagggt gaaacgcagg tcgccagcgg caccgcgcct tcggcggtg | 840 |
| aaattatcga tgagcgtggt ggttatgccg atcgcgtcac actacgtctg aacgtcgaaa | 900 |
| acccgaaact gtggagcgcc gaaatcccga atctctatcg tgcggtggtt gaactgcaca | 960 |
| ccgccgacgg cacgctgatt gaagcagaag cctgcgatgt cggtttccgc gaggtgcgga | 1020 |
| ttgaaaatgg tctgctgctg ctgaacggca agccgttgct gattcgaggc gttaaccgtc | 1080 |
| acgagcatca tcctctgcat ggtcaggtca tggatgagca gacgatggtg caggatatcc | 1140 |
| tgctgatgaa gcagaacaac tttaacgccg tgcgctgttc gcattatccg aaccatccgc | 1200 |
| tgtggtacac gctgtgcgac cgctacggcc tgtatgtggt ggatgaagcc aatattgaaa | 1260 |
| cccacggcat ggtgccaatg aatcgtctga ccgatgatcc gcgctggcta ccggcgatga | 1320 |
| gcgaacgcgt aacgcgaatg gtgcagcgcg atcgtaatca cccgagtgtg atcatctggt | 1380 |
| cgctggggaa tgaatcaggc cacggcgcta atcacgacgc gctgtatcgc tggatcaaat | 1440 |
| ctgtcgatcc ttcccgcccg gtgcagtatg aaggcggcgg agccgacacc acggccaccg | 1500 |
| atattatttg cccgatgtac gcgcgcgtgg atgaagacca gcccttcccg ctgtgccgaa | 1560 |
| aatggtccat caaaaaatgg ctttcgctac ctggagagac gcgcccgctg atcctttgcg | 1620 |
| aatacgccca cgcgatgggt aacagtcttg gcggtttcgc taaatactgg caggcgtttc | 1680 |
| gtcagtatcc ccgtttacag gcggcttcg tctgggactg ggtggatcag tcgctgatta | 1740 |
| aatatgatga aaacggcaac ccgtggtcgg cttacggcgg tgattttggc gatacgccga | 1800 |
| acgatcgcca gttctgtatg aacgtctggg tctttgccga ccgcacgccg catccagcgc | 1860 |
| tgacggaagc aaaacaccag cagcagtttt tccagttccg tttatccggg caaaccatcg | 1920 |

```
aagtgaccag cgaatacctg ttccgtcata gcgataacga gctcctgcac tggatggtgg    1980
cgctggatgg taagccgctg gcaagcggtg aagtgcctct ggatgtcgct ccacaaggta    2040
aacagttgat tgaactgcct gaactaccgc agccggagag cgccgggcaa ctctggctca    2100
cagtacgcgt agtgcaaccg aacgcgaccg catggtcaga agccgacac atcagcgcct     2160 ggcagcagtg gcgtctggct gaaaacctca gcgtgacact ccccgccgcg tcccacgcca    2220
tcccgcatct gaccaccagc gaaatggatt tttgcatcga gctgggtaat aagcgttggc    2280
aatttaaccg ccagtcaggc tttctttcac agatgtggat tggcgataaa aaacaactgc    2340
tgacgccgct cgcgatcag ttcacccgtg caccgctgga taacgacatt ggcgtaagtg     2400
aagcgacccg cattgaccct aacgcctggg tcgaacgctg gaaggcggcg ggccattacc    2460
aggccgaagc agcgttgttg cagtgcacg cagatacact tgctgatgcg gtgctgatta     2520
cgaccgctca cgcgtggcag catcagggga aaaccttatt tatcagccgg aaaacctacc    2580
ggattgatgg tagtggtcaa atggcgatta ccgttgatgt tgaagtggcg agcgatacac    2640
cgcatccggc gcggattggc ctgaactgcc agctggcgca ggtagcagag cgggtaaact    2700
ggctcggatt agggccgcaa gaaaactatc ccgaccgcct tactgccgcc tgttttgacc    2760
gctgggatct gccattgtca gacatgtata ccccgtacgc cttcccgagc gaaaacggtc    2820
tgcgctgcgg gacgcgcgaa ttgaattatg cccacacca gtggcgcggc gacttccagt     2880
tcaacatcag ccgctacagt caacagcaac tgatggaaac cagccatcgc catctgctgc    2940
acgcggaaga aggcacatgg ctgaatatcg acggtttcca tatgggatt ggtggcgacg     3000 actcctggag cccgtcagta tcggcggaat tccagctgag cgccggtcgc taccattacc    3060
agttggtctg gtgtcaaaaa taaaggagac c                                   3091
```

<210> SEQ ID NO 34
<211> LENGTH: 733
<212> TYPE: DNA
<213> ORGANISM: Artificial Sequence
<220> FEATURE:
<223> OTHER INFORMATION: GFP variant - GFPmut3

<400> SEQUENCE: 34

```
ggtctcgaat gagtaaagga gaagaacttt tcactggagt tgtcccaatt cttgttgaat     60
tagatggcga tgttaatggg caaaaattct ctgtcagtgg agagggtgaa ggtgatgcaa    120
catacggaaa acttaccctt aaatttattt gcactactgg gaagctacct gttccatggc    180
caacacttgt cactactttc gggtatggtg ttcaatgctt tgcgagatac ccagatcata    240
tgaaacagca tgacttttc aagagtgcca tgcccgaagg ttatgtacag gaaagaacta     300
tattttacaa agatgacggg aactacaaga cacgtgctga agtcaagttt gaaggtgata    360
cccttgttaa tagaatcgag ttaaaaggta ttgattttaa agaagatgga acattcttg     420 gacacaaaat ggaatacaac tataactcac ataatgtata catcatggca gacaaaccaa    480
agaatggaat caaagttaac ttcaaaatta gacacaacat taaagatgga agcgttcaat    540
tagcagacca ttatcaacaa aatactccaa ttggcgatgg ccctgtcctt ttaccagaca    600
accattacct gtccacacaa tctgcccttt ccaaagatcc caacgaaaag agagatcaca    660
tgatccttct tgagtttgta acagctgctg ggattacaca tggcatggat gaactataca    720
aataaaggag acc                                                       733
```

<210> SEQ ID NO 35
<211> LENGTH: 862

<212> TYPE: DNA
<213> ORGANISM: Artificial Sequence
<220> FEATURE:
<223> OTHER INFORMATION: GFP variant - GFPpest

<400> SEQUENCE: 35

```
ggtctcgaat ggtggcgccg ggcgaggagc tgttcaccgg ggtggtgccc atcctggtcg      60
agctggacgg cgacgtaaac ggccacaagt tcagcgtgtc cggcgagggc gagggcgatg     120
ccacctacgg caagctgacc ctgaagttca tctgcaccac cggcaagctg cccgtgccct     180
ggcccaccct cgtgaccacc ctgacctacg gcgtgcagtg cttcagccgc taccccgacc     240
acatgaagca gcacgacttc ttcaagtccg ccatgcccga aggctacgtc caggagcgca     300
ccatcttctt caaggacgac ggcaactaca agacccgcgc cgaggtgaag ttcgagggcg     360
acaccctggt gaaccgcatc gagctgaagg gcatcgactt caaggaggac ggcaacatcc     420
tggggcacaa gctggagtac aactacaaca gccacaacgt ctatatcatg gccgacaagc     480
agaagaacgg catcaaggtg aacttcaaga tccgccacaa catcgaggac ggcagcgtgc     540
agctcgccga ccactaccag cagaacaccc ccatcggcga cggccccgtg ctgctgcccg     600
acaaccacta cctgagcacc cagtccgccc tgagcaaaga ccccaacgag aagcgcgatc     660
acatggtcct gctggagttc gtgaccgccg ccgggatcac tctcggcatg gacgagctgt     720
acaagaagct tagccatggc ttcccgccgg aggtggagga gcaggatgat ggcacgctgc     780
ccatgtcttg tgcccaggag agcgggatgg accgtcaccc tgcagcctgt gcttctgcta     840
ggatcatcga ttaaaggaga cc                                              862
```

<210> SEQ ID NO 36
<211> LENGTH: 322
<212> TYPE: DNA
<213> ORGANISM: Saccharomyces cerevisiae

<400> SEQUENCE: 36

```
ggtctcgtaa agcgaatttc ttatgattta tgatttttat tattaaataa gttataaaaa      60
aaataagtgt atacaaattt taaagtgact cttaggtttt aaaacgaaaa ttcttattct     120
tgagtaactc tttcctgtag gtcaggttgc tttctcaggt atagcatgag gtcgctctta     180
ttgaccacac ctctaccggc atgccgagca aatgcctgca aatcgctccc catttcaccc     240
aattgtagat atgctaactc cagcaatgag ttgatgaatc tcggtgtgta ttttatgtcc     300
tcagaggaca acctcggaga cc                                              322
```

<210> SEQ ID NO 37
<211> LENGTH: 322
<212> TYPE: DNA
<213> ORGANISM: Saccharomyces cerevisiae

<400> SEQUENCE: 37

```
ggtctcgtaa agcggatctc ttatgtcttt acgatttata gttttcatta tcaagtatgc      60
ctatattagt atatagcatc tttagatgac agtgttcgaa gtttcacgaa taaaagataa     120
tattctactt tttgctccca ccgcgtttgc tagcacgagt gaacaccatc cctcgcctgt     180
gagttgtacc cattcctcta aactgtagac atggtagctt cagcagtgtt cgttatgtac     240
ggcatcctcc aacaaacagt cggttatagt ttgtcctgct cctctgaatc gtgtccctcg     300
atatttctca tcctcggaga cc                                              322
```

<210> SEQ ID NO 38

<211> LENGTH: 322
<212> TYPE: DNA
<213> ORGANISM: Saccharomyces cerevisiae

<400> SEQUENCE: 38

```
ggtctcgtaa aagcttttga ttaagccttc tagtccaaaa aacacgtttt tttgtcattt      60
atttcatttt cttagaatag tttagtttat tcattttata gtcacgaatg ttttatgatt     120
ctatataggg ttgcaaacaa gcatttttca ttttatgtta aaacaatttc aggtttacct     180
tttattctgc ttgtggtgac gcgtgtatcc gcccgctctt ttggtcaccc atgtatttaa     240
ttgcataaat aattcttaaa agtggagcta gtctatttct atttacatac ctctcatttc     300
tcatttcctc ccctcggaga cc                                              322
```

<210> SEQ ID NO 39
<211> LENGTH: 322
<212> TYPE: DNA
<213> ORGANISM: Saccharomyces cerevisiae

<400> SEQUENCE: 39

```
ggtctcgtaa agtctgaaga atgaatgatt tgatgatttc ttttcccctc cattttctt      60
actgaatata tcaatgatat agacttgtat agtttattat ttcaaattaa gtagctatat    120
atagtcaaga taacgtttgt ttgacacgat tacattattc gtcgacatct ttttttcagcc    180
tgtcgtggta gcaatttgag gagtattatt aattgaatag gttcattttg cgctcgcata    240
aacagttttc gtcagggaca gtatgttgga atgagtggta attaatggtg acatgacatg    300
ttatagcaat acctcggaga cc                                              322
```

<210> SEQ ID NO 40
<211> LENGTH: 322
<212> TYPE: DNA
<213> ORGANISM: Saccharomyces cerevisiae

<400> SEQUENCE: 40

```
ggtctcgtaa agcgatttaa tctctaatta ttagttaaag ttttataagc attttttatgt     60
aacgaaaaat aaattggttc atattattac tgcactgtca cttaccatgg aaagaccaga    120
caagaagttg ccgacagtct gttgaattgg cctggttagg cttaagtctg ggtccgcttc    180
tttacaaatt tggagaattt ctcttaaacg atatgtatat tcttttcgtt ggaaaagatg    240
tcttccaaaa aaaaaaccga tgaattagtg gaaccaagga aaaaaaaga ggtatccttg    300
attaaggaac acctcggaga cc                                              322
```

<210> SEQ ID NO 41
<211> LENGTH: 322
<212> TYPE: DNA
<213> ORGANISM: Saccharomyces cerevisiae

<400> SEQUENCE: 41

```
ggtctcgtaa aacaaatcgc tcttaaatat atacctaaag aacattaaag ctatattata     60
agcaaagata cgtaaatttt gcttatatta ttatacacat atcatatttc tatattttta    120
agatttggtt atataatgta cgtaatgcaa aggaaataaa ttttatacat tattgaacag    180
cgtccaagta actacattat gtgcactaat agtttagcgt cgtgaagact ttattgtgtc    240
gcgaaaagta aaaattttaa aaattagagc accttgaact tgcgaaaaag gttctcatca    300
actgtttaaa acctcggaga cc                                              322
```

<210> SEQ ID NO 42
<211> LENGTH: 322
<212> TYPE: DNA
<213> ORGANISM: Saccharomyces cerevisiae

<400> SEQUENCE: 42

```
ggtctcgtaa aattgaattg aattgaaatc gatagatcaa ttttttttctt ttctctttcc      60 ccatccttta cgctaaaata atagtttatt ttatttttg aatatttttt atttatatac      120
gtatatatag actattattt atcttttaat gattattaag attttatta aaaaaaaatt      180 cgctcctctt ttaatgcctt tatgcagttt ttttttccca ttcgatattt ctatgttcgg      240
gttcagcgta ttttaagttt aataactcga aaattctgcg ttcgttaaag ctttcgagaa      300
ggatattatt tcctcggaga cc                                              322
```

<210> SEQ ID NO 43
<211> LENGTH: 322
<212> TYPE: DNA
<213> ORGANISM: Saccharomyces cerevisiae

<400> SEQUENCE: 43

```
ggtctcgtaa atcctgttga agtagcattt aatcataatt tttgtcacat tttaatcaac      60
ttgatttttc tggtttaatt tttctaattt taattttaat tttttttatca atgggaactg      120 atacactaaa aagaattagg agccaacaag aataagccgc ttattcccta ctagagtttg      180
cttaaaattt catctcgaat tgtcattcta atattttatc cacacacaca ccttaaaatt      240
tttagattaa atggcatcaa ctcttagctt cacacacaca cacacaccga agctggttgt      300
tttatttgat tcctcggaga cc                                              322
```

<210> SEQ ID NO 44
<211> LENGTH: 322
<212> TYPE: DNA
<213> ORGANISM: Saccharomyces cerevisiae

<400> SEQUENCE: 44

```
ggtctcgtaa aggaagtatc tcggaaatat taatttaggc catgtccta tgcacgtttc      60 ttttgatact tacgggtaca tgtacacaag tatatctata tatataaatt aatgaaaatc      120
ccctatttat atatatgact ttaacgagac agaacagttt tttatttttt atcctatttg      180
atgaatgata cagtttctta ttcacgtgtt atacccacac caaatccaat agcaataccg      240
gccatcacaa tcactgtttc ggcagcccct aagatcagac aaaacatccg gaaccacctt      300
aaatcaacgt ccctcggaga cc                                              322
```

<210> SEQ ID NO 45
<211> LENGTH: 322
<212> TYPE: DNA
<213> ORGANISM: Saccharomyces cerevisiae

<400> SEQUENCE: 45

```
ggtctcgtaa aataaagcaa tcttgatgag gataatgatt tttttttgaa tatacataaa      60
tactaccgtt tttctgctag attttgtgaa gacgtaaata agtacatatt acttttaag      120 ccaagacaag attaagcatt aactttaccc ttttctcttc taagtttcaa tactagttat      180
cactgtttaa aagttatggc gagaacgtcg gcggttaaaa tatattaccc tgaacgtggt      240
gaattgaagt tctaggatgg tttaaagatt tttccttttt gggaaataag taaacaatat      300
attgctgcct tcctcggaga cc                                              322
```

<210> SEQ ID NO 46
<211> LENGTH: 322
<212> TYPE: DNA
<213> ORGANISM: Saccharomyces cerevisiae

<400> SEQUENCE: 46

| | | | | | |
|---|---|---|---|---|---|
| ggtctcgtaa | agtgaattta | ctttaaatct | tgcatttaaa | taaattttct | ttttatagct | 60 |
| ttatgactta | gtttcaattt | atatactatt | ttaatgacat | tttcgattca | ttgattgaaa | 120 |
| gctttgtgtt | ttttcttgat | gcgctattgc | attgttcttg | tctttttcgc | cacatgtaat | 180 |
| atctgtagta | gatacctgat | acattgtgga | tgctgagtga | aattttagtt | aataatggag | 240 |
| gcgctcttaa | taattttggg | gatattggct | tttttttta | aagtttacaa | atgaattttt | 300 |
| tccgccagga | tcctcggaga | cc | | | | 322 |

<210> SEQ ID NO 47
<211> LENGTH: 322
<212> TYPE: DNA
<213> ORGANISM: Saccharomyces cerevisiae

<400> SEQUENCE: 47

| | | | | | |
|---|---|---|---|---|---|
| ggtctcgtaa | aggagattga | taagactttt | ctagttgcat | atcttttata | tttaaatctt | 60 |
| atctattagt | taatttttg | taatttatcc | ttatatatag | tctggttatt | ctaaatatc | 120 |
| atttcagtat | ctaaaaattc | ccctcttttt | tcagttatat | cttaacaggc | gacagtccaa | 180 |
| atgttgattt | atcccagtcc | gattcatcag | ggttgtgaag | cattttgtca | atggtcgaaa | 240 |
| tcacatcagt | aatagtgcct | cttacttgcc | tcatagaatt | tctttctctt | aacgtcaccg | 300 |
| tttggtcttt | tcctcggaga | cc | | | | 322 |

<210> SEQ ID NO 48
<211> LENGTH: 322
<212> TYPE: DNA
<213> ORGANISM: Saccharomyces cerevisiae

<400> SEQUENCE: 48

| | | | | | |
|---|---|---|---|---|---|
| ggtctcgtaa | agagtaataa | ttattgcttc | catataatat | ttttatatac | ctcttatttt | 60 |
| tatgtattag | ttaattaagt | atttttatct | atctgcttat | cattttcttt | tcatataggg | 120 |
| ggggttggtg | ttttcttgcc | catcagattg | atgtcctcca | actcggcact | attttacaaa | 180 |
| gggttttttt | gtaagagaag | gagaagacag | atactaaacc | atacgttact | cgaaacaaaa | 240 |
| aaaaaaaaaa | tggaaaaagc | tgctatcaac | aaaagacggc | ctcatcaaac | ctaaagaaac | 300 |
| catgtcagcg | tcctcggaga | cc | | | | 322 |

<210> SEQ ID NO 49
<211> LENGTH: 322
<212> TYPE: DNA
<213> ORGANISM: Saccharomyces cerevisiae

<400> SEQUENCE: 49

| | | | | | |
|---|---|---|---|---|---|
| ggtctcgtaa | agattaatat | aattatataa | aaatattatc | ttcttttctt | tatatctagt | 60 |
| gttatgtaaa | ataaattgat | gactacggaa | agcttttta | tattgtttct | ttttcattct | 120 |
| gagccactta | aatttcgtga | atgttcttgt | aagggacggt | agatttacaa | gtgatacaac | 180 |
| aaaaagcaag | gcgcttttc | taataaaaag | aagaaaagca | tttaacaatt | gaacacctct | 240 |
| atatcaacga | agaatattac | tttgtctcta | aatccttgta | aaatgtgtac | gatctctata | 300 |
| tgggttactc | acctcggaga | cc | | | | 322 |

<210> SEQ ID NO 50
<211> LENGTH: 2857
<212> TYPE: DNA
<213> ORGANISM: Artificial Sequence
<220> FEATURE:
<223> OTHER INFORMATION: E. coli vector

<400> SEQUENCE: 50

```
cgtcaaaagg gcgacacacc tgcgcgctat agaagacact ataggtctcc tatacgtctc    60
ttatacgaca tcaccgatgg ggaacccaga cgctgagtac gtattctaaa tgcataataa   120
atactgataa catcttatag tttgtattat attttgtatt atcgttgaca tgtataattt   180
tgatatcaaa aactgatttt ccctttatta ttttcgagat ttatttttctt aattctcttt   240
aacaaactag aaatattgta tacaaaaaa atcataaata atagatgaat agtttaatta    300
taggtgttca tcaatcgaaa aagcaacgta tcttatttaa agtgcgttgc ttttttctca    360
tttataaggt taaataattc tcatatatca agcaaagtga caggcgccct taaatattct    420
gacaaatgct ctttccctaa actcccccca taaaaaaacc cgccgaagcg ggttttttacg   480
ttatttgcgg attaacgatt actcgttatc agaaccgccc aggggcccg agcttaagac    540
tggccgtcgt tttacaacac agaaagagtt tgtagaaacg caaaaaggcc atccgtcagg    600
ggccttctgc ttagtttgat gcctggcagt tccctactct cgccttccgc ttcctcgctc    660
actgactcgc tgcgctcggt cgttcggctg cggcgagcgg tatcagctca ctcaaaggcg    720
gtaatacggt tatccacaga atcagggat aacgcaggaa agaacatgtg agcaaaaggc    780
cagcaaaagg ccaggaaccg taaaaaggcc gcgttgctgg cgttttttcca taggctccgc   840
cccctgacg agcatcacaa aaatcgacgc tcaagtcaga ggtggcgaaa cccgacagga    900
ctataaagat accaggcgtt tccccctgga agctccctcg tgcgctctcc tgttccgacc    960
ctgccgctta ccggatacct gtccgccttt ctcccttcgg gaagcgtggc gctttctcat   1020
agctcacgct gtaggtatct cagttcggtg taggtcgttc gctccaagct gggctgtgtg   1080
cacgaacccc ccgttcagcc cgaccgctgc gccttatccg gtaactatcg tcttgagtcc   1140
aacccggtaa gacacgactt atcgccactg gcagcagcca ctggtaacag gattagcaga   1200
gcgaggtatg taggcggtgc tacagagttc ttgaagtggt gggctaacta cggctacact   1260
agaagaacag tatttggtat ctgcgctctg ctgaagccag ttaccttcgg aaaaagagtt   1320
ggtagctctt gatccggcaa acaaaccacc gctggtagcg gtggtttttt tgtttgcaag   1380
cagcagatta cgcgcagaaa aaaaggatct caagaagatc ctttgatctt ttctacgggg   1440
tctgacgctc agtggaacga cgcgcgcgta actcacgtta agggattttg gtcatgagct   1500
tgcgccgtcc cgtcaagtca gcgtaatgct ctgcttttac caatgcttaa tcagtgaggc   1560
acctatctca gcgatctgtc tatttcgttc atccatagtt gcctgactcc ccgtcgtgta   1620
gataactacg atacgggagg gcttaccatc tggccccagc gctgcgatga taccgcgaga   1680
accacgctca ccggctccgg atttatcagc aataaaccag ccagccggaa gggccgagcg   1740
cagaagtggt cctgcaactt tatccgcctc catccagtct attaattgtt gccgggaagc   1800
tagagtaagt agttcgccag ttaatagttt gcgcaacgtt gttgccatcg ctacaggcat   1860
cgtggtgtca cgctcgtcgt ttggtatggc ttcattcagc tccggttccc aacgatcaag   1920
gcgagttaca tgatccccca tgttgtgcaa aaaagcggtt agctccttcg gtcctccgat   1980
cgttgtcaga agtaagttgg ccgcagtgtt atcactcatg gttatggcag cactgcataa   2040
```

```
ttctcttact gtcatgccat ccgtaagatg cttttctgtg actggtgagt actcaaccaa    2100
gtcattctga gaatagtgta tgcggcgacc gagttgctct tgcccggcgt caatacggga    2160
taataccgcg ccacatagca gaactttaaa agtgctcatc attggaaaac gttcttcggg    2220
gcgaaaactc tcaaggatct taccgctgtt gagatccagt tcgatgtaac ccactcgtgc    2280
acccaactga tcttcagcat cttttacttt caccagcgtt tctgggtgag caaaaacagg    2340
aaggcaaaat gccgcaaaaa agggaataag ggcgacacgg aaatgttgaa tactcatatt    2400
cttccttttt caatattatt gaagcattta tcagggttat tgtctcatga gcggatacat    2460
atttgaatgt atttagaaaa ataaacaaat aggggtcagt gttacaacca attaaccaat    2520
tctgaacatt atcgcgagcc catttatacc tgaatatggc tcataacacc ccttgtttgc    2580
ctggcggcag tagcgcggtg gtcccacctg accccatgcc gaactcagaa gtgaaacgcc    2640
gtagcgccga tggtagtgtg gggactcccc atgcgagagt agggaactgc caggcatcaa    2700
ataaaacgaa aggctcagtc gaaagactgg gcctttcgcc cgggctaatt agggggggctg    2760 gatcgcttcg tgttccccat cggtgatgtc gtataggaag caggttatac gagacctata    2820
ggagacgtat atggtcttcg tgtcgccctt cgctgaa                              2857

<210> SEQ ID NO 51
<211> LENGTH: 50
<212> TYPE: DNA
<213> ORGANISM: Artificial Sequence
<220> FEATURE:
<223> OTHER INFORMATION: Connector 5

<400> SEQUENCE: 51
aagcgacttc caatcgcttt gcatatccag taccacaccc acaggcgttt              50

<210> SEQ ID NO 52
<211> LENGTH: 50
<212> TYPE: DNA
<213> ORGANISM: Artificial Sequence
<220> FEATURE:
<223> OTHER INFORMATION: Connector a

<400> SEQUENCE: 52
ttgcccatcg aacgtacaag tactcctctg ttctctcctt cctttgcttt              50

<210> SEQ ID NO 53
<211> LENGTH: 50
<212> TYPE: DNA
<213> ORGANISM: Artificial Sequence
<220> FEATURE:
<223> OTHER INFORMATION: Connector b

<400> SEQUENCE: 53
cggatcgatg tacacaaccg actgcaccca acgaacaca aatcttagca               50

<210> SEQ ID NO 54
<211> LENGTH: 50
<212> TYPE: DNA
<213> ORGANISM: Artificial Sequence
<220> FEATURE:
<223> OTHER INFORMATION: Connector c

<400> SEQUENCE: 54
acgctttccg gcatcttcca gaccacagta tatccatccg cctcctgttg              50

<210> SEQ ID NO 55
<211> LENGTH: 50
```

```
<212> TYPE: DNA
<213> ORGANISM: Artificial Sequence
<220> FEATURE:
<223> OTHER INFORMATION: Connector d

<400> SEQUENCE: 55
aacgttgtcc aggtttgtat ccacgtgtgt ccgttccgcc aatattccgc          50

<210> SEQ ID NO 56
<211> LENGTH: 50
<212> TYPE: DNA
<213> ORGANISM: Artificial Sequence
<220> FEATURE:
<223> OTHER INFORMATION: Connector e

<400> SEQUENCE: 56
aaataaccac aaacatcctt cccatatgct cggtcgtgct tgttgtacct          50

<210> SEQ ID NO 57
<211> LENGTH: 50
<212> TYPE: DNA
<213> ORGANISM: Artificial Sequence
<220> FEATURE:
<223> OTHER INFORMATION: Connector f

<400> SEQUENCE: 57
gaaaccttcg aatccagcca gcatgtcgac acccacaaga tgtagtgcac          50

<210> SEQ ID NO 58
<211> LENGTH: 50
<212> TYPE: DNA
<213> ORGANISM: Artificial Sequence
<220> FEATURE:
<223> OTHER INFORMATION: Connector g

<400> SEQUENCE: 58
caacacacaa gttccgcaac gatcgaagca gagtcgagta catccagatg          50

<210> SEQ ID NO 59
<211> LENGTH: 50
<212> TYPE: DNA
<213> ORGANISM: Artificial Sequence
<220> FEATURE:
<223> OTHER INFORMATION: Connector h

<400> SEQUENCE: 59
aaagccaaag ttcgcgttcc gaccttgcct cccaaatccg agttgcgatt          50

<210> SEQ ID NO 60
<211> LENGTH: 50
<212> TYPE: DNA
<213> ORGANISM: Artificial Sequence
<220> FEATURE:
<223> OTHER INFORMATION: Connector i

<400> SEQUENCE: 60
atatccgatg ccgtacgaat cccactcgcg cacacatgct tgcctttgtt          50

<210> SEQ ID NO 61
<211> LENGTH: 50
<212> TYPE: DNA
<213> ORGANISM: Artificial Sequence
<220> FEATURE:
<223> OTHER INFORMATION: Connector j

<400> SEQUENCE: 61
```
acaagacaat tcgtaccaag tacgtcgagc gctgcaatac accatacgta        50

<210> SEQ ID NO 62
<211> LENGTH: 50
<212> TYPE: DNA
<213> ORGANISM: Artificial Sequence
<220> FEATURE:
<223> OTHER INFORMATION: Connector k

<400> SEQUENCE: 62
atgccttgcg tgcatgccat ctcgaacgat tgtgtttcca gccaacttgc        50

<210> SEQ ID NO 63
<211> LENGTH: 50
<212> TYPE: DNA
<213> ORGANISM: Artificial Sequence
<220> FEATURE:
<223> OTHER INFORMATION: Connector 3

<400> SEQUENCE: 63
agaaagcctg tatgcgaagc cacaatcctt tccaacagac catactaagt        50

<210> SEQ ID NO 64
<211> LENGTH: 757
<212> TYPE: DNA
<213> ORGANISM: Artificial Sequence
<220> FEATURE:
<223> OTHER INFORMATION: Backbone entry vector

<400> SEQUENCE: 64
aagcgacttc caatcgcttt gcatatccag taccacaccc acaggcgttt gtgcggagac        60
cggcttacta aaagccagat aacagtatgc atatttgcgc gctgattttt gcggtataag       120
aatatatact gatatgtata cccgaagtat gtcaaaaaga ggtatgctat gaagcagcgt       180
attacagtga cagttgacag cgacagctat cagttgctca aggcatatat gatgtcaata       240
tctccggtct ggtaagcaca accatgcaga atgaagcccg tcgtctgcgt gccgaacgct       300
ggaaagcgga aaatcaggaa gggatggctg aggtcgcccg gtttattgaa atgaacggct       360
cttttgctga cgagaacagg ggctggtgaa atgcagttta aggtttacac ctataaaaga       420
gagagccgtt atcgtctgtt tgtggatgta cagagtgata ttattgacac gcccgggcga       480
cggatggtga tccccctggc cagtgcacgt ctgctgtcag ataaagtctc ccgtgaactt       540
tacccggtgg tgcatatcgg ggatgaaagc tggcgcatga tgaccaccga tatggccagt       600
gtgccggttt ccgttatcgg ggaagaagtg gctgatctca gccaccgcga aaatgacatc       660
aaaaacgcca ttaacctgat gttctgggga atataaggtc tcgcctcttg cccatcgaac       720
gtacaagtac tcctctgttc tctccttcct ttgcttt                               757

<210> SEQ ID NO 65
<211> LENGTH: 757
<212> TYPE: DNA
<213> ORGANISM: Artificial Sequence
<220> FEATURE:
<223> OTHER INFORMATION: Backbone entry vector

<400> SEQUENCE: 65
ttgcccatcg aacgtacaag tactcctctg ttctctcctt cctttgcttt gtgcggagac        60
cggcttacta aaagccagat aacagtatgc atatttgcgc gctgattttt gcggtataag       120
aatatatact gatatgtata cccgaagtat gtcaaaaaga ggtatgctat gaagcagcgt       180
attacagtga cagttgacag cgacagctat cagttgctca aggcatatat gatgtcaata       240

```
tctccggtct ggtaagcaca accatgcaga atgaagcccg tcgtctgcgt gccgaacgct    300
ggaaagcgga aaatcaggaa gggatggctg aggtcgcccg gtttattgaa atgaacggct    360
cttttgctga cgagaacagg ggctggtgaa atgcagttta aggtttacac ctataaaaga    420
gagagccgtt atcgtctgtt tgtggatgta cagagtgata ttattgacac gcccgggcga    480
cggatggtga tcccctggc cagtgcacgt ctgctgtcag ataaagtctc ccgtgaactt     540
tacccggtgg tgcatatcgg ggatgaaagc tggcgcatga tgaccaccga tatggccagt    600
gtgccggttt ccgttatcgg ggaagaagtg gctgatctca gccaccgcga aaatgacatc    660
aaaaacgcca ttaacctgat gttctgggga atataaggtc tcgcctccgg atcgatgtac    720
acaaccgact gcacccaaac gaacacaaat cttagca                             757
```

```
<210> SEQ ID NO 66
<211> LENGTH: 757
<212> TYPE: DNA
<213> ORGANISM: Artificial Sequence
<220> FEATURE:
<223> OTHER INFORMATION: Backbone entry vector

<400> SEQUENCE: 66
cggatcgatg tacacaaccg actgcaccca acgaacacaa atcttagca gtgcggagac    60 cggcttacta aaagccagat aacagtatgc atatttgcgc gctgattttt gcggtataag    120
aatatatact gatatgtata cccgaagtat gtcaaaaaga ggtatgctat gaagcagcgt    180
attacagtga cagttgacag cgacagctat cagttgctca aggcatatat gatgtcaata    240
tctccggtct ggtaagcaca accatgcaga atgaagcccg tcgtctgcgt gccgaacgct    300
ggaaagcgga aaatcaggaa gggatggctg aggtcgcccg gtttattgaa atgaacggct    360
cttttgctga cgagaacagg ggctggtgaa atgcagttta aggtttacac ctataaaaga    420
gagagccgtt atcgtctgtt tgtggatgta cagagtgata ttattgacac gcccgggcga    480
cggatggtga tcccctggc cagtgcacgt ctgctgtcag ataaagtctc ccgtgaactt     540
tacccggtgg tgcatatcgg ggatgaaagc tggcgcatga tgaccaccga tatggccagt    600
gtgccggttt ccgttatcgg ggaagaagtg gctgatctca gccaccgcga aaatgacatc    660
aaaaacgcca ttaacctgat gttctgggga atataaggtc tcgcctcacg ctttccggca    720
tcttccagac cacagtatat ccatccgcct cctgttg                              757
```

```
<210> SEQ ID NO 67
<211> LENGTH: 757
<212> TYPE: DNA
<213> ORGANISM: Artificial Sequence
<220> FEATURE:
<223> OTHER INFORMATION: Backbone entry vector

<400> SEQUENCE: 67
acgctttccg gcatcttcca gaccacagta tatccatccg cctcctgttg gtgcggagac    60
cggcttacta aaagccagat aacagtatgc atatttgcgc gctgattttt gcggtataag    120
aatatatact gatatgtata cccgaagtat gtcaaaaaga ggtatgctat gaagcagcgt    180
attacagtga cagttgacag cgacagctat cagttgctca aggcatatat gatgtcaata    240
tctccggtct ggtaagcaca accatgcaga atgaagcccg tcgtctgcgt gccgaacgct    300
ggaaagcgga aaatcaggaa gggatggctg aggtcgcccg gtttattgaa atgaacggct    360
cttttgctga cgagaacagg ggctggtgaa atgcagttta aggtttacac ctataaaaga    420
```

```
gagagccgtt atcgtctgtt tgtggatgta cagagtgata ttattgacac gcccgggcga    480
cggatggtga tccccctggc cagtgcacgt ctgctgtcag ataaagtctc ccgtgaactt    540
tacccggtgg tgcatatcgg ggatgaaagc tggcgcatga tgaccaccga tatggccagt    600
gtgccggttt ccgttatcgg ggaagaagtg gctgatctca gccaccgcga aaatgacatc    660
aaaaacgcca ttaacctgat gttctgggga atataaggtc tcgcctcaac gttgtccagg    720
tttgtatcca cgtgtgtccg ttccgccaat attccgc                             757

<210> SEQ ID NO 68
<211> LENGTH: 757
<212> TYPE: DNA
<213> ORGANISM: Artificial Sequence
<220> FEATURE:
<223> OTHER INFORMATION: Backbone entry vector

<400> SEQUENCE: 68
aacgttgtcc aggtttgtat ccacgtgtgt ccgttccgcc aatattccgc gtgcggagac     60
cggcttacta aaagccagat aacagtatgc atatttgcgc gctgattttt gcggtataag    120
aatatatact gatatgtata cccgaagtat gtcaaaaaga ggtatgctat gaagcagcgt    180
attacagtga cagttgacag cgacagctat cagttgctca aggcatatat gatgtcaata    240
tctccggtct ggtaagcaca accatgcaga atgaagcccg tcgtctgcgt gccgaacgct    300
ggaaagcgga aaatcaggaa gggatggctg aggtcgcccg gtttattgaa atgaacggct    360
cttttgctga cgagaacagg ggctggtgaa atgcagttta aggtttacac ctataaaaga    420
gagagccgtt atcgtctgtt tgtggatgta cagagtgata ttattgacac gcccgggcga    480
cggatggtga tccccctggc cagtgcacgt ctgctgtcag ataaagtctc ccgtgaactt    540
tacccggtgg tgcatatcgg ggatgaaagc tggcgcatga tgaccaccga tatggccagt    600
gtgccggttt ccgttatcgg ggaagaagtg gctgatctca gccaccgcga aaatgacatc    660
aaaaacgcca ttaacctgat gttctgggga atataaggtc tcgcctcaaa taaccacaaa    720
catccttccc atatgctcgg tcgtgcttgt tgtacct                             757

<210> SEQ ID NO 69
<211> LENGTH: 757
<212> TYPE: DNA
<213> ORGANISM: Artificial Sequence
<220> FEATURE:
<223> OTHER INFORMATION: Backbone entry vector

<400> SEQUENCE: 69
aaataaccac aaacatcctt cccatatgct cggtcgtgct tgttgtacct gtgcggagac     60
cggcttacta aaagccagat aacagtatgc atatttgcgc gctgattttt gcggtataag    120
aatatatact gatatgtata cccgaagtat gtcaaaaaga ggtatgctat gaagcagcgt    180
attacagtga cagttgacag cgacagctat cagttgctca aggcatatat gatgtcaata    240
tctccggtct ggtaagcaca accatgcaga atgaagcccg tcgtctgcgt gccgaacgct    300
ggaaagcgga aaatcaggaa gggatggctg aggtcgcccg gtttattgaa atgaacggct    360
cttttgctga cgagaacagg ggctggtgaa atgcagttta aggtttacac ctataaaaga    420
gagagccgtt atcgtctgtt tgtggatgta cagagtgata ttattgacac gcccgggcga    480
cggatggtga tccccctggc cagtgcacgt ctgctgtcag ataaagtctc ccgtgaactt    540
tacccggtgg tgcatatcgg ggatgaaagc tggcgcatga tgaccaccga tatggccagt    600
gtgccggttt ccgttatcgg ggaagaagtg gctgatctca gccaccgcga aaatgacatc    660
```

```
aaaaacgcca ttaacctgat gttctgggga atataaggtc tcgcctcgaa accttcgaat    720
ccagccagca tgtcgacacc cacaagatgt agtgcac                             757

<210> SEQ ID NO 70
<211> LENGTH: 757
<212> TYPE: DNA
<213> ORGANISM: Artificial Sequence
<220> FEATURE:
<223> OTHER INFORMATION: Backbone entry vector

<400> SEQUENCE: 70
gaaaccttcg aatccagcca gcatgtcgac acccacaaga tgtagtgcac gtgcggagac     60
cggcttacta aaagccagat aacagtatgc atatttgcgc gctgattttt gcggtataag    120
aatatatact gatatgtata cccgaagtat gtcaaaaaga ggtatgctat gaagcagcgt    180
attacagtga cagttgacag cgacagctat cagttgctca aggcatatat gatgtcaata    240
tctccggtct ggtaagcaca accatgcaga atgaagcccg tcgtctgcgt gccgaacgct    300
ggaaagcgga aaatcaggaa gggatggctg aggtcgcccg gtttattgaa atgaacggct    360
cttttgctga cgagaacagg ggctggtgaa atgcagttta aggtttacac ctataaaaga    420
gagagccgtt atcgtctgtt tgtggatgta cagagtgata ttattgacac gcccgggcga    480
cggatggtga tcccctggc cagtgcacgt ctgctgtcag ataaagtctc ccgtgaactt     540
tacccggtgg tgcatatcgg ggatgaaagc tggcgcatga tgaccaccga tatggccagt    600
gtgccggttt ccgttatcgg ggaagaagtg gctgatctca gccaccgcga aaatgacatc    660
aaaaacgcca ttaacctgat gttctgggga atataaggtc tcgcctccaa cacacaagtt    720
ccgcaacgat cgaagcagag tcgagtacat ccagatg                             757

<210> SEQ ID NO 71
<211> LENGTH: 757
<212> TYPE: DNA
<213> ORGANISM: Artificial Sequence
<220> FEATURE:
<223> OTHER INFORMATION: Backbone entry vector

<400> SEQUENCE: 71
caacacacaa gttccgcaac gatcgaagca gagtcgagta catccagatg gtgcggagac     60
cggcttacta aaagccagat aacagtatgc atatttgcgc gctgattttt gcggtataag    120
aatatatact gatatgtata cccgaagtat gtcaaaaaga ggtatgctat gaagcagcgt    180
attacagtga cagttgacag cgacagctat cagttgctca aggcatatat gatgtcaata    240
tctccggtct ggtaagcaca accatgcaga atgaagcccg tcgtctgcgt gccgaacgct    300
ggaaagcgga aaatcaggaa gggatggctg aggtcgcccg gtttattgaa atgaacggct    360
cttttgctga cgagaacagg ggctggtgaa atgcagttta aggtttacac ctataaaaga    420
gagagccgtt atcgtctgtt tgtggatgta cagagtgata ttattgacac gcccgggcga    480
cggatggtga tcccctggc cagtgcacgt ctgctgtcag ataaagtctc ccgtgaactt     540
tacccggtgg tgcatatcgg ggatgaaagc tggcgcatga tgaccaccga tatggccagt    600
gtgccggttt ccgttatcgg ggaagaagtg gctgatctca gccaccgcga aaatgacatc    660
aaaaacgcca ttaacctgat gttctgggga atataaggtc tcgcctcaaa gccaaagttc    720
gcgttccgac cttgcctccc aaatccgagt tgcgatt                             757

<210> SEQ ID NO 72
```

```
<211> LENGTH: 757
<212> TYPE: DNA
<213> ORGANISM: Artificial Sequence
<220> FEATURE:
<223> OTHER INFORMATION: Backbone entry vector

<400> SEQUENCE: 72
aaagccaaag ttcgcgttcc gaccttgcct cccaaatccg agttgcgatt gtgcggagac      60
cggcttacta aaagccagat aacagtatgc atatttgcgc gctgattttt gcggtataag     120
aatatatact gatatgtata cccgaagtat gtcaaaaaga ggtatgctat gaagcagcgt     180
attacagtga cagttgacag cgacagctat cagttgctca aggcatatat gatgtcaata     240
tctccggtct ggtaagcaca accatgcaga atgaagcccg tcgtctgcgt gccgaacgct     300
ggaaagcgga aaatcaggaa gggatggctg aggtcgcccg gtttattgaa atgaacggct     360
cttttgctga cgagaacagg ggctggtgaa atgcagttta aggtttacac ctataaaaga     420
gagagccgtt atcgtctgtt tgtggatgta cagagtgata ttattgacac gcccgggcga     480
cggatggtga tcccctggc cagtgcacgt ctgctgtcag ataaagtctc ccgtgaactt      540
tacccggtgg tgcatatcgg ggatgaaagc tggcgcatga tgaccaccga tatggccagt     600
gtgccggttt ccgttatcgg ggaagaagtg gctgatctca gccaccgcga aaatgacatc     660
aaaaacgcca ttaacctgat gttctgggga atataaggtc tcgcctcata tccgatgccg     720
tacgaatccc actcgcgcac acatgcttgc ctttgtt                              757

<210> SEQ ID NO 73
<211> LENGTH: 757
<212> TYPE: DNA
<213> ORGANISM: Artificial Sequence
<220> FEATURE:
<223> OTHER INFORMATION: Bacbone entry vector

<400> SEQUENCE: 73
atatccgatg ccgtacgaat cccactcgcg cacacatgct tgcctttgtt gtgcggagac      60
cggcttacta aaagccagat aacagtatgc atatttgcgc gctgattttt gcggtataag     120
aatatatact gatatgtata cccgaagtat gtcaaaaaga ggtatgctat gaagcagcgt     180
attacagtga cagttgacag cgacagctat cagttgctca aggcatatat gatgtcaata     240
tctccggtct ggtaagcaca accatgcaga atgaagcccg tcgtctgcgt gccgaacgct     300
ggaaagcgga aaatcaggaa gggatggctg aggtcgcccg gtttattgaa atgaacggct     360
cttttgctga cgagaacagg ggctggtgaa atgcagttta aggtttacac ctataaaaga     420
gagagccgtt atcgtctgtt tgtggatgta cagagtgata ttattgacac gcccgggcga     480
cggatggtga tcccctggc cagtgcacgt ctgctgtcag ataaagtctc ccgtgaactt      540
tacccggtgg tgcatatcgg ggatgaaagc tggcgcatga tgaccaccga tatggccagt     600
gtgccggttt ccgttatcgg ggaagaagtg gctgatctca gccaccgcga aaatgacatc     660
aaaaacgcca ttaacctgat gttctgggga atataaggtc tcgcctcaca agacaattcg     720
taccaagtac gtcgagcgct gcaatacacc atacgta                              757

<210> SEQ ID NO 74
<211> LENGTH: 757
<212> TYPE: DNA
<213> ORGANISM: Artificial Sequence
<220> FEATURE:
<223> OTHER INFORMATION: Backbone entry vector

<400> SEQUENCE: 74
```

```
acaagacaat tcgtaccaag tacgtcgagc gctgcaatac accatacgta gtgcggagac    60
cggcttacta aaagccagat aacagtatgc atatttgcgc gctgatttt gcggtataag    120 aatatatact gatatgtata cccgaagtat gtcaaaaaga ggtatgctat gaagcagcgt   180
attacagtga cagttgacag cgacagctat cagttgctca aggcatatat gatgtcaata   240
tctccggtct ggtaagcaca accatgcaga atgaagcccg tcgtctgcgt gccgaacgct   300
ggaaagcgga aaatcaggaa gggatggctg aggtcgcccg gtttattgaa atgaacggct   360
cttttgctga cgagaacagg ggctggtgaa atgcagttta aggtttacac ctataaaaga   420
gagagccgtt atcgtctgtt tgtggatgta cagagtgata ttattgacac gcccgggcga   480
cggatggtga tcccctggc cagtgcacgt ctgctgtcag ataaagtctc ccgtgaactt    540
tacccggtgg tgcatatcgg ggatgaaagc tggcgcatga tgaccaccga tatggccagt   600
gtgccggttt ccgttatcgg ggaagaagtg gctgatctca gccaccgcga aaatgacatc    660
aaaaacgcca ttaacctgat gttctgggga atataaggtc tcgcctcatg ccttgcgtgc    720
atgccatctc gaacgattgt gtttccagcc aacttgc                             757
```

`<210>` SEQ ID NO 75
`<211>` LENGTH: 757
`<212>` TYPE: DNA
`<213>` ORGANISM: Artificial Sequence
`<220>` FEATURE:
`<223>` OTHER INFORMATION: Backbone entry vector

`<400>` SEQUENCE: 75

```
ttgcccatcg aacgtacaag tactcctctg ttctctcctt cctttgcttt gtgcggagac   60
cggcttacta aaagccagat aacagtatgc atatttgcgc gctgatttt gcggtataag    120 aatatatact gatatgtata cccgaagtat gtcaaaaaga ggtatgctat gaagcagcgt   180
attacagtga cagttgacag cgacagctat cagttgctca aggcatatat gatgtcaata   240
tctccggtct ggtaagcaca accatgcaga atgaagcccg tcgtctgcgt gccgaacgct   300
ggaaagcgga aaatcaggaa gggatggctg aggtcgcccg gtttattgaa atgaacggct   360
cttttgctga cgagaacagg ggctggtgaa atgcagttta aggtttacac ctataaaaga   420
gagagccgtt atcgtctgtt tgtggatgta cagagtgata ttattgacac gcccgggcga   480
cggatggtga tcccctggc cagtgcacgt ctgctgtcag ataaagtctc ccgtgaactt    540
tacccggtgg tgcatatcgg ggatgaaagc tggcgcatga tgaccaccga tatggccagt   600
gtgccggttt ccgttatcgg ggaagaagtg gctgatctca gccaccgcga aaatgacatc   660
aaaaacgcca ttaacctgat gttctgggga atataaggtc tcgcctcaga aagcctgtat   720
gcgaagccac aatcctttcc aacagaccat actaagt                             757
```

`<210>` SEQ ID NO 76
`<211>` LENGTH: 757
`<212>` TYPE: DNA
`<213>` ORGANISM: Artificial Sequence
`<220>` FEATURE:
`<223>` OTHER INFORMATION: Backbone entry vector

`<400>` SEQUENCE: 76

```
cggatcgatg tacacaaccg actgcaccca aacgaacaca atcttagca gtgcggagac    60 cggcttacta aaagccagat aacagtatgc atatttgcgc gctgatttt gcggtataag    120 aatatatact gatatgtata cccgaagtat gtcaaaaaga ggtatgctat gaagcagcgt   180
```

| | |
|---|---|
| attacagtga cagttgacag cgacagctat cagttgctca aggcatatat gatgtcaata | 240 |
| tctccggtct ggtaagcaca accatgcaga atgaagcccg tcgtctgcgt gccgaacgct | 300 |
| ggaaagcgga aaatcaggaa gggatggctg aggtcgcccg gtttattgaa atgaacggct | 360 |
| cttttgctga cgagaacagg ggctggtgaa atgcagttta aggtttacac ctataaaaga | 420 |
| gagagccgtt atcgtctgtt tgtggatgta cagagtgata ttattgacac gcccgggcga | 480 |
| cggatggtga tcccctggc cagtgcacgt ctgctgtcag ataaagtctc ccgtgaactt | 540 |
| tacccggtgg tgcatatcgg ggatgaaagc tggcgcatga tgaccaccga tatggccagt | 600 |
| gtgccggttt ccgttatcgg ggaagaagtg gctgatctca gccaccgcga aaatgacatc | 660 |
| aaaaacgcca ttaacctgat gttctgggga atataaggtc tcgcctcaga aagcctgtat | 720 |
| gcgaagccac aatcctttcc aacagaccat actaagt | 757 |

```
<210> SEQ ID NO 77
<211> LENGTH: 757
<212> TYPE: DNA
<213> ORGANISM: Artificial Sequence
<220> FEATURE:
<223> OTHER INFORMATION: Backbone entry vector

<400> SEQUENCE: 77
```

| | |
|---|---|
| acgctttccg gcatcttcca gaccacagta tatccatccg cctcctgttg gtgcggagac | 60 |
| cggcttacta aaagccagat aacagtatgc atatttgcgc gctgattttt gcggtataag | 120 |
| aatatatact gatatgtata cccgaagtat gtcaaaaaga ggtatgctat gaagcagcgt | 180 |
| attacagtga cagttgacag cgacagctat cagttgctca aggcatatat gatgtcaata | 240 |
| tctccggtct ggtaagcaca accatgcaga atgaagcccg tcgtctgcgt gccgaacgct | 300 |
| ggaaagcgga aaatcaggaa gggatggctg aggtcgcccg gtttattgaa atgaacggct | 360 |
| cttttgctga cgagaacagg ggctggtgaa atgcagttta aggtttacac ctataaaaga | 420 |
| gagagccgtt atcgtctgtt tgtggatgta cagagtgata ttattgacac gcccgggcga | 480 |
| cggatggtga tcccctggc cagtgcacgt ctgctgtcag ataaagtctc ccgtgaactt | 540 |
| tacccggtgg tgcatatcgg ggatgaaagc tggcgcatga tgaccaccga tatggccagt | 600 |
| gtgccggttt ccgttatcgg ggaagaagtg gctgatctca gccaccgcga aaatgacatc | 660 |
| aaaaacgcca ttaacctgat gttctgggga atataaggtc tcgcctcaga aagcctgtat | 720 |
| gcgaagccac aatcctttcc aacagaccat actaagt | 757 |

```
<210> SEQ ID NO 78
<211> LENGTH: 757
<212> TYPE: DNA
<213> ORGANISM: Artificial Sequence
<220> FEATURE:
<223> OTHER INFORMATION: Backbone entry vector

<400> SEQUENCE: 78
```

| | |
|---|---|
| aacgttgtcc aggtttgtat ccacgtgtgt ccgttccgcc aatattccgc gtgcggagac | 60 |
| cggcttacta aaagccagat aacagtatgc atatttgcgc gctgattttt gcggtataag | 120 |
| aatatatact gatatgtata cccgaagtat gtcaaaaaga ggtatgctat gaagcagcgt | 180 |
| attacagtga cagttgacag cgacagctat cagttgctca aggcatatat gatgtcaata | 240 |
| tctccggtct ggtaagcaca accatgcaga atgaagcccg tcgtctgcgt gccgaacgct | 300 |
| ggaaagcgga aaatcaggaa gggatggctg aggtcgcccg gtttattgaa atgaacggct | 360 |
| cttttgctga cgagaacagg ggctggtgaa atgcagttta aggtttacac ctataaaaga | 420 |

| gagagccgtt atcgtctgtt tgtggatgta cagagtgata ttattgacac gcccgggcga | 480 |
| cggatggtga tcccctggc cagtgcacgt ctgctgtcag ataaagtctc ccgtgaactt | 540 |
| tacccggtgg tgcatatcgg ggatgaaagc tggcgcatga tgaccaccga tatggccagt | 600 |
| gtgccggttt ccgttatcgg ggaagaagtg gctgatctca gccaccgcga aaatgacatc | 660 |
| aaaaacgcca ttaacctgat gttctgggga atataaggtc tcgcctcaga aagcctgtat | 720 |
| gcgaagccac aatcctttcc aacagaccat actaagt | 757 |

<210> SEQ ID NO 79
<211> LENGTH: 757
<212> TYPE: DNA
<213> ORGANISM: Artificial Sequence
<220> FEATURE:
<223> OTHER INFORMATION: Backbone entry vector

<400> SEQUENCE: 79

| aaataaccac aaacatcctt cccatatgct cggtcgtgct tgttgtacct gtgcggagac | 60 |
| cggcttacta aaagccagat aacagtatgc atatttgcgc gctgatttt gcggtataag | 120 |
| aatatatact gatatgtata cccgaagtat gtcaaaaaga ggtatgctat gaagcagcgt | 180 |
| attacagtga cagttgacag cgacagctat cagttgctca aggcatatat gatgtcaata | 240 |
| tctccggtct ggtaagcaca accatgcaga atgaagcccg tcgtctgcgt gccgaacgct | 300 |
| ggaaagcgga aaatcaggaa gggatggctg aggtcgcccg gtttattgaa atgaacggct | 360 |
| cttttgctga cgagaacagg ggctggtgaa atgcagttta aggtttacac ctataaaaga | 420 |
| gagagccgtt atcgtctgtt tgtggatgta cagagtgata ttattgacac gcccgggcga | 480 |
| cggatggtga tcccctggc cagtgcacgt ctgctgtcag ataaagtctc ccgtgaactt | 540 |
| tacccggtgg tgcatatcgg ggatgaaagc tggcgcatga tgaccaccga tatggccagt | 600 |
| gtgccggttt ccgttatcgg ggaagaagtg gctgatctca gccaccgcga aaatgacatc | 660 |
| aaaaacgcca ttaacctgat gttctgggga atataaggtc tcgcctcaga aagcctgtat | 720 |
| gcgaagccac aatcctttcc aacagaccat actaagt | 757 |

<210> SEQ ID NO 80
<211> LENGTH: 757
<212> TYPE: DNA
<213> ORGANISM: Artificial Sequence
<220> FEATURE:
<223> OTHER INFORMATION: Backbone entry vector

<400> SEQUENCE: 80

| gaaaccttcg aatccagcca gcatgtcgac acccacaaga tgtagtgcac gtgcggagac | 60 |
| cggcttacta aaagccagat aacagtatgc atatttgcgc gctgatttt gcggtataag | 120 |
| aatatatact gatatgtata cccgaagtat gtcaaaaaga ggtatgctat gaagcagcgt | 180 |
| attacagtga cagttgacag cgacagctat cagttgctca aggcatatat gatgtcaata | 240 |
| tctccggtct ggtaagcaca accatgcaga atgaagcccg tcgtctgcgt gccgaacgct | 300 |
| ggaaagcgga aaatcaggaa gggatggctg aggtcgcccg gtttattgaa atgaacggct | 360 |
| cttttgctga cgagaacagg ggctggtgaa atgcagttta aggtttacac ctataaaaga | 420 |
| gagagccgtt atcgtctgtt tgtggatgta cagagtgata ttattgacac gcccgggcga | 480 |
| cggatggtga tcccctggc cagtgcacgt ctgctgtcag ataaagtctc ccgtgaactt | 540 |
| tacccggtgg tgcatatcgg ggatgaaagc tggcgcatga tgaccaccga tatggccagt | 600 |

```
gtgccggttt ccgttatcgg ggaagaagtg gctgatctca gccaccgcga aaatgacatc    660
aaaaacgcca ttaacctgat gttctgggga atataaggtc tcgcctcaga aagcctgtat    720
gcgaagccac aatcctttcc aacagaccat actaagt                             757

<210> SEQ ID NO 81
<211> LENGTH: 757
<212> TYPE: DNA
<213> ORGANISM: Artificial Sequence
<220> FEATURE:
<223> OTHER INFORMATION: Backbone entry vector

<400> SEQUENCE: 81
caacacacaa gttccgcaac gatcgaagca gagtcgagta catccagatg gtgcggagac     60
cggcttacta aaagccagat aacagtatgc atatttgcgc gctgattttt gcggtataag    120
aatatatact gatatgtata cccgaagtat gtcaaaaaga ggtatgctat gaagcagcgt    180
attacagtga cagttgacag cgacagctat cagttgctca aggcatatat gatgtcaata    240
tctccggtct ggtaagcaca accatgcaga atgaagcccg tcgtctgcgt gccgaacgct    300
ggaaagcgga aaatcaggaa gggatggctg aggtcgcccg gtttattgaa atgaacggct    360
cttttgctga cgagaacagg ggctggtgaa atgcagttta aggtttacac ctataaaaga    420
gagagccgtt atcgtctgtt tgtggatgta cagagtgata ttattgacac gcccgggcga    480
cggatggtga tccccctggc cagtgcacgt ctgctgtcag ataaagtctc ccgtgaactt    540
tacccggtgg tgcatatcgg ggatgaaagc tggcgcatga tgaccaccga tatggccagt    600
gtgccggttt ccgttatcgg ggaagaagtg gctgatctca gccaccgcga aaatgacatc    660
aaaaacgcca ttaacctgat gttctgggga atataaggtc tcgcctcaga aagcctgtat    720
gcgaagccac aatcctttcc aacagaccat actaagt                             757

<210> SEQ ID NO 82
<211> LENGTH: 757
<212> TYPE: DNA
<213> ORGANISM: Artificial Sequence
<220> FEATURE:
<223> OTHER INFORMATION: Backbone entry vector

<400> SEQUENCE: 82
aaagccaaag ttcgcgttcc gaccttgcct cccaaatccg agttgcgatt gtgcggagac     60
cggcttacta aaagccagat aacagtatgc atatttgcgc gctgattttt gcggtataag    120
aatatatact gatatgtata cccgaagtat gtcaaaaaga ggtatgctat gaagcagcgt    180
attacagtga cagttgacag cgacagctat cagttgctca aggcatatat gatgtcaata    240
tctccggtct ggtaagcaca accatgcaga atgaagcccg tcgtctgcgt gccgaacgct    300
ggaaagcgga aaatcaggaa gggatggctg aggtcgcccg gtttattgaa atgaacggct    360
cttttgctga cgagaacagg ggctggtgaa atgcagttta aggtttacac ctataaaaga    420
gagagccgtt atcgtctgtt tgtggatgta cagagtgata ttattgacac gcccgggcga    480
cggatggtga tccccctggc cagtgcacgt ctgctgtcag ataaagtctc ccgtgaactt    540
tacccggtgg tgcatatcgg ggatgaaagc tggcgcatga tgaccaccga tatggccagt    600
gtgccggttt ccgttatcgg ggaagaagtg gctgatctca gccaccgcga aaatgacatc    660
aaaaacgcca ttaacctgat gttctgggga atataaggtc tcgcctcaga aagcctgtat    720
gcgaagccac aatcctttcc aacagaccat actaagt                             757
```

<210> SEQ ID NO 83
<211> LENGTH: 757
<212> TYPE: DNA
<213> ORGANISM: Artificial Sequence
<220> FEATURE:
<223> OTHER INFORMATION: Backbone entry vector

<400> SEQUENCE: 83

| | |
|---|---:|
| atatccgatg ccgtacgaat cccactcgcg cacacatgct tgcctttgtt gtgcggagac | 60 |
| cggcttacta aaagccagat aacagtatgc atatttgcgc gctgattttt gcggtataag | 120 |
| aatatatact gatatgtata cccgaagtat gtcaaaaaga gtatgctat gaagcagcgt | 180 |
| attacagtga cagttgacag cgacagctat cagttgctca aggcatatat gatgtcaata | 240 |
| tctccggtct ggtaagcaca accatgcaga atgaagcccg tcgtctgcgt gccgaacgct | 300 |
| ggaaagcgga aaatcaggaa gggatggctg aggtcgcccg gtttattgaa atgaacggct | 360 |
| cttttgctga cgagaacagg ggctggtgaa atgcagttta aggtttacac ctataaaaga | 420 |
| gagagccgtt atcgtctgtt tgtggatgta cagagtgata ttattgacac gcccgggcga | 480 |
| cggatggtga tccccctggc cagtgcacgt ctgctgtcag ataaagtctc ccgtgaactt | 540 |
| tacccggtgg tgcatatcgg ggatgaaagc tggcgcatga tgaccaccga tatggccagt | 600 |
| gtgccggttt ccgttatcgg ggaagaagtg gctgatctca gccaccgcga aaatgacatc | 660 |
| aaaaacgcca ttaacctgat gttctgggga atataaggtc tcgcctcaga aagcctgtat | 720 |
| gcgaagccac aatcctttcc aacagaccat actaagt | 757 |

<210> SEQ ID NO 84
<211> LENGTH: 757
<212> TYPE: DNA
<213> ORGANISM: Artificial Sequence
<220> FEATURE:
<223> OTHER INFORMATION: Backbone entry vector

<400> SEQUENCE: 84

| | |
|---|---:|
| acaagacaat tcgtaccaag tacgtcgagc gctgcaatac accatacgta gtgcggagac | 60 |
| cggcttacta aaagccagat aacagtatgc atatttgcgc gctgattttt gcggtataag | 120 |
| aatatatact gatatgtata cccgaagtat gtcaaaaaga gtatgctat gaagcagcgt | 180 |
| attacagtga cagttgacag cgacagctat cagttgctca aggcatatat gatgtcaata | 240 |
| tctccggtct ggtaagcaca accatgcaga atgaagcccg tcgtctgcgt gccgaacgct | 300 |
| ggaaagcgga aaatcaggaa gggatggctg aggtcgcccg gtttattgaa atgaacggct | 360 |
| cttttgctga cgagaacagg ggctggtgaa atgcagttta aggtttacac ctataaaaga | 420 |
| gagagccgtt atcgtctgtt tgtggatgta cagagtgata ttattgacac gcccgggcga | 480 |
| cggatggtga tccccctggc cagtgcacgt ctgctgtcag ataaagtctc ccgtgaactt | 540 |
| tacccggtgg tgcatatcgg ggatgaaagc tggcgcatga tgaccaccga tatggccagt | 600 |
| gtgccggttt ccgttatcgg ggaagaagtg gctgatctca gccaccgcga aaatgacatc | 660 |
| aaaaacgcca ttaacctgat gttctgggga atataaggtc tcgcctcaga aagcctgtat | 720 |
| gcgaagccac aatcctttcc aacagaccat actaagt | 757 |

<210> SEQ ID NO 85
<211> LENGTH: 757
<212> TYPE: DNA
<213> ORGANISM: Artificial Sequence
<220> FEATURE:
<223> OTHER INFORMATION: Backbone entry vector

```
<400> SEQUENCE: 85
atgccttgcg tgcatgccat ctcgaacgat tgtgtttcca gccaacttgc gtgcggagac      60
cggcttacta aaagccagat aacagtatgc atatttgcgc gctgattttt gcggtataag     120
aatatatact gatatgtata cccgaagtat gtcaaaaaga ggtatgctat gaagcagcgt     180
attacagtga cagttgacag cgacagctat cagttgctca aggcatatat gatgtcaata     240
tctccggtct ggtaagcaca accatgcaga atgaagcccg tcgtctgcgt gccgaacgct     300
ggaaagcgga aaatcaggaa gggatggctg aggtcgcccg gtttattgaa atgaacggct     360
cttttgctga cgagaacagg ggctggtgaa atgcagttta aggtttacac ctataaaaga     420
gagagccgtt atcgtctgtt tgtggatgta cagagtgata ttattgacac gcccgggcga     480
cggatggtga tcccctggc cagtgcacgt ctgctgtcag ataaagtctc ccgtgaactt      540
tacccggtgg tgcatatcgg ggatgaaagc tggcgcatga tgaccaccga tatggccagt     600
gtgccggttt ccgttatcgg ggaagaagtg gctgatctca gccaccgcga aaatgacatc     660
aaaaacgcca ttaacctgat gttctgggga atataaggtc tcgcctcaga aagcctgtat     720
gcgaagccac aatcctttcc aacagaccat actaagt                              757

<210> SEQ ID NO 86
<211> LENGTH: 2749
<212> TYPE: DNA
<213> ORGANISM: Artificial Sequence
<220> FEATURE:
<223> OTHER INFORMATION: E.coli vector used for all backbone entry vectors with SEQ ID
      NOs: 64 to 85

<400> SEQUENCE: 86
aaaatgaagt gaagttccta tactttctag agaataggaa cttctatagt gagtcgaata      60
agggcgacac aaaatttatt ctaaatgcat aataaatact gataacatct tatagtttgt     120
attatatttt gtattatcgt tgacatgtat aattttgata tcaaaaactg attttccctt     180
tattattttc gagatttatt ttcttaattc tctttaacaa actagaaata ttgtatatac     240
aaaaaatcat aaataataga tgaatagttt aattataggt gttcatcaat cgaaaaagca     300
acgtatctta tttaaagtgc gttgcttttt tctcattttat aaggttaaat aattctcata     360
tatcaagcaa agtgacaggc gcccttaaat attctgacaa atgctctttc cctaaactcc     420
ccccataaaa aaacccgccg aagcgggttt ttacgttatt tgcggattaa cgattactcg     480
ttatcagaac cgcccagggg gcccgagctt aagactggcc gtcgttttac aacacagaaa     540
gagtttgtag aaacgcaaaa aggccatccg tcagggggcct tctgcttagt ttgatgcctg     600
gcagttccct actctcgcct tccgcttcct cgctcactga ctcgctgcgc tcggtcgttc     660
ggctgcggcg agcggtatca gctcactcaa aggcggtaat acggttatcc acagaatcag     720
gggataacgc aggaaagaac atgtgagcaa aaggccagca aaaggccagg aaccgtaaaa     780
aggccgcgtt gctggcgttt ttccataggc tccgcccccc tgacgagcat cacaaaaatc     840
gacgctcaag tcagaggtgg cgaaacccga caggactata aagataccag gcgtttcccc     900
ctggaagctc cctcgtgcgc tctcctgttc cgaccctgcc gcttaccgga tacctgtccg     960
cctttctccc ttcgggaagc gtggcgcttt ctcatagctc acgctgtagg tatctcagtt    1020
cggtgtaggt cgttcgctcc aagctgggct gtgtgcacga accccccgtt cagcccgacc    1080
gctgcgcctt atccggtaac tatcgtcttg agtccaaccc ggtaagacac gacttatcgc    1140
cactggcagc agccactggt aacaggatta gcagagcgag gtatgtaggc ggtgctacag    1200
```

-continued

```
agttcttgaa gtggtgggct aactacggct acactagaag aacagtattt ggtatctgcg    1260
ctctgctgaa gccagttacc ttcggaaaaa gagttggtag ctcttgatcc ggcaaacaaa    1320
ccaccgctgg tagcggtggt ttttttgttt gcaagcagca gattacgcgc agaaaaaaag    1380
gatctcaaga agatcctttg atcttttcta cggggtctga cgctcagtgg aacgacgcgc    1440
gcgtaactca cgttaaggga ttttggtcat gagcttgcgc cgtcccgtca agtcagcgta    1500
atgctctgct tttagaaaaa ctcatcgagc atcaaatgaa actgcaattt attcatatca    1560
ggattatcaa taccatattt tgaaaaagc cgtttctgta atgaaggaga aaactcaccg    1620
aggcagttcc ataggatggc aagatcctgg tatcggtctg cgattccgac tcgtccaaca    1680
tcaatacaac ctattaattt cccctcgtca aaaataaggt tatcaagtga aaatcacca    1740 tgagtgacga ctgaatccgg tgagaatggc aaaagtttat gcatttcttt ccagacttgt    1800
tcaacaggcc agccattacg ctcgtcatca aaatcactcg catcaaccaa accgttattc    1860
attcgtgatt gcgcctgagc gaggcgaaat acgcgatcgc tgttaaaagg acaattacaa    1920
acaggaatcg agtgcaaccg gcgcaggaac actgccagcg catcaacaat attttcacct    1980
gaatcaggat attcttctaa tacctggaac gctgttttc cggggatcgc agtggtgagt    2040
aaccatgcat catcaggagt acggataaaa tgcttgatgg tcggaagtgg cataaattcc    2100
gtcagccagt ttagtctgac catctcatct gtaacatcat tggcaacgct acctttgcca    2160
tgtttcagaa acaactctgg cgcatcgggc ttcccataca agcgatagat tgtcgcacct    2220
gattgcccga cattatcgcg agcccattta tacccatata atcagcatc catgttggaa    2280 tttaatcgcg gcctcgacgt ttcccgttga atatggctca tattcttcct ttttcaatat    2340
tattgaagca tttatcaggg ttattgtctc atgagcggat acatatttga atgtatttag    2400
aaaaataaac aaatagggt cagtgttaca accaattaac caattctgaa cattatcgcg    2460
agcccattta tacctgaata tggctcataa caccccttgt ttgcctggcg cagtagcgc    2520 ggtggtccca cctgacccca tgccgaactc agaagtgaaa cgccgtagcg ccgatggtag    2580
tgtggggact ccccatgcga gagtagggaa ctgccaggca tcaaataaaa cgaaaggctc    2640
agtcgaaaga ctgggccttt cgcccgggct aattaggggg tgtcgccctt attcgactct    2700
atagtgaagt tcctattctc tagaaagtat aggaacttct gaagtgggg              2749
```

```
<210> SEQ ID NO 87
<211> LENGTH: 22
<212> TYPE: DNA
<213> ORGANISM: Artificial Sequence
<220> FEATURE:
<223> OTHER INFORMATION: PCR primer

<400> SEQUENCE: 87
aagcgacttc caatcgcttt gc                                              22

<210> SEQ ID NO 88
<211> LENGTH: 21
<212> TYPE: DNA
<213> ORGANISM: Artificial Sequence
<220> FEATURE:
<223> OTHER INFORMATION: PCR primer

<400> SEQUENCE: 88
aaagcaaagg aaggagagaa c                                               21

<210> SEQ ID NO 89
<211> LENGTH: 20
```

<212> TYPE: DNA
<213> ORGANISM: Artificial Sequence
<220> FEATURE:
<223> OTHER INFORMATION: PCR primer

<400> SEQUENCE: 89
ttgcccatcg aacgtacaag                                               20

<210> SEQ ID NO 90
<211> LENGTH: 23
<212> TYPE: DNA
<213> ORGANISM: Artificial Sequence
<220> FEATURE:
<223> OTHER INFORMATION: PCR primer

<400> SEQUENCE: 90
tgctaagatt tgtgttcgtt tgg                                           23

<210> SEQ ID NO 91
<211> LENGTH: 20
<212> TYPE: DNA
<213> ORGANISM: Artificial Sequence
<220> FEATURE:
<223> OTHER INFORMATION: PCR primer

<400> SEQUENCE: 91
cggatcgatg tacacaaccg                                               20

<210> SEQ ID NO 92
<211> LENGTH: 23
<212> TYPE: DNA
<213> ORGANISM: Artificial Sequence
<220> FEATURE:
<223> OTHER INFORMATION: PCR primer

<400> SEQUENCE: 92
caacaggagg cggatggata tac                                           23

<210> SEQ ID NO 93
<211> LENGTH: 21
<212> TYPE: DNA
<213> ORGANISM: Artificial Sequence
<220> FEATURE:
<223> OTHER INFORMATION: PCR primer

<400> SEQUENCE: 93
acgctttccg gcatcttcca g                                             21

<210> SEQ ID NO 94
<211> LENGTH: 20
<212> TYPE: DNA
<213> ORGANISM: Artificial Sequence
<220> FEATURE:
<223> OTHER INFORMATION: PCR primer

<400> SEQUENCE: 94
gcggaatatt ggcggaacgg                                               20

<210> SEQ ID NO 95
<211> LENGTH: 22
<212> TYPE: DNA
<213> ORGANISM: Artificial Sequence
<220> FEATURE:
<223> OTHER INFORMATION: PCR primer

<400> SEQUENCE: 95

```
aacgttgtcc aggtttgtat cc                                      22

<210> SEQ ID NO 96
<211> LENGTH: 20
<212> TYPE: DNA
<213> ORGANISM: Artificial Sequence
<220> FEATURE:
<223> OTHER INFORMATION: PCR primer

<400> SEQUENCE: 96
aggtacaaca agcacgaccg                                         20

<210> SEQ ID NO 97
<211> LENGTH: 23
<212> TYPE: DNA
<213> ORGANISM: Artificial Sequence
<220> FEATURE:
<223> OTHER INFORMATION: PCR primer

<400> SEQUENCE: 97
aaataaccac aaacatcctt ccc                                     23

<210> SEQ ID NO 98
<211> LENGTH: 23
<212> TYPE: DNA
<213> ORGANISM: Artificial Sequence
<220> FEATURE:
<223> OTHER INFORMATION: PCR primer

<400> SEQUENCE: 98
gtgcactaca tcttgtgggt gtc                                     23

<210> SEQ ID NO 99
<211> LENGTH: 22
<212> TYPE: DNA
<213> ORGANISM: Artificial Sequence
<220> FEATURE:
<223> OTHER INFORMATION: PCR primer

<400> SEQUENCE: 99
gaaaccttcg aatccagcca gc                                      22

<210> SEQ ID NO 100
<211> LENGTH: 20
<212> TYPE: DNA
<213> ORGANISM: Artificial Sequence
<220> FEATURE:
<223> OTHER INFORMATION: PCR primer

<400> SEQUENCE: 100
catctggatg tactcgactc                                         20

<210> SEQ ID NO 101
<211> LENGTH: 21
<212> TYPE: DNA
<213> ORGANISM: Artificial Sequence
<220> FEATURE:
<223> OTHER INFORMATION: PCR primer

<400> SEQUENCE: 101
caacacacaa gttccgcaac g                                       21

<210> SEQ ID NO 102
<211> LENGTH: 20
<212> TYPE: DNA
<213> ORGANISM: Artificial Sequence
```

```
<220> FEATURE:
<223> OTHER INFORMATION: PCR primer

<400> SEQUENCE: 102
aatcgcaact cggatttggg                                            20

<210> SEQ ID NO 103
<211> LENGTH: 20
<212> TYPE: DNA
<213> ORGANISM: Artificial Sequence
<220> FEATURE:
<223> OTHER INFORMATION: PCR primer

<400> SEQUENCE: 103
aaagccaaag ttcgcgttcc                                            20

<210> SEQ ID NO 104
<211> LENGTH: 20
<212> TYPE: DNA
<213> ORGANISM: Artificial Sequence
<220> FEATURE:
<223> OTHER INFORMATION: PCR primer

<400> SEQUENCE: 104
aacaaaggca agcatgtgtg                                            20

<210> SEQ ID NO 105
<211> LENGTH: 22
<212> TYPE: DNA
<213> ORGANISM: Artificial Sequence
<220> FEATURE:
<223> OTHER INFORMATION: PCR primer

<400> SEQUENCE: 105
atatccgatg ccgtacgaat cc                                         22

<210> SEQ ID NO 106
<211> LENGTH: 21
<212> TYPE: DNA
<213> ORGANISM: Artificial Sequence
<220> FEATURE:
<223> OTHER INFORMATION: PCR primer

<400> SEQUENCE: 106
tacgtatggt gtattgcagc g                                          21

<210> SEQ ID NO 107
<211> LENGTH: 20
<212> TYPE: DNA
<213> ORGANISM: Artificial Sequence
<220> FEATURE:
<223> OTHER INFORMATION: PCR primer

<400> SEQUENCE: 107
acaagacaat tcgtaccaag                                            20

<210> SEQ ID NO 108
<211> LENGTH: 19
<212> TYPE: DNA
<213> ORGANISM: Artificial Sequence
<220> FEATURE:
<223> OTHER INFORMATION: PCR primer

<400> SEQUENCE: 108
gcaagttggc tggaaacac                                             19
```

<210> SEQ ID NO 109
<211> LENGTH: 21
<212> TYPE: DNA
<213> ORGANISM: Artificial Sequence
<220> FEATURE:
<223> OTHER INFORMATION: PCR primer

<400> SEQUENCE: 109
atgccttgcg tgcatgccat c                                          21

<210> SEQ ID NO 110
<211> LENGTH: 24
<212> TYPE: DNA
<213> ORGANISM: Artificial Sequence
<220> FEATURE:
<223> OTHER INFORMATION: PCR primer

<400> SEQUENCE: 110
acttagtatg gtctgttgga aagg                                       24

<210> SEQ ID NO 111
<211> LENGTH: 77
<212> TYPE: DNA
<213> ORGANISM: Artificial Sequence
<220> FEATURE:
<223> OTHER INFORMATION: PCR primer

<400> SEQUENCE: 111
ttgcccatcg aacgtacaag tactcctctg ttctctcctt cctttgcttt cttcgtacgc   60
tgcaggtcga cgaattc                                                77

<210> SEQ ID NO 112
<211> LENGTH: 75
<212> TYPE: DNA
<213> ORGANISM: Artificial Sequence
<220> FEATURE:
<223> OTHER INFORMATION: PCR primer

<400> SEQUENCE: 112
tgctaagatt tgtgttcgtt tgggtgcagt cggttgtgta catcgatccg taggccacta   60
gtggatctga tatcg                                                  75

<210> SEQ ID NO 113
<211> LENGTH: 1674
<212> TYPE: DNA
<213> ORGANISM: Artificial Sequence
<220> FEATURE:
<223> OTHER INFORMATION: PCR fragment KanMX marker equipped with
      connector a and b

<400> SEQUENCE: 113
ttgcccatcg aacgtacaag tactcctctg ttctctcctt cctttgcttt cttcgtacgc   60
tgcaggtcga cgaattctac cgttcgtata atgtatgcta tacgaagtta tagatctgtt  120
tagcttgcct cgtccccgcc gggtcacccg gccagcgaca tggaggccca gaatacccct  180
cttgacagtc ttgacgtgcg cagctcaggg gcatgatgtg actgtcgccc gtacatttag  240
cccatacatc cccatgtata atcatttgca tccatacatt ttgatggccg cacggcgcga  300
agcaaaaatt acggctcctc gctgcagacc tgcgagcagg gaaacgctcc cctcacagac  360
gcgttgaatt gtcccacgc cgcgcccctg tagagaaata taaaaggtta ggatttgcca  420
ctgaggttct tctttcatat acttcctttt aaaatcttgc taggatacag ttctcacatc  480

```
acatccgaac ataaacaacc atgggtaagg aaaagactca cgtttcgagg ccgcgattaa    540
attccaacat ggatgctgat ttatatgggt ataaatgggc tcgcgataat gtcgggcaat    600
caggtgcgac aatctatcga ttgtatggga agcccgatgc gccagagttg tttctgaaac    660
atggcaaagg tagcgttgcc aatgatgtta cagatgagat ggtcagacta aactggctga    720
cggaatttat gcctcttccg accatcaagc attttatccg tactcctgat gatgcatggt    780
tactcaccac tgcgatcccc ggcaaaacag cattccaggt attagaagaa tatcctgatt    840
caggtgaaaa tattgttgat gcgctggcag tgttcctgcg ccggttgcat tcgattcctg    900
tttgtaattg tcctttaac agcgatcgcg tatttcgtct cgctcaggcg caatcacgaa     960
tgaataacgg tttggttgat gcgagtgatt ttgatgacga gcgtaatggc tggcctgttg   1020
aacaagtctg gaaagaaatg cataagcttt tgccattctc accggattca gtcgtcactc   1080
atggtgattt ctcacttgat aaccttattt ttgacgaggg gaaattaata ggttgtattg   1140
atgttggacg agtcggaatc gcagaccgat accaggatct tgccatccta tggaactgcc   1200
tcggtgagtt ttctccttca ttacagaaac ggctttttca aaaatatggt attgataatc   1260
ctgatatgaa taaattgcag tttcatttga tgctcgatga gttttttctaa tcagtactga   1320 caataaaaag attcttgttt tcaagaactt gtcatttgta tagttttttt atattgtagt   1380
tgttctattt taatcaaatg ttagcgtgat ttatattttt tttcgcctcg acatcatctg   1440
cccagatgcg aagttaagtg cgcagaaagt aatatcatgc gtcaatcgta tgtgaatgct   1500
ggtcgctata ctgctgtcga ttcgatacta acgccgccat ccagtgtcga aaacgagctc   1560
ataacttcgt ataatgtatg ctatacgaac ggtagaattc gatatcagat ccactagtgg   1620
cctacggatc gatgtacaca accgactgca cccaaacgaa cacaaatctt agca         1674
```

<210> SEQ ID NO 114
<211> LENGTH: 19
<212> TYPE: DNA
<213> ORGANISM: Artificial Sequence
<220> FEATURE:
<223> OTHER INFORMATION: Forward primer on left flank INT1

<400> SEQUENCE: 114

```
cggcattatt gtgtatggc                                                  19
```

<210> SEQ ID NO 115
<211> LENGTH: 73
<212> TYPE: DNA
<213> ORGANISM: Artificial Sequence
<220> FEATURE:
<223> OTHER INFORMATION: rev primer on left flank INT1 adding connector
     5

<400> SEQUENCE: 115

```
aaacgcctgt gggtgtggta ctggatatgc aaagcgattg gaagtcgctt agggtttcaa    60
agatccatac ttc                                                        73
```

<210> SEQ ID NO 116
<211> LENGTH: 550
<212> TYPE: DNA
<213> ORGANISM: Artificial Sequence
<220> FEATURE:
<223> OTHER INFORMATION: Left flank with connector 5 for integration at
     INT1

<400> SEQUENCE: 116

```
cggcattatt gtgtatggct caataatttt ataaaaaaag gaactattgg ttcttagtat    60
```

```
tttcttgcta aaagacatat tcttaccaat cctttcataa gctaattatg ccatccatat      120
agcaagagaa tccggtgggg gcgccatgcc tatccggcgg caacattatt actctggtat      180
acgggcgtaa ctccataata tgccaccact tacctttaac atgttcatgg taggtacccc      240
acccagccat aaggaaattt tcaaaggcgt tggatcaaaa aataggcctt tatttcatcg      300
cgtgattgag gagcataaca tgtttagtga aggtttcttt tggaaaactt cagtcgctca      360
ttattagaac cagggaggtc caggcttttgc tggtgggaga gaaagcttat gaagctgggg      420
ttgcagattt gtcgattggt cgccagtaca cagtttttaaa aagtcagaga atgtagagaa      480
gtatggatct ttgaaaccct aagcgacttc caatcgcttt gcatatccag taccacaccc      540
acaggcgttt                                                             550

<210> SEQ ID NO 117
<211> LENGTH: 90
<212> TYPE: DNA
<213> ORGANISM: Artificial Sequence
<220> FEATURE:
<223> OTHER INFORMATION: forw primer on right flank INT1 adding
      connector 3

<400> SEQUENCE: 117
agaaagcctg tatgcgaagc cacaatcctt tccaacagac catactaagt attttatttt      60
acttttttta gaatgacctg ttcccgacac                                       90

<210> SEQ ID NO 118
<211> LENGTH: 24
<212> TYPE: DNA
<213> ORGANISM: Artificial Sequence
<220> FEATURE:
<223> OTHER INFORMATION: Reverse primer on left flank INT1

<400> SEQUENCE: 118
cacaagctta ttcttccaaa aatc                                             24

<210> SEQ ID NO 119
<211> LENGTH: 548
<212> TYPE: DNA
<213> ORGANISM: Artificial Sequence
<220> FEATURE:
<223> OTHER INFORMATION: Right flank with connector 3 for integration at
      INT1

<400> SEQUENCE: 119
agaaagcctg tatgcgaagc cacaatcctt tccaacagac catactaagt attttatttt      60
acttttttta gaatgacctg ttcccgacac tatgtaagat ctagctttta acatattatg      120
gaaacctgaa atgtaaaatc tgaattttg tatatgtgtt tatatttggg tagttctttt      180
gaggaaagca tgcatagact tgctgtacga actttatgtg acttgtagtg acgctgtttc      240
atgagacttt agcccttgga acatattatc atatctcagc ttgaaatact atagatttac      300
ttttgcagcc atttcttggt gctccaaggt tgtgcgtatc tattacttaa tttctgtcct      360
tgccaagttt tgcagcaggg cggtcacaag actcctctgc cgtcattcct tagtccttcg      420
ggaacacact tatttatgta tttgtattct acaattctac ggtgcacaag ggttgggcac      480
tgttgagctc agcacgcaac tattgctggc atgaagataa gattgatttt tggaagaata      540
agcttgtg                                                               548

<210> SEQ ID NO 120
```

<211> LENGTH: 1228
<212> TYPE: DNA
<213> ORGANISM: Aspergillus terreus

<400> SEQUENCE: 120

```
ggtctcgaat gggtcacggt gacactgaat ctccaaaccc aaccaccacc actgaaggtt      60
ctggtcaaaa cgaacctgaa agaagggtc gtgacattcc attatggaga agtgtgtta      120
tcactttcgt tgtttcctgg atgactttgg ttgtcacttt ctcctccacc tgtttgttgc     180
cagctgctcc agaaattgct aacgaattcg atatgaccgt cgaaaccatt aacatttcca     240
acgctggtgt tttggttgcc atgggttact cttctttgat ctggggtcca atgaacaaat     300
tggttggtag aagaacctct tacaacttgg ccatctccat gttgtgtgcc tgttctgctg     360
gtactgctgc tgccatcaac gaagaaatgt tcattgcttt ccgtgtcttg tctggcttga     420
ccggtacttc tttcatggtt tccggtcaaa ccgtcttggc tgatatcttt gaaccagttt     480
acagaggtac tgctgtcggt ttcttcatgg ctggtactct atccggtcca gccattggtc     540
catgtgtcgg tggtgtcatt gtcactttca cctcctggag agttatcttc tggttacaat     600
tgggtatgtc tggtttaggt ttggttttgt ctctattatt cttcccaaag atcgaaggta     660
actctgaaaa ggtttctact gctttcaagc caaccacttt ggtcaccatc atctccaagt     720
tctctccaac cgatgtcttg aagcaatggg tttacccaaa tgtcttttg gctgatttgt      780
gttgtggttt gttggccatc actcaatact ccatcttgac ttctgccaga gctatcttca     840
actccagatt ccatttgacc accgctttgg tttccggttt attctacttg gctccaggtg     900
ctggtttctt gattggttct ttggttggtg gtaaattgtc tgacagaacc gtcagaagat     960
acattgtcaa gagaggtttc agattacctc aagacagatt gcactctggt ttgatcactt    1020
tgtttgctgt cttgccagct ggtactttga tctacggttg gactttgcaa gaggacaagg    1080
gtgacatggt tgttccaatc attgctgctt tctttgctgg ttggggtttg atgggttctt    1140
tcaactgttt gaacacctac gttgctggtt tattccacac tttgatctac ttgttcccat    1200
tgtgtacctg tccacaataa aggagacc                                       1228
```

<210> SEQ ID NO 121
<211> LENGTH: 1492
<212> TYPE: DNA
<213> ORGANISM: Aspergillus terreus

<400> SEQUENCE: 121

```
ggtctcgaat gaccaagcaa tctgctgact ccaatgccaa gtctggtgtt acttctgaaa      60
tctgtcactg ggcttctaac ttggctaccg atgacatccc atctgatgtc ttggaaagag     120
ctaagtactt gatcttggac ggtattgctt gtgcttgggt tggtgccaga gttccatggt     180
ctgaaaagta cgttcaagct accatgtcct tcgaacctcc aggtgcttgt cgtgtcattg     240
gttacggtca aaaattgggt cctgttgctg ctgccatgac caactctgcc tttattcaag     300
ctactgaatt ggacgactac cactctgaag ctccattaca ttccgcttcc attgtcttac     360
cagctgtctt tgctgcttct gaagttttgg ctgaacaagg taagactatc tctggtatcg     420
atgtcatctt ggctgccatt gtcggtttcg aatccggtcc aagaatcggt aaggccatct     480
acggttccga tttgttgaac aacggttggc attgtggtgc cgtttacggt gccccagctg     540
gtgctttggc taccggtaag ctattaggtt tgactccaga ctccatggaa gatgctttgg     600
gtattgcctg tacccaagct tgtggttga tgtccgctca atacggtggt atggtcaaga     660
gagtccaaca cggtttcgct gccagaaacg gtttgttggg tggtttgttg gctcacggtg     720
```

```
gttacgaagc tatgaagggt gttttggaaa gatcttacgg tggtttcttg aagatgttca   780
ccaagggtaa cggtagagaa ccaccataca aggaagaaga agttgttgct ggtttaggtt   840
ctttctggca cactttcacc atcagaatca aattgtacgc ttgttgtggt ttagtccacg   900
gtccagttga agccatcgaa aacttgcaag gtagataccc agaattattg aacagagcta   960
acttgtccaa catcagacac gttcacgttc aattgtccac tgcttctaac tctcactgtg  1020
gttggatccc agaagaaaga ccaatttctt ccattgctgg tcaaatgtcc gttgcttaca  1080
ttttggctgt tcaattggtt gaccaacaat gtttgttgtc tcaattctct gaattcgatg  1140
acaacttgga aagaccagaa gtctgggact tggccagaaa ggttacctct tctcaatctg  1200
aagaattcga ccaagatggt aactgtctat ccgctggtcg tgtcagaatc gaattcaacg  1260
acggttcttc catcactgaa tctgttgaaa agccattggg tgtcaaggaa ccaatgccaa  1320
acgaaagaat tttgcacaaa tacagaactt tggctggttc cgtcactgac gaatccagag  1380
tcaaggaaat tgaagatttg gttttgggtt tagatcgttt gactgacatc tctccattat  1440
tggaattgtt gaactgtcca gtcaaatctc cattcgggat ctaaaggaga cc           1492
```

<210> SEQ ID NO 122
<211> LENGTH: 1468
<212> TYPE: DNA
<213> ORGANISM: Saccharomyces cerevisiae

<400> SEQUENCE: 122

```
ggtctcgaat gtccgctcaa atcaacaaca tcagaccaga atttgacaga gaaattgtcg    60
atatcgttga ctacgtcatg aactacgaaa tttcttccaa ggttgcttac gacactgctc   120
actactgttt gttggacact ttaggttgtg gtttggaagc tttggaatac ccagcctgta   180
agaaattgtt gggtccaatt gtcccaggta ccgttgttcc aaatggtgtc agagttccag   240
gtactcaatt ccaattggac ccagttcaag ctgctttcaa catcggtgcc atgatcagat   300
ggttagattt caacgacacc tggttagctg ctgaatgggg tcacccatct gacaacttgg   360
gtggtatctt ggccactgct gactggttat ccagaaacgc tgttgcttcc ggtaaggctc   420
cattgaccat gaagcaagtc ttgactgcca tgatcaaggc tcacgaaatc caaggttgta   480
ttgctttgga aaactctttc aaccgtgtcg gtttggacca tgtcttgttg gtcaaggttg   540
cctccactgc tgttgttgct gaaatgttgg gtttgaccag agaagaaatc ttgaacgccg   600
tttccttggc ttgggttgat ggtcaatctc taagaaccta cagacacgcc ccaaacaccg   660
gtaccagaaa gtcctgggct gctggtgatg ctacttccag agctgtcaga ttggctttga   720
tggccaagac cggtgaaatg ggttacccat ctgctttgac tgctccagtc tggggtttct   780
acgatgtctc tttcaaaggt gaatctttca gattccaaag accttacggt tcttacgtta   840
tggaaaacgt cttattcaag atttctttcc cagctgaatt ccactctcaa accgctgttg   900
aagctgctat gactttatac gaacaaatgc aagctgccgg taagactgct gctgacattg   960
aaaaggtcac catcagaacc cacgaagctt gtatcagaat tattgacaag aagggtcctt  1020
tgaacaaccc agctgatcgt gaccattgta tccaatacat ggttgccatc ccattattgt  1080
ttggtagatt gactgctgct gactacgaag ataatgttgc tcaagacaag agaattgatg  1140
ctttgagaga aagatcaac tgtttcgaag atccagcttt caccgctgat taccacgacc  1200
cagaaaagag agccattgcc aacgccatca ctttggaatt cactgacggt accagatttg  1260
aagaagttgt tgtcgaatac ccaattggtc acgctcgtcg tcgtcaagat ggtatcccaa  1320
```

| aattggtcga taaattcaag atcaacttgg ccagacaatt cccaaccaga caacaacaaa | 1380 |
| gaatcttgga agtttctttg dacagagcta gattggaaca aatgccagtc aacgaatact | 1440 |
| tggacttgta cgttatttaa aggagacc | 1468 |

<210> SEQ ID NO 123
<211> LENGTH: 3559
<212> TYPE: DNA
<213> ORGANISM: Saccharomyces cerevisiae

<400> SEQUENCE: 123

| ggtctcgaat gtcctcttcc aagatcttgg ctggtttgag agacaacttt tctttgttgg | 60 |
| gtgaaaagaa caagattttg gtcgccaaca gaggtgaaat cccaatcaga attttcagat | 120 |
| ctgctcacga attgtctatg agaactatcg ccatctactc tcacgaagat agattatcca | 180 |
| tgcacagatt gaaggctgat gaagcctacg ttatcggtga agaaggtcaa tacaccccag | 240 |
| tcggtgctta cttggccatg gacgaaatca tcgaaattgc caagaagcac aaggtcgatt | 300 |
| tcatccaccc aggttacggt ttcttgtctg aaaactctga atttgctgac aaggttgtta | 360 |
| aggctggtat tacctggatt ggtccaccag ctgaagtcat tgaatctgtt ggtgacaagg | 420 |
| tttctgccag acatttggct gctcgtgcca acgttccaac tgtcccaggt actccaggtc | 480 |
| ctatcgaaac cgttcaagaa gctctagatt tcgtcaatga atacggttac ccagttatca | 540 |
| tcaaggctgc tttcggtggt ggtggtcgtg gtatgagagt tgtcagagaa ggtgacgatg | 600 |
| tcgctgatgc tttccaaaga gccacttctg aagctagaac tgctttcggt aacggtactt | 660 |
| gtttcgtcga aagattcttg gacaagccaa agcacattga agttcaatta ttagctgaca | 720 |
| accacggtaa cgttgtccac ttgttcgaaa gagactgttc cgtccaaaga cgtcaccaaa | 780 |
| aggttgtcga agttgctcca gctaagactt accaagagaa gttagagat gctatcttga | 840 |
| ccgatgccgt taagttggct aaggttgtg gttacagaaa cgctggtact gctgaattct | 900 |
| tggttgacaa ccaaaacaga cattacttca ttgaaatcaa cccaagaatt caagtcgaac | 960 |
| acaccatcac tgaagaaatc actggtattg acattgtctc cgctcaaatc caaatcgccg | 1020 |
| ctggtgctac tttgactcaa ttaggtctat tacaagacaa aatcaccacc agaggtttct | 1080 |
| ctatccaatg tcgtatcacc actgaagatc catccaagaa cttccaacca gacactggtc | 1140 |
| gtttggaagt ctacgatccc gctggtggta acggtgtcag attggacggt ggtaacgcct | 1200 |
| acgctggtgc taccatctct ccacactacg actccatgtt ggttaagtgt tcctgttctg | 1260 |
| gttctaccta cgaaattgtc agaagaaaga tgatcgagagc tttgattgaa ttcagaatca | 1320 |
| gaggtgtcaa gaccaacatc ccattcttgt tgactttgtt gaccaaccca gttttcattg | 1380 |
| aagtacccta ctggaccact ttcatcgatg acactccaca attgttccaa atggtttcct | 1440 |
| ctcaaaacag agctcaaaaa ttgttgcact acttggctga cttggccgtc aacggttcct | 1500 |
| ctatcaaggg tcaaatcggt ttaccaaagt tgaagtccaa cccttccgtt ccacatttgc | 1560 |
| acgatgctca aggtaatgtc atcaacgtta ccaaatctgc cccaccatcc ggttggagac | 1620 |
| aagtcttgtt ggaaaagggt ccatccgaat tgccaagca agtcagacaa ttcaacggta | 1680 |
| cttttgttgat ggacaccacc tggagagatg ctcaccaatc tttgctagct accagagtca | 1740 |
| gaactcacga tttggccacc attgctccaa ccactgctca cgctttggct ggtgccttg | 1800 |
| ctttggaatg ttgggtggt gctactttcg atgtcgccat gagattcttg catgaggacc | 1860 |
| catgggaaag attgagaaaa ttgagatctt tggtcccaaa cattccattc caaatgttgt | 1920 |
| tgagaggtgc taacggtgtt gcttactcct ctttgccaga caacgccatt gaccatttcg | 1980 |

-continued

```
ttaagcaagc caaggacaat ggtgttgaca ttttcagagt ctttgacgct tgaacgact      2040 tggaacaatt gaaggttggt gttaatgctg tcaagaaggc tggtggtgtt gtcgaagcta      2100
ccgtttgtta ctctggtgac atgttgcaac caggtaagaa atacaacttg gactactact      2160
tagaagttgt cgaaaagatc gttcaaatgg gtactcacat cttgggtatc aaggacatgg      2220
ctggtaccat gaagccagct gctgccaaat tgttgattgg ttctttacgt accagatacc      2280
cagacttgcc aatccacgtt cactctcatg actccgctgg tactgctgtt gcttccatga      2340
ctgcttgtgc tttggccggt gctgatgttg ttgacgttgc cattaactcc atgtccggtt      2400
tgacctctca accatctatt aacgctttgt tggcctcctt ggaaggtaac attgacactg      2460
gtatcaacgt cgaacacgtt agagaattgg acgcttactg ggctgaaatg agattattat      2520
actcttgttt cgaagctgac ttgaagggtc cagaccctga agtttaccaa cacgaaattc      2580
caggtggtca attgaccaac ttgttgttcc aagctcaaca attaggtcta ggtgaacaat      2640
gggctgaaac caagagagct tacagagaag ctaactactt gttgggtgac attgttaagg      2700
tcaccccaac ttctaaggtc gttggtgatt tggctcaatt catggtttct aacaaattga      2760
cttctgatga catcagaaga ttagctaact ctttggactt cccagactcc gttatggact      2820
tcttcgaagg tttgatcggt caaccatacg gtggtttccc agaaccattg agatccgatg      2880
ttttgagaaa caagcgtcgt aaattgactt gtagaccagg tttagaattg gaaccattcg      2940
atttggaaaa gatcagagaa gatttgcaaa acagattcgg tgatatcgat gaatgtgatg      3000
ttgcctccta acacatgtat cctcgtgtct acgaagattt ccaaaagatt agagaaactt      3060
acggtgactt gtctgtctta ccaaccaaga acttcttggc tccagctgaa ccagacgaag      3120
aaatcgaagt caccattgaa caaggtaaga ctttgattat caaattacaa gctgttggtg      3180
atttgaacaa gaaaaccggt caaagagaag tctacttcga attgaacggt gaattgagaa      3240
agatcagagt tgctgacaaa tctcaaaaca ttcaatctgt tgccaagcca aaggctgatg      3300
tccacgacac ccaccaaatc ggtgctccaa tggctggtgt catcattgaa gtcaaggttc      3360
acaagggttc tttggtcaag aagggtgaat ctatcgccgt tttgtctgct atgaagatgg      3420
aaatggttgt ttcctctcca gctgatggtc aagtcaaaga tgtctttatc cgtgacggtg      3480
aatccgtcga tgcttctgac ttgttggttg ttttggaaga gaaactcta ccaccttctc      3540 aaaagaaata aaggagacc                                                  3559
```

<210> SEQ ID NO 124
<211> LENGTH: 961
<212> TYPE: DNA
<213> ORGANISM: Saccharomyces cerevisiae

<400> SEQUENCE: 124

```
ggtctcgaat gccatctact accaacactg ctgctgctaa cgtcattgaa agaagcctg       60 tttctttctc caacatcttg ctaggtgctt gtttgaactt gtctgaagtt accactttag      120
gtcaaccatt ggaagttgtc aagaccacca tggctgccaa cagaaacttc actttcttgg      180
aatctgtcaa gcacgtctgg tcccgtggtg gtattttggg ttactaccaa ggtttgattc      240
catgggcttg gattgaagct tccaccaagg gtgccgtctt gttgttcgtt tctgctgaag      300
ctgaataccg tttcaaatct ttgggtttga acaactttgc ttctggtatc ttaggtggtg      360
ttaccggtgg tgtcactcaa gcttacttga ccatgggttt ctgtacttgt atgaaaactg      420
tcgaaatcac cagacacaaa tctgcttctg ctggtggtgt tccacaatct tcctggtccg      480
```

-continued

| | |
|---|---|
| ttttcaagaa catctacaag aaggaaggta tcagaggtat caacaagggt gtcaatgctg | 540 |
| ttgccatcag acaaatgact aactgggggtt ccagattcgg tttgtccaga ttggttgaag | 600 |
| atggtatcag aaagatcact ggtaagacca acaaggacga caaattgaac ccattcgaaa | 660 |
| agattggtgc ttctgctttg ggtggtggtt tatctgcttg gaaccaacca attgaagtca | 720 |
| tcagagttga atgcaatcc aagaaggaag atccaaacag accaaagaac ttgaccgtcg | 780 |
| gtaagacttt caaatacatc taccaatcta acggtttgaa gggtttatac agaggtgtta | 840 |
| ctccaagaat tggtttgggt atctggcaaa ccgtctttat ggttggtttc ggtgacatgg | 900 |
| ccaaggaatt cgttgccaga tgaccggtg aaactccagt tgccaagcac taaaggagac | 960 |
| c | 961 |

<210> SEQ ID NO 125
<211> LENGTH: 991
<212> TYPE: DNA
<213> ORGANISM: Saccharomyces cerevisiae

<400> SEQUENCE: 125

| | |
|---|---|
| ggtctcgaat gtcctctgac aactccaagc aagacaaaca aatcgaaaag actgctgctc | 60 |
| aaaagatctc caaatttggt tctttcgttg ctggtggttt ggctgcttgt atcgctgtca | 120 |
| ctgttaccaa cccaattgaa ttgatcaaga tcagaatgca attgcaaggt gaaatgtctg | 180 |
| cttctgctgc caaggtctac aagaacccaa tccaaggtat ggccgttatc ttcaagaacg | 240 |
| aaggtatcaa gggtttgcaa aagggtttga cgctgctta catctaccaa attggtttga | 300 |
| acggttccag attaggtttc tacgaaccaa ttagatcttc tttgaaccaa ttattcttcc | 360 |
| cagaccaaga accacacaag gtccaatctg ttggtgttaa cgtcttttcc ggtgctgctt | 420 |
| ccggtattat cggtgccgtt atcggttctc cattattctt ggtcaagacc agattacaat | 480 |
| cttactctga attcatcaag attggtgaac aaacccacta cactggtgtc tggaacggtt | 540 |
| tagtcaccat tttcaagact gaaggtgtca agggtttgtt cagaggtatc gatgctgcca | 600 |
| ttttgagaac cggtgctggt tcttccgttc aattgccaat ctacaacact gccaagaaca | 660 |
| tcttggtcaa gaacgatttg atgaaggacg gtccagctct acatttgact gcttccacca | 720 |
| tctctggttt gggtgttgcc gttgttatga acccatggga tgtcatcttg accagaattt | 780 |
| acaaccaaaa gggtgacttg tacaagggtc aattgactg tttggtcaag actgttagaa | 840 |
| ttgaaggtgt cactgctttg tacaagggtt cgctgctca agttttcaga attgctcctc | 900 |
| acaccatcat gtgtttgact ttcatggaac aaaccatgaa attggtttac tccattgaat | 960 |
| ctcgtgtttt gggtcacaat taaaggagac c | 991 |

<210> SEQ ID NO 126
<211> LENGTH: 6493
<212> TYPE: DNA
<213> ORGANISM: Rasamsonia emersonii

<400> SEQUENCE: 126

| | |
|---|---|
| ggagttgctt gcccgggcag gatatcggtt ggcggcgtgg ttggacttga ttgcgaagca | 60 |
| gtagagacag gtattctgct gatagcatgg atttatatta tcaataagca gaggcctaaa | 120 |
| gacattcaac cagaagaaac gtccttcatg caacagcaag ctagaacata tacatatgag | 180 |
| aacaagcata gtgccaatca agcagaccta tactgtactc tattacaaca aactactatc | 240 |
| acggtagtcg tacactggtc aatgaaataa tgtgagtaaa aatgatcatg attctatgac | 300 |
| agaacagcta gtacgcttga tttattgggg tataaatttt actttattta ggtggttaag | 360 |

```
agccagcaga ctagatatat agctcagata taatataatt aatagtcaca gaaaaaaata    420
aataaaaata aaaatagcaa gatccatgat atggtataca caaaaaaata ataatcataa    480
atcacacaat tccatcctct ccaaaaccac ctagccagct cctaccaaac gatacatact    540
cagtccaagc aaatcccccg ttccgtcctc ccgtccgtcc gatcagtccc gaataccgac    600
caaaaaaaaa aagagacaaa atccaaatca cgggttcatt cacatcccca caggataccc    660
atggatcagt cgtcctactt actgtggtac agattagaac agaaaattag gtttttacac    720
aactcagggt ggttgcattg cattgcattg tgctgtggag ttagttaact tagttgtact    780
ccatccagtt catacgcagt acattattgg gcatttgacc ccatcagaca agatatctaa    840
ggataagagt agaaattagg taataatagt caaagagaa gaagagatac caagggaact    900
agatactaac aaccaatcag gatatgccac agtgtggaac agaatggaag cagacaggat    960
caacataact ggaaataacc ttttctttct ttcttcgtac agcatcttgg caggaagtaa   1020
cttgatattg ttaattaatg tccatgtcca tgtccatgtc tttgttatgt cttgtcttgt   1080 cttctcttgtg tgctacaagt acagtgtaac agattcatat ccgctgaaac agacataaca  1140
ttcgacacat ggaatacgga gataaagaaa taaattatac tatatacgga atgatatcaa   1200
taaatatccg tgttgtactc cttattaaga aagagtggcg cttggcgcgt ctacgtgcat   1260
ggactggtac tacatatttg attcttcga ttttttaataa caacaaccta gtagacgtat   1320
gtatgtcatg tgaaactttc gattgcgtgc tttcttgtct acttgtcgac ttgttacaat   1380
cttgtcgaat attaataata ataatccatc gcactgacat cttggcaagt actccgtaca   1440
tcaggttaca tacatactga ttctctaaag ctagataacg aataggattc tcgcacagac   1500
agtatgtgtc tcttgtctgt cagatgataa gcagatgaac aaagaaagta taactgctta   1560
ctacctacat gccgacattt agtcgattcc tttcggagaa tttattatgg attattaata   1620 gcatacccg ggattggcag aagggggtaaa aggtccgact agacaaggat atccatacag   1680
tacataccgt tgatacagat cgaatcacat gcatactgct gatggtgtga tgaatccttg   1740
aattagacaa tcatccagac ctgtctggac agagatcctg gcactgaaca atccactcat   1800
tgctatctat cggtactctg tacctgtttc agctgaagct tgccaatcgc agactgccat   1860
ctgcaactga tcagcgccag gatgcaggtc atgcataccc agcgttgttc ccgaggtgtc   1920
attgcttaaa cgcgttaacc agtgtgctaa acgtgctaaa cgtgctaaat gctaaactgc   1980
tgatgctatg cagctgcatc gccgaatctg gagaatgcag atcacctgcc gacggcgggc   2040
tccgggcacg tgcacggggg accccgtagg acagaaacgt ccatcgagag tacgagtac   2100 ggagtattac aagaccctgt ccatcagacc ctgtccatcg tcattgccaa gatctctcat   2160
tgtttgctgt ttcatgctcg gatcaccagt ggacagcaat gccccgtgaa cagcaagccg   2220
catgctggtc cgtgtcttgt ccgtgtgccg atgtagtatt gctaacgaga cccagaatgg   2280
catcaatgac gttgcggatg acagaatgag ggggatcatc agtacgtctg ctatcaggat   2340
gattatccta cggagtattt actcagctga agacaggaac aagatcgtct gatggatgag   2400
gcccacggcc agccagcaca gactccgtac tcttcagtct tctggatttg accgttcgac   2460
ggcgcctccg acgtagcatc tcgctagcct gatccttggc tgcgcctatc gtcggctcat   2520
gcccctgttg atgacgggga agtggagcgg cgccgcgata aggttgcctt gctaatttag   2580
cgcctgcacg ctccagccaa aaagaccaat attgaggtcg atcgtctccc ctggctccgt   2640
gctgctggcc tgcgatcgcc ggcgcgatca taccctgcaa tcacgccgcc agcctatcac   2700
```

```
agaccatgcg gtccttgcac catctgggag ctcgagctct cctgactgcc gtcgggcgt      2760 caatgcgtcc ggagcctccg acgagggcct ctgctcctcg tctgtcctac tggagcttgt      2820
ccgtcagacg tcgcatcctg agccgtgtgc tgatatcgcc atggctctga cgtgatcgac      2880
tgcgagcggc cggcgaggct ataagaagcc gcaacttgct gctcgaagta ccgtctccca      2940
tccatcgatc agacagtcag cagtcctcac tcagtcagtc ctcagtcgtc cttcaccacc      3000
atgggtctgt ccaaagcctt cgtgtctgca ctctcgctgt gctccgccgt cgccgtggcc      3060
gccccgaccg ggccagctcc caacgtgcag ttctccctga gcaggtcgc ggtgccccgg      3120 accaagcctc gtgcgccccc agctgccgac tacgcgcgcg ctctggccaa gtatggcgct      3180
ccaattccgt cgtctgtgcg gacggccgcg tccggcacgc agagcggctc tgcggccaac      3240
acgcccgtcg ccggcgacag cttgtatctc acgcccgtta ccatcggcca gagcacgctg      3300
aacctggact ttgacacggg ctctgcggat ctgtaagtgt cccaactctc gcaagaacaa      3360
gaacggagca gctgactcgt ccagctgggt cttctccaac gagacgccct ccagcgagcg      3420
cggcaaccac gccatctaca agcccagctc gacggccaag aagctgaacg ctacacctg      3480 gagcatctcg tacggcgacg gcagctcggc cggcggcgac gtctaccagg acagcgtctc      3540
ggtgggcggc gtcaacgcct ccaaccaggc ggtcgaggcc gccaccaagg tcagctccga      3600
gttcacgcag gagccgggcg acggcttgct gggcctggcc ttcagcagca tcaacaccgt      3660
caagcccaag ccgcagacga ccttcttcga cacggtcaag tcctcgctcg ccaagccgct      3720
gttcgccgtc accctcaagc acaacgagcc cggcagctac gactttggct acatcgacag      3780
ctccaagtac aagggcagca tccagtacac ccaggtcgac aactcgcagg gcttctggca      3840
gttcacggcc gacggctact cgattggcgg cagcagcggc agcggtggct ccatttctgg      3900
cattgctggt aagaactccc cctacatcag agttatctag atgctgattt cgcagacacc      3960
ggcaccaccc tcctcctgct cgacgaccag atcgtcaacg agtactacca gcaggtccag      4020
ggcgcgcaga acgaccagaa cgccggcggc tacaccttcc cgtgcgacgc gcagctgccc      4080
gagctgagct tcaccatcgg ccagtacacc gccaccgtgc cggccgagta cctcaacttc      4140
cagcccgtgt cgcagggcag ccagacctgc ttcggcggtc tgcagtccaa ccagggcatt      4200
ggcttctcca tcttcggcga cgtcttcctc aagagccagt acgtcgtctt tgactcggac      4260
ggtcctcagc tgggctttgc tgctcaggcg tagaccagtc gtcctccagc ccaggttggt      4320
tggtaggaga tgattttcg atcgatcgat tatcatggtg attgatagga tatgtgcatg      4380
agcagttgcc tgtacataca tacataatga tttattgaat caattagtta tgatcaatct      4440
cgaatatatt ttcagtgaaa tacgtacatg gtcatagcat aacgatatac tccgttttct      4500
tcaggtagct agtaaatata cacaaattca tcgttctccc ggtccgtcag gtccaggaag      4560
gctttgtctc cgatcgtccc gtcgggatca ctctcgctgg tatcgtgata gcgctccctc      4620
atcgagtaat caaccacctt ggccggcttt ccattccgca cgcgccgccg ctcctgcatc      4680
cggttcagca cgaccaaatt cgcccactgc gccagcacga cggccaccag cgccacgaag      4740
atggccagac aagcccgcac gcccggccga tacgccggcg cgtccttctt gctgaagagc      4800
agcgggccga cgatgttgcc cgccgagctg gccgcgttgt acaggctcat cagcgccgat      4860
ttcttcgttg tgccgcccgt gttgcccacg atccacgtca cgatcagtgg gttgccgccg      4920
aagagaaacg cgagcaggta gtagcctacc aggagggagg gttcgactga gttttgcttc      4980
gtgctgttat tactgcgtgg cacggcgtac agaattgcca ggcccgcgac taccggcagc      5040
atgaagccgg ccagcacgac gcccttcatc cgcgcccgct gcgccagata gctccccgcc      5100
```

```
aggatgacca gcagctgcag cgcgccaaac ggcatgttga gcagactcgt cgtgtacgcg    5160 tcgtaccccca ggccgttgag gatcagcggg ccgaacgtgt tgctcacgct ggcgccgacg   5220
ttcagcagca tcgccatgcc gatccagagg taggttttgg gctcgagcgc tgcctcgacg   5280
acgtgccgga tcttgaactc gcggctccct gtgcccgtct ggttcgcgcg cagccgctcg   5340
atggcctgcg cttttttccgt ctccgtcagg aaccgcgctg aggggatgtc gttgtctagt  5400
ttccagtaga tgaacggcac tgagatgatg gtcaggaggc cgacggtgag gaagatactg   5460
cgccagtcgt cagcagtcag tcagtcagcg ttcggggtag aaggggagta catctgccat   5520
ggcctcagaa caggcgactc gatatggccc aacccgtacg acagggccgc cgcgatgaca   5580
gtcgccgcgc cgttggtact gtaccaggcc gcaatgcgca gcggctgctc ggcgcggcgg   5640
taccactggc tggtgatgac gctgaacagc ggcagacagg cggcctcgaa caggccgagg   5700
aagaagcgcg cggccatcag ggaggcgaaa ctgcgacagg cggccatggc ggcctgggcg   5760
acgccccagc ccagacacag cgcgggcatc aggcggcgat gcggcacgcg cacgatcagc   5820
cacgacgaga acggctgcca gacgagctgg gcgatgggcg cgatcgaccc cagcagcgag   5880
tactggttgc ccgtcaggtg cgtgtcggcc tgcaagccga aggtgccccc gtacccgagc   5940
accgacttgt ccaggatctg caggaagtac acccacacga ggatggccag gatgacgcgg   6000
tctgtcttgc gccggatgcg cttgctgtcg gcgtccgtga gtgggattct ctgctggccg   6060
atcaggcgga gcgccgtgtc gccgtggacg gcgggttgct cttcttcatg ggtgacggtc   6120
ggtttggatg ccatggtagc gattactaga tgtaatcaag ttgtaatggg agacaaacga   6180
ccaagttctc tctcgacgtt ttataccggc ttatatgtct gttcagcagc attgcaagtc   6240
aagtaatgac atcggaattc ctccggttcc ccgcattgcg cggcgatcat cggctggcac   6300
tagcagtata gctagctcag agtccgtatt actggattct attgcattgc gctgattgca   6360
gacgttgact gacagcagga gctttgactc tattaccccc acgcttcggc aattccccgc   6420
gtgctcgggc ctctatgcac ccccacgtgg gggaacattc cagagtatgc aggcagtagt   6480
atgcagcatg gat                                                      6493
```

<210> SEQ ID NO 127
<211> LENGTH: 1194
<212> TYPE: DNA
<213> ORGANISM: Rasamsonia emersonii

<400> SEQUENCE: 127

```
atgggtctgt ccaaagcctt cgtgtctgca ctctcgctgt gctccgccgt cgccgtggcc    60
gccccgaccg ggccagctcc caacgtgcag ttctccctga gcaggtcgc ggtgccccgg   120 accaagcctc gtcgcccccc agctgccgac tacgcgcgcg ctctggccaa gtatggcgct   180
ccaattccgt cgtctgtgcg gacggccgcg tccggcacgc agagcggctc tgcggccaac   240
acgcccgtcg ccggcgacag cttgtatctc acgcccgtta ccatcggcca gagcacgctg   300
aacctggact ttgacacggg ctctgcggat ctctgggtct tctccaacga gacgccctcc   360
agcgagcgcg gcaaccacgc catctacaag cccagctcga cggccaagaa gctgaacggc   420
tacacctgga gcatctcgta cggcgacggc agctcggccg cggcgacgt ctaccaggac   480 agcgtctcgg tgggcggcgt caacgcctcc aaccaggcgg tcgaggccgc caccaaggtc   540
agctccgagt tcacgcagga gccgggcgac ggcttgctgg gcctggcctt cagcagcatc   600
aacaccgtca agcccaagcc gcagacgacc ttcttcgaca cggtcaagtc ctcgctcgcc   660
```

```
aagccgctgt tcgccgtcac cctcaagcac aacgagcccg gcagctacga ctttggctac      720
atcgacagct ccaagtacaa gggcagcatc cagtacaccc aggtcgacaa ctcgcagggc      780
ttctggcagt tcacggccga cggctactcg attggcggca gcagcggcag cggtggctcc      840
atttctggca ttgctgacac cggcaccacc ctcctcctgc tcgacgacca gatcgtcaac      900
gagtactacc agcaggtcca gggcgcgcag aacgaccaga acgccggcgg ctacaccttc      960
ccgtgcgacg cgcagctgcc cgagctgagc ttcaccatcg ccagtacac cgccaccgtg     1020 ccggccgagt acctcaactt ccagcccgtg tcgcagggca gccagacctg cttcggcggt     1080
ctgcagtcca accagggcat tggcttctcc atcttcggcg acgtcttcct caagagccag     1140
tacgtcgtct ttgactcgga cggtcctcag ctgggctttg ctgctcaggc gtag            1194
```

<210> SEQ ID NO 128
<211> LENGTH: 397
<212> TYPE: PRT
<213> ORGANISM: Rasamsonia emersonii

<400> SEQUENCE: 128

```
Met Gly Leu Ser Lys Ala Phe Val Ser Ala Leu Ser Leu Cys Ser Ala
1               5                   10                  15

Val Ala Val Ala Ala Pro Thr Gly Pro Ala Pro Asn Val Gln Phe Ser
                20                  25                  30

Leu Lys Gln Val Ala Val Pro Arg Thr Lys Pro Arg Ala Pro Pro Ala
            35                  40                  45

Ala Asp Tyr Ala Arg Ala Leu Ala Lys Tyr Gly Ala Pro Ile Pro Ser
        50                  55                  60

Ser Val Arg Thr Ala Ala Ser Gly Thr Gln Ser Gly Ser Ala Ala Asn
65                  70                  75                  80

Thr Pro Val Ala Gly Asp Ser Leu Tyr Leu Thr Pro Val Thr Ile Gly
                85                  90                  95

Gln Ser Thr Leu Asn Leu Asp Phe Asp Thr Gly Ser Ala Asp Leu Trp
            100                 105                 110

Val Phe Ser Asn Glu Thr Pro Ser Ser Glu Arg Gly Asn His Ala Ile
        115                 120                 125

Tyr Lys Pro Ser Ser Thr Ala Lys Lys Leu Asn Gly Tyr Thr Trp Ser
    130                 135                 140

Ile Ser Tyr Gly Asp Gly Ser Ala Gly Gly Asp Val Tyr Gln Asp
145                 150                 155                 160

Ser Val Ser Val Gly Gly Val Asn Ala Ser Asn Gln Ala Val Glu Ala
                165                 170                 175

Ala Thr Lys Val Ser Ser Glu Phe Thr Gln Glu Pro Gly Asp Gly Leu
            180                 185                 190

Leu Gly Leu Ala Phe Ser Ser Ile Asn Thr Val Lys Pro Lys Pro Gln
        195                 200                 205

Thr Thr Phe Phe Asp Thr Val Lys Ser Ser Leu Ala Lys Pro Leu Phe
    210                 215                 220

Ala Val Thr Leu Lys His Asn Glu Pro Gly Ser Tyr Asp Phe Gly Tyr
225                 230                 235                 240

Ile Asp Ser Ser Lys Tyr Lys Gly Ser Ile Gln Tyr Thr Gln Val Asp
                245                 250                 255

Asn Ser Gln Gly Phe Trp Gln Phe Thr Ala Asp Gly Tyr Ser Ile Gly
            260                 265                 270

Gly Ser Ser Gly Ser Gly Gly Ser Ile Ser Gly Ile Ala Asp Thr Gly
        275                 280                 285
```

```
Thr Thr Leu Leu Leu Leu Asp Asp Gln Ile Val Asn Glu Tyr Tyr Gln
    290                 295                 300
Gln Val Gln Gly Ala Gln Asn Asp Gln Asn Ala Gly Gly Tyr Thr Phe
305                 310                 315                 320
Pro Cys Asp Ala Gln Leu Pro Glu Leu Ser Phe Thr Ile Gly Gln Tyr
                325                 330                 335
Thr Ala Thr Val Pro Ala Glu Tyr Leu Asn Phe Gln Pro Val Ser Gln
            340                 345                 350
Gly Ser Gln Thr Cys Phe Gly Gly Leu Gln Ser Asn Gln Gly Ile Gly
        355                 360                 365
Phe Ser Ile Phe Gly Asp Val Phe Leu Lys Ser Gln Tyr Val Val Phe
    370                 375                 380
Asp Ser Asp Gly Pro Gln Leu Gly Phe Ala Ala Gln Ala
385                 390                 395

<210> SEQ ID NO 129
<211> LENGTH: 1066
<212> TYPE: DNA
<213> ORGANISM: Artificial Sequence
<220> FEATURE:
<223> OTHER INFORMATION: A.nidulans gpdA promoter and 5' part of the ble
      coding region

<400> SEQUENCE: 129
agacagctct ggcggctctg aggtgcagtg gatgattatt aatccgggac cggccgcccc     60
tccgccccga agtggaaagg ctggtgtgcc cctcgttgac caagaatcta ttgcatcatc    120
ggagaatatg gagcttcatc gaatcaccgg cagtaagcga aggagaatgt gaagccaggg    180
gtgtatagcc gtcggcgaaa tagcatgcca ttaacctagg tacagaagtc caattgcttc    240
cgatctggta aaagattcac gagatagtac cttctccgaa gtaggtagag cgagtacccg    300
gcgcgtaagc tccctaattg gcccatccgg catctgtagg gcgtccaaat atcgtgcctc    360
tcctgctttg cccggtgtat gaaaccggaa aggccgctca ggagctggcc agcggcgcag    420
accgggaaca caagctggca gtcgacccat ccggtgctct gcactcgacc tgctgaggtc    480
cctcagtccc tggtaggcag cttttgccccg tctgtccgcc cggtgtgtcg gcggggttga    540
caaggtcgtt gcgtcagtcc aacatttgtt gccatatttt cctgctctcc ccaccagctg    600
ctcttttctt ttctctttct tttcccatct tcagtatatt catcttccca tccaagaacc    660
tttatttccc ctaagtaagt actttgctac atccatactc catccttccc atcccttatt    720
cctttgaacc tttcagttcg agctttccca cttcatcgca gcttgactaa cagctaccccc   780 gcttgagcag acatcaccat ggccaagttg accagtgccg ttccggtgct caccgcgcgc    840
gacgtcgccg gagcggtcga gttctggacc gaccggctcg ggttctcccg ggacttcgtg    900
gaggacgact cgccggtgt ggtccgggac gacgtgaccc tgttcatcag cgcggtccag    960
gaccaggtgg tgccggacaa cacctggcc tgggtgtggg tgcgcggcct ggacgagctg   1020
tacgccgagt ggtcggaggt cgtgtccacg aacttccggg acgcct              1066

<210> SEQ ID NO 130
<211> LENGTH: 1065
<212> TYPE: DNA
<213> ORGANISM: Artificial Sequence
<220> FEATURE:
<223> OTHER INFORMATION: 3' part of the ble coding region and A.nidulans
      TrpC terminator
<220> FEATURE:
<221> NAME/KEY: misc_feature
```

<220> FEATURE:
<221> NAME/KEY: misc_feature
<222> LOCATION: (685)..(685)
<223> OTHER INFORMATION: n is a, c, g, or t
<220> FEATURE:
<221> NAME/KEY: misc_feature
<222> LOCATION: (893)..(893)
<223> OTHER INFORMATION: n is a, c, g, or t
<220> FEATURE:
<221> NAME/KEY: misc_feature
<222> LOCATION: (984)..(984)
<223> OTHER INFORMATION: n is a, c, g, or t

<400> SEQUENCE: 130

```
accagtgccg ttccggtgct caccgcgcgc gacgtcgccg gagcggtcga gttctggacc      60
gaccggctcg ggttctcccg ggacttcgtg gaggacgact tcgccggtgt ggtccgggac     120
gacgtgaccc tgttcatcag cgcggtccag gaccaggtgg tgccggacaa caccctggcc     180
tgggtgtggg tgcgcggcct ggacgagctg tacgccgagt ggtcggaggt cgtgtccacg     240
aacttccggg acgcctccgg gccggccatg accgagatcg gcgagcagcc gtggggggcgg    300
gagttcgccc tgcgcgaccc ggccggcaac tgcgtgcact tcgtggccga ggagcaggac     360
tgaccgacgc cgaccaacac cgccggtccg acggcggccc acgggtccca ggagcttgag     420
atccacttaa cgttactgaa atcatcaaac agcttgacga atctggatat aagatcgttg     480
gtgtcgatgt cagctccgga gttgagacaa atggtgttca ggatctcgat aagatacgtt     540
catttgtcca agcagcaaag agtgccttct agtgatttaa tagctccatg tcaacaagaa     600
taaaacgcgt tttcgggttt acctcttcca gatacagctc atctgcaatg cattaatgca     660
ttgactgcaa cctagtaacg ccttncaggc tccggcgaag agaagaatag cttagcagag     720
ctattttcat tttcgggaga cgagatcaag cagatcaacg gtcgtcaaga gacctacgag     780
actgaggaat ccgctcttgg ctccacgcga ctatatattt gtctctaatt gtactttgac     840
atgctcctct tctttactct gatagcttga ctatgaaaat tccgtcacca gcncctgggt     900
tcgcaaagat aattgcatgt ttcttccttg aactctcaag cctacaggac acacattcat     960
cgtaggtata aacctcgaaa tcanttccta ctaagatggt atacaatagt aaccatgcat    1020
ggttgcctag tgaatgctcc gtaacaccca atacgccggc cggcc                    1065
```

<210> SEQ ID NO 131
<211> LENGTH: 1500
<212> TYPE: DNA
<213> ORGANISM: Penicillium chrysogenum

<400> SEQUENCE: 131

```
acttttttgg tcctgattga aaatggtagc gtggtctagg agaggtgaag gaagatctag      60
cactgcttga taacgggtgc aattgtccag taaagaaagg cgtgcctatc gtgcgattga     120
aacagagagc ggatgatatg tggcggatct cccagtacaa ggcatgttac atctctcccc     180
tagtcgtaat tgcaaggatc aaacgttggg tcaatggaat tcagagagct tttcgtacga     240
agtgcgtaat gtacgtagca ttttatggta gcatgcaaag cacattttgc tgcaacccca     300
atttaatgcg gtcctgctca ataattgatc tgcactaagg ccttggcgat ggggccagaa     360
aagggttgtt cagtggtgtg tactccgtaa tggtcaagcc gatttcgaga atgaccgtag     420
tgttcattca tcagtgcgat attaaatcag ttagctactc tatctgaaag ctaataaatt     480
tcttttaccac taacaatact cttctctgac tgaaagtacc ttttccactc ccctcatact    540
tcatgtttta agctcaaccg taggaaagcc tgtatatctt aaaagatttg gatttactct     600
tccagcgctt actgtctgct ctttcggccg agcgaacctt ggcagtatga tcggactatg     660
```

```
tactttgtta cacaaaagga gaagcgggc tgccactgag acaacccct gttcaaggc      720
tagcatcccg ctgtaagccc acccatccca ccttgaagta tgcaactttt gaccgcctag    780
accatgtgag cttatgttac tgaaatacta cccgcgaatc atttcctaat ttgctttggc    840
tcgaatccac cccagcccta cgtaacacaa cggggagctg ccttacagct tggctgtatc    900
acagtatcac atagatacat acatagtata gtgcctttgc cttttcgacc tataagcatc    960
cgccatatgc taaaccttct catataccaa cattttggat ttggagatca tttcctagtg   1020
aaacaacttt atcaaatgca atgcagccat cgtcctttgc agatccgagt ggcccagtca   1080
ccgtgtcaac gtgtcagccg tttttctctgc tttttaggaa atgattacca ctaggtaagc   1140
ccaaaaatat cttcctggta aacaagtagt gcatcttacc ccggaggctg aagcaggtaa   1200
gggattttgg agagagccca cccgtaagaa tataccagcc aagaggtcca gtatcctgaa   1260
gtatgtgagg cattaatgtc attggagaag tcatgcaatc cataagctgc cacccccaag   1320
atgactgcat tggacctgag cattgtatgt gtcacctttc acacagagct catgatctgg   1380
tttataaagg cggcttcatg accctcaatt ccatatagta tcactcccat cacagcattt   1440
cgatatcttc aaccacttta accttctcca gaggatcatc atctcaacac cgtcaaaatg   1500

<210> SEQ ID NO 132
<211> LENGTH: 819
<212> TYPE: DNA
<213> ORGANISM: T. thermophilus

<400> SEQUENCE: 132
atgaagggct cctctgctgc ctccgtcctc cttgctctcc ttgccggtat caccgcacc     60
tcggcccacg gctacgtgtc gaacattgtc gtcaacggtg tctactaccg tggatggttg    120
cctggtgagg accctacaa ccctgaccct cccatcggtg ttggctggga gactcccaac    180
ctgggtaacg gattcgtcac ccccgaggag gcctccactg atgccatcat ctgccacaag    240
gaagccaagc cgcccgtgg ccacgccacc gtcaaggccg gtgacaagat ctacatccag    300
tggcagccca tccctggcc cgagagccac cacggtcccg tccttgacta ccttgctgct    360
tgcaacggtg actgcgagac tgttgacaag acctccctcc gcttcttcaa gatctccaac    420
aagggtctga tcgatggcag ctctcctcct ggatactggg cggatgacca gttgattgag    480
aacggcaacg gctggctcgt ccagattcct gaagatatca gcccggaaa ctacgtgctc    540
cgtcacgaga tcattgcgct gcacgctgct ggcaacccca acggtgctca gctctacccc    600
cagtgcttca acctccacat caccggcagc ggtaccgttg agcccaggg tatccccgcc    660
accgagctgt actctcccga tgaccctggt atcctgatca acatctacca gcctctgacc    720
acctacgaag tccccggtcc tacccccatt cccaggctg ttgaaattga gcagtcctcc    780
tctgccatca ccgccactgg caccccact cctgcttaa                           819

<210> SEQ ID NO 133
<211> LENGTH: 301
<212> TYPE: DNA
<213> ORGANISM: Penicillium chrysogenum

<400> SEQUENCE: 133
aaggctcttg atgacgagcc aatgcatctt ttgtatgtag cttcaaccga ctccgtcttc     60
acttcttcgc ccgcactgcc taccgtttgt accatctgac tcatataaat gtctagcccc    120
tacctacact atacctaagg gagagaagcg tagagtgatt aacgtacggg cctatagtac    180
cccgatctct agatagaaca tttagtagag attaggatgc ctaactaatt taacttgagc    240
```

```
attgtcccgt tcatattgat tttcagtcca ttatacactc ttaatcgttt cccggtagaa    300
g                                                                  301
```

<210> SEQ ID NO 134
<211> LENGTH: 1501
<212> TYPE: DNA
<213> ORGANISM: Rasamsonia emersonii

<400> SEQUENCE: 134

```
ccaattattc aaatcttcaa cctgggtcct ttgcgactag actcggcact atacccacct    60
gagtcgaatc tccgctggac gatttttttt cttagaagaa aaaaagcttc agaggctaag   120
gattaggctt ccgtacggac tccatgccct atcagacaga gactccgcaa ctcatctgat   180
ctcttcgatg gagggaaaat ctgctgtttt tcgcaaattt ccaacccacc agaaacaccc   240
agaactgtca cgactcacac gtcctacggt ctttgtgtga gtataactga ttatattcac   300
agatgggtta ctcaatgcag gtacaaactt tgatcgcgct ctttttggga ccgtctatca   360
accggcttcg aaaaatggct cgactagcca atctgacagg aaattgcgat gttgcaaccg   420
tgtatacgga gtcctctgta caacctctgc caacctctgc cacctcggta catgtacgga   480
gtagctcccc gcagccgcga ttggatgcat taaagtgggt caaccgcagt ggcttgcagt   540
ccgctgcacg agtccgtatg caataattct tgacacacac gagtgcacat aataatagga   600
aagcagacaa actttgagct gaaggctgtc gagcttggca aattgcagga tctggctagt   660
ttcgaagtcg acttcgcgcg cgcagcagta ttgcattatt gagtgtgacc tgctgcgtgg   720
gattagcgtc gcaccggccg aaagctagtc tcatccaagg ctgagcctga gcgctaatta   780
ccccggatca gccaagccct aatggatcta atgaggtgcc tcctccagca ttcggcctgc   840
atggtgcggc gacccctctc tccacgtcca ataattgctg ttgcgcctgt cgaaccctgc   900
caccgcatct ttgccgtttt actccgagat ctgaaaagcc tgctgtggat ggcagttcgc   960
aatatgcact ctcaatcagg tctgtagcat ctttttaacta ttattctatt actaattgct  1020
tctggaaggc ttgtggggtg tggtttgtca tcaagttggc tccctgagcg ccgcgttgca  1080
atctccacgc gcggttgtac ggagtatatt catgcggatc cccggggcag agccgtagtg  1140
catgtgacac taatcgatca tccgctcaat tggatcctgg atttcgaccc tggcttgaac  1200
atatccaatg atcttccagg gacgaaccga cccggtcatg ctttgttacc tacgtacgga  1260
gtagcggcct gggtgatggt tccggaaggt ctgctaaaag gagatcgagt atacccccg   1320
gggtccgtct gagacttata aagggctctc tgcaactctc cggccgactt ttttcttcat  1380
tcgacagcca tcactcgttt atctggtcga ttctgcagac ttgcccaagg agcaaagagc  1440
atcttcatac gcgcatcatc catctccagc tttctctctc caaacataca ccgtcaaaat  1500
g                                                                 1501
```

<210> SEQ ID NO 135
<211> LENGTH: 825
<212> TYPE: DNA
<213> ORGANISM: T. languinosa

<400> SEQUENCE: 135

```
atgaagggct ccaccaccgc ctcgctactc cttcctctcc ttgcctccgt cacccgtacc    60
tccgctcacg gtttcgtttc caacctggtc atcaacggtg tgttctaccg cggctggctc   120
cccaccgagg acccctacaa ggccgaccct cccattggtg ttggctggga gactcccaac   180
```

| | |
|---|---|
| cttggcaacg gcttcgtcct ccccgaggag gccagcactg atgccattgt ctgccacaag | 240 |
| gaggctgagc ctgctcgtgg atacgcctcc gttgctgctg gtgacaagat ctacatccag | 300 |
| tggcagccca cccctggcc tgagtctcac cacggtcccg tcatcgacta ccttgctcct | 360 |
| tgcaacggtg actgctcgac cgtcaacaag acctccctgg agttcttcaa gattgatggt | 420 |
| gttggtctga tcgatggcag ctctcctcct ggcaagtggg cggatgatga attgattgcc | 480 |
| aacggcaacg gctggttggt gcagatcccc gaggacatca agcccggtaa ctacgtcctg | 540 |
| cgccacgaga tcattgctct ccacgaagcg ttcaaccaga acggtgctca gatctacccc | 600 |
| cagtgcttca acctgcagat caccggaagc ggtaccgtcg agcccgaagg aactcctgcc | 660 |
| accgagctct actctcccac cgaccccggt atcctggtcg acatctacaa ccctctctcc | 720 |
| acctacgtgg tccccggtcc taccctcatc ccccaggctg ttgaaatcga gcagtccagc | 780 |
| tctgccgtca ctgccactgg aactcccacc cccgctgccg cctaa | 825 |

<210> SEQ ID NO 136
<211> LENGTH: 301
<212> TYPE: DNA
<213> ORGANISM: Aspergillus nidulans

<400> SEQUENCE: 136

| | |
|---|---|
| ctaataagtg tcagatagca atttgcacaa gaaatcaata ccagcaactg taaataagcg | 60 |
| ctgaagtgac catgccatgc tacgaaagag cagaaaaaaa cctgccgtag aaccgaagag | 120 |
| atatgacacg cttccatctc tcaaaggaag aatcccttca gggttgcgtt ccagtctag | 180 |
| acacgtataa cggcacaagt gtctctcacc aaatggggtta tatctcaaat gtgatctaag | 240 |
| gatggaaagc ccagaatatt ggctgggttg atggctgctt cgagtgcagt ctcatgctgc | 300 |
| c | 301 |

<210> SEQ ID NO 137
<211> LENGTH: 62
<212> TYPE: DNA
<213> ORGANISM: Artificial Sequence
<220> FEATURE:
<223> OTHER INFORMATION: Gibson primer 5' RePepA region-Ppaf

<400> SEQUENCE: 137

| | |
|---|---|
| gctagataac gaataggatt ctcgcacaga cagtgcactt ttttggtcct gattgaaaat | 60 |
| gg | 62 |

<210> SEQ ID NO 138
<211> LENGTH: 30
<212> TYPE: DNA
<213> ORGANISM: Artificial Sequence
<220> FEATURE:
<223> OTHER INFORMATION: Gibson primer TpenDE

<400> SEQUENCE: 138

| | |
|---|---|
| gaggcttcta ccgggaaacg attaagagtg | 30 |

<210> SEQ ID NO 139
<211> LENGTH: 65
<212> TYPE: DNA
<213> ORGANISM: Artificial Sequence
<220> FEATURE:
<223> OTHER INFORMATION: Gibson primer TpenDE-Ppra

<400> SEQUENCE: 139

| | |
|---|---|
| cattatacac tcttaatcgt ttcccggtag aagcctcgtg ccaattattc aaatcttcaa | 60 | cctgg                                                                          65

<210> SEQ ID NO 140
<211> LENGTH: 33
<212> TYPE: DNA
<213> ORGANISM: Artificial Sequence
<220> FEATURE:
<223> OTHER INFORMATION: Gibson primer Tamds

<400> SEQUENCE: 140
gggcagcatg agactgcact cgaagcagcc atc                                           33

<210> SEQ ID NO 141
<211> LENGTH: 62
<212> TYPE: DNA
<213> ORGANISM: Artificial Sequence
<220> FEATURE:
<223> OTHER INFORMATION: Gibson primer Tamds-loxP-gpd-ble

<400> SEQUENCE: 141
gatggctgct tcgagtgcag tctcatgctg ccctctaccg ttcgtataat gtatgctata            60
cg                                                                             62

<210> SEQ ID NO 142
<211> LENGTH: 29
<212> TYPE: DNA
<213> ORGANISM: Artificial Sequence
<220> FEATURE:
<223> OTHER INFORMATION: Gibson primer 5' RePepA region

<400> SEQUENCE: 142
ctgtctgtgc gagaatccta ttcgttatc                                                29

<210> SEQ ID NO 143
<211> LENGTH: 7890
<212> TYPE: DNA
<213> ORGANISM: Rasamsonia emersonii

<400> SEQUENCE: 143
ggagcctggc tcagcatgct cacggactgc aggatgaaca cgcgtctccg aaggtgcaac            60
cggggagaag ataaccaccg tccttgaggg aagaacatct gtcatcatcg aaacagaagc           120
agtctcagtc tcggtctcgg tctcagtccc gtcatctata gtcgtcacag ttgggatcgg           180
aaacgtggcc gaccagtccc tggtcttgta ccaggtgtta ttctcgtatc gcggcggcgc           240
gatcatgtcg agcgcctcac caatccttcc gaggacatag cccatcctga acccgccctg           300
gaggcgctcg atgaagttgt tggcgggatg aacggcggtg aaagggatgg catggaagat           360
gccgaggatg ccatggcca tggagaacat gaacaggccg aaggggtcca tggtgatgat            420
gattcgatcg atatcagaca gctgaatatg tattagcttt ccaaatttct tctatcatga           480
aattcgacag gaaatagaaa agaaaggat gctggctttg attaaagaga gtagctgggt            540
cttatcacaa gagattaaaa agtgtcttaa acaaagacaa gacaagacaa gcatccgtct           600
gatgcatgag tttcgagata tatataatac aaaggatgga ttcactgaac agttcgttga           660
cttctgaaga acaaaggctg gtctctgcat gcccgagaat agtaacaaca ataaagagca           720
aatacaacgt tgtgtacagc aagcgaatga cctgccttga atgagtctgg cagatttatt           780
cccccatcta ctaccttcaa gtacctcatc agatggccag cagaaggtgc aagtgggtat           840
atcttctcat tcgaagaact tagtgtttag ttttctgagc agcaatatag ctagttgcaa           900

```
gttagaaaag agtataaaga accgtttccg caacaccagc taccctcaaa gaaaggaatt    960
gaacaaactg ggaactaccg attactacca agctggaggg cataggcaat gaacgccagg   1020
aattggtaaa gactgaagat aggaaggtat ggtgaatact gcatagtgca atgtagacct   1080
tcagtatcat aaggatcatc cattcattat agacgctaat ataaagtatt tctgaaaaaa   1140
aatgttggag aggagatcaa gtctttttat tcaacggctt tcaaagacta aaagctggaa   1200
aaggcaggct atcatcatga tacctagcat agcataccat gtttgcgttt atcacttcat   1260
attcaggaca acctcctgcc caggaccacg ccataggcaa ctgtcgccag gagaccgccc   1320
aggttgacca gcgtcgagat tccatgcagc ttggcaaact tcttgttgag ctcggtcatc   1380
tccttggagt gaggaggcgg gtcataactc ttcttgccgt cgatcgattc tgccagagat   1440
catatatatc agcccgtacc tatacagtgt actcgtgcgt actcggcagc agccaaaccg   1500
gtaggtagta ggcaggtacc aaccttgctg ccacctctgc ttgataactc ccacaacctt   1560
cggggtcaga tagagcaggt tggtcagtcc cgaaacgaag acgatcgaaa gcggcagcaa   1620
caccgtcaga cgattctcct cgagaagcac ccccgcgagg ctagagggcc cagttcccag   1680
gaccgttctg gctcccgggt aggtcagcgc tgcgacaacg gggagagcgc tctgcagggt   1740
gaagtagatc gggaacaggc tattctggag cgtcgagaac tgctgacggg gaagcgtcct   1800
gaacgcgacg gttccgccaa cgaaggtcta catatataac ggaatgttgt aggagctttt   1860
gatgagttat ctatcctcct gaccaattga ccagaaacaa aactcaggat gtcaaacctg   1920
atagatctcg actcccagaa gggtgccgta gctgattgaa gtgtgatgtc agccgatcta   1980
ttagtagcag ccgtagtact ggtgacgcac cttagtatgt ggaagggggcc caggatagac   2040
atcctgctct gttgtactga tatggaaaca cctcgtgact ggaacagaac tatatgggat   2100
tatacttaga cagataccccc actgactggg aattcagagg gaagagtaag ttgtgttatg   2160
ctacgggtag gttagagaag ctgtcaagct tgggtctccc gagctaacgc tagctgcatg   2220
tggggcatgt tcttatctcc acggcccgct caaacctaga tctgcttcca acaaagcaca   2280
aatatctata cacacggcct tttccgtaag gcccacgcac cttcccgacg tcatgtgcac   2340
tcgcgtctgc cgcgcctcaa aaaggaaata tcacgcgtct gcctggaggc gctccttagt   2400
catagaaaga aacgcatcta cgccatgcag tgatttattt atctgacatt tccttcctct   2460
tcgttgcagc aggagggaca gctgacatct cttttgcaaa atggctgaca aggaggccac   2520
cgtctacgtg atcgatgtgg gaaagtccat ggggaggcgc cgccatggac ggccggtatc   2580
tgacctggaa tgggcaatgc aatatgtctg ggacaagatt acgacaaccg tatgctgaca   2640
cttgatccgg tctcctggaa attaaattcc tgcgttgaga actgacatat cttctgttag   2700
gttgccacgg ggcggaaaac ggctacaatt ggagtggtcg ggctgaggac agatggtgag   2760
attttaccgt gcccgaatca ggtaaatatg atttactgat gtatctggac agaaacatcg   2820
aacgacttgc aggatgatga cagctattcg cacatctctg tctttcagga aattggacag   2880
tatgtgcctc agctgacact gatgactagt gacttttcct cgcatatact aaataaatca   2940
ctgccagggt cctcatgcct gatctgcgaa aactgcgcga cctgatcaag cctagcaaca   3000
ctgatgaagg agatggtgag ttttgcccgt atcttcggac tcatttgatt tgatattgag   3060
acctatctac ctatagctat ctcctccctt gtcgtcgcga tccagatgat caccacttat   3120
accaaaaagc tgaagtatcg acggaaaaat attctcgtga cgaacgggga aggatccatg   3180
agtaccgatg tcttgatga gatcgtgaaa aagctcaagt ccgatagcat tgaattggtg   3240
gtcttgtatg ttttttcactt ctctttgact tttcttgtgg ctggtatgca aaatggctaa   3300
```

```
actggtttcg ttgcaggggt gttgactttg atgatcctga atttggtgtc aaagaggagg    3360
acaagaatcc agcaaaagta ttcaatgttt tttttttagc aggttggaag agttgctgat    3420
tcgatctgcc gcaggctgag aatgaagcgg tcctcagagg tctcgttgat tcctgcgacg    3480
gagtctacgg gacattacaa caggccatat tggagctgga cacaccgcgt gtgaaggttg    3540
ttcgtggaat accctccttt agaggagagc tccgactggg gaaccctgaa gagtattcgt    3600
ctgcccttcg tatcccagtc gaaagatact accgaactta tgttgccaag ccgccgacag    3660
cgagctcctt tgtcctacga tctgacgctg cagctggtca gagggtgcag gagaatgcac    3720
tgacaagcgt ccgaaacgca cggacatatc acgtcagtga tgagtccgca ccaggaggca    3780
agagagacgt ggagcgagaa gatctcgcca agggctacga gtatgggaga accgcggtgc    3840
acattagtga gtccgatgag aatatcacca aactccagac gaaccctggt ctggaaatca    3900
tcggcttcat tcagagtgac catgtatgtt tctcgtcaag ggtatctcat ctgaaccgtg    3960
attaacctag gatccagtac gaccgataca tgcacatgtc taccagcaat gtcataattg    4020
cacagaaagc aaacgaaaag gcgatccttg ctctttcatc tttcattcac gccttgttcg    4080
agttggactt ttatgctgtg gccagacttg ttaccaagga caacaagccc ccactcatcg    4140
tattactggc accatctatt gaagcagact ttgaatgtct tctagaagtc cagctcccctt   4200 ttgctgaaga tgttcggtcg taccgttttcc ctcccttgga caaggtggtc actgtctctg   4260
gaaagacagt caaagagcac cgacatctcc caagtgacga attgctgaat gcgatgagca   4320
aatacgtcga cagcatggag ctcgtcgaca aggatgaaaa cgggtgagtc atcacaggga   4380
aaccgtcatg ctgctcatct caagtatact gacaactcca cagagaacca gttgacagcc   4440
tggctcccag actggaggat tcgtactctc cactgctgca caggatcgag caagctatcc   4500
ggtggcgtgc catccatcca aacgagcctc ttccgccccc ttctgagaag ttgacgcagc   4560
tgtcacgacc gccagcagat ctgcaagcgc gcgcgaagaa atacctggat cgggtcattg   4620
ccgccgccga tgtgaagaaa ggtctgtcaa cttctacgct cccccagaat gcatctgact   4680
aaaaaatgct gcacagttcc accaaaagca aaggtcgca agcggaatcg cgaagccgac     4740 aaaccctat cgggtcttga cgttgacgag ctccttcgtc gcgagaagcg cgccaagatc     4800
tcagccaaca acgccatccc cgagttcaaa cagtcgctgg tcaacgccga gaccatcgac    4860
gccgtccgtg acgcagtcag ccagatggaa agcatcatcg agaaccacat ccgaagcagc    4920
tttggagacg ccaactacga ccgcgtgatc gaggagctgg gtgtcctccg cgaggagctg    4980
atcgcctacg aagagccgga tctctacaac gacttcctgc ggaggctgaa ggacaagatc    5040
ctcaatgagg agctgggcgg agacagacga gagctgtggt ggctcgtcag gaggcaacgg    5100
gtcggtctga tagacaagaa ggcgtcggaa cgggttgaag ttactgaaca ggaagccagg    5160
gaggtaagta agcagataca ttattccttt agttccatta aacgagctgc atgatgagct    5220
gacttttgtt cactagttca tgacctcgaa ataaaatagt ccattattgc tatgtatgtc    5280
aaggcgcctg gccgtagtag tcttaacatg ctgatgctgt gaatcaaagc gccagatgaa    5340
caataataga aataatacca cttggtagct gtctccattc tcacagatag acaacgttaa    5400 agaaagaaa aacgtaaaaa gagggtatat gtggtctagt aacgccgcaa ggaaaaaaaa    5460
actcatacgt tagtttcgaa cgcaaatctc aaaatcgagc acttcgagta aatactctgt    5520
cgtatcgttt cgcctcagga tatcttcccg agccttctct ttccgatatc gattttccgt    5580
tgtaatctag ttattattac tccagttagt aaatgcacga cgggcagtat tgtaaataat    5640
```

-continued

```
gaaatcagca gcgagagtac gaacatgtcc acatcctcat cggctttccg gagcaactcg    5700
ttctggatct ccagctcatt gttaatggcg atccccagct ccttctgtcg agcgacgatt    5760
ttcatcaact cctccacgct ccggtcctgc tcttccatcg tctgcttctg cagctggagc    5820
acgccctggt tgtcgagttc ccgcgtcttg tccgtttcct tgcccaggac tcgtccagaa    5880
cggggtttgg cgctccccac cagggcgtcc ttgtcctgca tcgaagcgac agcgttgtcg    5940
agcttgctct tcgtcaccat cgcgttgtgc agattctcca atccgtcctt ctctttcttg    6000
gcgctcgcga tgagatcctt cctccgacgg atctctccct cgcctaacct gctgccgccc    6060
catccagacg acttgtcgct caggttcttc agcccttcct caagagcgcc gatcatcgac    6120
cctgctttca ccaagctgct tttggcctgt gccgagctct cgtgttgttt ctgtggagtc    6180
gtggcctgat cacgtctcgt cagatgcagc ctcgtctcgt gtaagtgcgc cttcatctcc    6240
cggtagcaat ccagccacag gactggatcc gtgatcggtc cgccgcctgg cgcgcccggt    6300
tccgtgatgg acttgtgaag cttcgatgcg gcagagctat ccgacagggc ttgggagggg    6360
aggtttagaa aggacctcca gacgcttgtt tgacgccatc gcgggtcctc gctctcgttg    6420
atggcccgca ggtatctttc caggcctttg cgccgctctt cgcgcagagt ctcgttcgag    6480
ttcgtgttgg aaaaccagga cttcccgggc agagcgacgg gtggttgggc gccaacctgg    6540
cggactagtg cgtcatggaa cgatgcaaat tctgaatagc gtttctggac aacgaacgac    6600
cgtagaggca gccggatggt gatgttgtat agcgtatacg gactgggagc gtccgcgatg    6660
gtggctgtcg ggatggaaat ttcgacattc ggggccatga ttatagttca gacgggaaaa    6720
agaacaaaac aaagagcagg cccttgttat cgaccaggaa gcataattcc cgccgcttct    6780
cttgcggtat ctctgtcgtt gcagagttgg ttgcagagta gtggagtcgg ccggcgggtg    6840
gaaactcccg caatgacgca ggcgccccat cttcttctgc caccgccgat ctgtggctta    6900
gcttcttctt gtcaagactc gactccacca tcgcgactcc aggcagcacg aatcgcacga    6960
ttgccgaaaa actacaccgt actaggggaa ggcctaatta atctattacc ctagctaaaa    7020
atggggttgt caaacttatc atatagccgt gcgacccgcc cttggaggtc actagatcca    7080
acctgcgcac ggcctggtta cggttgatgg gagctaaaat tagaacgaaa gatatactgg    7140
cggtccgtcc ccgcgtctat ccacaatcca aaactcgtat gcagagttat ctacaggtcg    7200
atccaatcat gagtcctttg tgacatgtcg ttgaatacat ggtctcaatc gagtctgccg    7260
ttcttacatg accatcctca ccaagatcaa tgtcccgtga ttcgactgtc agccaagata    7320
cgtctcacct ggccccatct ctactgtcga caacgtctgc ctatactgta ggtgatcaga    7380
atacgcagtc ccggggagtc tactcgcgat ggggtggttc atacgtcggc tcctcgtcga    7440
cgttgtctct gggtccgtcg gagagcgtca atatagacgg gagacgaaag ttgctcttga    7500
tctatatcca tggcttcatg ggtgaagaag cgagcttcca caagttccct gctcatgtcc    7560
ataaccttgt caccattgct ctggccgagt cgcacgttgt gtattcgaag gtatatcctc    7620
gatacaaatc ccgccgagca atggacattg cacgtgatga tttcagtcga tggtgcgttt    7680
gcagactggc atatctctct ttagagatca tcctagaaag aaacgcatga tactaagtgt    7740
cgaataggct atcaccgcat gagtcggaag atacagatgt gatcctactc ggccacagcc    7800
tgggtgggat cctagccgca gaggttgcgc tgctcccatc agcccctggg agcaaggaga    7860
tcttcgagca tcgtatcctg ggactcatca                                     7890
```

<210> SEQ ID NO 144
<211> LENGTH: 2145

<212> TYPE: DNA
<213> ORGANISM: Rasmsonia emersonii

<400> SEQUENCE: 144

```
atggctgaca aggaggccac cgtctacgtg atcgatgtgg aaagtccat ggggaggcgc      60
cgccatggac ggccggtatc tgacctggaa tgggcaatgc aatatgtctg ggacaagatt    120
acgacaaccg ttgccacggg gcggaaaacg gctacaattg gagtggtcgg gctgaggaca    180
gatgaaacat cgaacgactt gcaggatgat gacagctatt cgcacatctc tgtctttcag    240
gaaattggac aggtcctcat gcctgatctg cgaaaactgc gcgacctgat caagcctagc    300
aacactgatg aaggagatgc tatctcctcc cttgtcgtcg cgatccagat gatcaccact    360
tataccaaaa agctgaagta tcgacggaaa atcattctcg tgacgaacgg ggaaggatcc    420
atgagtaccg atggtcttga tgagatcgtg aaaaagctca agtccgatag cattgaattg    480
gtggtcttgg gtgttgactt tgatgatcct gaatttggtg tcaaagagga ggacaagaat    540
ccagcaaaag ctgagaatga agcggtcctc agaggtctcg ttgattcctg cgacggagtc    600
tacgggacat tacaacaggc catattggag ctggacacac cgcgtgtgaa ggttgttcgt    660
ggaatacact cctttagagg agagctccga ctggggaacc ctgaagagta ttcgtctgcc    720
cttcgtatcc cagtcgaaag atactaccga acttatgttg ccaagccgcc gacagcgagc    780
tcctttgtcc tacgatctga cgctgcagct ggtcaagagg gtgcagagaa tgcactgaca    840
agcgtccgaa acgcacggac atatcacgtc agtgatgagt ccgcaccagg aggcaagaga    900
gacgtggagc gagaagatct cgccaagggc tacgagtatg ggagaaccgc ggtgcacatt    960
agtgagtccg atgagaatat caccaaactc cagacgaacc ctggtctgga aatcatcggc   1020
ttcattcaga gtgaccatta cgaccgatac atgcacatgt ctaccagcaa tgtcataatt   1080
gcacagaaag caaacgaaaa ggcgatcctt gctctttcat ctttcattca cgccttgttc   1140
gagttggact gttatgctgt ggccagactt gttaccaagg acaacaagcc cccactcatc   1200
gtattactgg caccatctat tgaagcagac tttgaatgtc ttctagaagt ccagctccct   1260
tttgctgaag atgttcggtc gtaccgtttc cctcccttgg acaaggtggt cactgtctct   1320
ggaaagacag tcaaagagca ccgacatctc ccaagtgacg aattgctgaa tgcgatgagc   1380
aaatacgtcg acagcatgga gctcgtcgaa aaggatgaaa acggagaacc agttgacagc   1440
ctggctccca gactggagga ttcgtactct ccactgctgc acaggatcga gcaagctatc   1500
cggtggcgtg ccatccatcc aaacgagcct cttccgcccc cttctgagaa gttgacgcag   1560
ctgtcacgac cgccagcaga tctgcaagcg cgcgcgaaga aatacctgga tcgggtcatt   1620
gccgccgccg atgtgaagaa agttccacca aaagcaaaag gtcgcaagcg gaatcgcgaa   1680
gccgacaaac ccctatcggg tcttgacgtt gacgagctcc ttcgtcgcga gaagcgcgcc   1740
aagatctcag ccaacaacgc catccccgag ttcaaacagt cgctggtcaa cgccgagacc   1800
atcgacgccg tccgtgacgc agtcagccag atggaaagca tcatcgagaa ccacatccga   1860
agcagctttg gagacgccaa ctacgaccgc gtgatcgagg agctgggtgt cctccgcgag   1920
gagctgatcg cctacgaaga gccggatctc tacaacgact tcctgcggag gctgaaggac   1980
aagatcctca atgaggagct gggcggagac agacgagagc tgtggtggct cgtcaggagg   2040
caacgggtcg gtctgataga caagaaggcg tcggaacggg ttgaagttac tgaacaggaa   2100
gccagggagt ccattattgc tatctgtctc cattctcaca gatag                    2145
```

<210> SEQ ID NO 145

```
<211> LENGTH: 714
<212> TYPE: PRT
<213> ORGANISM: Rasamsonia emersonii

<400> SEQUENCE: 145

Met Ala Asp Lys Glu Ala Thr Val Tyr Val Ile Asp Val Gly Lys Ser
1               5                   10                  15

Met Gly Arg Arg Arg His Gly Arg Pro Val Ser Asp Leu Glu Trp Ala
            20                  25                  30

Met Gln Tyr Val Trp Asp Lys Ile Thr Thr Val Ala Thr Gly Arg
            35                  40                  45

Lys Thr Ala Thr Ile Gly Val Val Gly Leu Arg Thr Asp Glu Thr Ser
 50                  55                  60

Asn Asp Leu Gln Asp Asp Ser Tyr Ser His Ile Ser Val Phe Gln
 65                  70                  75                  80

Glu Ile Gly Gln Val Leu Met Pro Asp Leu Arg Lys Leu Arg Asp Leu
                85                  90                  95

Ile Lys Pro Ser Asn Thr Asp Glu Gly Asp Ala Ile Ser Ser Leu Val
            100                 105                 110

Val Ala Ile Gln Met Ile Thr Thr Tyr Thr Lys Lys Leu Lys Tyr Arg
        115                 120                 125

Arg Lys Ile Ile Leu Val Thr Asn Gly Glu Gly Ser Met Ser Thr Asp
130                 135                 140

Gly Leu Asp Glu Ile Val Lys Lys Leu Lys Ser Asp Ser Ile Glu Leu
145                 150                 155                 160

Val Val Leu Gly Val Asp Phe Asp Asp Pro Glu Phe Gly Val Lys Glu
                165                 170                 175

Glu Asp Lys Asn Pro Ala Lys Ala Glu Asn Glu Ala Val Leu Arg Gly
            180                 185                 190

Leu Val Asp Ser Cys Asp Gly Val Tyr Gly Thr Leu Gln Gln Ala Ile
        195                 200                 205

Leu Glu Leu Asp Thr Pro Arg Val Lys Val Val Arg Gly Ile Pro Ser
210                 215                 220

Phe Arg Gly Glu Leu Arg Leu Gly Asn Pro Glu Glu Tyr Ser Ser Ala
225                 230                 235                 240

Leu Arg Ile Pro Val Glu Arg Tyr Tyr Arg Thr Tyr Val Ala Lys Pro
                245                 250                 255

Pro Thr Ala Ser Ser Phe Val Leu Arg Ser Asp Ala Ala Gly Gln
            260                 265                 270

Glu Gly Ala Glu Asn Ala Leu Thr Ser Val Arg Asn Ala Arg Thr Tyr
        275                 280                 285

His Val Ser Asp Glu Ser Ala Pro Gly Gly Lys Arg Asp Val Glu Arg
290                 295                 300

Glu Asp Leu Ala Lys Gly Tyr Glu Tyr Gly Arg Thr Ala Val His Ile
305                 310                 315                 320

Ser Glu Ser Asp Glu Asn Ile Thr Lys Leu Gln Thr Asn Pro Gly Leu
                325                 330                 335

Glu Ile Ile Gly Phe Ile Gln Ser Asp His Tyr Asp Arg Tyr Met His
            340                 345                 350

Met Ser Thr Ser Asn Val Ile Ala Gln Lys Ala Asn Glu Lys Ala
        355                 360                 365

Ile Leu Ala Leu Ser Ser Phe Ile His Ala Leu Phe Glu Leu Asp Cys
370                 375                 380

Tyr Ala Val Ala Arg Leu Val Thr Lys Asp Asn Lys Pro Pro Leu Ile
```

```
                385                 390                 395                 400
        Val Leu Leu Ala Pro Ser Ile Glu Ala Asp Phe Glu Cys Leu Leu Glu
                        405                 410                 415

Val Gln Leu Pro Phe Ala Glu Asp Val Arg Ser Tyr Arg Phe Pro Pro
                        420                 425                 430

Leu Asp Lys Val Val Thr Val Ser Gly Lys Thr Val Lys Glu His Arg
                        435                 440                 445

His Leu Pro Ser Asp Glu Leu Leu Asn Ala Met Ser Lys Tyr Val Asp
                    450                 455                 460

Ser Met Glu Leu Val Asp Lys Asp Glu Asn Gly Glu Pro Val Asp Ser
        465                 470                 475                 480

Leu Ala Pro Arg Leu Glu Asp Ser Tyr Ser Pro Leu Leu His Arg Ile
                        485                 490                 495

Glu Gln Ala Ile Arg Trp Arg Ala Ile His Pro Asn Glu Pro Leu Pro
                        500                 505                 510

Pro Pro Ser Glu Lys Leu Thr Gln Leu Ser Arg Pro Pro Ala Asp Leu
                        515                 520                 525

Gln Ala Arg Ala Lys Lys Tyr Leu Asp Arg Val Ile Ala Ala Ala Asp
                    530                 535                 540

Val Lys Lys Val Pro Pro Lys Ala Lys Gly Arg Lys Arg Asn Arg Glu
        545                 550                 555                 560

Ala Asp Lys Pro Leu Ser Gly Leu Asp Val Asp Glu Leu Leu Arg Arg
                        565                 570                 575

Glu Lys Arg Ala Lys Ile Ser Ala Asn Asn Ala Ile Pro Glu Phe Lys
                        580                 585                 590

Gln Ser Leu Val Asn Ala Glu Thr Ile Asp Ala Val Arg Asp Ala Val
                        595                 600                 605

Ser Gln Met Glu Ser Ile Ile Glu Asn His Ile Arg Ser Ser Phe Gly
                    610                 615                 620

Asp Ala Asn Tyr Asp Arg Val Ile Glu Glu Leu Gly Val Leu Arg Glu
        625                 630                 635                 640

Glu Leu Ile Ala Tyr Glu Glu Pro Asp Leu Tyr Asn Asp Phe Leu Arg
                        645                 650                 655

Arg Leu Lys Asp Lys Ile Leu Asn Glu Glu Leu Gly Gly Asp Arg Arg
                        660                 665                 670

Glu Leu Trp Trp Leu Val Arg Arg Gln Arg Val Gly Leu Ile Asp Lys
                        675                 680                 685

Lys Ala Ser Glu Arg Val Glu Val Thr Glu Gln Glu Ala Arg Glu Ser
                    690                 695                 700

Ile Ile Ala Ile Cys Leu His Ser His Arg
        705                 710

<210> SEQ ID NO 146
<211> LENGTH: 11
<212> TYPE: DNA
<213> ORGANISM: Artificial Sequence
<220> FEATURE:
<223> OTHER INFORMATION: 5' bridge used for all promoters

<400> SEQUENCE: 146
ggtctcggtg c                                                           11

<210> SEQ ID NO 147
<211> LENGTH: 11
<212> TYPE: DNA
<213> ORGANISM: Artificial Sequence
```

```
<220> FEATURE:
<223> OTHER INFORMATION: 3' bridge used for all promoters

<400> SEQUENCE: 147
aatgggagac c                                                              11

<210> SEQ ID NO 148
<211> LENGTH: 11
<212> TYPE: DNA
<213> ORGANISM: Artificial Sequence
<220> FEATURE:
<223> OTHER INFORMATION: 5' bridge used for all ORFs

<400> SEQUENCE: 148
ggtctcgaat g                                                              11

<210> SEQ ID NO 149
<211> LENGTH: 11
<212> TYPE: DNA
<213> ORGANISM: Artificial Sequence
<220> FEATURE:
<223> OTHER INFORMATION: 3' bridge used for all ORFs

<400> SEQUENCE: 149
taaaggagac c                                                              11

<210> SEQ ID NO 150
<211> LENGTH: 11
<212> TYPE: DNA
<213> ORGANISM: Artificial Sequence
<220> FEATURE:
<223> OTHER INFORMATION: 5' bridge used for all terminators

<400> SEQUENCE: 150
ggtctcgtaa a                                                              11

<210> SEQ ID NO 151
<211> LENGTH: 11
<212> TYPE: DNA
<213> ORGANISM: Artificial Sequence
<220> FEATURE:
<223> OTHER INFORMATION: 3' bridge used for all terminators

<400> SEQUENCE: 151
cctcggagac c                                                              11

<210> SEQ ID NO 152
<211> LENGTH: 11
<212> TYPE: DNA
<213> ORGANISM: Artificial Sequence
<220> FEATURE:
<223> OTHER INFORMATION: Bridge between left connector sequence and 5'
      part of promoter

<400> SEQUENCE: 152
gtgcggagac c                                                              11

<210> SEQ ID NO 153
<211> LENGTH: 11
<212> TYPE: DNA
<213> ORGANISM: Artificial Sequence
<220> FEATURE:
<223> OTHER INFORMATION: Bridge between 3' part of the terminator and
      the right connector sequence
```

```
<400> SEQUENCE: 153
ggtctcgcct c                                                                11
```

CLONING METHOD

CROSS REFERENCE TO RELATED APPLICATIONS

This application is a §371 National Stage Application of PCT/EP2013/056623, filed Mar. 27, 2013, which claims priority to U.S. Provisional Application No. 61/616,254, filed Mar. 27, 2012, all of which are incorporated by reference in their entireties.

BACKGROUND

Field of the Invention

The present invention relates to a method for the preparation of standardized expression cassettes. The invention also relates to a method for recombining such standardized expression cassettes in vivo in a host cell. Further the invention relates to a method for the integration of a nucleic acid sequence at a target locus. Also, the invention relates to a system for preparing standardized expression cassettes and to a system for producing a nucleic acid construct of interest incorporated at a target locus.

Description of Related Art

Modern biotechnology applies genetic engineering to develop organisms with novel phenotypes that are used for bio-based conversion processes with applications in food, feed, pharma, materials and energy. This includes the design and creation of novel phenotypes normally not found in the production host of interest or not (in known) nature at all. Examples of applications include, but are not limed to, the microbial production of chemical precursors, industrial enzymes, antibiotics, and biofuels.

Novel technologies are required to design better, build faster and test more DNA constructs for faster and more optimal strain engineering. This can be approached by standardization, modularization and automation of DNA construction. In addition, the ability to re-use existing elements, or so-called biobricks will help to better characterize these elements and reduce the costs of construct synthesis and/or assembly. Such biobricks can for example be promoters (P), 5'UTR (U), Signal Sequences (S), open reading frames (O), genomic sequences (G), terminators (T) and other functional or regulatory DNA elements.

Scientists are combing biological and engineering tools to develop novel methods for the engineering of cells. Complex DNA cassettes can be designed and are required to engineer cells for novel purposes and highly efficient conversions. Therfore a need exists to develop high-throughput low-cost DNA assembly methods for the practical handling and exploration of larger sets of designs. Required DNA cassettes can be produced by gene-synthesis and ligation. However, this is typically a costly process that has to be repeated for each construct. The re-use of DNA building blocks and modular cassettes has been proposed to reduce cost and time. Therefore, for optimal usage and exploration of gene combinations and tuning of metabolic pathways, also called synthetic biology, there is a need to develop novel methods to physically assemble complex DNA molecules containing large numbers of natural or artificial genes in a wide variety of arrangements. For the modular construction of DNA cassettes one needs efficient methods to physically assemble and build these using basic building blocks. Current available methods for assembling expression cassettes are reviewed by Wang T. et al. (2012). Appl Microbiol Biotechnol (2012) 93:1853-1863, and include like GoldenBraid (Sarrion-Perdigones A. (2012), PLoS ONE 6 (7): e21622) and Modular Cloning (Weber E. (2011), PLoS ONE 6(2): e16765 and EP2395087).

However, these methods are rather complex since they include sequential in vitro steps, or reiterative recombination (Wingler L M (2011) PNAS USA 108(37):15135-15140) for the in vivo assembly of libraries of multigene pathways.

Although much progress has been made in the past few years, physical construction of large recombinant DNA molecules represents a major bottleneck that still does not have appropriate solutions for every application (Weber E. (2011), PLoS ONE 6(2): e16765 and EP2395087). Recombinant DNA molecules have traditionally been constructed using type II restriction enzymes and ligase. Although very versatile, such approach is slow and tedious and only allows creation of constructs of relatively small size and containing only few genes. In particular, this approach is limited by the fact that designing cloning strategies becomes extremely difficult for large constructs since all restriction enzymes available will cut many times in such constructs. In the past few years, a number of different approaches have been developed to overcome these limitations. These include recombinase-based cloning, ligation-independent cloning, cloning based of homologous recombination and PCR-based assembly. Recombinase-based cloning eliminates the problems coming from the multiple occurrence of restriction sites in large constructs but is limited by the fact that recombination sites are left in the final construct, preventing the seamless assembly of protein coding sequences (Weber E. (2011), PLoS ONE 6(2): e16765 and EP2395087). Moreover, recombinase-based cloning is limited by the fact that, so far, only 4 fragments can be assembled in one construct simultaneously.

While all of these technologies have advantages on their own and are very valuable for specific applications, none has all the requirements needed for the task of generating the multiple genetic variant combinations required for the successful design and construction of organisms with novel phenotypes.

Methods for DNA construct assembly are described by Wang et al 2012. Studies in the structural biology of the multicomponent protein complex, metabolic engineering, and synthetic biology frequently rely on the efficient overexpression of these subunits or enzymes in the same cell. As a first step, constructing the multiple expression cassettes will be a complicated and time-consuming job if the classic and conventional digestion and ligation based cloning method is used. Some more efficient methods have been developed, including (1) the employment of a multiple compatible plasmid expression system, (2) the rare-cutter-based design of vectors, (3) in vitro recombination (sequence and ligation independent cloning, the isothermally enzymatic assembly of DNA molecules in a single reaction), and (4) in vivo recombination using recombination-efficient yeast (in vivo assembly of overlapping fragments, reiterative recombination for the chromosome integration of foreign expression cassettes).

Recently, cloning methods based on type IIs restriction enzymes have been developed (WO 2008/095927). Engler et al. PLoS ONE 4 (2009) e5553) describe a protocol to assemble in one step and one tube at least nine separate DNA fragments together into an acceptor vector using type IIs restriction enzymes by simply subjecting a mix of 10 undigested input plasmids to a restriction-ligation reaction and transforming the resulting mix into competent cells. This protocol was named "Golden Gate" cloning.

Although synthetic biology represents a new field, it nevertheless makes use of genetic engineering and should therefore learn from existing mature technologies such as mechanical engineering. An important consideration for successful engineering of complex devices consists of standardization of parts. For synthetic biology, standardization would allow to re-use at will previously validated modules from one project to the next and therefore make engineering new biological functions or organisms more efficient. One important aspect of standardization is that a predictive value can be associated with each part, for example a defined activity for a promoter (although it is understood that promoter activity can be affected by enhancer sequences present in nearby sequences), or a specific enzymatic activity for a given polypeptide. This is extremely important since engineering new functions or organisms will require such a large number of parts working in concert that the number of gene combinations that will need to be tested for many projects is likely to be too large to be physically possible. This element is an essential element that will be required to achieve the potential of synthetic biology.

SUMMARY

We have developed a hybrid in vitro/in vivo methods that applies standardized bio-elements to form complex DNA cassettes for expression in a host of interest via an intermediate Golden Gate assembly step (Engler C. (2008) PLoS ONE 3(11): e3647) and specially designed entry vectors for further usage in standardized cassette assembly.

Use of this novel efficient two-step method allows the construction of modular DNA cassettes in an highly efficient way. Additionally, we have developed and show a mini-pathway characterization method to measure promoter strength, including two internal reference measurements (see Example 1). In the example, GFP, LacZ and RFP are combined in one pathway. The method is also applied to characterize terminator sequences, and can be used similarly for characterizing signal sequences, 5'UTR, or any other regulating part, or mutation, insertion or deletion one is interested in.

Methods based on homologous recombination are valuable, but require a minimum amount of sequence in common between modules, limiting the ability to freely combine standard modules of different sequence. However, the method of the invention circumvents this issue by using standardized connector elements of about 9 bp (or longer) for in vitro assembly or about 25 bp (or longer) for in vivo assembly. Both approaches can be applied to assemble expression cassettes, or to develop knock-out or insertion sequences as explained in the sequel. Moreover, by efficient usage of PCR methods using standardized primers at connector sequences, one can efficiently recover modular cassettes from backbone cassettes containing standardized connector sequences. Connector sequences might contain a type IIS restriction enzyme recognizition sites to cut exactly at a required position in the proceeding step to allow for seamless in vivo homologous recombination in case this is needed to maintain or recover functionality of a DNA construct.

Accordingly, the invention provides a system of nucleic acid molecules that can be used for in vivo assembly of a nucleic acid cassette of interest from a desired number of, preferably, at least 3 fragments, and integration at a target locus, where at least one fragment contains a functional expression element. Functional expression elements contain, but are not limited to, a promoter DNA sequence (pro), an open reading frame DNA sequence (orf), a terminator DNA sequence (ter) and left and right flanking DNA sequences, called connectors (lcon and rcon, respectively) that are used for in vivo assembly.

The system of DNA molecules contains a set of at least 2 or 3 backbone (bbn) entry vectors designed with at least one lcon and one rcon sequence in an entry vector that can be applied in an one-pot Golden-Gate assembly reaction together with element vectors to create functional expression elements (M) and the usage of a single type II restriction enzyme in a functional order. For example: lcon-pro-orf-ter-rcon.

The system should be scalable to the assembly of nucleic acid constructs of interest from many expression elements while avoiding the need for constructing as many backbone vectors as the number of fragments or expression elements constituting the nucleic acid cassette of interest.

The system of nucleic acid molecules of the invention allows assembly of a number of expression elements that is smaller than the number of backbone vectors present in the system, as well as higher than the number of backbone vectors present in the system. The invention provides a system of standardized connector nucleic acid molecules than can be used for assembling any nucleic acid cassette of interest from a desired number of expression elements.

Accordingly, the present invention provides a method for the preparation of two or more standardized expression cassettes, which method comprises:
  a. providing two or more sets of element sequences,
     each set of element sequences together comprising at least one functional expression cassette,
     each element sequence being flanked on both sides by a type IIs restriction endonuclease cleavage site followed by the recognition site thereof,
     the type IIs restriction endonuclease recognition sites and cleavage sites being selected so that the sets of element sequences may be assembled into a functional expression cassette;
  b. providing at least two backbone entry vectors,
     each backbone entry vector comprising in this order (i) a restriction enzyme with its recognition site and a first connector sequence (LF); (ii) a vector backbone comprising a selectable marker gene; and (iii) a second at connector sequence (RF) and a restriction enzyme recognition site with its cleavage sequence, and; (iv) optionally, an insert between the recognition sites of (i) and (iii),
     the connector sequences, RF and LF, on any backbone entry vector being selected so that they can assemble with a LF or RF connector sequence respectively on the same or a different backbone entry vector; and
  c. assembling the two or more sets of element sequences as functional expression cassettes in the at least two backbone entry vectors, using a method based on the use of restriction enzyme digestion and ligation via the cleavage sites,
  thereby to prepare two or more standardized expression cassettes.

The invention also provides:
  a method for recombining two or more standardized expression cassettes in vivo in a host cell at a target locus, which method comprises
    a. preparing two or more standardized expression cassettes according to the method set out above, wherein,
       i. the RF and LF connector sequences comprise homologous recombination sequences; and ii. the RF and LF sequences on any backbone entry vector are selected so that they can assemble by recombination in vivo with a LF or RF connector sequence, respectively, with the same or a different backbone entry vector and/or with a sequence flanking the target locus; and b. recovering the expression cassettes from the backbone entry vectors including the LF and RF sequences; and c. recombining the recovered expression cassettes in vivo in a host cell with each other at the target locus; and a method for recombining two or more standardized expression cassettes in vivo in a host cell at a target locus, which method comprises a. preparing two or more standardized modular expression cassettes according to the method set out above, wherein, i. the RF and LF connector sequences comprise at least 9-base pair homologous sequences; and ii. the RF and LF sequences on any backbone entry vector are selected so that they can assemble using these sequences by an in vitro method with a LF or RF connector sequence, respectively, with the same or a different backbone entry vector and/or with a sequence flanking the target locus; and b. assembling and recovering the expression cassettes from the backbone entry vectors in vitro connected by a LF and RF sequence; and c. recombining the recovered and assembled expression cassettes in vivo in a host cell at the target locus.

Further provided by the invention is:

a system for preparing two or more standardized expression cassettes, said system comprising:

a. two or more sets of element sequences,
   each set of element sequences together comprising at least one functional expression cassette,
   each element sequence being flanked on both sides by a type IIs restriction endonuclease cleavage site followed by the recognition site thereof,
   the type IIs restriction endonuclease recognition sites and cleavage sites being selected so that the sets of element sequences may be assembled into a functional expression cassette;

b. at least two backbone entry vectors,
   each backbone entry vector comprising in this order (i) a restriction enzyme with its recognition site and a first connector sequence (LF); (ii) a vector backbone comprising a selectable marker gene; and (iii) a second at connector sequence (RF) and a restriction enzyme recognition site with its cleavage sequence, and; (iv) optionally, an insert between the recognition sites of (i) and (iii),
   the connector sequences, RF and LF, on any backbone entry vector being selected so that they can assemble with a LF or RF connector sequence respectively on the same or a different backbone entry vector; and a system for producing a nucleic acid construct of interest incorporated at a target locus, said system comprising:

a. a system as set out above; and b. at least two integration sequences, one of which recombines with a first expression cassette and a sequence flanking the target locus, and the second of which recombines with a second expression cassette and a sequence flanking the other side of target locus.

BRIEF DESCRIPTION OF THE SEQUENCE LISTING

Figure 1A:
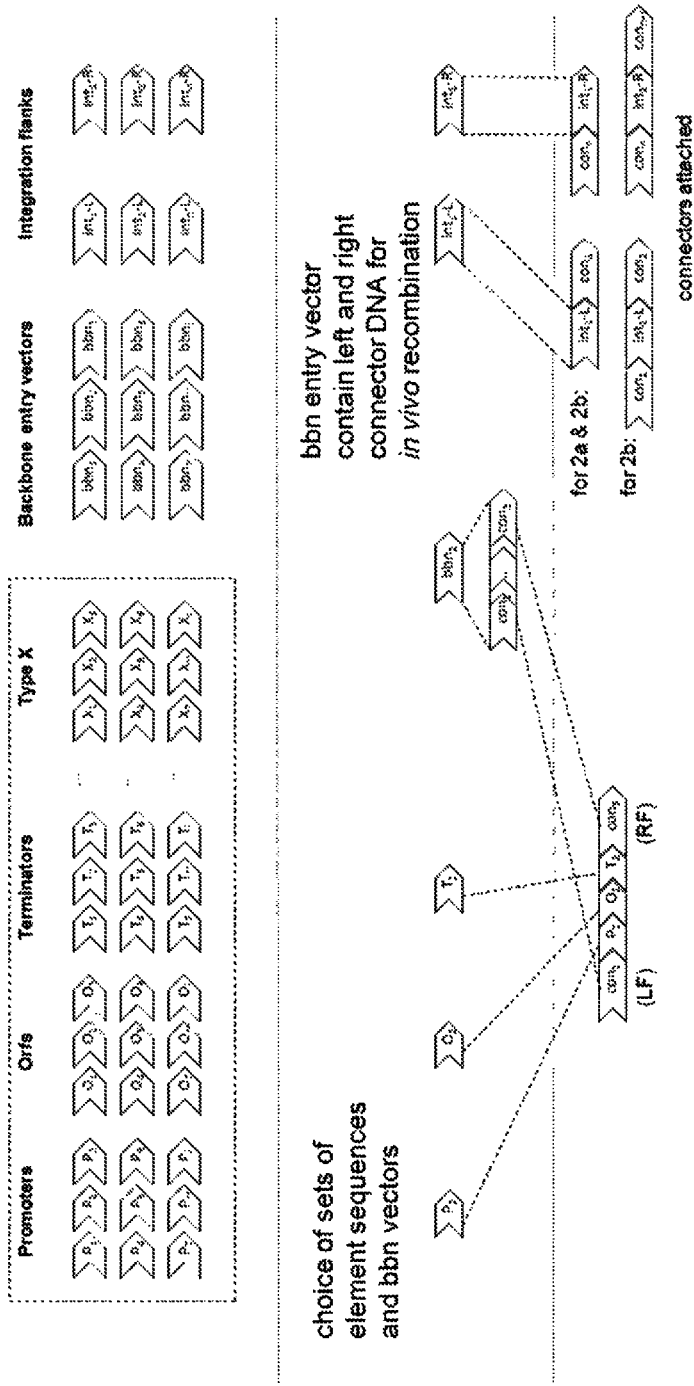
FIGS. 1A and 1B provide an overview of a 2-step cloning and transformation system for producing a nucleic acid construct of interest: Level 0 (FIG. 1A): A set of element sequences is prepared or available in a suitable vector with type IIs restriction endonuclease recognition sites and standardized cleavage sites (preferably 4-bp), selected such that after assembly using Golden gate cloning a functional expression cassette is formed. At Level 0 (FIG. 1A), also a set of backbone vectors is prepared or available, that contain left and right connector sequences suitable for assembly using sequence homology, for assembly of modular cassettes at Level 2 (FIG. 1B). A subset of element sequences is selected together with backbone (bbn) vectors. At level 1 (FIG. 1A), these are assembled using Golden Gate cloning resulting in functional expression cassettes that contain at least sequences that code together for a promoter, orf and terminator. Also one can select left and right flanks for integration at a target locus at Level 2 (FIG. 1B), and add a left or right connector sequence, or both. For example via cloning in an appropriate bbn vector, or via a PCR reaction where the con sequences are part of the primers one uses. Level 2 (FIG. 1B): in vivo assembly of functional expression cassettes, with integration flanks (int) and possibly other DNA sequences containing connector (con) sequences for in vivo assembly takes place and in a suitable host cell and recombination at a target locus. Typically all DNA parts to be assembled can be recovered by a PCR reaction from the vectors resulting from Level 1 for usage at Level 2, or for example using a method to cut out these fragments via a second appropriate IIs restriction enzymes and their recognition sites designed outside the con-vectors and cleaving the con vector including the DNA-sequence in between. Both option A and B provide a scheme for assembly of a modular cassette at a target locus. In option B, one adds additional left and right integration sites for a second host. Option B is followed by Level 3. Level 3 (FIG. 1B): recovery of the modular cassettes (or in parts) from 2B, for example via a PCR reaction, or other method. The recovered DNA is use for transformation and subsequent integration of the modular DNA cassette at a target locus in a second host.

SEQ ID NOs: 1 to 30 set out the sequences of promoter elements as follows: SEQ ID NO:1 Promoter element Sc.ENO1.Pro; Seq ID NO:2 Promoter element Sc PDC1.pro; Seq ID NO:3 Promoter element Sc ENO2.pro; Seq IDNO: 4 Promoter element Sc FBA1.pro; Seq ID NO:5 Promoter element Sc PGI1.pro; Seq IDNO: 6Promoter element Sc PGK1.pro; Seq ID NO:7 Promoter element Sc GPM1.pro; Seq ID NO:8 Promoter element Sc PMA1_1.pro; Seq ID NO:9 Promoter element Sc OYE2.pro; Seq ID NO:10 Promoter element Sc TAL1 .pro; Seq ID NO:11 Promoter element Sc TDH1.pro; Seq ID NO:12 Promoter element Sc TDH3.pro; Seq ID NO:13 Promoter element Sc TEF1.pro; Seq ID NO:14 Promoter element Sc TPI1.pro; Seq ID NO:15Promoter element Sc ACT1.pro; Seq ID NO:16 Promoter element Ag Tef1.pro; Seq ID NO:17 Promoter element Sc PRE3.pro; Seq ID NO:18 Promoter element Sc VPS68.pro; Seq ID NO:19 Promoter element KLLA0A09185g (*K. lactis* promoter 1); Seq ID NO:20 Promoter element KLLA0A11011g (*K. lactis* promoter 2); Seq ID NO:21Promoter element KLLA0B08998g (*K. lactis* promoter 3); Seq ID NO:22 Promoter element KLLA0B14839g (*K. lactis* promoter 4); Seq ID NO:23 Promoter element KLLA0B14883g (*K. lactis* promoter 5); Seq ID NO:24 Promoter element KLLA0C05566g (*K. lactis* promoter 6); Seq ID NO:25 Promoter element KLLA0D00979g (*K. lactis* promoter 7); Seq ID NO:26 Promoter element KLLA0D07634g (*K. lactis* promoter 8); Seq ID NO:27 Promoter element KLLA0E01057g (*K. lactis* promoter 9); Seq ID NO:28Promoter element KLLA0F18260g (*K. lactis* promoter 10); Seq ID NO:29 Promoter element KLLA0F20031g (*K. lactis* promoter 11); and Seq ID NO:30 Promoter element KLLA0F20988g (*K. lactis* promoter 12).

SEQ ID NOs: 31 to 35 set out the sequences of ORFs as follows: Seq ID NO:31ORF element vGFP; Seq ID NO:32 ORF element RFP; Seq ID NO:33 ORF element LacZ; Seq ID NO:34 ORF element GFPmut3; and Seq ID NO:35 ORF element GFP-pest.

SEQ ID NOs: 36 to 49 set out the sequences of terminator sequences as follows: Seq ID NO:36 element ADH1 terminator; Seq ID NO:37 element ADH2 terminator; Seq ID NO:38 element ENO1 terminator; Seq ID NO:39 element GPM1 terminator; Seq ID NO:40 element PDC1 terminator; Seq ID NO:41 element PGI1 terminator; Seq ID NO:42 element PGK1 terminator; Seq ID NO:43 element PMA1 terminator; Seq ID NO:44 element TAL1 terminator; Seq ID NO:45 element TDH1 terminator; Seq ID NO:46 element TDH3 terminator; Seq ID NO:47 element TEF1 terminator; Seq ID NO:48 element TEF2 terminator; and Seq ID NO:49 element TPI1 terminator.

SEQ ID NO: 50 sets out the sequence of the *E.coli* vector used for all elements with SEQ ID NO: 1 to 49.

SEQ ID NO: 51 to 63 set out the sequence of the connectors (see the Example).

Seq ID NO: 64 to SEQ ID NO: 85 set out the sequence of Backbone Entry Vectors (see the Example).

Seq ID NO: 86 sets out the sequence of the *E.coli* vector used for all backbone entry vectors with SEQ ID NO: 64 to 85.

SEQ ID NO: 87 to SEQ ID NO: 112 set out PCR primer sequences as follows: Seq ID NO:87 cons forw; Seq ID NO:88 cona rev; Seq ID NO:89 cona forw; Seq ID NO:90 conb rev; Seq ID NO:91 conb forw; Seq ID NO:92 conc rev; Seq ID NO:93 conc forw; Seq ID NO:94 conD rev; Seq ID NO:95 conD forw; Seq ID NO:96 conE rev; Seq ID NO:97 conE forw; Seq ID NO:98 conF rev; Seq ID NO:99 conF forw; Seq ID NO:100conG rev; Seq ID NO:101 conG forw; Seq ID NO:102 conH rev; Seq ID NO:103 conH forw; Seq ID NO:104 conI rev; Seq ID NO:105 conI forw; Seq ID NO:106 conJ rev; Seq ID NO:107 conJ forw; Seq ID NO:108 conK rev; Seq ID NO:109 conK fw; Seq ID NO:110 con3 rev; Seq IDNO:111 5950 forward primer on KanMX adding connector; and Seq ID NO:112 5951 reverse primer on KanMX adding connector b.

Seq ID NO: 113 sets out the sequence of the PCR fragment KanMX marker equipped with connector a and b.

SEQ ID: 114 sets out the sequence of the Forward primer on the left flank INT1 .

SEQ ID NO: 115 sets out the rev primer sequence on the left flank INT1 adding connector 5.

SEQ ID NO: 116 sets out the sequence of the Left flank with connector 5 for integration at INT1

SEQ ID NO: 117 sets out the sequence of the forward primer on the right flank INT1 adding connector 3

SEQ ID NO: 118 sets out the sequence of the Reverse primer on the left flank INT1 .

SEQ ID NO: 119 sets out the sequence of the Right flank with the connector 3 for integration at INT1 .

SEQ ID NOs 120, 121, 122, 123, 124 and 125 set out open reading frames that were specifically synthesized for the construction of the metabolic pathway for itaconic acid production in *S.cerevisiae* (see Table 5).

SEQ ID NO: 126 sets out the sequence of the *R. emersonii* RePepA (genomic sequence including flanks)

SEQ ID NO: 127 sets out the sequence of the *R. emersonii* RePepA (cDNA)

SEQ ID NO: 128 sets out the sequence of the *R. emersonii* RePepA (protein)

SEQ ID NO: 129 sets out the sequence of the *A.nidulans* gpdA promoter and 5' part of the ble coding region SEQ ID NO: 130 sets out the sequence of the 3' part of the ble coding region and *A.nidulans* TrpC terminator SEQ ID NO: 131 sets out the sequence of the *P. chrysogenum* Paf promoter SEQ ID NO: 132 sets out the sequence of the *T. thermophilus* GH61

SEQ ID NO: 133 sets out the sequence of the *P. chrysogenum* penDE terminator

SEQ ID NO: 134 sets out the sequence of the *R. emersonii* promoter 2

SEQ ID NO: 135 sets out the sequence of the *T. lanuginosa* GH61

SEQ ID NO: 136 sets out the sequence of the *A.nidulans* AmdS terminator

SEQ ID NO: 137 sets out the sequence of the forward Gibson primer 5' RePepA region-Ppaf for the joining of the pEBA1013 vector part and EBA328expression cassette SEQ ID NO: 138 sets out the sequence of the reverse Gibson primer TpenDE SEQ ID NO: 139 sets out the sequence of the forward Gibson primer TpenDE-Ppra for the joining of the EBA328 and EBA332 expression cassettes SEQ ID NO: 140 sets out the sequence of the reverse Gibson primer Tamds SEQ ID NO: 141 sets out the sequence of the forward Gibson primer Tamds-IoxP-gpd-ble for the joining of the EBA332 expression cassettes and the pEBA1013vector part SEQ ID NO: 142 sets out the sequence of the reverse Gibson primer 5' RePepA SEQ ID NO: 143 sets out the sequence of the ReKu80 (genomic sequence, coding region with flanks)

SEQ ID NO: 144 sets out the sequence of the ReKu80 (cDNA)

SEQ ID NO: 145 sets out the sequence of the ReKu80 (protein)

SEQ ID NO: 146 sets out the sequence of the 5' bridge of the promoters

SEQ ID NO: 147 sets out the sequence of the 3' bridge of the promoters

SEQ ID NO: 148 sets out the sequence of the 5' bridge of the ORFs

SEQ ID NO: 149 sets out the sequence of the 3' bridge of the ORFs

SEQ ID NO: 150 sets out the sequence of the 5' bridge of the terminators

SEQ ID NO: 151 sets out the sequence of the 3' bridge of the terminators

SEQ ID NO: 152 sets out the sequence of the bridge between the left connector sequence and the 5' part of the promoter SEQ ID NO: 153 sets out the sequence of the bridge between the 3' part of the terminator and the right connector sequence

DETAILED DESCRIPTION OF A PREFERRED EMBODIMENT

Throughout the present specification and the accompanying claims, the words "comprise", "include" and "having" and variations such as "comprises", "comprising", "includes" and "including" are to be interpreted inclusively. That is, these words are intended to convey the possible inclusion of other elements or integers not specifically recited, where the context allows.

The articles "a" and "an" are used herein to refer to one or to more than one (i.e. to one or at least one) of the grammatical object of the article. By way of example, "an element" may mean one element or more than one element.

The system of the invention comprises a defined set of components that have a high versatility and flexibility, whereby a given system can be easily applied to many different applications. Notably, a given system can be used for applications comprising different numbers of expression elements to be assembled in a nucleic acid cassette of interest. It is a great advantage of the invention that many different expression elements can be combined with a number of backbone vectors that is smaller than the number of expression elements to be combined. Therefore, the system can be scaled to the combination of many different expression elements and expression element numbers with no extra cloning work for the adaption of connectors to a large number of expression elements.

According to the invention, there is thus provided a method for the preparation of two or more standardized modular expression cassettes, which method comprises:

a. providing two or more sets of element sequences,
   each set of element sequences together comprising at least one functional expression cassette,
   each element sequence being flanked on both sides by a type IIs restriction endonuclease cleavage site followed by the recognition site thereof,
   the type IIs restriction endonuclease recognition sites and cleavage sites being selected so that the sets of element sequences may be assembled into a functional expression cassette;

b. providing at least two backbone entry vectors,
   each backbone entry vector comprising in this order (i) a restriction enzyme with its recognition site and a first connector sequence (LF), typically at least about 9 bp in length; (ii) a vector backbone comprising a selectable marker gene; and (iii) a second connector sequence (RF), again typically at least about 9 bp in length, and a restriction enzyme recognition site with its cleavage sequence, and; (iv) optionally, an insert between the recognition sites of (i) and (iii),
   the connector sequences, RF and LF, on any backbone entry vector being selected so that they can assemble with a LF or RF connector sequence respectively on the same or a different backbone entry vector;

c. assembling the two or more set of element sequences as functional expression cassettes in the at least two backbone entry vectors, using a method based on the use of restriction enzyme digestion and ligation via the cleavage sites,
   thereby to prepare two or more standardized expression cassettes.

The standardized, expression cassettes may readily be recombined in vivo. Accordingly, the invention provides a method for recombining two or more standardized modular expression cassettes in vivo in a host cell at a target locus, which method comprises a. preparing two or more standardized modular expression cassettes according to the method set out herein, wherein,
   i. the RF and LF connector sequences comprise homologous recombination sequences, typically at least 25-base pairs in length; and
   ii. the RF and LF sequences on each on any backbone entry vector are selected so that they can assemble by recombination in vivo with a LF or RF connector sequence, respectively, with the same or a different backbone entry vector and/or with a sequence flanking the target locus; and
b. recovering an expression cassettes from the backbone entry vectors including the LF and RF sequences; and
c. recombining the recovered expression cassettes in vivo in a host cell with each other at the target locus.

Also provided is a method for recombining two or more standardized expression cassettes in vivo in a host cell at a target locus, which method comprises a. preparing two or more standardized modular expression cassettes according to the method set out above, wherein, i. the RF and LF connector sequences comprise at least 9-base pair homologous sequences; and
ii. the RF and LF sequences on any backbone entry vector are selected so that they can assemble using these sequences by an in vitro method with a LF or RF connector sequence, respectively, with the same or a different backbone entry vector and/or with a sequence flanking the target locus; and
b. assembling and recovering the expression cassettes from the backbone entry vectors in vitro connected by a LF and RF sequence; and
c. recombining the recovered and assembled expression cassettes in vivo in a host cell at the target locus.

In the invention, a nucleic acid construct of interest is assembled and, typically, integrated at a target locus. Typically, a series of expression cassettes may be integrated at a target locus.

The method according to the invention involves recombination of nucleic acid molecules with each other and with a target locus. Recombination refers to a process in which a molecule of nucleic acid is broken and then joined to a different one. The recombination process of the invention typically involves the artificial and deliberate recombination of disparate nucleic acid molecules, which may be from the same or different organism, so as to create recombinant nucleic acids.

The method of the invention typically relies on homologous recombination reactions. "Homologous recombination" refers to a reaction between nucleotide sequences having corresponding sites containing a similar nucleotide sequence (i.e., homologous sequences) through which the molecules can interact (recombine) to form a new, recombinant nucleic acid sequence. The sites of similar nucleotide sequence are each referred to herein as a "homologous sequence". Generally, the frequency of homologous recombination increases as the length of the homology sequence increases. Thus, while homologous recombination can occur between two nucleic acid sequences that are less than identical, the recombination frequency (or efficiency) declines as the divergence between the two sequences increases.

A series of assembled expression cassettes may be incorporated at a target locus (typically by homologous recombination) using the method of the invention.

The target locus is any location where it is desired to integrate an assembled nucleic acid. The locus may be a chromosomal locus, i.e. within the genome of the host cell, or an extra-chromosomal locus, for example a plasmid or an artificial chromosome. The sequences used to for targeting a selected target locus will typically be sequences which flank the target locus. Integration of nucleic acid sequence at a target locus may result in that sequence being integrated with no loss of sequence at the target locus. Alternatively, the integration may be accompanied by loss of sequence from the target locus. Thus, integration of nucleic acid sequence at the target locus may result in the partial or full deletion of a coding sequence, for example, such that one or more genes are partially or fully knocked-out.

Figure 1B:
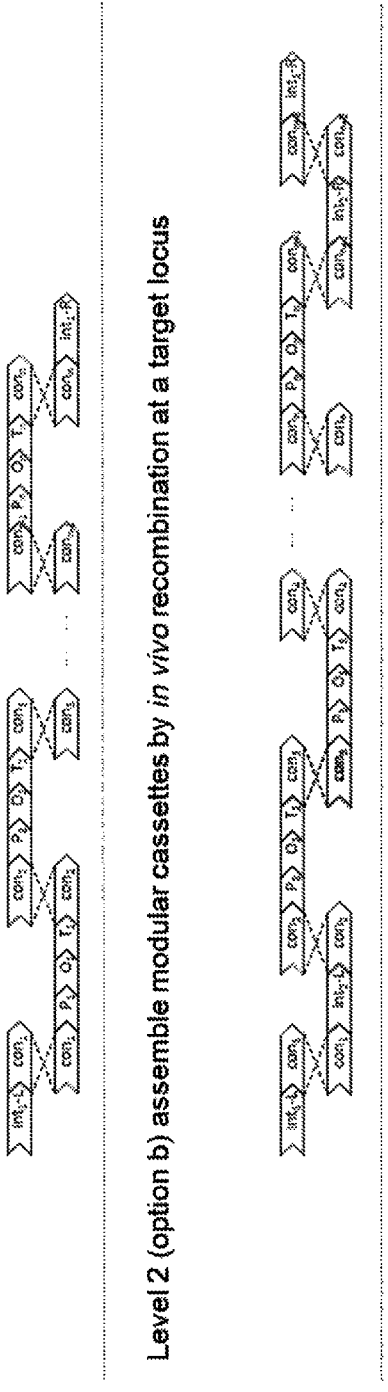
Figure 1B:
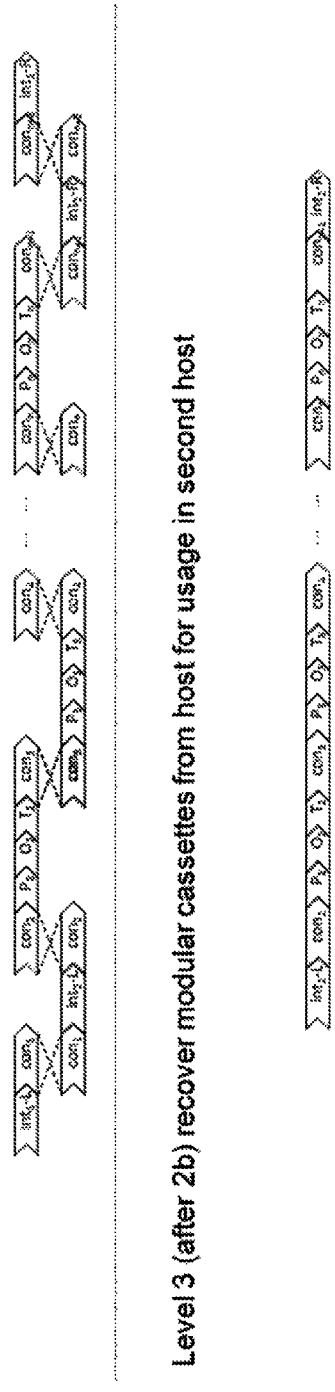
Figure 2A:
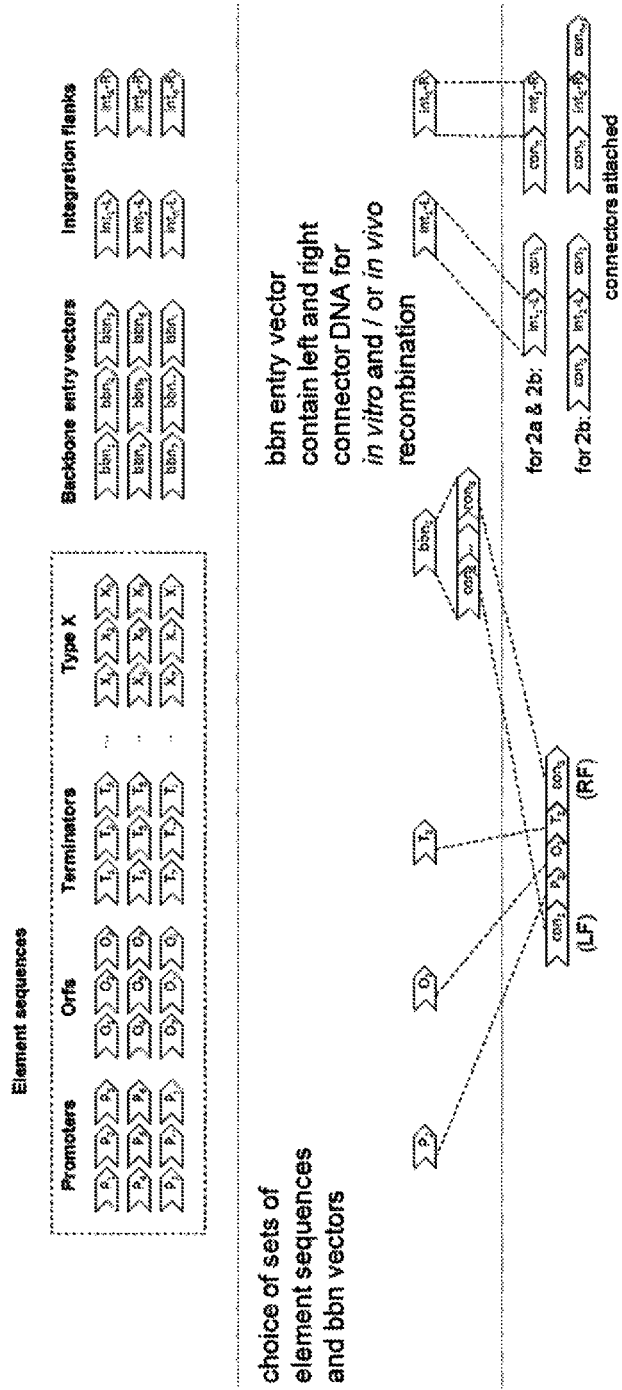
FIGS. 2A and 2B provide an overview of a 2-step cloning and transformation system for producing a nucleic acid construct of interest: Level 0 (FIG. 2A): A set of element sequences is prepared or available in a suitable vector with type IIs restriction endonuclease recognition sites and standardized cleavage sites (preferably 4-bp), selected such that after assembly using Golden gate cloning a functional expression cassette is formed. At Level 0, also a set of backbone vectors is prepared or available, that contain left and right connector sequences suitable for assembly using sequence homology, for assembly of modular cassettes at Level 2 (FIG. 2B). A subset of element sequences is selected together with backbone (bbn) vectors. At level 1 (FIG. 2A), these are assembled using Golden Gate cloning resulting in functional expression cassettes that contain at least sequences that code together for a promoter, orf and terminator. Also one can select left and right flanks for integration at a target locus at Level 2 step b (FIG. 2B), and add a left or right connector sequence, or both. For example via cloning in an appropriate bbn vector, or via a PCR reaction where the con sequences are part of the primers one uses. Typically all DNA parts to be assembled can be recovered by a PCR reaction from the vectors resulting from Level 1 for usage at Level 2 step a, or for example using a method to cut out these fragments via a second appropriate IIs restriction enzymes and their recognition sites designed outside the con-vectors and cleaving the con vector including the DNA-sequence in between. Level 2 step a (FIG. 2B): one or more functional expression cassettes and / or integration flanks with connector sequences are assembled together using an in vitro assembly reactions, for examples Gibson cloning, to form modular cassettes. Next at Level 2 step b (FIG. 2B): in vivo assembly of modular cassettes, including separate or already as modular cassette, integration flanks (int) and possibly other DNA sequences containing connector (con) sequences for in vivo assembly takes place and in a suitable host cell and recombination at a target locus. Both option A and B provide a scheme for assembly of a modular cassette at a target locus. In option B, one adds additional left and right integration sites for a second host. Option B is followed by Level 3. Level 3 (FIG. 2B): recovery of the modular cassettes (or in parts) from 2B, for example via a PCR reaction, or other method. The recovered DNA is use for transformation and subsequent integration of the modular DNA cassette at a target locus in a second host.
Figure 2B:
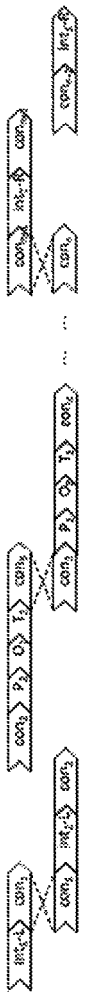
Figure 2B:
Figure 2B:

Two or more expression cassettes may be assembled in a modular way in a 2-step method according to the invention (see FIG. 1 and FIG. I.2).

At Level 1, sets of element sequences are assembled together with a backbone DNA sequence containing left and right connector DNA sequences (LF and RF con sequences) that allow for assembly of functional cassettes, typically containing at least 2 elements comprising promoter, orf and terminator sequences.

At Level 2, in vivo assembly of the at least one expression cassette takes place, but typically two or more expression cassettes, with a 5' DNA flank for targeted integration and a 3' DNA flank for targeted integration, and integration at a target locus takes place.

Additionally, at Level 3 a step can be made to obtain an assembled expression cassette from the host cell for further processing outside the host cell and/or using to modify another host cell, or being a DNA product. This may be achieved by providing the sequences used for integration with additional sequences designed to allow integration a a second target locus, typically in a second host cell.

In FIG. 1, Level 2 describes the assembly of modular expression cassettes from functional expression cassettes and 5' and '3 cassettes by in vivo DNA recombination at a target locus. FIG. 2 describes an alternative scheme where Level 2 is split in a and b, namely first an in vitro assembly step to obtain modular expression cassettes, that are further recombined in vivo at Level 2b into the complete modular DNA expression cassette at a target locus in a host.

At Level 2a (FIG. 2) one can apply, but is not limited to methods called SLIC, Gibson, and CPEC. These are related methods that offer standardized, scarless, (largely) sequence-independent, multi-part DNA assembly. Since the starting materials and final products are the same for these three methods, all can be applied using same homologous connector sequences of at least 9 bp and might be required longer for efficiency of specific methods (j5.jbei.org/j5manual/pages/22.html).

At level 1, restriction is catalysed typically by a single type IIs restriction endonuclease. However, multiple type IIs restriction endonuclease could be applied as well, or a combination of type IIs restriction endonuclease for the element sequence vectors, with a type II restriction enzyme that creates a overhang compatible with those designed for the left and right element of the elements that are used to assemble a functional expression cassette or expression cassette with a integration flank (int) sequence. Ligation is catalysed by a ligase.

The method of the invention allows the production of expression cassettes of interest from sets of element sequences by assembling nucleic acid fragment constructs via single-stranded overhangs formed at both ends of the fragments using type IIs restriction endonucleases. In the invention, type IIs restriction enzymes may be used. The type IIs restriction endonuclease recognition site is a recognition site of a restriction endonuclease recognizing a double-stranded DNA and cleaving the double-stranded DNA at a cleavage site that is outside the recognition site on the double stranded DNA. The type IIs restriction endonuclease cleaves such that, depending on the specific type IIs restriction endonuclease, overhangs of from 3 to 6 nucleotides are produced. Typically, in the method of the invention, enzymes giving rise to 4 nucleotide overhangs may be used. However, it is also possible to use type IIs endonucleases producing longer single-stranded overhangs. The nucleotide range that forms the overhangs upon cleavage is referred to herein as cleavage site. Since the nucleotides of the cleavage site are not part of the recognition site, they can be chosen as desired without destroying cleavage activity of the type IIs restriction endonuclease. Examples of type IIs restriction endonucleases suitable for the methods of the invention are given in Table 5.

For practicing the invention, any type IIs restriction enzyme that provides "sticky" ends sufficient for efficient ligation at its cleavage sites can be used. A selection of such enzymes is provided on the REBASE webpage (rebase.n- eb.com/cgi-bin/asymmlist) and in the review of Szybalsky et al. (1991, Gene, 100:13-26). Type II restriction enzymes with asymmetric recognition sites (e.g. those shown in this webpage) that have cleavage site outside of recognition site and provide upon cleavage of at least three, preferably 4 or more nucleotide residues overhangs (e.g. Bli736I; BpuAl, VpaK321, SfaNI, etc.) can be used in the invention.

It is recommended that the recognition site contains at least 4, more preferably at least 6 or more base pairs in order to minimize the chance for such site to be found in a sequence portion of interest. Type IIs restriction nucleases with 5 bp recognition sites (e.g. SfaNI) also can be used. Type IIs restriction endonucleases that produce 4 nt single-stranded overhangs at the extremities of digested fragments can theoretically generate ends with 256 possible sequences. Type IIs restriction enzymes having even longer recognition sites, e.g. comprising ten or more base pairs have been engineered. The largest recognition site among natural type IIs enzymes is for the enzyme SapI which has a 7 bp recognition site. A preferred solution is the use of artificial type IIs enzymes engineered to have a long recognition site (Lippow et al, 2009, Nucleic acides Res., 37:3061-3073). For example, a type IIs enzyme with a 18 bp recognition sites would be expected to cut only a few times per eukaryotic genome at most, and would allow to make most entry modules without having to change any nucleotide of the native sequence.

Level 2, option b (FIG. 1), one can include additional backbones with a left and right DNA flank for later integration in a second host, after recovery at Level 3.

The method of the invention may be carried out, wherein the recombination step is carried out in the presence of two integration sequences, one of which recombines with a first expression cassette and a sequence flanking the target locus, and the second of which recombines with a second expression cassette and a sequence flanking the other side of target locus.

Alternatively, integration sequences may be provided by two of the backbone entry vectors. Accordingly, the method of the invention may be carried out so that in the recombination step, a first expression cassette comprises an integration sequence which recombines with a sequence flanking the target locus, and a second expression cassette comprises an integration sequence which recombines with a sequence flanking the other side of target locus.

The integration sequences may comprise additional sequences for recombination with a second target locus, optionally a locus in a host cell of species different than the first target locus.

The integration sequences will typically allow recombination at the target locus via homologous recombination. That is to say, the integration sequences will typically have sufficient homology with sequences at the target locus so as to enable integration of two or more expression cassettes at a target locus via homologous recombination.

The lengths of the sequences mediating homologous recombination between assembled expression cassettes and the target locus may be at least about 20 bp, at least about 30 bp, at least about 50 bp, at least about 0.1 kb, at least about 0.2 kb, at least about 0.5 kb, at least about 1 kb or at least about 2 kb.

Alternatively, the integration sequences could be sequences which are recognized by a site-specific recombinase. That is to say, the integration sequences could allow integration via site-specific recombination in the presence of the appropriate recombinase enzyme.

In the method of the invention, there may be provided integration sequences which provide for recombination with a first target locus in one host cell species and then for recombination with a target locus in a second host cell species. A selection marker (for selection in the first host cell species) may conveniently be provided between such integration sequences. Clearly, it is one necessary to place such a marker between two integration sites located on one side of the expression cassettes. For example integration sites may be provided at the 5' and 3' ends of the expression cassettes which are specific a target locus in a first host cell species. A selection marker may then be provided adjacent to one of the integration sites, located between the integration site and one end of the expression cassettes. That selection marker will typically be suitable for selection in the first host cell species. Additional integration sites for a second host cell species may then be provided. One of these will be located between the selection marker and one end of the expression cassettes. Another will then be located between the other end of the expression cassette and an integration site (specific for the first host cell species).

Figure 23:
FIG. 23 shows the use of selection marker cassettes. In option 1 one or more promoter-open reading frame-terminator (POT) cassettes encode for selectable marker(s) for assembly in host 1 and application in host 2; might be shared, for example $POT_2$. In option 2, one or more POT cassettes outside the inner flanks encode for selectable marker(s) for assembly in host 1 and another one or more POT within inner flanks for application in host 2, for example $POT_2$ for host 1 and $POT_S$ for host 2.
Figure 23:

This approach is illustrated in FIG. 23 which shows the use of selection marker cassettes. In option 1 one or more promoter-open reading frame-terminator (POT) cassettes encode for selectable marker(s) for assembly in host 1 and application in host 2; might be shared, for example POT$_2$. In option 2, one or more POT cassettes outside the inner flanks encode for selectable marker(s) for assembly in host 1 and another one or more POT within inner flanks for application in host 2, for example POT$_2$ for host 1 and POT$_3$ for host 2.

In the method of the invention, a series of expression cassettes, for example at least about 2, 3, 4, 5, 6, 7, 8, 9, 10, 11, 12, 13, 14, 15, 16, 17, 18, 19 or 20 or more expression cassettes may be assembled and recombined in a predetermined order in series at a target locus.

The method may be carried out so that at least one expression cassette is capable of expressing a marker. That is to say, at least one expression vector may encode a polypeptide which can act as a marker.

In the method of the invention, one or more expression cassettes not produced according to the method of the invention may be used.

In the method of the invention, at least two sets of element sequences are provided. Each set of element sequences will typically be capable of being assembled as an expression cassette. An expression cassette in the context of this invention is intended to indicate a nucleic acid sequence that directs a cell's machinery to make RNA and protein. Typically, an expression cassette will comprise a coding sequence and the sequences controlling expression of that coding sequence. Typically, an expression cassette may comprise at least a promoter, an open reading frame and a terminator sequence.

The term "control sequences" is defined herein to include all components, which are necessary or advantageous for the production of mRNA or a polypeptide, either in vitro or in a host cell. Each control sequence may be native or foreign to the nucleic acid sequence encoding the polypeptide. Such control sequences include, but are not limited to, a leader, Shine-Delgarno sequence, optimal translation initiation sequences (as described in Kozak, 1991, J. Biol. Chem. 266:19867-19870), a polyadenylation sequence, a pro-peptide sequence, a pre-pro-peptide sequence, a promoter, a signal sequence, and a transcription termination signal. At a minimum, the control sequences typically include a promoter, and a transcriptional stop signal (terminator or termination signal). Translational start and stop signals may typically also be present. Control sequences may be optimized to their specific purpose.

The term "promoter" is defined herein as a DNA sequence that binds RNA polymerase and directs the polymerase to the correct downstream transcriptional start site of a nucleic acid sequence encoding a biological compound to initiate transcription. RNA polymerase effectively catalyzes the assembly of messenger RNA complementary to the appropriate DNA strand of a coding region. The term "promoter" will also be understood to include the 5'-non-coding region (between promoter and translation start) for translation after transcription into mRNA, cis-acting transcription control elements such as enhancers, and other nucleotide sequences capable of interacting with transcription factors.

The method of the invention is typically carried out such that the elements of an expression cassette are assembled in a backbone entry vector such that they are in operable linkage. The term "operable linkage" or "operably linked" or the like are defined herein as a configuration in which a control sequence is appropriately placed at a position relative to the coding sequence of the DNA sequence such that the control sequence directs the production of an mRNA or a polypeptide.

Accordingly, an element in the context of this invention is any constituent of an expression cassette. A set of elements is a group of elements that together may give rise to an expression cassette. The method of the invention requires that provision of two sets of element sequences. This means that enough elements are to be provided so that at least two different expression cassettes may result. This implies that there must be at least two different species of at least one element provided. That is to say, one promoter, taken in combination with two ORFs and two termination signals constitutes two sets of element sequences for the purposes of this invention.

In a method of the invention, typically at least two of the sets of element sequences comprise a promoter element, an open reading frame element and a termination signal element.

In a method according to the invention, one or more of the sets of elements may comprise "partial" element sequences, such as UTRs, signal peptides and split-open reading frames.

Each set of element sequences is provided in a form so that the set may be assembled into a functional expression cassette in a backbone entry vector. Typically then, each element is flanked by on both sides by a type IIs restriction endonuclease cleavage site followed by the recognition site thereof, the type IIs restriction endonuclease recognition sites and cleavage sites being selected so that the sets of element sequences may be assembled into a functional expression cassette. Each element sequence and flanking sequence therefore typically comprises in order from one end to the other: type IIs restriction endonuclease recognition site; cleavage site thereof; element sequence; type IIs restriction endonuclease cleavage site; recognition site thereof.

Accordingly, the sets of elements are prepared or provided in a suitable vector with type IIs restriction endonuclease recognition sites and standardized cleavage sites (preferably 4-bp), selected such that after assembly, for example using a one-pot approach, such as Golden gate cloning, a functional expression cassette is formed.

A set of backbone entry vectors is prepared or provided. These vectors comprise contain left and right connector sequences suitable for assembly using sequence homology, for assembly of modular cassettes at (see Level 1 in FIGS. 1 and 2).

In more details, each backbone entry vector typically comprises, in this order: (i) a restriction enzyme cleavage site with its recognition site and a first connector sequence (LF); (ii) a vector backbone comprising a selectable marker gene; and (iii) a second connector sequence (RF) and a restriction enzyme recognition site with its cleavage sequence, and; (iv) optionally, an insert between the recognition sites of (i) and (iii), the connector sequences, RF and LF, on any backbone entry vector being selected so that they can assemble with a LF or RF connector sequence respectively on the same or a different backbone entry vector.

A subset of element sequences is selected together with backbone (bbn) entry vectors. These may be assembled, for example using Golden Gate cloning, resulting in functional expression cassettes comprised within the backbone entry vectors.

In the method according to the invention, the elements in each set are defined so that the expression cassette is assembled in a pre-determined order. Also, the connector sequences in the backbone entry vectors may also be selected so that the expression cassettes may be assembled in a pre-determined order.

The left and right flanks for integration at a target locus (see Level 2 in FIGS. 1 and 2) may be provided by the backbone entry vectors themselves or may be added as additional sequences. Integration sequences may be provided via a PCR reaction where they are part of the primers used.

In level 2, in vivo assembly of functional expression cassettes, with integration flanks (int) and possibly other DNA sequences containing connector (con) sequences for in vivo assembly takes place and in a suitable host cell and recombination at a target locus.

Typically all DNA parts to be assembled can be recovered by a PCR reaction from the vectors resulting from Level 1 for usage at Level 2, or for example, using a method to cut out these fragments via appropriate IIs restriction enzymes and their recognition sites designed oudside the con-vectors and cleaving the con vector including the DNA-sequence in between.

Both options a and b in FIG. 1 provide a scheme for assembly of a modular cassette at a target locus. In option b, additional left and right integration sites are added for a second host. Option b may be followed by Level 3.

In Level 3 (see FIGS. 1. and 2), the modular cassettes (or in parts) may be recovered from 2b, for example via a PCR reaction, or other method. The recovered DNA is use for transformation and subsequent integration of the modular DNA cassette at a target locus in a second host.

In the method of the invention, the connector sequences enable recombination between expression cassettes from different backbone entry vectors. The length of such sequences may vary depending on the type of assembly to be carried out, i.e. in vivo or in vitro, and/or the species in which recombination is to take place. Connectors which are recombined in vivo will typically be from about 20 bp to about 500 bp in length, for example about 25 bp in length (for example in the case of yeast). Connectors which are to be recombined in vitro, for example in a Gibson reaction, may be about 9 bp, 10 bp, 11 bp, 12 bp, 13 bp, 14 bp, 15 bp or longer in length.

In order to promote targeted integration at a targeted locus and to ensure assembly of the connector sequences for integration are provided. Such sequences may be from at least about 20 bp, at least about 30 bp, at least about 50 bp, at least about 0.1 kb, at least about 0.2 kb in length to at least about 0.5 kb, at least about 1 kb, at least about 2 kb in length or at least about 5 kb in length.

Figure 3:
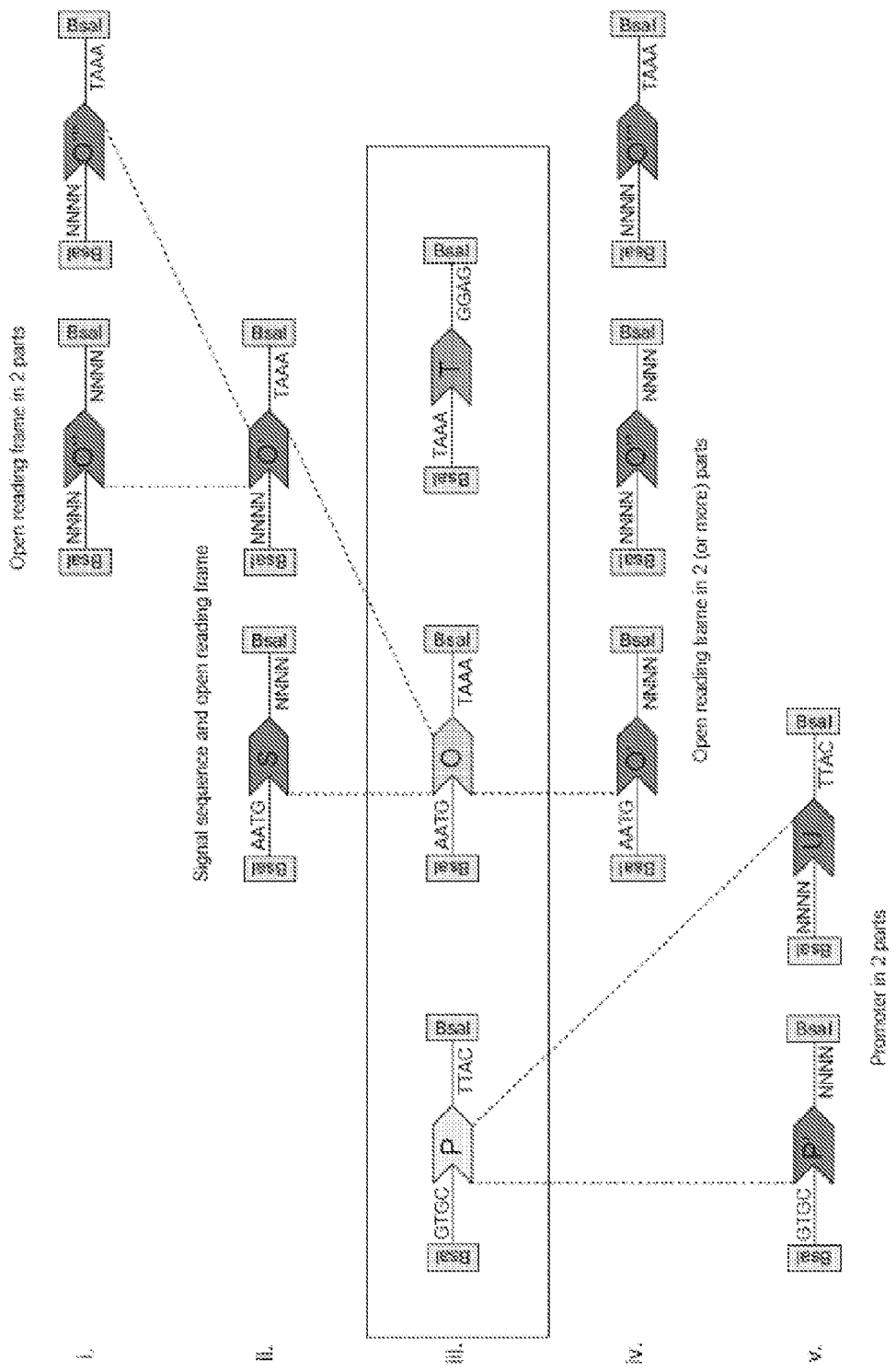
FIG. 3, parts i.-v., shows assembly options at Level 1 (but not limited to these) with item iii. being a preferred method for assembly of functional expression cassettes using preferably a single type IIS endonucleases and 4-bp overhangs after cleavage and ligation. Ii. Show that an open reading frame can be split in a signal sequences and a separate part of the open reading frame, or i. and open reading frame in multiple fragments, for example due to size or modular character of a protein, e.g. an enzyme with a separate domains, like PKS, NRPS, cellulose, etc, or just due to size or for protein engineering purposes to create a library sequence for part of an orf. Item iv. shows a split in 3 pieces for an orf. Item v. shows a promoter being split in a promoter, where part of the 5'UTR of a gene is added separately. Note that these are examples, and basically one can design a split DNA sequence in multi-parts and ligate using type-IIs systems to create scarf-free DNA sequences. In the shown case, AATG is used at the methione start of a protein. Here the last nucleotide of a promoter sequenced is modified always in an A. For the bridge to the terminator, TAAA is chosen, where a stop codon of a gene is modified in TAA and the first position of a terminator sequence being modified with an A or extended by an A at the 5'. Note that for efficient use of the Golden Gate (or other type IIS dependent cloning system) all sequences are preferable (made) free of the recognition sites of the restriction enzymes being used for cleavage.

FIG. 3 shows assembly options at Level 1 (but not limited to these) with item iii. being a preferred method for assembly of functional expression cassettes using preferably a single type IIS endonucleases and 4-bp overhangs after cleavage and ligation. Ii. Show that an open reading frame can be split in a signal sequences and a separate part of the open reading frame, or i. and open reading frame in multiple fragments, for example due to size or modular character of a protein, e.g. a enzyme with a separate domains, like PKS, NRPS, cellulose, etc, or just due to size or for protein engineering purposes to create a library sequence for part of an orf. Item iv. shows a split in 3 pieces for an orf. Item v. shows a promoter being split in a promoter, where part of the 5'UTR of a gene is added separately. Note that these are examples, and basically one can design a split DNA sequence in multi-parts and ligate using type-IIs systems to create scarf-free DNA sequences. In the shown case, AATG is used at the methione start of a protein. Here the last nucleotide of a promoter sequenced is modified always in an A. For the bridge to the terminator, TAAA is chosen, where a stop codon of a gene is modified in TAA and the first position of a terminator sequence being modified with an A or extended by an A at the 5'. Note that for efficient use of the Golden Gate (or other type IIS dependent cloning system) all sequences are preferable (made) free of the recognition sites of the restriction enzymes being used for cleavage.

Figure 4:
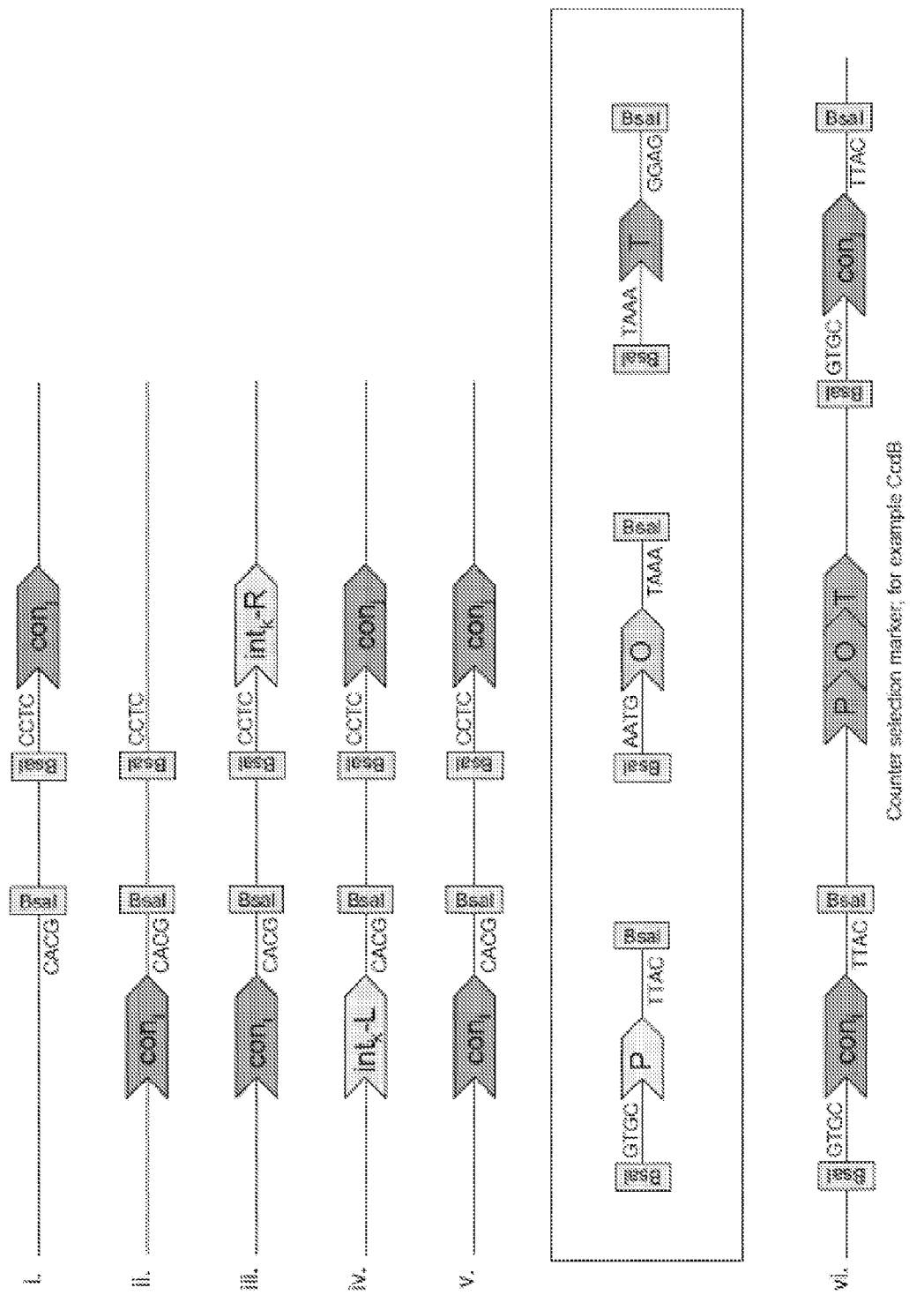
FIG. 4, parts i.-v., shows backbone (bbn) vector variants for the connector (con) part of these vectors. Item v. shows the variant typically applied to create functional expression cassettes at Level 1 (FIGS. 1A & 1B, and 2A & 2B) with specified, but not limited to, the given 4-bp connectors. Item iv. and ii. Provide variant bbn vectors where one of the connectors is replaced by or combined with a left and right integration flank for integration at a target locus, respectively. Item ii and i. are variants were only a left or right connector is part of the backbone. These are typically ones that can only be applied at the end of a modular cassette, for example to us etogether with integration flanks and store these in a vector. Item vi. Show that one could use a counter selection marker for Golden Gate cloning (or other) within the type IIs restriction sites used to insert the element sequences. Note that the method is not limited to use of BsaI as type IIs restriction enzymes, nor to the use of IIS restriction enzymes, as long as the flanks resulting from restriction are compatible with the ones of the single or modular element or int / flank sequence to be inserted.

FIG. 4 shows backbone (bbn) vector variants for the connector (con) part of these vectors. Item v. shows the variant typically applied to create functional expression cassettes at Level 1 (FIGS. 1 and 2) with specified, but not limited to, the given 4-bp connectors. Item iv. and ii. Provide variant bbn vectors where one of the connectors is replaced by or combined with a left and right integration flank for integration at a target locus, respectively. Item ii and i. are variants were only a left or right connector is part of the backbone. These are typically ones that can only be applied at the end of a modular cassette, for example to use together with integration flanks and store these in a vector. Item vi. Show that one could use a counter selection marker for Golden Gate cloning (or other) within the type IIs restriction sites used to insert the element sequences. Note that the method is not limited to use of BsaI as type IIs restriction enzymes, nor to the use of IIS restriction enzymes, as long as the flanks resulting from restriction are compatible with the ones of the single or modular element or int/flank sequence to be inserted.

In a method of the invention, a plurality of expression cassettes may be assembled, each cassette comprising a member of a biological pathway. The term "pathway", as used herein, is to be interpreted broadly, and may refer to a series of simultaneous, sequential or separate chemical reactions, effected by activities that convert substrates or beginning elements into end compounds or desired products via one or more intermediates. An activity sometimes is conversion of a substrate to an intermediate or product (e.g., catalytic conversion by an enzyme) and sometimes is binding of molecule or ligand, in certain embodiments. The term "identical pathway" as used herein, refers to pathways from related or unrelated organisms that have the same number and type of activities and result in the same end product. The term "similar pathway" as used herein, refers to pathways from related or unrelated organisms that have one or more of: a different number of activities, different types of activities, utilize the same starting or intermediate molecules, and/or result in the same end product.

A method according to any one of the preceding claims, wherein variants of at least one element in at least one set of elements are provided so that variants of are least one standardized modular expression cassette are generated.

In this way, pathway improvement and optimization can be attained, for example, by harnessing naturally occurring genetic diversity and/or engineered genetic diversity. Naturally occurring genetic diversity can be harnessed by testing subgroup polynucleotides from different organisms. Engineered genetic diversity can be harnessed by testing subgroup polynucleotides that have been codon-optimized or mutated, for example. For codon-optimized diversity, amino acid codon triplets can be substituted for other codons, and/or certain nucleotide sequences can be added, removed or substituted. For example, native codons may be substituted for more or less preferred codons. In certain embodiments, pathways can be optimized by substituting a related or similar activity for one or more steps from a similar but not identical pathway. A polynucleotide in a subgroup also may have been genetically altered such that, when encoded, effects an activity different than the activity of a native counterpart that was utilized as a starting material for genetic alteration. Nucleic acid and/or amino acid sequences altered by the hand of a person as known in the art can be referred to as "engineered" genetic diversity.

All variants of any given element may all share at least about 50% sequence identity with each other.

A metabolic pathway can be seen as a series of reaction steps which convert a beginning substrate or element into a final product. Each step may be catalyzed by one or more activities. In a pathway where substrate A is converted to end product D, intermediates B and C are produced and converted by specific activities in the pathway. Each specific activity of a pathway can be considered a species of an activity subgroup and a polypeptide that encodes the activity can be considered a species of a counterpart polypeptide subgroup.

Any peptides, polypeptides or proteins, or an activity catalyzed by one or more peptides, polypeptides or proteins may be encoded by a polynucleotide subgroup. Representative proteins include enzymes (e.g., part or all of a metabolic pathway), antibodies, serum proteins (e.g., albumin), membrane bound proteins, hormones (e.g., growth hormone, erythropoietin, insulin, etc.), cytokines, etc., and include both naturally occurring and exogenously expressed polypeptides. Representative activities (e.g., enzymes or combinations of enzymes which are functionally associated to provide an activity or group of activities as in a metabolic pathway) include any activities associated with a desired metabolic pathway. The term "enzyme" as used herein may refer to a protein which can act as a catalyst to induce a chemical change in other compounds, thereby producing one or more products from one or more substrates.

It will be understood that the methods and compositions described in embodiments presented herein can be used to; (i) optimize any metabolic pathway that produces a desirable end product, and/or (ii) optimize subdomains within an activity subgroup of a metabolic pathway. The term "protein" as used herein refers to a molecule having a sequence of amino acids linked by peptide bonds. This term includes fusion proteins, oligopeptides, peptides, cyclic peptides, polypeptides and polypeptide derivatives, whether native or recombinant, and also includes fragments, derivatives, homologs, and variants thereof. A protein or polypeptide sometimes is of intracellular origin (e.g., located in the nucleus, cytosol, or interstitial space of host cells in vivo) and sometimes is a cell membrane protein in vivo. In some embodiments (described above, and in further detail below in Engineering and Alteration Methods), a genetic modification can result in a modification (e.g., increase, substantially increase, decrease or substantially decrease) of a target activity.

In a method of the invention, the expression cassettes used may constitute a biological pathway which enables the production of a compound of interest in the host cell. The compound of interest is a primary metabolite, a secondary metabolite, a polypeptide or a mixture of polypeptides.

Figure 5:
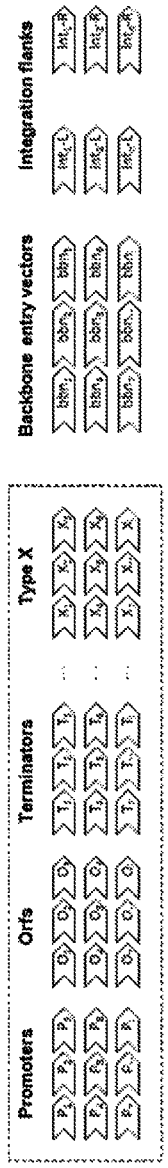
FIG. 5 show the modularity of the system and methods described in this document at level 1. By selecting multiple elements from level 0 and use in one pot Golden Gate (or other) cloning reaction, one creates a library of functional expression cassettes, to be used a library at Level 2 (FIGS. 1A & 1B or 2A & B) and possibly can be combined with step 2 of FIG. 6.
Figure 5:
Figure 5:

Accordingly, the method of the invention may be used in a modular format at level 1 (see FIG. 5). By selecting multiple elements from level 0 and use in one pot Golden Gate (or other) cloning reaction, one creates a library of functional expression cassettes, to be used as a library at Level 2 (FIG. 1 or 2) and may be combined with step 2 of FIG. 6.

The method may be used in modular format at level 2 (for example in a method as set out in FIG. 1). Accordingly, a library of functional expression cassettes can be added for one or more modules to be assembled via in vivo assembly and recombination resulting in a library of host cells containing a diversity of modular DNA cassettes at a target locus (see FIG. 6). Optionally such a library can be recovered at Level 3.

Such a modular approach level 2 may be carried out with an intermediate in vitro step at Level 2 (for example in a method as set out in FIG. 2). Accordingly, a library of functional expression cassettes can be added for one or more modules to be assembled via in vitro assembly (see FIG. 7). This step can be proceeded by in vivo assembly of the resulting (and possibly recovered) multi-part DNA sequences resulting in a library of host cells containing a diversity of modular DNA cassettes at a target locus. Optionally such a library can be recovered at Level 3.

Multiple variants at Level 2 (see FIGS. 8(A)-(E)) using the same backbone (bbn) vectors with unique at least 25-bp connector sequences can be applied to create in vivo knock out or integration constructs. Level 1 shows how the various elements (but not limited to) at Level 0 can be inserted in backbone vectors (see also FIG. 4) can be assembled to create modular elements flanked by required one or two connector sequences for in vivo assembly in a specified order at Level 2. These unique connector make efficient reuse of these element vector possible, and allow for usage in a combinatorial way directly or as a library to create for example knock-out of a stretch of DNA covering multiple genes, or in a library with int-L and int-R sequences (Level 2C) to create a library of host cells with reduced plasmids, chromosomes or other pieces of DNA in a host cell. Typically a functional marker cassette will be applied together with at least one int-L and one int-R sequence (being in that order at a target locus, but not necessarily connected).

Several strategies, but not limited to, follow: (A) create an insertion with a marker to replace a orf at a target locus; (B) create a insertion with a marker to replace a selected part of DNA at a target locus defined by int-L and int_R; (C) create a insertion with a marker to replace a selected part of DNA at a target locus defined by combinatorial possibilities of int-L and in_t R sequences added as a library, resulting a small to larger parts of DNA being replaced depending on the maximal distance of the int-L and int-R sequences selected for at least one chromosome, plasmid or other target DNA; (D) shows that part (B) can be adapted to insert a specific element or part of it at a target locus. This can be applied for exchange of signal sequence, promoter, 5'UTR or modular parts in a protein in a standardized modular fashion, either by rational design or as a library approach. A possible example is promoter tuning, or another one creation of variants of modular proteins like NRPS, PKS, cellulases and other modular proteins, etc; (E) shows that when using more than one marker and a second set of non-compatible connector sequences with first one, one can do multiple actions at once.

Note that for (D) the int-R needs a correct match with the target locus in order not to disturb the original reading frame.

Figure 6A:
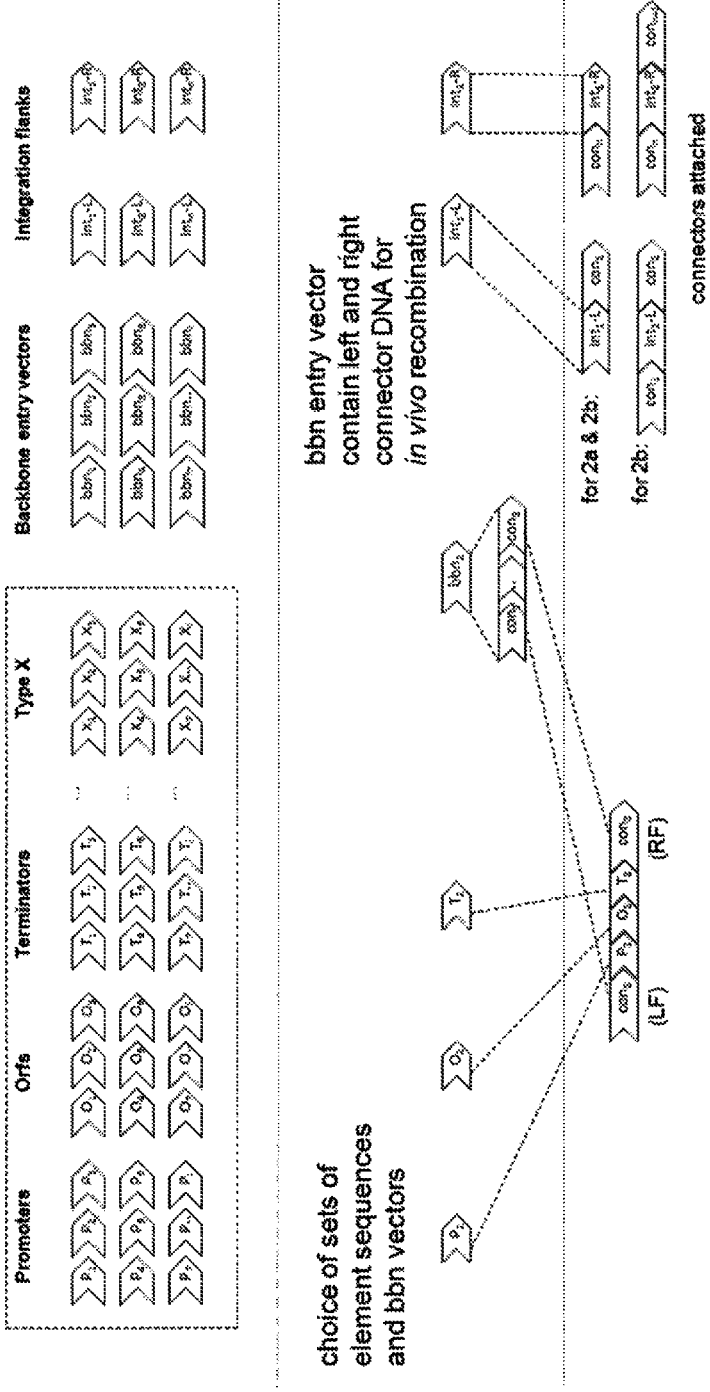
FIGS. 6A and 6B show modularity of the system and methods described in this document at level 2 (for FIGS. 1A & 1B). A library of functional expression cassettes can be added for one or more modules to be assembled via in vivo assembly and recombination resulting in a library of host cells containing a diversity of modular DNA cassettes at a target locus. Optionally such a library can be recovered at Level 3.
Figure 6B:
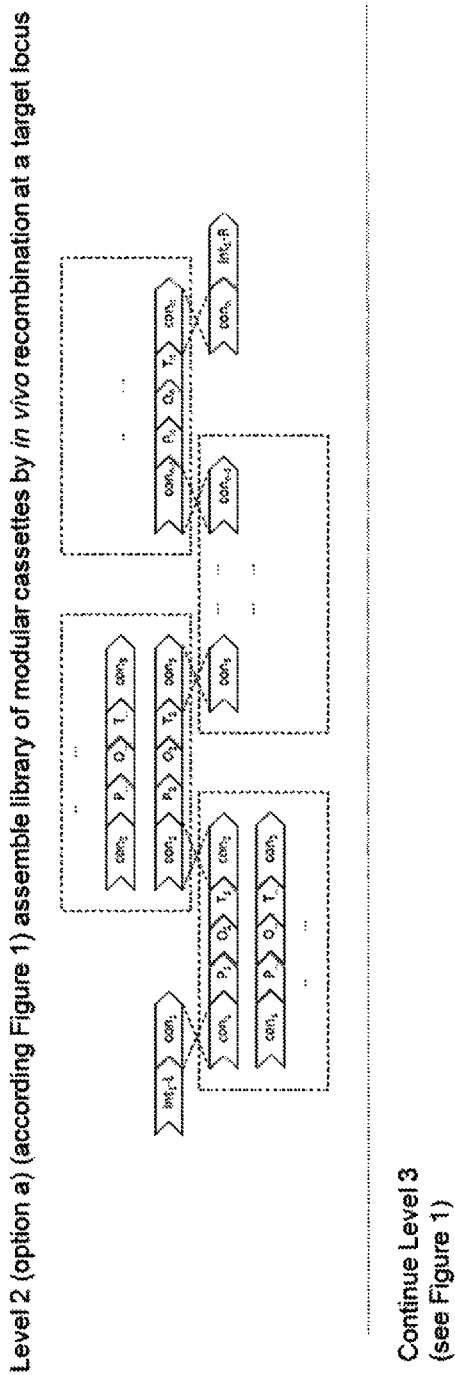
Figure 7A:
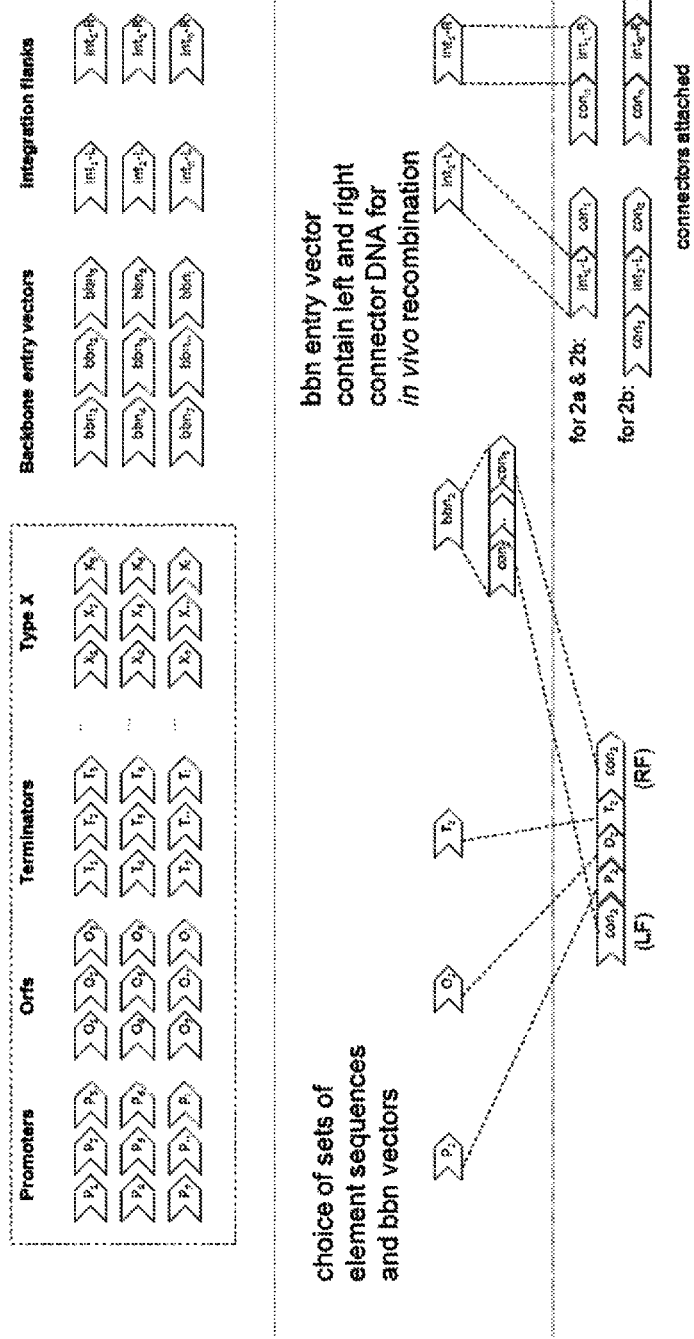
FIGS. 7A and 7B show modularity of the system and methods described in this document at level 2 (for FIGS. 2A & 2B). Similar to FIGS. 6A and 6B, but then with an intermediate in vitro ste at Level 2 step a (FIG. 7B): A library of functional expression cassettes can be added for one or more modules to be assembled via in vitro assembly. This step can be proceeded by in vivo assembly of the resulting (and possibly recovered) multi-part DNA sequences resulting in a library of host cells containing a diversity of modular DNA cassettes at a target locus. Optionally such a library can be recovered at Level 3.
Figure 7B:
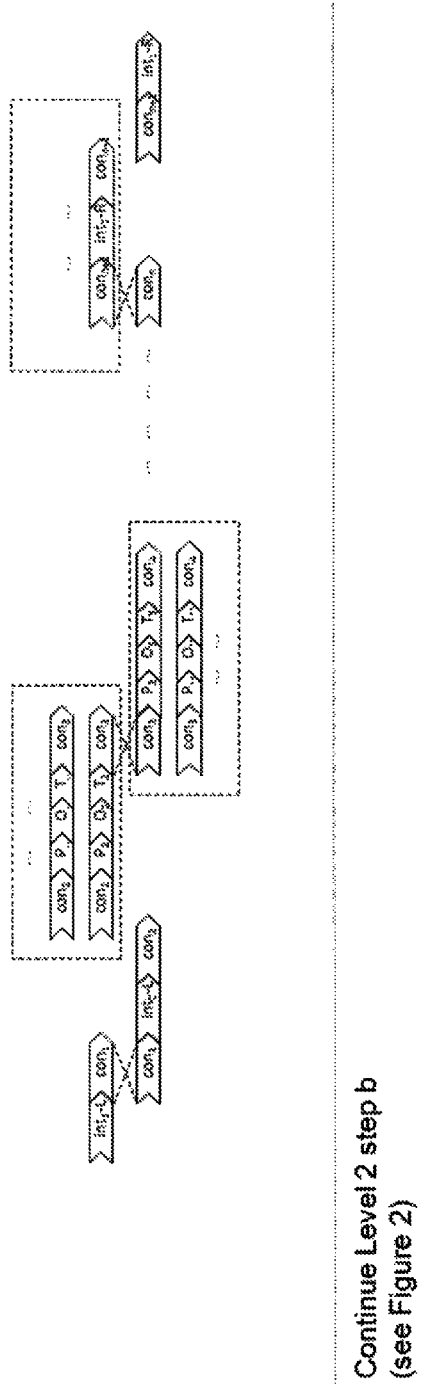
Figure 8A:
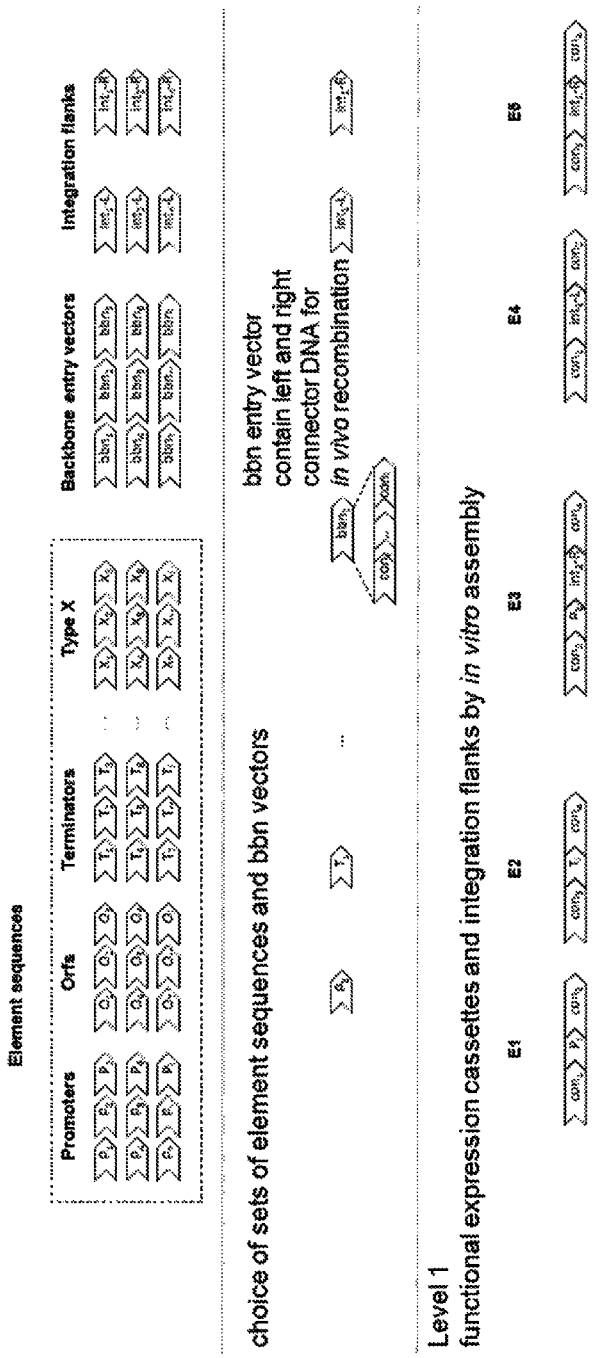
FIGS. 8A and 8B show and described in multiple variants at Level 2(A)-(E), but not limited to these, that the same backbone (bbn) vectors with unique at least 25-bp connector sequences can be applied to create in vivo knock out or integration constructs as described below. Level 1 (FIG. 8A) shows how the various elements (but not limited to) at Level 0 can be inserted in backbone vectors (see also FIG. 4) can be assembled to create modular elements flanked by required one or two connector sequences for in vivo assembly in a specified order at Level 2 (FIG. 8B). These unique connector make efficient reuse of these element vector possible, and allow for usage in a combinatorial way directly or as a library to create for example knock-out of a stretch of DNA covering multiple genes, or in a library with int-L and int-R sequences (Level 2C) to create a library of host cells with reduced plasmids, chromosomes or other pieces of DNA in a host cell. Typically a functional marker cassette will be applied together with at least one int-L and one int-R sequence (being in that order at a target locus, but not necessarily connected). Several strategies, but not limited to, follow: (A) create an insertion with a marker to replace a orf at a target locus; (B) create a insertion with a marker to replace a selected part of DNA at a target locus defined by int-L and int_R; (C) create a insertion with a marker to replace a selected part of DNA at a target locus defined by combinatorial possibilities of int-L and int_R sequences added as a library, resulting a small to larger parts of DNA being replaced depending on the maximal distance of the int-L and int-R sequences selected for at least one chromosome, plasmid or other target DNA; (D) shows that part (B) can be adapted to insert a specific element or part of it at a target locus. This can be applied for exchange of signal sequence, promoter, 5'UTR or modular parts in a protein in a standardized modular fashion, either by rational design or as a library approach. A possible example is promoter tuning, or another one creation of variants of modular proteins like NRPS, PKS, cellulases and other modular proteins, etc; (E) shows that when using more than one marker and a second set of non-compatible connector sequences with first one, one can do multiple actions at once. Note that for (D) the int-R needs a correct match with the target locus in order not to disturb the original reading frame. Of course the method of FIGS. 8A and 8B can be combined with FIGS. 1A and 1B or FIGS. 2A and 2B have insertion of one or more modular DNA cassettes one or more target loci, while inserting a marker at a second position together with removal or insertion of a DNA sequence as described in FIGS. 8A and 8B, either as one or more pre-defined sequences or as library approaches (FIGS. 5, 6A, 6B, 7A, 7B).
Figure 8B:
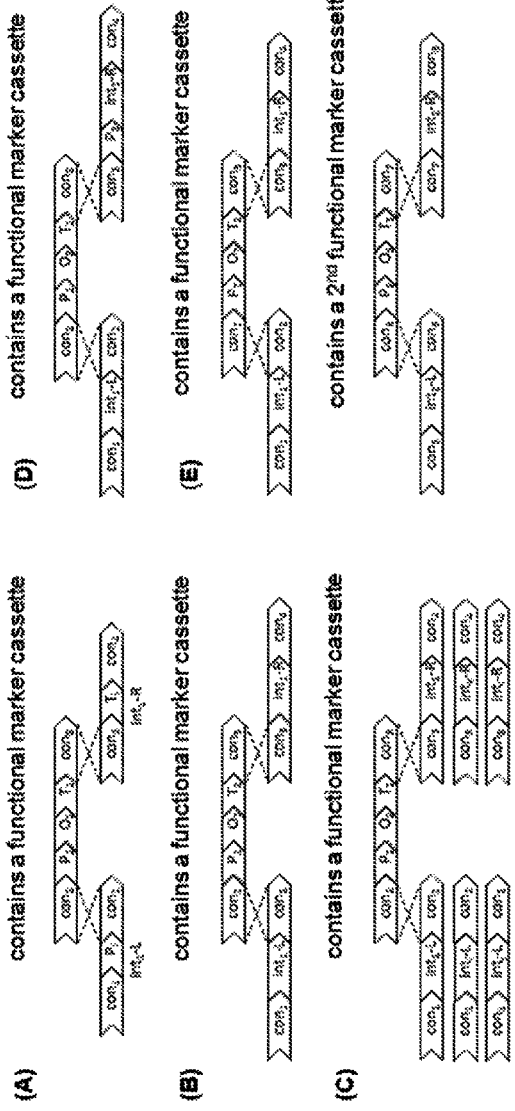

Of course, a method as illustrated in FIG. 8 can be combined with one as illustrated in FIG. 1 or FIG. 2, so as to have insertion of one or more modular DNA cassettes one or more target loci, while inserting a marker at a second position together with removal or insertion of a DNA sequence as described in FIG. 8, either as a or more pre-defined sequences or as library approaches (FIG. 5-7).

Accordingly the invention provides a general 2-step pathway building method, which is fast, efficient and flexible method due to the standardized genetic elements for the golden gate cloning combined with the standardized connectors providing homology for the in vivo recombination.

The invention thus provides a method for integration of a nucleic acid sequence at a target locus.

Such a method for integration of a DNA sequence at a target locus comprises:

a. providing: (i) a set of at least two left (int-L) and two right (int-R) integration sequence for homologous recombination to at least one target locus in a host cell of at least about 200 base pairs in length, wherein
   the left (int-L) sequence is flanked by one at least about 25-base pair connector sequence,
   the right (int-R) sequence is flanked by one at least about 25-base pair connector sequence; and
   (ii) at least one expression cassette flanked on both sides by an at least about 25-base pair connector sequence; and
b. assembling in vivo the sets of at least three sequences from step (a) by recombination at the homologous target loci of the int-L and int-R sequences, so that at least one left and at least one right integration sequence are in this order at a target locus in the host cell,
   wherein after in vivo assembly, at least one expression cassette is present at a target locus, optionally which expression cassettes are capable of expressing a functional marker.

In such a method at least one expression cassette may be assembled via two or more nucleic acid sequences in step (b) resulting in at least one functional expression cassette, for example containing a marker polypeptide-encoding ORF.

Such a method may comprise:
a. preparing two or more standardized modular expression cassettes according to the method of claim 1, wherein,
   i. The int-L and int-R sequences are part of a promoter, orf or terminator sequence;
   ii. the RF and LF connector sequences comprise at least 25-base pair homologous recombination sequences; and
   iii. the RF and LF sequences on any backbone entry vector are selected so that they can assemble by recombination in vivo with a LF or RF connector sequence, respectively, with the same or a different backbone entry vector and/or with a sequence flanking the target locus; and b. recovering an expression cassettes from the backbone entry vectors including the LF and RF sequences; and
c. recombining the recovered expression cassettes in vivo in a host cell with each other at the target locus.

A method for integration of a DNA sequence at a target locus may comprise the selection of two or more int-L and two or more int-R sequences for use in one in vivo assembly and recombination reactions resulting in a plurality of host cells with combinations of DNA targeting to at least 2 allowed combinations by the selected int-L and int-R sequences, wherein
 i. at least two int_L sequences are left from at least one int-R sequence at the target DNA sequence, or
 ii. at least two int_R sequences are right from at least one int-L sequence at the target DNA sequence.

In these methods, a second functional marker cassette may be integrated at a second target locus. Accordingly, the method may be used to generate double or triple mutants, or mutants containing 4, 5, 6, 7, 8, 9, 10 or more mutations.

Such methods may result in the functional knock-out or downregulation of a functional gene or set of functional genes lying together at a target locus. That is to say, the invention may be used to carry out deletion or knock-out or knock-down of a gene at a target locus In such a method of the invention, at least one int-R sequence may be homologous to the at least first 200 base-pairs of an open reading frame, and functionally coupled at the left side to a DNA sequence to be inserted before the open reading frame, resulting in a open reading frame with a modified 5'UTR sequence of at least 50 base-pairs. This enables insertion of a new promoter and/or the replacement of a signal sequence.

Most preferred are the following type IIs restriction endonucleases: BsaI, BbsI, BsmBI, SapI, BspMI, AarI, Esp3I, BpiI, and HgaI. Many of the cited restriction endonucleases are available from New England Biolabs. Sources of these enzymes can also be found on the REBASE webpage mentioned above.

Examples of ligases to be used in the invention include T4 DNA ligase, *E. coli* DNA ligase, Taq DNA ligase, all of which are commercially available from New England Biolabs.

A host cell suitable for use in the invention can include one or more of the following features: aerobe, anaerobe, filamentous, non-filamentous, monoploid, dipoid, auxotrophic and/or non-auxotrophic.

A host cell suitable for use in the invention may be a prokaryotic microorganism (e.g., bacterium) or a non-prokaryotic microorganism. A suitable host cell may be a eukaryotic microorganism (e.g., yeast, fungi, amoeba, and algae). A suitable host cell may be from a non-microbial source, for example a mammalian or insect cell.

"Fungi" are herein defined as eukaryotic microorganisms and include all species of the subdivision Eumycotina (Alexopoulos, C. J., 1962, In: Introductory Mycology, John Wiley & Sons, Inc., New York). The term fungus thus includes both filamentous fungi and yeast. "Filamentous fungi" are herein defined as eukaryotic microorganisms that include all filamentous forms of the subdivision Eumycotina and Oomycota (as defined by Hawksworth et. al., 1995, supra). The filamentous fungi are characterized by a mycelial wall composed of chitin, cellulose, glucan, chitosan, mannan, and other complex polysaccharides. Vegetative growth is by hyphal elongation and carbon catabolism is obligately aerobic. Filamentous fungal strains include, but are not limited to, strains of *Acremonium, Aspergillus, Aureobasidium, Cryptococcus, Filibasidium, Fusarium,* *Humicola, Magnaporthe, Mucor, Myceliophthora, Neocallimastix, Neurospora, Paecilomyces, Penicillium, Piromyces, Schizophyllum, Talaromyces, Thermoascus, Thielavia, Tolypocladium,* and *Trichoderma.*

"Yeasts" are herein defined as eukaryotic microorganisms and include all species of the subdivision Eumycotina that predominantly grow in unicellular form. Yeasts may either grow by budding of a unicellular thallus or may grow by fission of the organism.

The host cells according to the invention are preferably fungal host cell whereby a fungus is defined as herein above. Preferred fungal host cells are fungi that are used in industrial fermentation processes for the production of fermentation products as described below. A large variety of filamentous fungi as well as yeasts are use in such processes. Preferred filamentous fungal host cells may be selected from the genera: *Aspergillus, Trichoderma, Humicola, Acremonium, Fusarium, Rhizopus, Mortierella, Penicillium, Myceliophthora, Chrysosporium, Mucor, Sordaria, Neurospora, Podospora, Monascus, Agaricus, Pycnoporus, Schizophylum, Trametes* and *Phanerochaete.* Preferred fungal strains that may serve as host cells, e.g. as reference host cells for the comparison of fermentation characteristics of transformed and untransformed cells, include e.g. *Aspergillus niger* CBS120.49, CBS 513.88, *Aspergillus oryzae* ATCC16868, ATCC 20423, IFO 4177, ATCC 1011, ATCC 9576, ATCC14488-14491, ATCC 11601, ATCC12892, *Aspergillus fumigatus* AF293 (CBS101355), *P. chrysogenum* CBS 455.95, *Penicillium citrinum* ATCC 38065, *Penicillium chrysogenum* P2, *Acremonium chrysogenum* ATCC 36225, ATCC 48272, *Trichoderma reesei* ATCC 26921, ATCC 56765, ATCC 26921, *Aspergillus sojae* ATCC11906, *Chrysosporium lucknowense* ATCC44006 and derivatives of all of these strains. Particularly preferred as filamentous fungal host cell are *Aspergillus niger* CBS 513.88 and derivatives thereof.

Any suitable yeast may be selected as a host cell. Preferred yeast host cells may be selected from the genera: *Saccharomyces* (e.g., *S. cerevisiae, S. bayanus, S. pastorianus, S. carlsbergensis), Kluyveromyces, Candida* (e.g., *C. revkaufi, C. pulcherrima, C. tropicalis, C. utilis), Pichia* (e.g., *P. pastoris), Schizosaccharomyces, Hansenula, Kloeckera, Schwanniomyces,* and *Yarrowia* (e.g., *Y. lipolytica* (formerly classified as *Candida lipolytica*).

Any suitable prokaryote may be selected as a host cell. A Gram negative or Gram positive bacteria may be selected. Examples of bacteria include, but are not limited to, *Bacillus* bacteria (e.g., *B. subtilis, B. megaterium), Acinetobacter* bacteria, *Norcardia* bacteria, *Xanthobacter* bacteria, *Escherichia* bacteria (e.g., *E. coli* (e.g., strains DH 1 OB, Stbl2, DH5-alpha, DB3, DB3.1), DB4, DB5, JDP682 and ccdA-over (e.g., U.S. application Ser. No. 09/518,188))), *Streptomyces* bacteria, *Erwinia* bacteria, *Klebsiella* bacteria, *Serratia* bacteria (e.g., *S. marcessans), Pseudomonas* bacteria (e.g., *P. aeruginosa), Salmonella* bacteria (e.g., *S. typhimurium, S. typhi*). Bacteria also include, but are not limited to, photosynthetic bacteria (e.g., green non-sulfur bacteria (e.g., *Choroflexus* bacteria (e.g., *C. aurantiacus), Chloronema* bacteria (e.g., *C. gigateum*)), green sulfur bacteria (e.g., *Chlorobium* bacteria (e.g., *C. limicola), Pelodictyon* bacteria (e.g., *P. luteolum*), purple sulfur bacteria (e.g., *Chromatium* bacteria (e.g., *C. okenii*)), and purple non-sulfur bacteria (e.g., *Rhodospirillum* bacteria (e.g., *R. rubrum), Rhodobacter* bacteria (e.g., *R. sphaeroides, R. capsulatus*), and *Rhodomicrobium* bacteria (e.g., *R. vanellii*)).

Cells from non-microbial organisms can be utilized as a host cell. Examples of such cells, include, but are not limited to, insect cells (e.g., *Drosophila* (e.g., *D. melanogaster*), *Spodoptera* (e.g., *S. frugiperda* Sf9 or Sf21 cells) and *Trichoplusa* (e.g., High-Five cells); nematode cells (e.g., *C. elegans* cells); avian cells; amphibian cells (e.g., *Xenopus laevis* cells); reptilian cells; and mammalian cells (e.g., NIH3T3, 293, CHO, COS, VERO, C127, BHK, Per-C6, Bowes melanoma and HeLa cells).

Microorganisms or cells suitable for use as host cells in the invention are commercially available.

Eukaryotic cells have at least two separate pathways (one via homologous recombination (HR) and one via non-homologous recombination (NHR)) through which nucleic acids (in particular DNA) can be integrated into the host genome. The yeast *Saccharomyces cerevisiae* is an organism with a preference for homologous recombination (HR). The ratio of non-homologous to homologous recombination (NHR/HR) of this organism may vary from about 0.07 to 0.007.

WO 02/052026 discloses mutants of *S. cerevisiae* having an improved targeting efficiency of DNA sequences into its genome. Such mutant strains are deficient in a gene involved in NHR (KU70).

Contrary to *S. cerevisiae*, most higher eukaryotes such as filamentous fungal cells up to mammalian cells have a preference for NHR. Among filamentous fungi, the NHR/HR ratio ranges between 1 and more than 100. In such organisms, targeted integration frequency is rather low.

Thus, to improve the efficiency of polynucletide assembly at the target locus, it is preferred that the efficiency of homologous recombination (HR) is enhanced in the host cell in the method according to the invention.

Accordingly, preferably in the method according to the invention, the host cell is, preferably inducibly, increased in its efficiency of homologous recombination (HR).

Since the NHR and HR pathways are interlinked, the efficiency of HR can be increased by modulation of either one or both pathways. Increase of expression of HR components will increase the efficiency of HR and decrease the ratio of NHR/HR. Decrease of expression of NHR components will also decrease the ratio of NHR/HR The increase in efficiency of HR in the host cell of the vector-host system according to the invention is preferably depicted as a decrease in ratio of NHR/HR and is preferably calculated relative to a parent host cell wherein the HR and/or NHR pathways are not modulated. The efficiency of both HR and NHR can be measured by various methods available to the person skilled in the art. A preferred method comprises determining the efficiency of targeted integration and ectopic integration of a single vector construct in both parent and modulated host cell. The ratio of NHR/HR can then be calculated for both cell types. Subsequently, the decrease in NHR/HR ration can be calculated. In WO2005/095624, this preferred method is extensively described.

Host cells having a decreased NHR/HR ratio as compared to a parent cell may be obtained by modifying the parent eukaryotic cell by increasing the efficiency of the HR pathway and/or by decreasing the efficiency of the NHR pathway. Preferably, the NHR/HR ratio thereby is decreased at least twice, preferably at least 4 times, more preferably at least 10 times. Preferably, the NHR/HR ratio is decreased in the host cell of the vector-host system according to the invention as compared to a parent host cell by at least 5%, more preferably at least 10%, even more preferably at least 20%, even more preferably at least 30%, even more preferably at least 40%, even more preferably at least 50%, even more preferably at least 60%, even more preferably at least 70%, even more preferably at least 80%, even more preferably at least 90% and most preferably by at least 100%.

According to one embodiment, the ratio of NHR/HR is decreased by increasing the expression level of an HR component. HR components are well-known to the person skilled in the art. HR components are herein defined as all genes and elements being involved in the control of the targeted integration of polynucleotides into the genome of a host, said polynucleotides having a certain homology with a certain pre-determined site of the genome of a host wherein the integration is targeted.

The ratio of NHR/HR may be decreased by decreasing the expression level of an NHR component. NHR components are herein defined as all genes and elements being involved in the control of the integration of polynucleotides into the genome of a host, irrespective of the degree of homology of said polynucleotides with the genome sequence of the host. NHR components are well-known to the person skilled in the art.

Preferred NHR components are a component selected from the group consisting of the homolog or ortholog for the host cell of the vector-host system according to the invention of the yeast genes involved in the NHR pathway: KU70, KU80, RAD50, MRE11, XRS2, LIG4, LIF1, NEJ1 and SIR4 (van den Bosch et al., 2002, Biol. Chem. 383: 873-892 and Allen et al., 2003, Mol. Cancer Res. 1:913-920). Most preferred are one of KU70, KU80, and LIG4 and both KU70 and KU80. The decrease in expression level of the NHR component can be achieved using the methods as described herein for obtaining the deficiency of the essential gene.

Since it is possible that decreasing the expression of components involved in NHR may result in adverse phenotypic effects, it is preferred that in the host cell of the vector-host system according to the invention, the increase in efficiency in homologous recombination is inducible. This can be achieved by methods known to the person skilled in the art, for example by either using an inducible process for an NHR component (e.g. by placing the NHR component behind an inducible promoter) or by using a transient disruption of the NHR component, or by placing the gene encoding the NHR component back into the genome.

IN the invention, a marker gene (or selection marker or marker or similar) may be used. Any suitable marker gene may be used and such genes are well known to determine whether a nucleic acid is included in a cell. An assembled polynucleotide prepared according to the invention may comprise two or more marker genes, where one functions efficiently in one organism and another functions efficiently in another organism.

Examples of marker genes include, but are not limited to, (1) nucleic acid segments that encode products that provide resistance against otherwise toxic compounds (e.g., antibiotics); (2) nucleic acid segments that encode products that are otherwise lacking in the recipient cell (e.g., essential products, tRNA genes, auxotrophic markers); (3) nucleic acid segments that encode products that suppress the activity of a gene product; (4) nucleic acid segments that encode products that can be readily identified (e.g., phenotypic markers such as antibiotic resistance markers (e.g., β-lactamase), β-galactosidase, fluorescent or other coloured markers, such as green fluorescent protein (GFP), yellow fluorescent protein (YFP), red fluorescent protein (RFP) and cyan fluorescent protein (CFP), and cell surface proteins); (5) nucleic acid segments that bind products that are otherwise detrimental to cell survival and/or function; (6) nucleic acid segments that otherwise inhibit the activity of any of the nucleic acid segments as described in 1-5 above (e.g., antisense oligonucleotides); (7) nucleic acid segments that bind products that modify a substrate (e.g., restriction endonucleases); (8) nucleic acid segments that can be used to isolate or identify a desired molecule (e.g., specific protein binding sites); (9) nucleic acid segments that encode a specific nucleotide sequence that can be otherwise non-functional (e.g., for PCR amplification of subpopulations of molecules); (10) nucleic acid segments that, when absent, directly or indirectly confer resistance or sensitivity to particular compounds; (11) nucleic acid segments that encode products that either are toxic or convert a relatively non-toxic compound to a toxic compound (e.g., Herpes simplex thymidine kinase, cytosine deaminase) in recipient cells; (12) nucleic acid segments that inhibit replication, partition or heritability of nucleic acid molecules that contain them; (13) nucleic acid segments that encode conditional replication functions, e.g., replication in certain hosts or host cell strains or under certain environmental conditions (e.g., temperature, nutritional conditions, and the like); and/or an essential gene which is preferably a gene that has not been shown to be non-essential, more preferably, a gene whose deficiency renders the host cell non-viable. More preferably, an essential gene is a gene whose deficiency renders the host cell non-viable under all conditions and on any medium, in particular complex (undefined) medium. An essential gene in the context of the present invention may be a gene that renders the host cell non-viable when another (non-essential) gene has been rendered deficient.

Amino acid or nucleotide sequences are said to be homologous when exhibiting a certain level of similarity. Two sequences being homologous indicate a common evolutionary origin. Whether two homologous sequences are closely related or more distantly related is indicated by "percent identity" or "percent similarity", which is high or low respectively. Although disputed, to indicate "percent identity" or "percent similarity", "level of homology" or "percent homology" are frequently used interchangeably. For the purposes of the invention, a comparison of sequences and determination of percent identity between two sequences can be accomplished using a mathematical algorithm. The skilled person will be aware of the fact that several different computer programs are available to align two sequences and determine the homology between two sequences (Kruskal, J. B. (1983) An overview of sequence comparison In D. Sankoff and J. B. Kruskal, (ed.), Time warps, string edits and macromolecules: the theory and practice of sequence comparison, pp. 1-44 Addison Wesley).

The percent identity between two nucleic acid or amino acid sequences can be determined using the Needleman and Wunsch algorithm for the alignment of two sequences. (Needleman, S. B. and Wunsch, C. D. (1970) J. Mol. Biol. 48, 443-453). The algorithm aligns amino acid sequences as well as nucleotide sequences. The Needleman-Wunsch algorithm has been implemented in the computer program NEEDLE. For the purpose of this invention the NEEDLE program from the EMBOSS package was used (version 2.8.0 or higher, EMBOSS: The European Molecular Biology Open Software Suite (2000) Rice,P. Longden,l. and Bleasby, A. Trends in Genetics 16, (6) pp276-277, emboss.bioinformatics.nl/). For protein sequences, EBLOSUM62may be used for the substitution matrix. For nucleotide sequences, EDNAFULL may be used. Other matrices can be specified. The optional parameters used for alignment of amino acid sequences are a gap-open penalty of 10 and a gap extension penalty of 0.5. The skilled person will appreciate that all these different parameters will yield slightly different results but that the overall percentage identity of two sequences is not significantly altered when using different algorithms.

The homology or identity is the percentage of identical matches between the two full sequences over the total aligned region including any gaps or extensions. The homology or identity between the two aligned sequences may be calculated as follows: Number of corresponding positions in the alignment showing an identical amino acid or nucleic acid residue in both sequences divided by the total length of the alignment including the gaps. The identity defined as herein can be obtained from NEEDLE and is labelled in the output of the program as "IDENTITY".

The homology or identity between the two aligned sequences may be calculated as follows: Number of corresponding positions in the alignment showing an identical amino acid or nucleic acid residue in both sequences divided by the total length of the alignment after subtraction of the total number of gaps in the alignment. The identity defined as herein can be obtained from NEEDLE by using the NOBRIEF option and is labeled in the output of the program as "longest-identity".

Sequence identity can also be determined by hybridization assays conducted under stringent conditions. As use herein, the term "stringent conditions" refers to conditions for hybridization and washing. Stringent conditions are known to those skilled in the art and can be found in Current Protocols in Molecular Biology, John Wiley & Sons, N.Y., 6.3.1-6.3.6 (1989). Aqueous and non-aqueous methods are described in that reference and either can be used. An example of stringent hybridization conditions is hybridization in 6× sodium chloride/sodium citrate (SSC) at about 45° C., followed by one or more washes in 0.2×SSC, 0.1% SDS at 50° C. Another example of stringent hybridization conditions are hybridization in 6× sodium chloride/sodium citrate (SSC) at about 45° C., followed by one or more washes in 0.2×SSC, 0.1% SDS at 55° C. A further example of stringent hybridization conditions is hybridization in 6× sodium chloride/sodium citrate (SSC) at about 45° C., followed by one or more washes in 0.2×SSC, 0.1% SDS at 60° C. Often, stringent hybridization conditions are hybridization in 6× sodium chloride/sodium citrate (SSC) at about 45° C., followed by one or more washes in 0.2×SSC, 0.1% SDS at 65° C. More often, stringency conditions are 0.5M sodium phosphate, 7% SDS at 65° C., followed by one or more washes at 0.2×SSC, 1 SDS at 65° C.

A reference herein to a patent document or other matter which is given as prior art is not to be taken as an admission that that document or matter was known or that the information it contains was part of the common general knowledge as at the priority date of any of the claims.

The disclosure of each reference set forth herein is incorporated herein by reference in its entirety.

The present invention is further illustrated by the following Examples:

EXAMPLES

General

Standard genetic techniques, such as overexpression of enzymes in the host cells, as well as for additional genetic modification of host cells, are known methods in the art, such as described in Sambrook and Russel (2001) "Molecular Cloning: A Laboratory Manual ($3^{rd}$ edition), Cold Spring Harbor Laboratory, Cold Spring Harbor Laboratory Press, or F. Ausubel et al, eds., "Current protocols in molecular biology", Green Publishing and Wiley Interscience, New York (1987).

Chromosomal DNA Isolation from Yeast

Yeast cells were grown in YEP-medium containing 2% glucose, in a rotary shaker (overnight, at 30° C. and 280 rpm). 1.5 ml of these cultures were transferred to an eppendorf tube and centrifuged for 1 minute at maximum speed. The supernatant was decanted and the pellet was resuspended in 200 µl of YCPS (0.1% SB3-14 (Sigma Aldrich, the Netherlands) in 10 mM Tris.HCl pH 7.5; 1 mM EDTA) and 1 µl RNase (20 mg/ml RNase A from bovine pancreas, Sigma, the Netherlands). The cell suspension was incubated for 10 minutes at 65° C. The suspension was centrifuged in an Eppendorf centrifuge for 1 minute at 7000 rpm. The supernatant was discarded. The pellet was carefully dissolved in 200 µl CLS (25 mM EDTA, 2% SDS) and 1 µl RNase A. After incubation at 65° C. for 10 minutes, the suspension was cooled on ice. After addition of 70 µl PPS (10M ammonium acetate) the solutions were thoroughly mixed on a Vortex mixer. After centrifugation (5 minutes in Eppendorf centrifuge at maximum speed), the supernatant was mixed with 200 µl ice-cold isopropanol. The DNA readily precipitated and was pelleted by centrifugation (5 minutes, maximum speed). The pellet was washed with 400 µl ice-cold 70% ethanol. The pellet was dried at room temperature and dissolved in 50 ill TE (10 mM Tris.HCl pH7.5, 1 mM EDTA).

General Methods for *Rasamsonia emersonii*

Strains

*Rasamsonia* (*Talaromyces*) *emersonii* strain TEC-142 is deposited at CENTRAAL BUREAU VOOR SCHIMMELCULTURES, Uppsalalaan 8, P.O. Box 85167, NL-3508 AD Utrecht, The Netherlands on 1 Jul. 2009 having the Accession Number CBS 124902. TEC-142S is a single isolate of TEC-142.

Other suitable strains, such as strains described above, can be equally used in the present examples to show the effect and advantages of the invention. For example TEC-101, TEC-142, TEC-192, TEC-201 or TEC-210 are suitable *Rasamsonia* strains which are described in WO2011/000949, Media and Solutions:

Potato dextrose agar, PDA, (Fluka, Cat. No. 70139): per litre: Potato extrac 4 g; Dextrose 20 g; Bacto agar 15 g; pH 5.4; Sterilize 20 min at 120° C.

*Rasamsonia* agar medium: per litre: Salt fraction no. 3 15 g; Cellulose 30 g; Bacto peptone 7.5 g; Grain flour 15 g; KH2PO4 5 g; CaCl2.2aq 1 g; Bacto agar 20 g; pH 6.0; Sterilize 20 min at 120° C.

Salt fraction composition: The "salt fraction no. 3" was fitting the disclosure of WO98/37179, Table 1. Deviations from the composition of this table were CaCl2.2aq 1.0 g/l, KCl 1.8 g/L, citric acid 1 aq 0.45 g/L (chelating agent).

Shake Flask Media for *Rasamsonia*

*Rasamsonia* medium 1: Per litre: Glucose 20 g; Yeast extract (Difco) 20 g; Clerol FBA3107 (AF) 4 drops; MES 30 g; pH 6.0; Sterilize 20 min at 120° C.

*Rasamsonia* medium 2: Per litre: Salt fraction no. 3 10 g; glucose 10 g; KH2PO4 5 g; NaH2PO4 2 g; (NH4)2SO4 5 g; MES 30 g; pH 5.4; Sterilize 20 min at 120° C.

*Rasamsonia* medium 3: Per litre: Salt fraction no. 3 10 g; cellulose 20 g; KH2PO4 5 g; NaH2PO4 2 g; (NH4)2SO4 5 g; MES 30 g; pH 5.4; Sterilize 20 min at 120° C.

*Rasamsonia* medium 4: Per litre: Salt fraction no. 3 10 g; cellulose 15 g; glucose 5 g; KH2PO4 5 g; NaH2PO4 2 g; (NH4)2SO4 5 g; MES 30 g; pH 5.4; Sterilize 20 min at 120° C.

Spore Batch Preparation for *Rasamsonia*

Strains were grown from stocks on *Rasamsonia* agar medium in 10 cm diameter Petri dishes for 5-7 days at 40° C. For MTP fermentations, strains were grown in 96-well plates containing *Rasamsonia* agar medium. Strain stocks were stored at −80° C. in 10% glycerol.

Chromosomal DNA Isolation

Strains were grown in YGG medium (per liter: 8 g KCI, 16 g glucose.H20, 20 ml of 10% yeast extract, 10 ml of 100×pen/strep, 6.66 g YNB+amino acids, 1.5 g citric acid, and 6 g K2HPO4). for 16 hours at 42° C., 250 rpm, and chromosomal DNA was isolated using the DNEASY® plant mini kit (Qiagen, Hilden, Germany).

Shake Flask Growth Protocol of *Rasamsonia*

Spores were inoculated into 100 ml shake flasks containing 20 ml of *Rasamsonia* medium 1 and incubated at 45° C. at 250 rpm in an incubator shaker for 1 day (preculture 1) and 1 or 2 ml of biomass from preculture 1 was transferred to 100 ml shake flasks containing 20 ml of *Rasamsonia* medium 2 and grown under conditions as described above for 1 day (preculture 2). Subsequently, 1 or 2 ml of biomass from preculture 2 was transferred to 100 ml shake flasks containing 20 ml of *Rasamsonia* medium 3 or 4 and grown under conditions described above for 3 days.

Protein Analysis

Protein samples were separated under reducing conditions on NuPAGE 4-12% Bis-Tris gel (Invitrogen, Breda, The Netherlands) and stained. Gels were stained with either InstantBlue (Expedeon, Cambridge, United Kingdom), SimplyBlue safestain (Invitrogen, Breda, The Netherlands) or Sypro Ruby (Invitrogen, Breda, The Netherlands) according to manufacturer's instructions.

Total Protein Content

Protein content of the recovered supernatant was determined according to Bradford method. The amount of protein in the enzyme samples was determined with Bradford Protein assay, using Coomassie protein reagent. 25 µl of appropriately diluted enzyme sample was mixed with 1.2 ml Coomassie reagent. After 10 minutes at room temperature the absorbance of the mixture at 595 nm was determined using a spectrophotometer (Uvikon XL). Protein content was calculated in comparison to BSA standard.

Corn Stover Assay

In order to measure cellulase activity a corn stover activity assay was performed. Cellulase activity was measured in supernatants (the liquid part of the broth wherein the cells were cultured) of an empty strain and the transformant:

Preparation of Pre-Treated, Corn Stover Substrate.

Dilute-acid pre-treated corn stover was obtained as described in Schell, D. J., Applied Biochemistry and Biotechnology (2003), vol. 105-108, pp 69-85. A pilot scale pretreatment reactor was used operating at steady state conditions of 190° C., 1 min residence time and an effective H2SO4 acid concentration of 1.45% (w/w) in the liquid phase.

Measurement of Cellulase Activity on 2% Unwashed Acid Pretreated Corn Stover

Since glucose release by cellulases is not a linear function of the quantity of enzyme in the composition, in other words, twice the amount of enzyme does not automatically result in twice the amount of glucose at a fixed time point. Therefore the activity of the cellulose enzyme mixture has been assessed in a dose response based assay, in which the dosage is based on equal amount of protein per cellulose mixture tested.

Overall cellulase activity of the mixture measured with unwashed acid pretreated corn stover as substrate. The frozen enzyme samples were thawed and a series of 6 dilutions was made ranging from undiluted in steps of two-fold up to 32-fold in 50 mM citrate buffer pH 4.5.

200 µl of sample was transferred to a vial containing 800 µL of 2.5% (w/w) dry matter of the acid pretreated corn stover in 50 mM citrate buffer, buffered at pH 4.5. Another 200 µl sample was transferred to a vial, referred to as blank, containing 800 µl of 50 mM citrate buffer, buffered at pH 4.5. In addition, a sugar background of corn stover was determined by incubating 800 µL 2.5% (w/w) dry matter of the acid pretreated corn stover in 50 mM citrate buffer, buffered at pH 4.5 with 200 µl of 50 mM citrate buffer. All vials were incubated for 72 hr at 65° C.

After incubation, 100 µl of internal standard solution (20 g/L maleic acid, 40 g/L EDTA in D2O) was added to the vials. All vials containing pretreated corn stover were centrifuged for 30 minutes at 5300 g and, subsequently, 600 µl of the supernatant was transferred to a new vial containing 400 µl of H2O/D2O 9:1.

The 1D 1H-NMR spectra were recorded on an Avance III Bruker operating at a proton frequency of 500 MHz, using a pulse program with water suppression, at a temperature of 27° C. Glucose quantification (arbitrary units) was performed based on the signal at 5.20 ppm, relative to 4,4-Dimethyl-4-silapentane sulfonic acid with relation to the internal standard signal at 6.30 ppm. The relative glucose release (ΔGlc) was calculated by correcting the glucose measured in the samples by the residual sugar present in the enzyme solution (measured from the blank) and the residual sugar present in the acid pretreated corn stover.

Since the protein concentration of the samples was known the sugar release can be depicted as a function of protein mg/ml of the tested diluted sample versus the relative glucose release at time point 72 hours.

Example 1

Standardized Pathway Building System for Yeast 1.1 General Introduction to the Standardized Pathway Building System for Yeast This method enables the fast introduction of genes/pathways with large flexibility into the yeast (*S. cerevisiae*) genome. Level One (see FIG. 9) is focused on cloning so-called standardized genetic elements, promoters, open reading frame's (ORF's) and terminators into functional expression cassettes flanked by standardized 50 bp connectors using a method called "Golden Gate Cloning" (Engler C. et al (2008) PLoS ONE 3(11): e3647 and Engler C. et al (2009) PLoS ONE 4 (5): e5553

The standardized 50 bp connectors are part of the backbone entry vectors and are used in Level Two (see FIG. 9) where the standardized 50 bp connectors provide the necessary homology between multiple expression cassettes, so that they to built up and integrated as pathways via in vivo homologous recombination into the yeast genome.

Standardization of the design of the desired genetic elements (e.g. promoter, open reading frame (ORF) and terminator) in combination with the use of standardized connectors, enables maximal speed and flexibility during cloning and transformations.

Figure 9A:
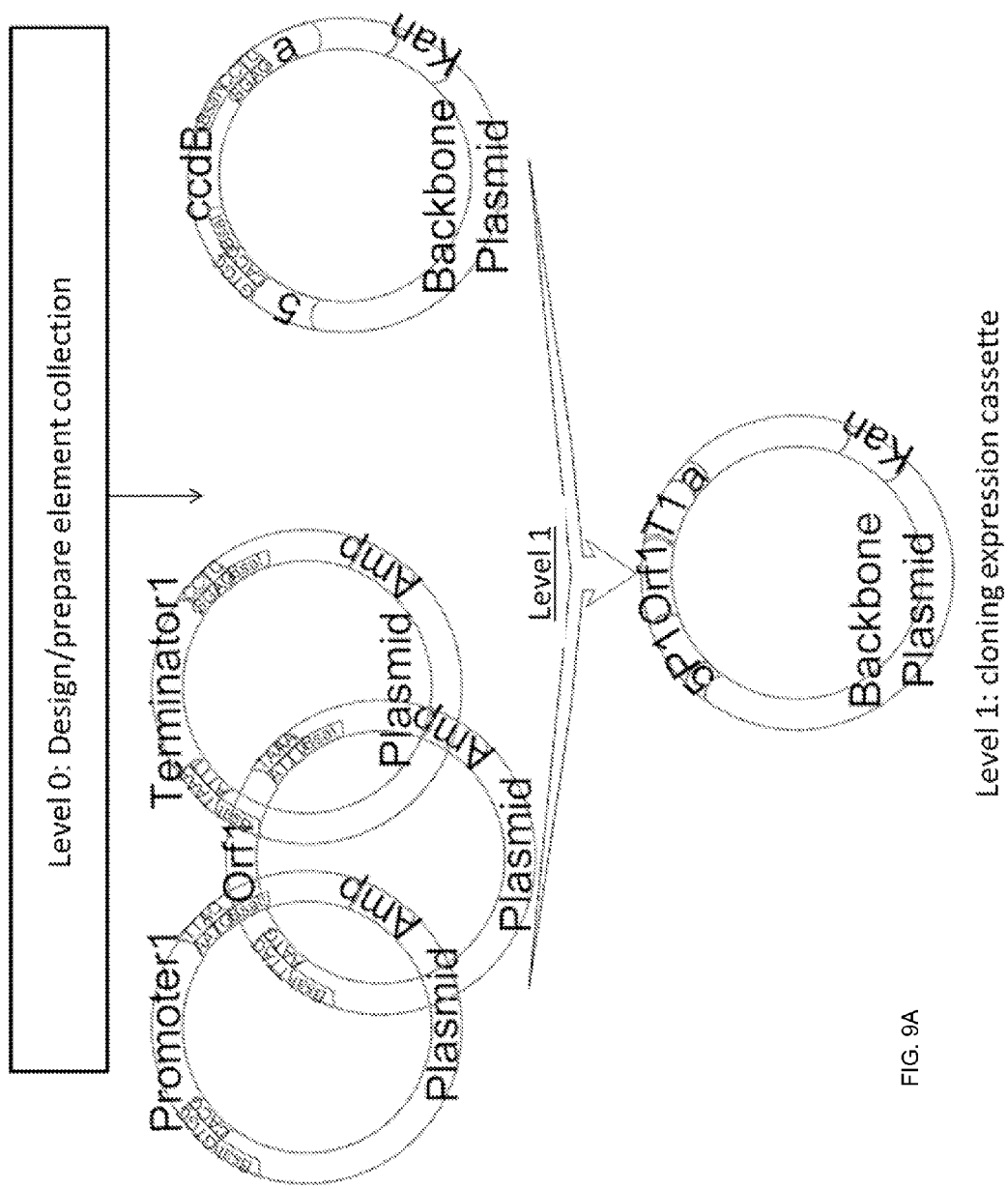
FIGS. 9A and 9B show the general scheme of the 2-step pathway building method, a fast, efficient and flexible method due to the standardized genetic elements for the golden gate cloning combined with the standardized connectors providing homology for the in vivo recombination.
Figure 9B:
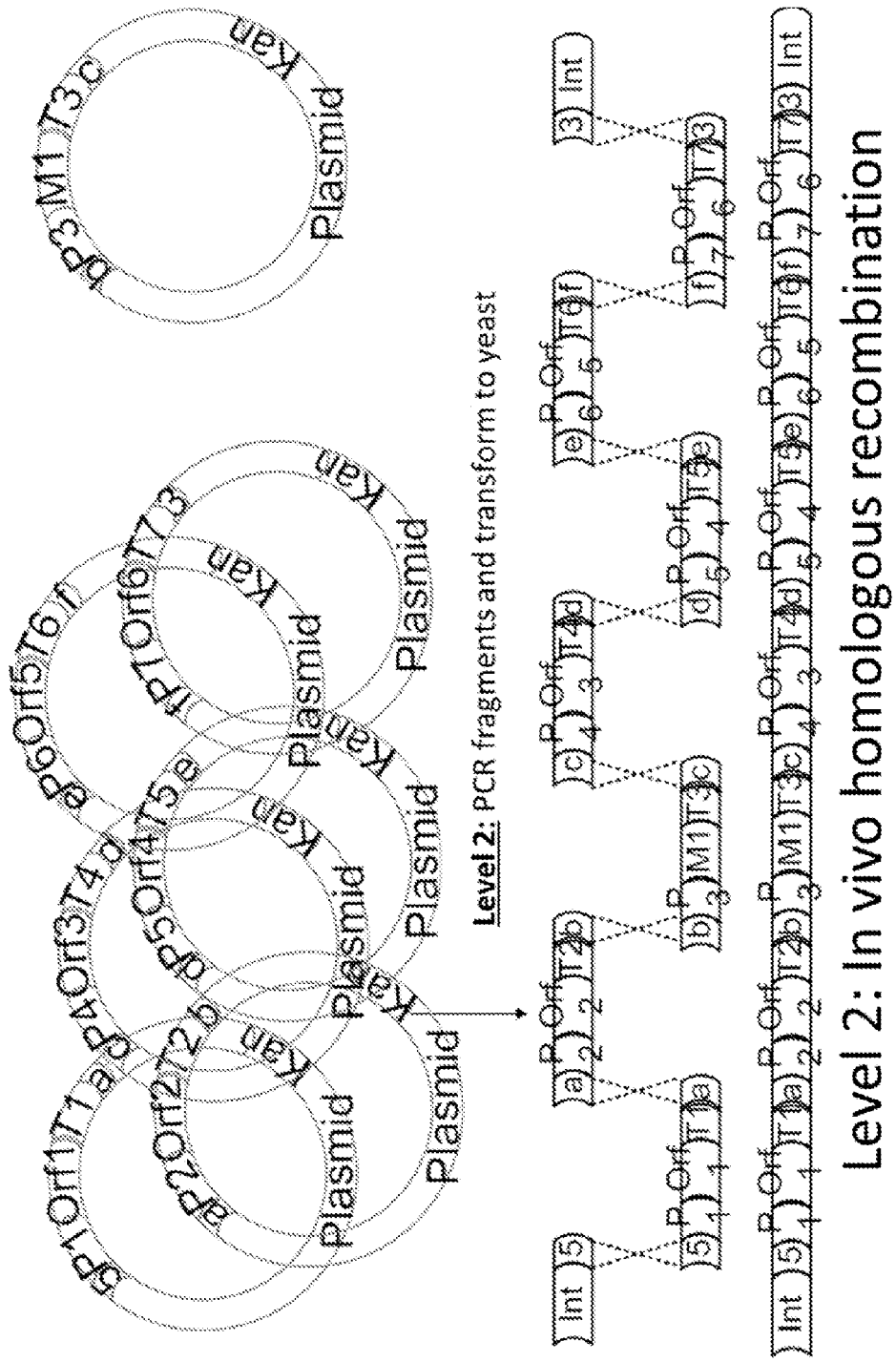

FIG. 9 is a schematic representation of the standardized pathway building method. In the Example described herein, the method was used to determine the influence of a set of promoters and terminators on the expression of five selected reporter genes.

1.2 Design of the Genetic Elements Promoter, ORF and Terminator

Each genetic element was designed to a standard so that it is possible to clone the elements with the typeIIS restriction enzyme BsaI into a vector, thus creating a functional expression cassette comprising a promoter, ORF and terminator.

First, all elements were cured of internal BsaI sites by the introduction of a point mutation. For ORF's, changes in amino-acid sequences were avoided. For promoters and terminators, the point mutation was chosen so as not to affect, to the best of our knowledge, the functionality of the element. Each element was provided with a 4nt bridges at both sides in combination with a BsaI recognition site. The BsaI recognition site was placed so that cutting with the type IIS restriction enzyme created the standardized 4 nucleotide overhang, referred to "the bridge". In this way, a set of 30 promoters (SEQ ID NOs: 1 to 30), 5 ORF's (reporter genes; SEQ ID NOs: 31 to 35) and 14 terminators (SEQ ID NOs: 36 to 49) were designed. The specific rules for each element are described hereafter in more detail, starting with rules for promoters, followed by ORF's and terminators.

Specific design rules for promoters
  as stated before, all BsaI sites were removed from the promoter sequence
  a standardized size was set to 600 base pairs for most promoters; exceptions were made where previously it had been shown that a larger or shorter promoter was a better choice or had historically been set to a certain length
sequence:

```
5'GGTCTCGGTGC (SEQ ID NO: 146)+
(promoter sequence-the last bp)+

AATGGGAGACC (SEQ ID NO: 147)3'
```

GTGC (underlined) on the 5' part of the promoter is the 4 nucleotide sequence bridge to the backbone entry vector (discussed in 1.3)
  AATG (underlined) on the 3'part of the promoter is the 4 nucleotide sequence bridge to the ORF, where ATG is the start codon of the ORF and the first A of the AATG is a standardized last base pair A of the promoter sequence Specific design rules for ORF's
  all BsaI sites were removed from the ORF sequence
sequence

```
5'GGTCTCGAATG (SEQ ID NO: 148)+
(ORFsequence)+TAAAGGAGACC (SEQ ID NO: 149)3'
``` the ORF sequence is without stop and start codon (included in 4 nt bridges)
  AATG (underlined) on the 5' part of the ORF is the 4 nucleotide bridge to the promoter sequence
  TAAA (underlined) on the 3' part of the ORF is the 4 nucleotide bridge to the terminator sequence Specific design rules for terminators
  all BsaI sites were removed from the terminator sequence
sequence

```
5'GGTCTCGTAAA+ (SEQ ID NO: 150)
(Terminator sequence)+CCTCGGAGACC
(SEQ ID NO: 151)3'
```

TAAA (underlined) on the 5' part of the terminator is the 4 nucleotide bridge to the ORF sequence CCTC (underlined) on the 3' part of the terminator is the 4 nucleotide bridge to the backbone entry vector (discussed in 1.3)

All of the genetic elements (promoter, ORF and terminators) were synthesized and cloned by DNA2.0 (Menlo Park, Calif. USA) in a standard vector having the *E. coli* ampicillin resistance marker. The standard *E. coli* cloning vector used by DNA2.0 is set out in SEQ ID NO: 50.

1.3 Design of the Backbone Entry Vector

The backbone entry vector was constructed with two BsaI sites that, after cutting, create the 4 nucleotide bridges/sticky ends to clone in an expression vector (i.e. an assembled promoter, ORF and terminator combination). To improve the efficiency of the Golden Gate Cloning reaction, a ccdB gene for counter selection in *E. coli* was positioned between the BsaI sites. This prevented the selection of original backbone vector. Furthermore, the backbone entry vector had the selection marker kanamycin for propagation of the backbone plasmid in *E. coli*, as opposed to the ampicillin marker for vectors containing the input elements (promoter, ORF and terminator). Selection on kanamycin was therefore used to prevent unwanted selection of the element vectors.

Another important feature of the backbone entry vectors were the standardized 50 bp sequences that are referred to as "connectors". The connectors provided the necessary homology for recombination in Level 2 of the standardized pathway building method. The connectors flanked the 4nt bridges in such a way that after cloning of the promoter, ORF and terminator in the vector, the created expression cassette was flanked by a connector on the left and right.

Thirteen unique 50 bp connectors, named connector 5, connector A to connector K and connector 3, (SEQ ID NOs: 51 to 63) were designed with random sequences not containing any homology to the yeast genome. These connector sequences were used to design the 22 backbone vectors listed in Table 1.

TABLE 1

All backbone entry vectors with their connectors and corresponding SEQ ID identifier

| Backbone entry vectors | Connectors | | SEQ ID NO: |
|---|---|---|---|
| Sc 5a.bbn | Left connector 5 | Right connector a | SEQ ID NO: 64 |
| Sc ab.bbn | Left connector a | Right connector b | SEQ ID NO: 65 |
| Sc bc.bbn | Left connector b | Right connector c | SEQ ID NO: 66 |
| Sc cd.bbn | Left connector c | Right connector d | SEQ ID NO: 67 |
| Sc de.bbn | Left connector d | Right connector e | SEQ ID NO: 68 |
| Sc ef.bbn | Left connector e | Right connector f | SEQ ID NO: 69 |
| Sc fg.bbn | Left connector f | Right connector g | SEQ ID NO: 70 |
| Sc gh.bbn | Left connector g | Right connector h | SEQ ID NO: 71 |
| Sc hi.bbn | Left connector h | Right connector i | SEQ ID NO: 72 |
| Sc ij.bbn | Left connector i | Right connector j | SEQ ID NO: 73 |
| Sc jk.bbn | Left connector j | Right connector k | SEQ ID NO: 74 |
| Sc a3.bbn | Left connector a | Right connector 3 | SEQ ID NO: 75 |
| Sc b3.bbn | Left connector b | Right connector 3 | SEQ ID NO: 76 |
| Sc c3.bbn | Left connector c | Right connector 3 | SEQ ID NO: 77 |
| Sc d3.bbn | Left connector d | Right connector 3 | SEQ ID NO: 78 |
| Sc e3.bbn | Left connector e | Right connector 3 | SEQ ID NO: 79 |
| Sc f3.bbn | Left connector f | Right connector 3 | SEQ ID NO: 80 |
| Sc g3.bbn | Left connector g | Right connector 3 | SEQ ID NO: 81 |
| Sc h3.bbn | Left connector h | Right connector 3 | SEQ ID NO: 82 |
| Sc i3.bbn | Left connector i | Right connector 3 | SEQ ID NO: 83 |
| Sc j3.bbn | Left connector j | Right connector 3 | SEQ ID NO: 84 |
| Sc k3.bbn | Left connector k | Right connector 3 | SEQ ID NO: 85 |

The sequences listed as SEQ ID NOs: 64 to 85 were the specific sequences synthesized and cloned into a standard *E. coli* vector by DNA2.0 to create the backbone vectors. The *E. coli* vector used for cloning SEQ ID NOs: 64 to 85 contained the kanamycin marker and its sequence is listed as SEQ ID NO: 86.

The backbone vectors fulfil two important functions. One, they contained the bridges to the promoter and terminator making it possible to close the circle in the Golden Gate reaction. Two, they decorated the expression cassettes with the connectors for the in vivo recombination step (referred to as Level 2). For example, cloning an expression cassette with the Golden Gate reaction in the Sc 5A.bbn will equip the expression cassette on the left part with connector 5 and on the right part with connector A. The group of backbone entry vectors with the designed connectors, listed in Table 1, were ordered and synthesized at DNA2.0 (Menlo Park, Calif. USA). All features of the backbone entry vectors are summarized hereafter.

Summarizing the specific design for the backbones

*E. coli* vector sequence with kanamycin marker (SEQ ID NO: 86)

two BsaI sites creating after the cut 4 nt bridges compatible with the bridge on the 5' of the promoter and the 3' of the terminator counterselection with ccdB sequence located between the BsaI sites connector sequences left and right from the bridges the design of the actual sequences ordered and cloned in the vector by DNA2.0:

```
5'L con - GTGCGGAGACC (SEQ ID NO: 152) -
ccdB sequence -

GGTCTCGCCTC (SEQ ID NO: 153) - R con 3'
```

GTGC (underlined) bridge to 5' part of the promoter

CCTC (underlined) bridge to the 3' part of the terminator

"L con" and "R con" are the left connector sequence and right connector sequence respectively 1.4 Assembly of Expression Cassettes with Golden Gate Cloning Assembly was carried out as described in the Golden Gate cloning publications (Engler C. et al (2008) PLoS ONE 3(11): e3647 and Engler C. et al (2009) PLoS ONE 4 (5): e5553. In a one pot reaction, BsaI and ligase was added in combination with the three element input vectors and the backbone entry vectors. The most preferred reaction conditions were 50 cycle reactions of 2 minutes 37° C. and 5 minutes 16° C. Typically, 2 clones were checked by sequencing the complete insert. When both clones showed incorrect, additional clones were checked with sequencing. A list of all assembled expression cassettes can be found in table 2.

TABLE 2

An overview of all expression cassettes cloned into the
backbone entry vectors with the golden gate reaction

| Assembly nr | Promoter element | ORF element | Terminator element | Backbone |
|---|---|---|---|---|
| Assembly 1 | Sc ENO1.pro | vGFP | ADH1 terminator | Sc 5a.bbn |
| Assembly 2 | Sc PDC1.pro | vGFP | ADH1 terminator | Sc 5a.bbn |
| Assembly 3 | Sc ENO2.pro | vGFP | ADH1 terminator | Sc 5a.bbn |
| Assembly 4 | Sc FBA1.pro | vGFP | ADH1 terminator | Sc 5a.bbn |
| Assembly 5 | Sc PGI1.pro | vGFP | ADH1 terminator | Sc 5a.bbn |
| Assembly 6 | Sc PGK1.pro | vGFP | ADH1 terminator | Sc 5a.bbn |
| Assembly 7 | Sc GPM1.pro | vGFP | ADH1 terminator | Sc 5a.bbn |
| Assembly 8 | Sc PMA1_1.pro | vGFP | ADH1 terminator | Sc 5a.bbn |
| Assembly 9 | Sc OYE2.pro | vGFP | ADH1 terminator | Sc 5a.bbn |
| Assembly 10 | Sc TAL1.pro | vGFP | ADH1 terminator | Sc 5a.bbn |
| Assembly 11 | Sc TDH1.pro | vGFP | ADH1 terminator | Sc 5a.bbn |
| Assembly 12 | Sc TDH3.pro | vGFP | ADH1 terminator | Sc 5a.bbn |
| Assembly 13 | Sc TEF1.pro | vGFP | ADH1 terminator | Sc 5a.bbn |
| Assembly 14 | Sc TPI1.pro | vGFP | ADH1 terminator | Sc 5a.bbn |
| Assembly 15 | Sc ACT1.pro | vGFP | ADH1 terminator | Sc 5a.bbn |
| Assembly 16 | Ag Tef1.pro | vGFP | ADH1 terminator | Sc 5a.bbn |
| Assembly 17 | Sc PRE3.pro | vGFP | ADH1 terminator | Sc 5a.bbn |
| Assembly 18 | Sc VPS68.pro | vGFP | ADH1 terminator | Sc 5a.bbn |
| Assembly 19 | Sc ENO1.pro | LacZ | ADH2 terminator | Sc bc.bbn |
| Assembly 20 | Sc PDC1.pro | LacZ | ADH2 terminator | Sc bc.bbn |
| Assembly 21 | Sc ENO2.pro | LacZ | ADH2 terminator | Sc bc.bbn |
| Assembly 22 | Sc FBA1.pro | LacZ | ADH2 terminator | Sc bc.bbn |
| Assembly 23 | Sc PGI1.pro | LacZ | ADH2 terminator | Sc bc.bbn |
| Assembly 24 | Sc PGK1.pro | LacZ | ADH2 terminator | Sc bc.bbn |
| Assembly 25 | Sc GPM1.pro | LacZ | ADH2 terminator | Sc bc.bbn |
| Assembly 26 | Sc PMA1_1.pro | LacZ | ADH2 terminator | Sc bc.bbn |
| Assembly 27 | Sc OYE2.pro | LacZ | ADH2 terminator | Sc bc.bbn |
| Assembly 28 | Sc TAL1.pro | LacZ | ADH2 terminator | Sc bc.bbn |
| Assembly 29 | Sc TDH1.pro | LacZ | ADH2 terminator | Sc bc.bbn |
| Assembly 30 | Sc TDH3.pro | LacZ | ADH2 terminator | Sc bc.bbn |
| Assembly 31 | Sc TEF1.pro | LacZ | ADH2 terminator | Sc bc.bbn |
| Assembly 32 | Sc TPI1.pro | LacZ | ADH2 terminator | Sc bc.bbn |
| Assembly 33 | Sc ACT1.pro | LacZ | ADH2 terminator | Sc bc.bbn |
| Assembly 34 | Ag Tef1.pro | LacZ | ADH2 terminator | Sc bc.bbn |
| Assembly 35 | Sc PRE3.pro | LacZ | ADH2 terminator | Sc bc.bbn |
| Assembly 36 | Sc VPS68.pro | LacZ | ADH2 terminator | Sc bc.bbn |
| Assembly 37 | Sc ENO1.pro | RFP | ENO1 terminator | Sc c3.bbn |
| Assembly 38 | Sc PDC1.pro | RFP | ENO1 terminator | Sc c3.bbn |
| Assembly 39 | Sc ENO2.pro | RFP | ENO1 terminator | Sc c3.bbn |
| Assembly 40 | Sc FBA1.pro | RFP | ENO1 terminator | Sc c3.bbn |
| Assembly 41 | Sc PGI1.pro | RFP | ENO1 terminator | Sc c3.bbn |
| Assembly 42 | Sc PGK1.pro | RFP | ENO1 terminator | Sc c3.bbn |
| Assembly 43 | Sc GPM1.pro | RFP | ENO1 terminator | Sc c3.bbn |
| Assembly 44 | Sc PMA1_1.pro | RFP | ENO1 terminator | Sc c3.bbn |
| Assembly 45 | Sc OYE2.pro | RFP | ENO1 terminator | Sc c3.bbn |
| Assembly 46 | Sc TAL1.pro | RFP | ENO1 terminator | Sc c3.bbn |
| Assembly 47 | Sc TDH1.pro | RFP | ENO1 terminator | Sc c3.bbn |
| Assembly 48 | Sc TDH3.pro | RFP | ENO1 terminator | Sc c3.bbn |
| Assembly 49 | Sc TEF1.pro | RFP | ENO1 terminator | Sc c3.bbn |
| Assembly 50 | Sc TPI1.pro | RFP | ENO1 terminator | Sc c3.bbn |
| Assembly 51 | Sc ACT1.pro | RFP | ENO1 terminator | Sc c3.bbn |
| Assembly 52 | Ag Tef1.pro | RFP | ENO1 terminator | Sc c3.bbn |
| Assembly 53 | Sc PRE3.pro | RFP | ENO1 terminator | Sc c3.bbn |
| Assembly 54 | Sc VPS68.pro | RFP | ENO1 terminator | Sc c3.bbn |
| Assembly 55 | Sc ACT1.pro | vGFP | ADH1 terminator | Sc 5a.bbn |
| Assembly 56 | Sc ACT1.pro | vGFP | ADH2 terminator | Sc 5a.bbn |
| Assembly 57 | Sc ACT1.pro | vGFP | ENO1 terminator | Sc 5a.bbn |
| Assembly 58 | Sc ACT1.pro | vGFP | GPM1 terminator | Sc 5a.bbn |
| Assembly 59 | Sc ACT1.pro | vGFP | PDC1 terminator | Sc 5a.bbn |
| Assembly 60 | Sc ACT1.pro | vGFP | PGI1 terminator | Sc 5a.bbn |
| Assembly 61 | Sc ACT1.pro | vGFP | PGK1 terminator | Sc 5a.bbn |
| Assembly 62 | Sc ACT1.pro | vGFP | PMA1 terminator | Sc 5a.bbn |
| Assembly 63 | Sc ACT1.pro | vGFP | TAL1 terminator | Sc 5a.bbn |
| Assembly 64 | Sc ACT1.pro | vGFP | TDH1 terminator | Sc 5a.bbn |
| Assembly 65 | Sc ACT1.pro | vGFP | TDH3 terminator | Sc 5a.bbn |
| Assembly 66 | Sc ACT1.pro | vGFP | TEF1 terminator | Sc 5a.bbn |
| Assembly 67 | Sc ACT1.pro | vGFP | TEF2 terminator | Sc 5a.bbn |
| Assembly 68 | Sc ACT1.pro | vGFP | TPI1 terminator | Sc 5a.bbn |
| Assembly 69 | Sc ENO1.pro | GFPmut3 | ADH1 terminator | Sc 5a.bbn |
| Assembly 70 | Sc PDC1.pro | GFPmut3 | ADH1 terminator | Sc 5a.bbn |
| Assembly 71 | Sc ENO2.pro | GFPmut3 | ADH1 terminator | Sc 5a.bbn |
| Assembly 72 | Sc FBA1.pro | GFPmut3 | ADH1 terminator | Sc 5a.bbn |
| Assembly 73 | Sc PGI1.pro | GFPmut3 | ADH1 terminator | Sc 5a.bbn |
| Assembly 74 | Sc PGK1.pro | GFPmut3 | ADH1 terminator | Sc 5a.bbn |

TABLE 2-continued

An overview of all expression cassettes cloned into the backbone entry vectors with the golden gate reaction

| Assembly nr | Promoter element | ORF element | Terminator element | Backbone |
|---|---|---|---|---|
| Assembly 75 | Sc GPM1.pro | GFPmut3 | ADH1 terminator | Sc 5a.bbn |
| Assembly 76 | Sc PMA1_1.pro | GFPmut3 | ADH1 terminator | Sc 5a.bbn |
| Assembly 77 | Sc OYE2.pro | GFPmut3 | ADH1 terminator | Sc 5a.bbn |
| Assembly 78 | Sc TAL1.pro | GFPmut3 | ADH1 terminator | Sc 5a.bbn |
| Assembly 79 | Sc TDH1.pro | GFPmut3 | ADH1 terminator | Sc 5a.bbn |
| Assembly 80 | Sc TDH3.pro | GFPmut3 | ADH1 terminator | Sc 5a.bbn |
| Assembly 81 | Sc TEF1.pro | GFPmut3 | ADH1 terminator | Sc 5a.bbn |
| Assembly 82 | Sc TPI1.pro | GFPmut3 | ADH1 terminator | Sc 5a.bbn |
| Assembly 83 | Sc ACT1.pro | GFPmut3 | ADH1 terminator | Sc 5a.bbn |
| Assembly 84 | Ag Tef1.pro | GFPmut3 | ADH1 terminator | Sc 5a.bbn |
| Assembly 85 | Sc PRE3.pro | GFPmut3 | ADH1 terminator | Sc 5a.bbn |
| Assembly 86 | Sc VPS68.pro | GFPmut3 | ADH1 terminator | Sc 5a.bbn |
| Assembly 87 | Sc ENO1.pro | GFP-pest | ADH1 terminator | Sc 5a.bbn |
| Assembly 88 | Sc PDC1.pro | GFP-pest | ADH1 terminator | Sc 5a.bbn |
| Assembly 89 | Sc ENO2.pro | GFP-pest | ADH1 terminator | Sc 5a.bbn |
| Assembly 90 | Sc FBA1.pro | GFP-pest | ADH1 terminator | Sc 5a.bbn |
| Assembly 91 | Sc PGI1.pro | GFP-pest | ADH1 terminator | Sc 5a.bbn |
| Assembly 92 | Sc PGK1.pro | GFP-pest | ADH1 terminator | Sc 5a.bbn |
| Assembly 93 | Sc GPM1.pro | GFP-pest | ADH1 terminator | Sc 5a.bbn |
| Assembly 94 | Sc PMA1_1.pro | GFP-pest | ADH1 terminator | Sc 5a.bbn |
| Assembly 95 | Sc OYE2.pro | GFP-pest | ADH1 terminator | Sc 5a.bbn |
| Assembly 96 | Sc TAL1.pro | GFP-pest | ADH1 terminator | Sc 5a.bbn |
| Assembly 97 | Sc TDH1.pro | GFP-pest | ADH1 terminator | Sc 5a.bbn |
| Assembly 98 | Sc TDH3.pro | GFP-pest | ADH1 terminator | Sc 5a.bbn |
| Assembly 99 | Sc TEF1.pro | GFP-pest | ADH1 terminator | Sc 5a.bbn |
| Assembly 100 | Sc TPI1.pro | GFP-pest | ADH1 terminator | Sc 5a.bbn |
| Assembly 101 | Sc ACT1.pro | GFP-pest | ADH1 terminator | Sc 5a.bbn |
| Assembly 102 | Ag Tef1.pro | GFP-pest | ADH1 terminator | Sc 5a.bbn |
| Assembly 103 | Sc PRE3.pro | GFP-pest | ADH1 terminator | Sc 5a.bbn |
| Assembly 104 | Sc VPS68.pro | GFP-pest | ADH1 terminator | Sc 5a.bbn |
| Assembly 105 | KLLA0A09185g | vGFP | ADH1 terminator | Sc 5a.bbn |
| Assembly 106 | KLLA0A11011g | vGFP | ADH1 terminator | Sc 5a.bbn |
| Assembly 107 | KLLA0B08998g | vGFP | ADH1 terminator | Sc 5a.bbn |
| Assembly 108 | KLLA0B14839g | vGFP | ADH1 terminator | Sc 5a.bbn |
| Assembly 109 | KLLA0B14883g | vGFP | ADH1 terminator | Sc 5a.bbn |
| Assembly 110 | KLLA0C05566g | vGFP | ADH1 terminator | Sc 5a.bbn |
| Assembly 111 | KLLA0D00979g | vGFP | ADH1 terminator | Sc 5a.bbn |
| Assembly 112 | KLLA0D07634g | vGFP | ADH1 terminator | Sc 5a.bbn |
| Assembly 113 | KLLA0E01057g | vGFP | ADH1 terminator | Sc 5a.bbn |
| Assembly 114 | KLLA0F18260g | vGFP | ADH1 terminator | Sc 5a.bbn |
| Assembly 115 | KLLA0F20031g | vGFP | ADH1 terminator | Sc 5a.bbn |
| Assembly 116 | KLLA0F20988g | vGFP | ADH1 terminator | Sc 5a.bbn |

1.5 Preparation and Purification of PCR Fragments for Transformation

Amplification of expression cassettes with connector sequences from the plasmids was carried out with a standard set of primers binding to the connectors. The primers are set out in SEQ ID NOs: 87 to 110 and named after the connector and the direction of amplification. For example "con 5 fw" was the forward primer on connector 5. Only a subset of the primers was used in this experiment. Table 3 shows the primers used with the corresponding PCR templates used in the PCR reactions. PCR reactions were performed with PhucionPHUSION® polymerase (Finnzymes) according to the manual.

TABLE 3

An overview of all PCR reactions generating expression cassettes equipped with connectors used in the transformation of S. cerevisiae

| Template DNA | Basic backbone | Primers used | Short description |
|---|---|---|---|
| Assembly 1-18 | Sc 5a.bbn | Con 5 fw / Con a rev | Test S. cerevisiae promoters with vGFP in 5a position |
| Assembly 19-36 | Sc bc.bbn | Con b fw / Con c rev | Test S. cerevisiae promoters with lacZ in bc position |
| Assembly 37-54 | Sc c3.bbn | Con c fw / Con 3 rev | Test S. cerevisiae promoters with lacZ in c3 position |
| Assembly 55-68 | Sc 5a.bbn | Con 5 fw / Con a rev | Test S. cerevisiae terminators with vGFP in 5a position |
| Assembly 69-85 | Sc 5a.bbn | Con 5 fw / Con a rev | Test S. cerevisiae promoters with GFP-var1 in 5a position |
| Assembly 87-104 | Sc 5a.bbn | Con 5 fw / Con a rev | Test S. cerevisiae promoters with GFP-var2 in 5a position |
| Assembly 105-116 | Sc 5a.bbn | Con 5 fw / Con a rev | Test K. lactis promoters with vGFP in 5a position |

The dominant marker KanMX (conferring resistance to G418) was used for selection in yeast. It was PCR amplified using a standard plasmid containing this marker as template with the forward primer 5950 (SEQ ID NO: 111) adding connector a and the reverse primer 5951 (SEQ ID NO: 112) adding connector b. The marker cassette was therefore placed at position ab. The resulting PCR fragment was used in all transformations (SEQ ID NO: 113).

For the Example, the constructs were integrated into an intergenic region on chromosome XV referred to as INT1 herein. The left flank for integration into the chromosomal INT1 site in the genome of S. cerevisiae was PCR amplified with forward primer 02500 (SEQ ID NO: 114) and reverse primer 05510 (SEQ ID NO: 115) adding connector 5. The sequence of the left flank with connector 5 is set out as SEQ ID NO: 116. The right flank for integration into the chromosomal INT1 site in the genome of S. cerevisiae was PCR amplified with forward primer 05511 (SEQ ID NO: 117) adding the connector sequence 3 and reverse primer 02523 (SEQ ID NO: 118). The sequence of the right flank with connector 3 is listed as SEQ ID NO: 119. Chromosomal DNA isolated from CenPK-1137D was used as template. The added connectors 5 and 3 on the flanks provided homology to the expression cassettes. All DNA fragments added during transformation, integration flanks, expression cassettes and marker cassette were able to recombine via the connectors and the complete assembled fragment is able to integrate into the genome on the INT1 site.

All amplified PCR fragments were checked on size with standard agarose electrophoresis techniques. PCR amplified DNA fragments were purified with the PCR purification kit from Qiagen, according to the manual. DNA concentration was measured using A260/A280 on a Nanodrop ND-1000 spectrophotometer. When not enough PCR product was obtained after purification, additional PCR reactions were performed and purified until sufficient amount of DNA was available.

1.6 Transformation of the Fragments to S. cerevisiae

Transformation of S. cerevisiae was done as described by Gietz and Woods (2002; Transformation of the yeast by the LiAc/SS carrier DNA/PEG method. Methods in Enzymology 350: 87-96). CEN.PK1137D (MATa URA3 HIS3 LEU2 TRP1 MAL2-8 SUC2) was transformed with 1 μg of each of the amplified and purified PCR fragments. Table 4 shows an overview of the transformations performed and the PCR fragments added for each individual transformation. Each transformation will result in a "reporter gene pathway" with a GFP, KanMX marker, lacZ and RFP integrated into the INT1 locus on the genome.

TABLE 4

An overview of the transformations and the fragments added for each transformation

| | LFL_5 | cassette 5a | | | marker ab | cassette bc | | | cassette c3 | | | 3_RFL |
|---|---|---|---|---|---|---|---|---|---|---|---|---|
| nr | INT1_5 | prom | orf | Term | marker | prom | orf | term | prom | orf | term | 3_INT1 |
| 1 | INT1_5 | pENO1 | vGFP | tADH1 | Kanmx | pPRE3 | LacZ | tADH2 | pACT1 | RFP | tENO1 | 3_INT1 |
| 2 | INT1_5 | pPDC1 | vGFP | tADH1 | Kanmx | pPRE3 | LacZ | tADH2 | pACT1 | RFP | tENO1 | 3_INT1 |
| 3 | INT1_5 | pENO2 | vGFP | tADH1 | Kanmx | pPRE3 | LacZ | tADH2 | pACT1 | RFP | tENO1 | 3_INT1 |
| 4 | INT1_5 | pFBA1 | vGFP | tADH1 | Kanmx | pPRE3 | LacZ | tADH2 | pACT1 | RFP | tENO1 | 3_INT1 |
| 5 | INT1_5 | pPGI1 | vGFP | tADH1 | Kanmx | pPRE3 | LacZ | tADH2 | pACT1 | RFP | tENO1 | 3_INT1 |
| 6 | INT1_5 | pPGK1 | vGFP | tADH1 | Kanmx | pPRE3 | LacZ | tADH2 | pACT1 | RFP | tENO1 | 3_INT1 |
| 7 | INT1_5 | pGPM1 | vGFP | tADH1 | Kanmx | pPRE3 | LacZ | tADH2 | pACT1 | RFP | tENO1 | 3_INT1 |
| 8 | INT1_5 | pPMA1 | vGFP | tADH1 | Kanmx | pPRE3 | LacZ | tADH2 | pACT1 | RFP | tENO1 | 3_INT1 |
| 9 | INT1_5 | pOYE2 | vGFP | tADH1 | Kanmx | pPRE3 | LacZ | tADH2 | pACT1 | RFP | tENO1 | 3_INT1 |
| 10 | INT1_5 | pTAL1 | vGFP | tADH1 | Kanmx | pPRE3 | LacZ | tADH2 | pACT1 | RFP | tENO1 | 3_INT1 |
| 11 | INT1_5 | pTDH1 | vGFP | tADH1 | Kanmx | pPRE3 | LacZ | tADH2 | pACT1 | RFP | tENO1 | 3_INT1 |
| 12 | INT1_5 | pTDH3 | vGFP | tADH1 | Kanmx | pPRE3 | LacZ | tADH2 | pACT1 | RFP | tENO1 | 3_INT1 |
| 13 | INT1_5 | pTEF1 | vGFP | tADH1 | Kanmx | pPRE3 | LacZ | tADH2 | pACT1 | RFP | tENO1 | 3_INT1 |
| 14 | INT1_5 | pTPI1 | vGFP | tADH1 | Kanmx | pPRE3 | LacZ | tADH2 | pACT1 | RFP | tENO1 | 3_INT1 |
| 15 | INT1_5 | pACT1 | vGFP | tADH1 | Kanmx | pPRE3 | LacZ | tADH2 | pACT1 | RFP | tENO1 | 3_INT1 |
| 16 | INT1_5 | Ag pTef1 | vGFP | tADH1 | Kanmx | pPRE3 | LacZ | tADH2 | pACT1 | RFP | tENO1 | 3_INT1 |
| 17 | INT1_5 | pPRE3 | vGFP | tADH1 | Kanmx | pPRE3 | LacZ | tADH2 | pACT1 | RFP | tENO1 | 3_INT1 |
| 18 | INT1_5 | pVPS68 | vGFP | tADH1 | Kanmx | pPRE3 | LacZ | tADH2 | pACT1 | RFP | tENO1 | 3_INT1 |
| 19 | INT1_5 | pENO1 | vGFP | tADH1 | Kanmx | pPRE3 | LacZ | tADH2 | pTDH3 | RFP | tENO1 | 3_INT1 |
| 20 | INT1_5 | pPDC1 | vGFP | tADH1 | Kanmx | pPRE3 | LacZ | tADH2 | pACT3 | RFP | tENO1 | 3_INT1 |
| 21 | INT1_5 | pENO2 | vGFP | tADH1 | Kanmx | pPRE3 | LacZ | tADH2 | pTDH3 | RFP | tENO1 | 3_INT1 |
| 22 | INT1_5 | pFBA1 | vGFP | tADH1 | Kanmx | pPRE3 | LacZ | tADH2 | pTDH3 | RFP | tENO1 | 3_INT1 |
| 23 | INT1_5 | pPGI1 | vGFP | tADH1 | Kanmx | pPRE3 | LacZ | tADH2 | pTDH3 | RFP | tENO1 | 3_INT1 |
| 24 | INT1_5 | pPGK1 | vGFP | tADH1 | Kanmx | pPRE3 | LacZ | tADH2 | pTDH3 | RFP | tENO1 | 3_INT1 |
| 25 | INT1_5 | pGPM1 | vGFP | tADH1 | Kanmx | pPRE3 | LacZ | tADH2 | pTDH3 | RFP | tENO1 | 3_INT1 |
| 26 | INT1_5 | pPMA1 | vGFP | tADH1 | Kanmx | pPRE3 | LacZ | tADH2 | pTDH3 | RFP | tENO1 | 3_INT1 |
| 27 | INT1_5 | pOYE2 | vGFP | tADH1 | Kanmx | pPRE3 | LacZ | tADH2 | pTDH3 | RFP | tENO1 | 3_INT1 |
| 28 | INT1_5 | pTAL1 | vGFP | tADH1 | Kanmx | pPRE3 | LacZ | tADH2 | pTDH3 | RFP | tENO1 | 3_INT1 |
| 29 | INT1_5 | pTDH1 | vGFP | tADH1 | Kanmx | pPRE3 | LacZ | tADH2 | pTDH3 | RFP | tENO1 | 3_INT1 |
| 30 | INT1_5 | pTDH3 | vGFP | tADH1 | Kanmx | pPRE3 | LacZ | tADH2 | pTDH3 | RFP | tENO1 | 3_INT1 |
| 31 | INT1_5 | pTEF1 | vGFP | tADH1 | Kanmx | pPRE3 | LacZ | tADH2 | pTDH3 | RFP | tENO1 | 3_INT1 |
| 32 | INT1_5 | pTPI1 | vGFP | tADH1 | Kanmx | pPRE3 | LacZ | tADH2 | pTDH3 | RFP | tENO1 | 3_INT1 |
| 33 | INT1_5 | pACT1 | vGFP | tADH1 | Kanmx | pPRE3 | LacZ | tADH2 | pTDH3 | RFP | tENO1 | 3_INT1 |
| 34 | INT1_5 | Ag pTef1 | vGFP | tADH1 | Kanmx | pPRE3 | LacZ | tADH2 | pTDH3 | RFP | tENO1 | 3_INT1 |
| 35 | INT1_5 | pPRE3 | vGFP | tADH1 | Kanmx | pACT1 | LacZ | tADH2 | pTDH3 | RFP | tENO1 | 3_INT1 |
| 36 | INT1_5 | pVPS68 | vGFP | tADH1 | Kanmx | pPRE3 | LacZ | tADH2 | pTDH3 | RFP | tENO1 | 3_INT1 |
| 37 | INT1_5 | pTDH3 | VGFP | tADH1 | Kanmx | pENO1 | LacZ | tADH2 | pACT1 | RFP | tENO1 | 3_INT1 |
| 38 | INT1_5 | pTDH3 | VGFP | tADH1 | Kanmx | pPDC1 | LacZ | tADH2 | pACT1 | RFP | tENO1 | 3_INT1 |
| 39 | INT1_5 | pTDH3 | vGFP | tADH1 | Kanmx | pENO2 | LacZ | tADH2 | pACT1 | RFP | tENO1 | 3_INT1 |
| 40 | INT1_5 | pTDH3 | vGFP | tADH1 | Kanmx | pFBA1 | LacZ | tADH2 | pACT1 | RFP | tENO1 | 3_INT1 |
| 41 | INT1_5 | pTDH3 | vGFP | tADH1 | Kanmx | pPGI1 | LacZ | tADH2 | pACT1 | RFP | tENO1 | 3_INT1 |
| 42 | INT1_5 | pTDH3 | vGFP | tADH1 | Kanmx | pPGK1 | LacZ | tADH2 | pACT1 | RFP | tENO1 | 3_INT1 |
| 43 | INT1_5 | pTDH3 | vGFP | tADH1 | Kanmx | pGPM1 | LacZ | tADH2 | pACT1 | RFP | tENO1 | 3_INT1 |
| 44 | INT1_5 | pTDH3 | vGFP | tADH1 | Kanmx | pPMA1 | LacZ | tADH2 | pACT1 | RFP | tENO1 | 3_INT1 |
| 45 | INT1_5 | pTDH3 | vGFP | tADH1 | Kanmx | pOYE2 | LacZ | tADH2 | pACT1 | RFP | tENO1 | 3_INT1 |
| 46 | INT1_5 | pTDH3 | vGFP | tADH1 | Kanmx | pTAL1 | LacZ | tADH2 | pACT1 | RFP | tENO1 | 3_INT1 |

TABLE 4-continued

An overview of the transformations and the fragments added for each transformation

| | LFL_5 | | cassette 5a | | marker ab | cassette bc | | | cassette c3 | | | 3_RFL |
|---|---|---|---|---|---|---|---|---|---|---|---|---|
| nr | INT1_5 | prom | orf | Term | marker | prom | orf | term | prom | orf | term | 3_INT1 |
| 47 | INT1_5 | pTDH3 | vGFP | tADH1 | Kanmx | pTDH1 | LacZ | tADH2 | pACT1 | RFP | tENO1 | 3_INT1 |
| 48 | INT1_5 | pTDH3 | vGFP | tADH1 | Kanmx | pTDH3 | LacZ | tADH2 | pACT1 | RFP | tENO1 | 3_INT1 |
| 49 | INT1_5 | pTDH3 | vGFP | tADH1 | Kanmx | PTEF1 | LacZ | tADH2 | pACT1 | RFP | tENO1 | 3_INT1 |
| 50 | INT1_5 | pTDH3 | vGFP | tADH1 | Kanmx | pTPI1 | LacZ | tADH2 | pACT1 | RFP | tENO1 | 3_INT1 |
| 51 | INT1_5 | pTDH3 | vGFP | tADH1 | Kanmx | pACT1 | LacZ | tADH2 | pACT1 | RFP | tENO1 | 3_INT1 |
| 52 | INT1_5 | pTDH3 | vGFP | tADH1 | Kanmx | Ag pTef1 | LacZ | tADH2 | pACT1 | RFP | tENO1 | 3_INT1 |
| 53 | INT1_5 | pTDH3 | vGFP | tADH1 | Kanmx | pPRE3 | LacZ | tADH2 | pACT1 | RFP | tENO1 | 3_INT1 |
| 54 | INT1_5 | pTDH3 | vGFP | tADH1 | Kanmx | pVPS68 | LacZ | tADH2 | pACT1 | RFP | tENO1 | 3_INT1 |
| 55 | INT1_5 | pACT1 | vGFP | tADH1 | Kanmx | pPRE3 | LacZ | tADH2 | pACT1 | RFP | tENO1 | 3_INT1 |
| 56 | INT1_5 | pACT1 | vGFP | tADH2 | Kanmx | pPRE3 | LacZ | tADH2 | pACT1 | RFP | tENO1 | 3_INT1 |
| 57 | INT1_5 | pACT1 | vGFP | tENO1 | Kanmx | pPRE3 | LacZ | tADH2 | pACT1 | RFP | tENO1 | 3_INT1 |
| 58 | INT1_5 | pACT1 | vGFP | tGPM1 | Kanmx | pPRE3 | LacZ | tADH2 | pACT1 | RFP | tENO1 | 3_INT1 |
| 59 | INT1_5 | pACT1 | vGFP | tPDC1 | Kanmx | pPRE3 | LacZ | tADH2 | pACT1 | RFP | tENO1 | 3_INT1 |
| 60 | INT1_5 | pACT1 | vGFP | tPGI1 | Kanmx | pPRE3 | LacZ | tADH2 | pACT1 | RFP | tENO1 | 3_INT1 |
| 61 | INT1_5 | pACT1 | vGFP | tPGK1 | Kanmx | pPRE3 | LacZ | tADH2 | pACT1 | RFP | tENO1 | 3_INT1 |
| 62 | INT1_5 | pACT1 | vGFP | tPMA1 | Kanmx | pPRE3 | LacZ | tADH2 | pACT1 | RFP | tENO1 | 3_INT1 |
| 63 | INT1_5 | pACT1 | vGFP | tTAL1 | Kanmx | pPRE3 | LacZ | tADH2 | pACT1 | RFP | tENO1 | 3_INT1 |
| 64 | INT1_5 | pACT1 | vGFP | tTDH1 | Kanmx | pPRE3 | LacZ | tADH2 | pACT1 | RFP | tENO1 | 3_INT1 |
| 65 | INT1_5 | pACT1 | vGFP | tTDH3 | Kanmx | pPRE3 | LacZ | tADH2 | pACT1 | RFP | tENO1 | 3_INT1 |
| 66 | INT1_5 | pACT1 | vGFP | tTEF1 | Kanmx | pPRE3 | LacZ | tADH2 | pACT1 | RFP | tENO1 | 3_INT1 |
| 67 | INT1_5 | pACT1 | vGFP | tTEF2 | Kanmx | pPRE3 | LacZ | tADH2 | pACT1 | RFP | tENO1 | 3_INT1 |
| 68 | INT1_5 | pACT1 | vGFP | tTPI1 | Kanmx | pPRE3 | LacZ | tADH2 | pACT1 | RFP | tENO1 | 3_INT1 |
| 69 | INT1_5 | pACT1 | vGFP | tADH1 | Kanmx | pPRE3 | LacZ | tADH2 | pTDH3 | RFP | tENO1 | 3_INT1 |
| 70 | INT1_5 | pACT1 | vGFP | tADH2 | Kanmx | pPRE3 | LacZ | tADH2 | pTDH3 | RFP | tENO1 | 3_INT1 |
| 71 | INT1_5 | pACT1 | vGFP | tENO1 | Kanmx | pPRE3 | LacZ | tADH2 | pTDH3 | RFP | tENO1 | 3_INT1 |
| 72 | INT1_5 | pACT1 | vGFP | tGPM1 | Kanmx | pPRE3 | LacZ | tADH2 | pTDH3 | RFP | tENO1 | 3_INT1 |
| 73 | INT1_5 | pACT1 | VGFP | tPDC1 | Kanmx | pPRE3 | LacZ | tADH2 | pTDH3 | RFP | tENO1 | 3_INT1 |
| 74 | INT1_5 | pACT1 | vGFP | tPGI1 | Kanmx | pPRE3 | LacZ | tADH2 | pTDH3 | RFP | tENO1 | 3_INT1 |
| 75 | INT1_5 | pACT1 | vGFP | tPGK1 | Kanmx | pPRE3 | LacZ | tADH2 | pTDH3 | RFP | tENO1 | 3_INT1 |
| 76 | INT1_5 | pACT1 | vGFP | tPMA1 | Kanmx | pPRE3 | LacZ | tADH2 | pTDH3 | RFP | tENO1 | 3_INT1 |
| 77 | INT1_5 | pACT1 | vGFP | tTAL1 | Kanmx | pPRE3 | LacZ | tADH2 | pTDH3 | RFP | tENO1 | 3_INT1 |
| 78 | INT1_5 | pACT1 | vGFP | tTDH1 | Kanmx | pPRE3 | LacZ | tADH2 | pTDH3 | RFP | tENO1 | 3_INT1 |
| 79 | INT1_5 | pACT1 | vGFP | tTDH3 | Kanmx | pPRE3 | LacZ | tADH2 | pTDH3 | RFP | tENO1 | 3_INT1 |
| 80 | INT1_5 | pACT1 | vGFP | tTEF1 | Kanmx | pPRE3 | LacZ | tADH2 | pTDH3 | RFP | tENO1 | 3_INT1 |
| 81 | INT1_5 | pACT1 | vGFP | tTEF2 | Kanmx | pPRE3 | LacZ | tADH2 | pTDH3 | RFP | tENO1 | 3_INT1 |
| 82 | INT1_5 | pACT1 | vGFP | tTPI1 | Kanmx | pPRE3 | LacZ | tADH2 | pTDH3 | RFP | tENO1 | 3_INT1 |
| 83 | INT1_5 | pENO1 | GFPmut3 | tADH1 | Kanmx | pPRE3 | LacZ | tADH2 | pACT1 | RFP | tENO1 | 3_INT1 |
| 84 | INT1_5 | pPDC1 | GFPmut3 | tADH1 | Kanmx | pPRE3 | LacZ | tADH2 | pACT1 | RFP | tENO1 | 3_INT1 |
| 85 | INT1_5 | pENO2 | GFPmut3 | tADH1 | Kanmx | pPRE3 | LacZ | tADH2 | pACT1 | RFP | tENO1 | 3_INT1 |
| 86 | INT1_5 | pFBA1 | GFPmut3 | tADH1 | Kanmx | pPRE3 | LacZ | tADH2 | pACT1 | RFP | tENO1 | 3_INT1 |
| 87 | INT1_5 | pPGI1 | GFPmut3 | tADH1 | Kanmx | pPRE3 | LacZ | tADH2 | pACT1 | RFP | tENO1 | 3_INT1 |
| 88 | INT1_5 | pPGK1 | GFPmut3 | tADH1 | Kanmx | pPRE3 | LacZ | tADH2 | pACT1 | RFP | tENO1 | 3_INT1 |
| 89 | INT1_5 | pGPM1 | GFPmut3 | tADH1 | Kanmx | pPRE3 | LacZ | tADH2 | pACT1 | RFP | tENO1 | 3_INT1 |
| 90 | INT1_5 | pPMA1 | GFPmut3 | tADH1 | Kanmx | pPRE3 | LacZ | tADH2 | pACT1 | RFP | tENO1 | 3_INT1 |
| 91 | INT1_5 | pOYE2 | GFPmut3 | tADH1 | Kanmx | pPRE3 | LacZ | tADH2 | pACT1 | RFP | tENO1 | 3_INT1 |
| 92 | INT1_5 | pTAL1 | GFPmut3 | tADH1 | Kanmx | pPRE3 | LacZ | tADH2 | pACT1 | RFP | tENO1 | 3_INT1 |
| 93 | INT1_5 | pTDH1 | GFPmut3 | tADH1 | Kanmx | pPRE3 | LacZ | tADH2 | pACT1 | RFP | tENO1 | 3_INT1 |
| 94 | INT1_5 | pTDH3 | GFPmut3 | tADH1 | Kanmx | pPRE3 | LacZ | tADH2 | pACT1 | RFP | tENO1 | 3_INT1 |
| 95 | INT1_5 | pTEF1 | GFPmut3 | tADH1 | Kanmx | pPRE3 | LacZ | tADH2 | pACT1 | RFP | tENO1 | 3_INT1 |
| 96 | INT1_5 | pTPI1 | GFPmut3 | tADH1 | Kanmx | pPRE3 | LacZ | tADH2 | pACT1 | RFP | tENO1 | 3_INT1 |
| 97 | INT1_5 | pACT1 | GFPmut3 | tADH1 | Kanmx | pPRE3 | LacZ | tADH2 | pACT1 | RFP | tENO1 | 3_INT1 |
| 98 | INT1_5 | Ag pTef1 | GFPmut3 | tADH1 | Kanmx | pPRE3 | LacZ | tADH2 | pACT1 | RFP | tENO1 | 3_INT1 |
| 99 | INT1_5 | pPRE3 | GFPmut3 | tADH1 | Kanmx | pPRE3 | LacZ | tADH2 | pACT1 | RFP | tENO1 | 3_INT1 |
| 100 | INT1_5 | pVPS68 | GFPmut3 | tADH1 | Kanmx | pPRE3 | LacZ | tADH2 | pACT1 | RFP | tENO1 | 3_INT1 |
| 101 | INT1_5 | pENO1 | GFPmut3 | tADH1 | Kanmx | pPRE3 | LacZ | tADH2 | pTDH3 | RFP | tENO1 | 3_INT1 |
| 102 | INT1_5 | pPDC1 | GFPmut3 | tADH1 | Kanmx | pPRE3 | LacZ | tADH2 | pTDH3 | RFP | tENO1 | 3_INT1 |
| 103 | INT1_5 | pENO2 | GFPmut3 | tADH1 | Kanmx | pPRE3 | LacZ | tADH2 | pTDH3 | RFP | tENO1 | 3_INT1 |
| 104 | INT1_5 | pFBA1 | GFPmut3 | tADH1 | Kanmx | pPRE3 | LacZ | tADH2 | pTDH3 | RFP | tENO1 | 3_INT1 |
| 105 | INT1_5 | pPGI1 | GFPmut3 | tADH1 | Kanmx | pPRE3 | LacZ | tADH2 | pTDH3 | RFP | tENO1 | 3_INT1 |
| 106 | INT1_5 | pPGK1 | GFPmut3 | tADH1 | Kanmx | pPRE3 | LacZ | tADH2 | pTDH3 | RFP | tENO1 | 3_INT1 |
| 107 | INT1_5 | pGPM1 | GFPmut3 | tADH1 | Kanmx | pPRE3 | LacZ | tADH2 | pTDH3 | RFP | tENO1 | 3_INT1 |
| 108 | INT1_5 | pPMA1 | GFPmut3 | tADH1 | Kanmx | pPRE3 | LacZ | tADH2 | pTDH3 | RFP | tENO1 | 3_INT1 |
| 109 | INT1_5 | pOYE2 | GFPmut3 | tADH1 | Kanmx | pPRE3 | LacZ | tADH2 | pTDH3 | RFP | tENO1 | 3_INT1 |
| 110 | INT1_5 | pTAL1 | GFPmut3 | tADH1 | Kanmx | pPRE3 | LacZ | tADH2 | pTDH3 | RFP | tENO1 | 3_INT1 |
| 111 | INT1_5 | pTDH1 | GFPmut3 | tADH1 | Kanmx | pPRE3 | LacZ | tADH2 | pTDH3 | RFP | tENO1 | 3_INT1 |
| 112 | INT1_5 | pTDH3 | GFPmut3 | tADH1 | Kanmx | pPRE3 | LacZ | tADH2 | pTDH3 | RFP | tENO1 | 3_INT1 |
| 113 | INT1_5 | pTEF1 | GFPmut3 | tADH1 | Kanmx | pPRE3 | LacZ | tADH2 | pTDH3 | RFP | tENO1 | 3_INT1 |
| 114 | INT1_5 | pTPI1 | GFPmut3 | tADH1 | Kanmx | pPRE3 | LacZ | tADH2 | pTDH3 | RFP | tENO1 | 3_INT1 |
| 115 | INT1_5 | pACT1 | GFPmut3 | tADH1 | Kanmx | pPRE3 | LacZ | tADH2 | pTDH3 | RFP | tENO1 | 3_INT1 |
| 116 | INT1_5 | Ag pTef1 | GFPmut3 | tADH1 | Kanmx | pPRE3 | LacZ | tADH2 | pTDH3 | RFP | tENO1 | 3_INT1 |
| 117 | INT1_5 | pPRE3 | GFPmut3 | tADH1 | Kanmx | pPRE3 | LacZ | tADH2 | pTDH3 | RFP | tENO1 | 3_INT1 |
| 118 | INT1_5 | pVPS68 | GFPmut3 | tADH1 | Kanmx | pPRE3 | LacZ | tADH2 | pTDH3 | RFP | tENO1 | 3_INT1 |
| 119 | INT1_5 | pENO1 | GFP-pest | tADH1 | Kanmx | pPRE3 | LacZ | tADH2 | pACT1 | RFP | tENO1 | 3_INT1 |
| 120 | INT1_5 | pPDC1 | GFP-pest | tADH1 | Kanmx | pPRE3 | LacZ | tADH2 | pACT1 | RFP | tENO1 | 3_INT1 |

TABLE 4-continued

An overview of the transformations and the fragments added for each transformation

| | LFL_5 | cassette 5a | | | marker ab | cassette bc | | | cassette c3 | | | 3_RFL |
|---|---|---|---|---|---|---|---|---|---|---|---|---|
| nr | INT1_5 | prom | orf | Term | marker | prom | orf | term | prom | orf | term | 3_INT1 |
| 121 | INT1_5 | pENO2 | GFP-pest | tADH1 | Kanmx | pPRE3 | LacZ | tADH2 | pACT1 | RFP | tENO1 | 3_INT1 |
| 122 | INT1_5 | pFBA1 | GFP-pest | tADH1 | Kanmx | pPRE3 | LacZ | tADH2 | pACT1 | RFP | tENO1 | 3_INT1 |
| 123 | INT1_5 | pPGI1 | GFP-pest | tADH1 | Kanmx | pPRE3 | LacZ | tADH2 | pACT1 | RFP | tENO1 | 3_INT1 |
| 124 | INT1_5 | pPGK1 | GFP-psst | tADH1 | Kanmx | pPRE3 | LacZ | tADH2 | pACT1 | RFP | tENO1 | 3_INT1 |
| 125 | INT1_5 | pGPM1 | GFP-pest | tADH1 | Kanmx | pPRE3 | LacZ | tADH2 | pACT1 | RFP | tENO1 | 3_INT1 |
| 126 | INT1_5 | pPMA1 | GFP-pest | tADH1 | Kanmx | pPRE3 | LacZ | tADH2 | pACT1 | RFP | tENO1 | 3_INT1 |
| 127 | INT1_5 | pOYE2 | GFP-pest | tADH1 | Kanmx | pPRE3 | LacZ | tADH2 | pACT1 | RFP | tENO1 | 3_INT1 |
| 128 | INT1_5 | pTAL1 | GFP-pest | tADH1 | Kanmx | pPRE3 | LacZ | tADH2 | pACT1 | RFP | tENO1 | 3_INT1 |
| 129 | INT1_5 | pTDH1 | GFP-pest | tADH1 | Kanmx | pPRE3 | LacZ | tADH2 | pACT1 | RFP | tENO1 | 3_INT1 |
| 130 | INT1_5 | pTDH3 | GFP-pest | tADH1 | Kanmx | pPRE3 | LacZ | tADH2 | pACT1 | RFP | tENO1 | 3_INT1 |
| 131 | INT1_5 | pTEF1 | GFP-pest | tADH1 | Kanmx | pPRE3 | LacZ | tADH2 | pACT1 | RFP | tENO1 | 3_INT1 |
| 132 | INT1_5 | pTPI1 | GFP-pest | tADH1 | Kanmx | pPRE3 | LacZ | tADH2 | pACT1 | RFP | tENO1 | 3_INT1 |
| 133 | INT1_5 | pACT1 | GFP-pest | tADH1 | Kanmx | pPRE3 | LacZ | tADH2 | pACT1 | RFP | tENO1 | 3_INT1 |
| 134 | INT1_5 | Ag pTef1 | GFP-pest | tADH1 | Kanmx | pPRE3 | LacZ | tADH2 | pACT1 | RFP | tENO1 | 3_INT1 |
| 135 | INT1_5 | pPRE3 | GFP-pest | tADH1 | Kanmx | pPRE3 | LacZ | tADH2 | pACT1 | RFP | tENO1 | 3_INT1 |
| 136 | INT1_5 | pVPS68 | GFP-pest | tADH1 | Kanmx | pPRE3 | LacZ | tADH2 | pACT1 | RFP | tENO1 | 3_INT1 |
| 137 | INT1_5 | pENO1 | GFP-pest | tADH1 | Kanmx | pPRE3 | LacZ | tADH2 | pTDH3 | RFP | tENO1 | 3_INT1 |
| 138 | INT1_5 | pPDC1 | GFP-pest | tADH1 | Kanmx | pPRE3 | LacZ | tADH2 | pTDH3 | RFP | tENO1 | 3_INT1 |
| 139 | INT1_5 | pENO2 | GFP-pest | tADH1 | Kanmx | pPRE3 | LacZ | tADH2 | pTDH3 | RFP | tENO1 | 3_INT1 |
| 140 | INT1_5 | pFBA1 | GFP-pest | tADH1 | Kanmx | pPRE3 | LacZ | tADH2 | pTDH3 | RFP | tENO1 | 3_INT1 |
| 141 | INT1_5 | pPGI1 | GFP-pest | tADH1 | Kanmx | pPRE3 | LacZ | tADH2 | pTDH3 | RFP | tENO1 | 3_INT1 |
| 142 | INT1_5 | pPGK1 | GFP-pest | tADH1 | Kanmx | pPRE3 | LacZ | tADH2 | pTDH3 | RFP | tENO1 | 3_INT1 |
| 143 | INT1_5 | pGPM1 | GFP-pest | tADH1 | Kanmx | pPRE3 | LacZ | tADH2 | pTDH3 | RFP | tENO1 | 3_INT1 |
| 144 | INT1_5 | pPMA1 | GFP-pest | tADH1 | Kanmx | pPRE3 | LacZ | tADH2 | pTDH3 | RFP | tENO1 | 3_INT1 |
| 145 | INT1_5 | pOYE2 | GFP-pest | tADH1 | Kanmx | pPRE3 | LacZ | tADH2 | pTDH3 | RFP | tENO1 | 3_INT1 |
| 146 | INT1_5 | pTAL1 | GFP-pest | tADH1 | Kanmx | pPRE3 | LacZ | tADH2 | pTDH3 | RFP | tENO1 | 3_INT1 |
| 147 | INT1_5 | pTDH1 | GFP-pest | tADH1 | Kanmx | pPRE3 | LacZ | tADH2 | pTDH3 | RFP | tENO1 | 3_INT1 |
| 148 | INT1_5 | pTDH3 | GFP-pest | tADH1 | Kanmx | pPRE3 | LacZ | tADH2 | pTDH3 | RFP | tENO1 | 3_INT1 |
| 149 | INT1_5 | pTEF1 | GFP-pest | tADH1 | Kanmx | pPRE3 | LacZ | tADH2 | pTDH3 | RFP | tENO1 | 3_INT1 |
| 150 | INT1_5 | pTPI1 | GFP-pest | tADH1 | Kanmx | pPRE3 | LacZ | tADH2 | pTDH3 | RFP | tENO1 | 3_INT1 |
| 151 | INT1_5 | pACT1 | GFP-pest | tADH1 | Kanmx | pPRE3 | LacZ | tADH2 | pTDH3 | RFP | tENO1 | 3_INT1 |
| 152 | INT1_5 | Ag pTef1 | GFP-pest | tADH1 | Kanmx | pPRE3 | LacZ | tADH2 | pTDH3 | RFP | tENO1 | 3_INT1 |
| 153 | INT1_5 | pPRE3 | GFP-pest | tADH1 | Kanmx | pPRE3 | LacZ | tADH2 | pTDH3 | RFP | tENO1 | 3_INT1 |
| 154 | INT1_5 | pVPS68 | GFP-pest | tADH1 | Kanmx | pPRE3 | LacZ | tADH2 | pTDH3 | RFP | tENO1 | 3_INT1 |
| 155 | INT1_5 | KL prom1 | vGFP | tADH1 | Kanmx | pPRE3 | LacZ | tADH2 | pACT1 | RFP | tENO1 | 3_INT1 |
| 156 | INT1_5 | KL prom2 | vGFP | tADH1 | Kanmx | pPRE3 | LacZ | tADH2 | pACT1 | RFP | tENO1 | 3_INT1 |
| 157 | INT1_5 | KL prom3 | vGFP | tADH1 | Kanmx | pPRE3 | LacZ | tADH2 | pACT1 | RFP | tENO1 | 3_INT1 |
| 158 | INT1_5 | KL prom4 | vGFP | tADH1 | Kanmx | pPRE3 | LacZ | tADH2 | pACT1 | RFP | tENO1 | 3_INT1 |
| 159 | INT1_5 | KL prom5 | vGFP | tADH1 | Kanmx | pPRE3 | LacZ | tADH2 | pACT1 | RFP | tENO1 | 3_INT1 |
| 160 | INT1_5 | KL prom6 | vGFP | tADH1 | Kanmx | pPRE3 | LacZ | tADH2 | pACT1 | RFP | tENO1 | 3_INT1 |
| 161 | INT1_5 | KL prom7 | vGFP | tADH1 | Kanmx | pPRE3 | LacZ | tADH2 | pACT1 | RFP | tENO1 | 3_INT1 |
| 162 | INT1_5 | KL prom8 | vGFP | tADH1 | Kanmx | pPRE3 | LacZ | tADH2 | pACT1 | RFP | tENO1 | 3_INT1 |
| 163 | INT1_5 | KL prom9 | vGFP | tADH1 | Kanmx | pPRE3 | LacZ | tADH2 | pACT1 | RFP | tENO1 | 3_INT1 |
| 164 | INT1_5 | KL prom10 | vGFP | tADH1 | Kanmx | pPRE3 | LacZ | tADH2 | pACT1 | RFP | tENO1 | 3_INT1 |
| 165 | INT1_5 | KL prom11 | vGFP | tADH1 | Kanmx | pPRE3 | LacZ | tADH2 | pACT1 | RFP | tENO1 | 3_INT1 |
| 166 | INT1_5 | KL prom12 | vGFP | tADH1 | Kanmx | pPRE3 | LacZ | tADH2 | pACT1 | RFP | tENO1 | 3_INT1 |
| 167 | INT1_5 | KL prom1 | vGFP | tADH1 | Kanmx | pPRE3 | LacZ | tADH2 | pTDH3 | RFP | tENO1 | 3_INT1 |
| 168 | INT1_5 | KL prom2 | vGFP | tADH1 | Kanmx | pPRE3 | LacZ | tADH2 | pTDH3 | RFP | tENO1 | 3_INT1 |
| 169 | INT1_5 | KL prom3 | vGFP | tADH1 | Kanmx | pPRE3 | LacZ | tADH2 | pTDH3 | RFP | tENO1 | 3_INT1 |
| 170 | INT1_5 | KL prom4 | vGFP | tADH1 | Kanmx | pPRE3 | LacZ | tADH2 | pTDH3 | RFP | tENO1 | 3_INT1 |
| 171 | INT1_5 | KL prom5 | vGFP | tADH1 | Kanmx | pPRE3 | LacZ | tADH2 | pTDH3 | RFP | tENO1 | 3_INT1 |
| 172 | INT1_5 | KL prom6 | vGFP | tADH1 | Kanmx | pPRE3 | LacZ | tADH2 | pTDH3 | RFP | tENO1 | 3_INT1 |
| 173 | INT1_5 | KL prom7 | vGFP | tADH1 | Kanmx | pPRE3 | LacZ | tADH2 | pTDH3 | RFP | tENO1 | 3_INT1 |
| 174 | INT1_5 | KL prom8 | vGFP | tADH1 | Kanmx | pPRE3 | LacZ | tADH2 | pTDH3 | RFP | tENO1 | 3_INT1 |
| 175 | INT1_5 | KL prom9 | vGFP | tADH1 | Kanmx | pPRE3 | LacZ | tADH2 | pTDH3 | RFP | tENO1 | 3_INT1 |
| 176 | INT1_5 | KL prom10 | vGFP | tADH1 | Kanmx | pPRE3 | LacZ | tADH2 | pTDH3 | RFP | tENO1 | 3_INT1 |
| 177 | INT1_5 | KL prom11 | vGFP | tADH1 | Kanmx | pPRE3 | LacZ | tADH2 | pTDH3 | RFP | tENO1 | 3_INT1 |
| 178 | INT1_5 | KL prom12 | vGFP | tADH1 | Kanmx | pPRE3 | LacZ | tADH2 | pTDH3 | RFP | tENO1 | 3_INT1 |
| 179 | INT1_5 | pTDH3 | vGFP | tADH1 | Kanmx | pPRE3 | LacZ | tADH2 | pENO1 | RFP | tENO1 | 3_INT1 |
| 180 | INT1_5 | pTDH3 | vGFP | tADH1 | Kanmx | pPRE3 | LacZ | tADH2 | pPDC1 | RFP | tENO1 | 3_INT1 |
| 181 | INT1_5 | pTDH3 | vGFP | tADH1 | Kanmx | pPRE3 | LacZ | tADH2 | pENO2 | RFP | tENO1 | 3_INT1 |
| 182 | INT1_5 | pTDH3 | vGFP | tADH1 | Kanmx | pPRE3 | LacZ | tADH2 | pFBA1 | RFP | tENO1 | 3_INT1 |
| 183 | INT1_5 | pTDH3 | vGFP | tADH1 | Kanmx | pPRE3 | LacZ | tADH2 | pPGI1 | RFP | tENO1 | 3_INT1 |
| 184 | INT1_5 | pTDH3 | vGFP | tADH1 | Kanmx | pPRE3 | LacZ | tADH2 | pPGK1 | RFP | tENO1 | 3_INT1 |
| 185 | INT1_5 | pTDH3 | vGFP | tADH1 | Kanmx | pPRE3 | LacZ | tADH2 | pGPM1 | RFP | tENO1 | 3_INT1 |
| 186 | INT1_5 | pTDH3 | vGFP | tADH1 | Kanmx | pPRE3 | LacZ | tADH2 | pPMA1 | RFP | tENO1 | 3_INT1 |
| 187 | INT1_5 | pTDH3 | vGFP | tADH1 | Kanmx | pPRE3 | LacZ | tADH2 | pOYE2 | RFP | tENO1 | 3_INT1 |
| 188 | INT1_5 | pTDH3 | vGFP | tADH1 | Kanmx | pPRE3 | LacZ | tADH2 | pTAL1 | RFP | tENO1 | 3_INT1 |

After the transformation procedure and ON recovery mixtures were plated on YEPhD-agar (BBL Phytone peptone 20.0 g/l, Yeast Extract 10.0 g/l, Sodium Chloride 5.0 g/l, Agar 15.0 g/l and 2% glucose) containing G418 (400 µg/ml). After 3 days incubation at 30° C., colonies appeared on the plates, whereas the negative control (i.e. no addition of DNA in the transformation experiment) resulted in an empty plate. Four colonies per transformation were picked and transferred to a MTP containing 240 µl YEPhD agar with G418 (200 µg/ml). The MTP plates were incubated for 3 days at 30° C. These plates were used as source for further analysis of the strains.

1.9 Reporter Gene Assays on Transformants after MTP Incubation

The yeast strains were grown in MTP under standard conditions to end-log phase. For all assays and measurements the cultures were diluted 10 times.

The OD600 was measured with a µQuant Microplate Spectrophotometer (BioTek Instruments, Inc, US) in a MTP plate containing 200 µl of the 10 times diluted culture per well. For the LacZ assay 70 µl of the 10 times diluted culture was used in the assay which was performed as described in the manual of the yeast beta-galactosidase assay kit used (Thermo Scientific). The absorption as a result from the lacZ assay was measured at 420 nm with a µQuant plater reader. Final lacZ activity for each culture was calculated with a correction factor for the OD600 measured. The GFP fluorescence (excitation 485 nm, emission 538 nm, gain 55) and RFP fluorescence (excitation 544nm, emission 620 nm, gain 70) were measured with a FLUOSTAR® plate reader (BMG Labtech, US).

Figure 10:
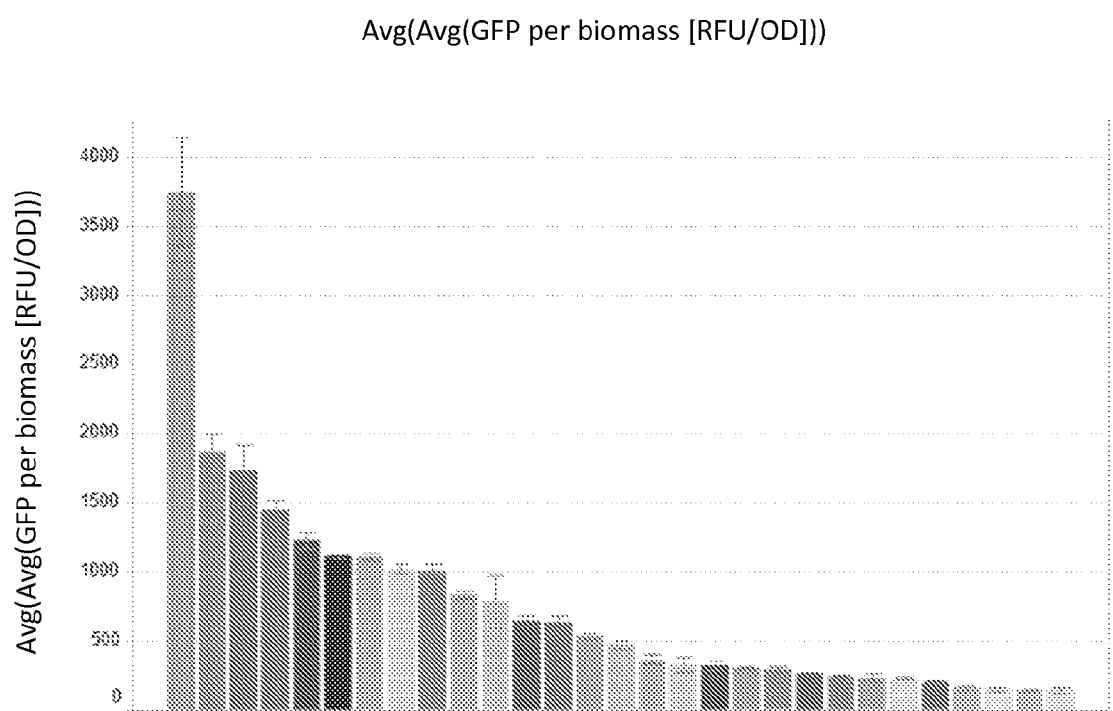
FIG. 10 shows the ranking of promoter expression strength based upon the GFP results obtained. The efficacy of the method is shown by the small standard deviation indicating the high number of correct transformants.
Figure 11:
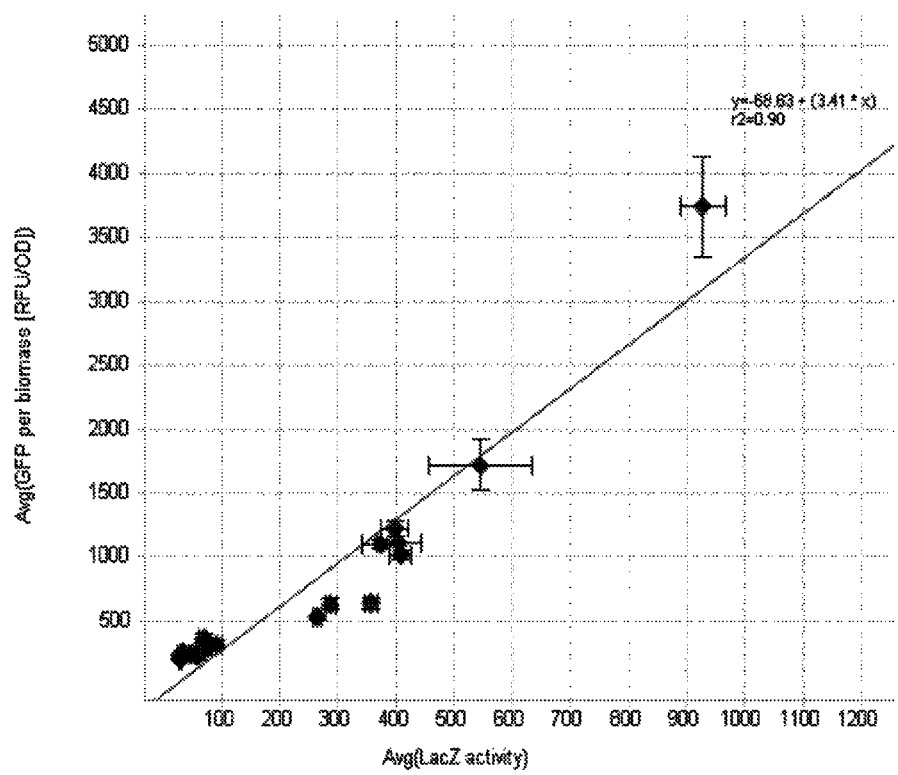
FIG. 11 shows the correlation between the results obtained in the lacZ and GFP reporter assay for each individual promoter is acceptable; the reporter gene assays confirm and strengthen the results obtained for each promoter.
Figure 12:
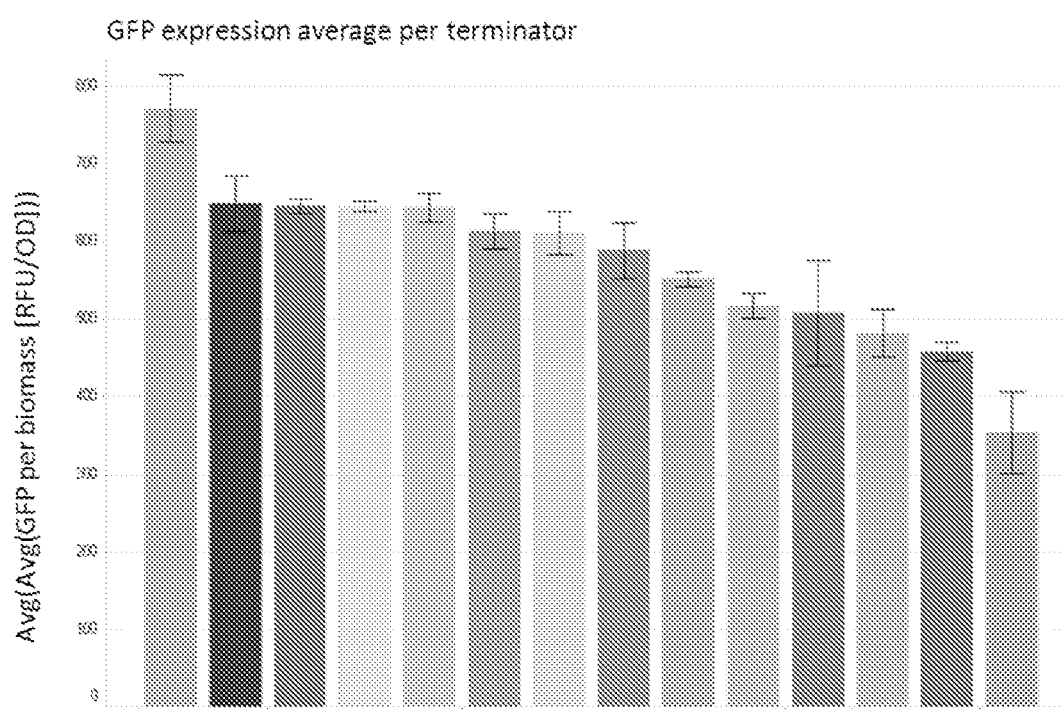
FIG. 12 sets out of the influence of the terminators on GFP expression. Again a small standard deviation for each series of 4 tested colonies, indicating a high percentage of correct transformants. The large standard deviation found for the terminator depicted in darkest gray is caused by a transformant without GFP signal (one of the few exceptions of incorrect transformants).

Results were further processed into graphics. FIG. 10 shows the ranking of promoters based upon the vGFP expression results obtained. Roughly 90% of the transformants show consistent results with low variance in the expression levels of reporter genes within a group of transformants from the same transformation, showing the efficacy of the method. The exceptions were mostly transformants without any reporter gene being expressed. These were left out of the figures; they are considered random integrants of the marker. For each promoter there is good correlation between the different reporter gene assays. This is shown in FIG. 11 for lacZ and vGFP expression. Exceptions to the rule are the transformations where genetic elements were used twice in a reporter gene pathway. For example, when promoter pACT1 was used to express vGFP and RFP, results showed more variation in the expression data indicating probably incorrect integration due to the internal homology. FIG. 12 shows the influence of the terminators on GFP expression. Again a small variance within each series of 4 tested colonies per terminator was observed, indicating the high percentage of correct transformants. The results clearly show that terminators can significantly influence expression of GFP.

The unstable protein variants of GFP, GFPmut and GFPpest, did not perform as well (low to very low GFP-signal) as the vGFP and were therefore not taken along in the results presented.

It can be concluded from the results that the described method enables the introduction of genes or complete pathways into hosts with high efficiency and efficacy.

Example 2

Building a Metabolic Pathway for Itaconic Acid Production in *Saccharomyces cerevisiae*

2.1 Step 1: building the expression constructs from biobricks

As in Example 1, promoter, open reading frame and terminator are all separate DNA sequences designed according to the standard rules described in the patent. The sequences are synthesized and cloned by DNA2.0 in a standard cloning vector. The nucleotide sequences of SEQ ID NOs 120, 121, 122, 123, 124 and 125, all open reading frames, were specifically synthesized for the construction of the metabolic pathway for itaconic acid production in *S. cerevisiae* (see Table 5 and the sequence list for details). The open reading frames were used in golden gate reactions together with a set of the in Example 1 described promoters, terminators and backbone vectors thereby creating the cassettes as shown in Table 6. The formed expression cassettes (cassette 117, cassette 120, cassette 133, cassette 136, cassette 124 and cassette 126) were used as a template to PCR amplify the DNA fragments used in the transformation.

TABLE 5

Description of the ORF's involved in the construction
of a metabolic route to itaconic acid in *S. cerevisiae*

| Nucleic acid | Id* | UniProt | Organism |
| --- | --- | --- | --- |
| SEQ ID NO: 120 | ITE_01 | Q0C8L2 | *A. terreus* |
| SEQ ID NO: 121 | CAD_01 | mCAD3 | *A. terreus* |
| SEQ ID NO: 122 | ACO_01 | A7A1I8 | *S. cerevisiae* |
| SEQ ID NO: 123 | PYC_01 | P32327 | *S. cerevisiae* |
| SEQ ID NO: 124 | CTP_01 | Q04013 | *S. cerevisiae* |
| SEQ ID NO: 125 | OTP_01 | P32332 | *S. cerevisiae* |

2.2 Preparation and Purification of PCR Fragments for Transformation

Assembly and integration of the itaconic acid pathways was carried out according to the methods described in Example 1. Amplification of expression cassettes with connector sequences from the plasmids was carried out with a standard set of primers binding to the connectors. The primers are set out in SEQ ID NOs: 87 to 110 and named after the connector and the direction of amplification. For example "con 5 fw" was the forward primer on connector 5. Only a subset of the primers was used in this experiment. Error! Reference source not found.6 shows the primers used with the corresponding PCR templates in the PCR reactions. PCR reactions were performed with PHUSION® polymerase (Finnzymes) according to the manual.

TABLE 6

Overview of all cassettes, the content of the cassettes and the primer combinations for generating expression cassettes equipped with connectors used in the transformation of S. cerevisiae

| cassette Nos | forward | reverse | PRO | ORF | TER | BBN |
|---|---|---|---|---|---|---|
| CAS117 | con5 forw | conA rev | Sc Act1.pro | SEQ ID NO: 120 | ADH1 terminator | Sc 5a.bbn |
| CAS120 | conB forw | conC rev | Sc TDH3.pro | SEQ ID NO: 121 | TDH1 terminator | Sc bc.bbn |
| CAS133 | conC forw | conD rev | Sc FBA1.pro | SEQ ID NO: 122 | GPM1 terminator | Sc cd.bbn |
| CAS136 | con D forw | con E rev | Sc PGK1.pro | SEQ ID NO: 123 | TPI1 terminator | Sc de.bbn |
| CAS124 | conE forw | conF rev | Sc Tef1.pro | SEQ ID NO: 124 | PDC1 terminator | Sc ef.bbn |
| CAS126 | conF forw | con3 rev | Sc ENO2.pro | SEQ ID NO: 125 | TAL1 terminator | Sc f3.bbn |

The dominant marker KanMX was amplified using a standard plasmid containing the fragments as template DNA. The 5' and 3' INT1 deletion flanks were amplified by PCR using CEN.PK113-7D genomic DNA as template. The dominant marker, integration flanks and the primers used are the same as described in example 1. Size of the PCR fragments was checked with standard agarose electrophoresis techniques. PCR amplified DNA fragments were purified with the NucleoMag® 96 PCR magnetic beads kit of Macherey-Nagel, according to the manual. DNA concentration was measured using the Trinean DropSense® 96 of GC biotech.

2.3 Transformation of the Fragments to S. cerevisiae

Transformation of S. cerevisiae was done as described by Gietz and Woods (2002; Transformation of the yeast by the LiAc/SS carrier DNA/PEG method. Methods in Enzymology 350: 87-96).

CEN.PK1137D (MATa URA3 HIS3 LEU2 TRP1 MAL2-8 SUC2) was transformed with up to 1 µg of each of the amplified and purified PCR fragments. The transformation will result in a "itaconic acid pathway" with the itaconic acid cassettes and KanMX marker integrated into the INT1 locus on the genome. Transformation mixtures were plated on YEPhD-agar (BBL Phytone peptone 20.0 g/l, Yeast Extract 10.0 g/l, Sodium Chloride 5.0 g/l, Agar 15.0 g/l and 2% glucose) containing G418 (400 µg/ml). After 3 days of incubation at 30° C., colonies appeared on the plates, whereas the negative control (i.e., no addition of DNA in the transformation experiment) resulted in blank plates.

2.4 Cultivation of the Transformants

Two single colonies of the transformation were picked and transferred to a MTP agar well containing 200 µl YEPhD-agar containing 400 µg/ml G418. After 3 days incubation of the plate at 30° C., the colonies were inoculated by transferring some colony material with a pin tool in a MTP plate with standard lid containing in each well 200 µL Verduyn medium (Verduyn et al., Yeast 8:501-517, 1992, where the (NH4)2SO4 was replaced with 2 g/l Urea) with a C-source based on starch and an enzyme providing release of glucose during cultivation. As a control the empty strain CEN.PK1137D was grown in the same growth protocol. The MTP was incubated in a MTP shaker (INFORS HT Multitron) at 30° C., 550 rpm and 80% humidity for 72 hours. After this pre-culture phase a production phase was started by transferring 80 µl of the broth to 4 ml Verduyn media (again with the urea replacing (NH4)2SO4) with a C-source based on starch and an enzyme providing release of glucose during cultivation. After 7 days growth in the shaker at 550 rpm, 30° C. and 80% humidity the plate was centrifuged for 10 minutes at 2750 rpm in a Heraeus Multifuge 4. Itaconic acid levels in the supernatant were measured with a hereafter described LC-MS method.

2.5 Detection of Itaconic Acid in the Samples

UPLC-MS/MS analysis method for the determination of itaconic acid, and other compounds of the Krebs cycle. A Waters HSS T3 column 1.7 µm, 100 mm*2.1 mm was used for the separation of itaconic, succinic, citric, iso-citric, malic and fumaric acid with gradient elution. Eluens A consists of LC/MS grade water, containing 0.1% formic acid, and eluens B consists of acetonitrile, containing 0.1% formic acid. The flow-rate was 0.35 ml/min and the column temperature was kept constant at 40° C. The gradient started at 95% A and was increased linear to 30% B in 10 minutes, kept at 30% B for 2 minutes, then immediately to 95% A and stabilized for 5 minutes. The injection volume used was 2 ul.

A Waters Xevo API was used in electrospray (ESI) in negative ionization mode, using multiple reaction monitoring (MRM). The ion source temperature was kept at 130° C., whereas the desolvation temperature is 350° C., at a flow-rate of 500 L/hr.

For itaconic acid and the other compounds of the Krebs cycle the deprotonated molecule was fragmented with 10 eV, resulting in specific fragments from losses of $H_2O$ and $CO2$. The standards of reference compounds spiked in blank fermentation broth were analyzed to confirm retention time, calculate a response factor for the respective ions, and was used to calculate the concentrations in fermentation samples. Samples were diluted appropriately (5-25 fold) in eluens A to overcome ion suppression and matrix effects during LC-MS analysis. To confirm the elemental composition of the compounds analyzed accurate mass analyses was performed with the same chromatographic system as described above, coupled to a LTQ orbitrap (ThermoFisher). Mass calibration was performed in constant infusion mode, using a NaTFA mixture (ref), in such a way that during the experimental set-up the accurate mass analyzed could be fitted within 2 ppm from the theoretical mass, of all compounds analyzed. A concentration of 95 mg/l itaconic acid was found in the samples of the transformed strains, the empty strain did not produce itaconic acid.

2.6 Genetic Analysis of the Transformants

Genetic analysis was performed in order to show correct integration of the cassettes in the genome of the transformants. Genomic DNA was isolated and PCR reactions were used to show correct integration and assembly of the cassettes. PCR was performed with phusionPHUSION® polymerase (Finnzymes) according to the manual. PCR reactions and primer pairs used for the analysis are listed in Table 7. From each PCR reaction 5 µl was analysed on an 0.8% agarose gel using standard electrophoresis techniques.

TABLE 7

The PCR reactions, their corresponding primer pair combinations and expected band size for each PCR result.

| PCR reaction | clone | fw primer | rev primer | expected band size |
|---|---|---|---|---|
| 1.1 | 1 | con 5 fw | con b rev | 3.8 kb |
| 2.1 | 2 | con 5 fw | con b rev | 3.8 kb |
| 1.2 | 1 | con b fw | con d rev | 5.7 kb |
| 2.2 | 2 | con b fw | con d rev | 5.7 kb |
| 1.3 | 1 | con d fw | con f rev | 6.5 kb |
| 2.3 | 2 | con d fw | con f rev | 6.5 kb |

Figure 13:
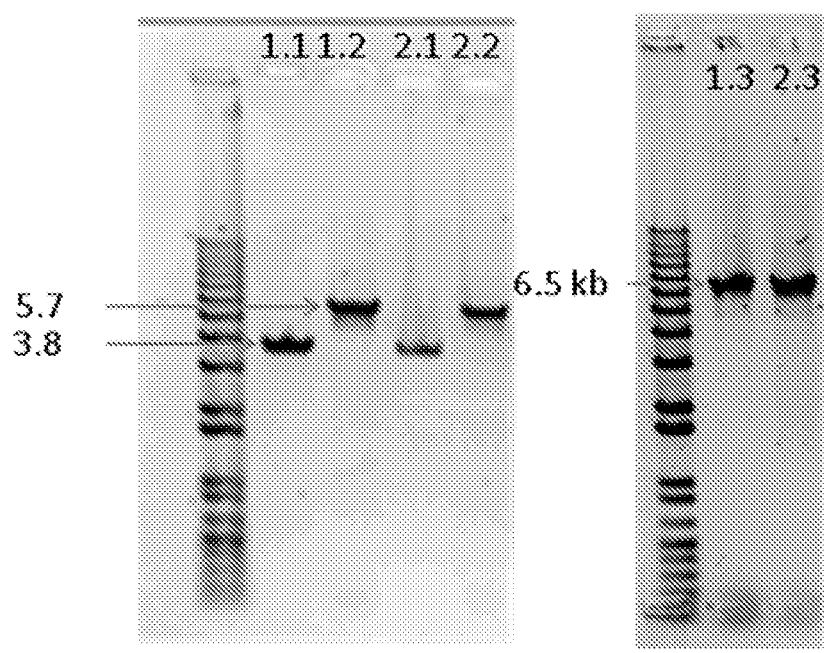
FIG. 13 sets out the results from PCR reactions analyzed on gel for assembly of an itaconic acid pathway. The PCR reactions result in the correct band sizes indicating the correct integration and assembly of the pathway in the genome.

FIG. 13 shows the pictures from the results. The transformants give the expected band sizes as a result from the PCR. The PCR reaction and itaconic acid production results clearly show the correct integration of the active itaconic acid metabolic pathway in the yeast genome. It therefore demonstrates the efficiency and effectiveness of the method described herein.

Example 3

Standardized Pathway Building in *Rasamsonia Emersonii*

3.1 General Introduction to the Standardized Pathway Building System in *Rasamsonia emersonii*

This method enables the fast introduction of genes/pathways into the filamentous fungus *Rasamsonia emersonii*. Level 1 (see FIG. 9) is focused on cloning so-called standardized genetic elements, promoters, open reading frame's (ORF's) and terminators into functional expression cassettes using a method called "Golden Gate Cloning" (Engler C. et al (2008) PLoS ONE 3(11): e3647 and Engler C. et al (2009) PLoS ONE 4 (5): e5553. Assembly of multiple expression cassettes (Level 2) is performed using Gibson cloning (Gibson D G, Young L, Chuang R Y, Venter J C, Hutchison C A 3rd, Smith H O. (2009). "Enzymatic assembly of DNA molecules up to several hundred kilobases". Nature Methods 6 (5): 343-345).

The multi cassette fragment was cloned in one of the two vectors of which the insert fragments together can be applied in the so-called "bipartite gene-targeting" method (Nielsen et al., 2006, 43: 54-64). This method is using two non-functional DNA fragments of a selection marker which are overlapping (see also WO2008113847 for further details of the bipartite method) together with gene-targeting sequences. Upon correct homologous recombination the selection marker becomes functional by integration at a homologous target locus. In this example, the cassettes were targeted to the RePepA locus. As also detailed in WO 2008113847, two different deletion vectors, Te pep.bbn and pEBA1006, were designed and constructed to be able to provide the two overlapping DNA molecules for bipartite gene-targeting. Te pep.bbn is the backbone entry vector suitable for Golden gate cloning.

3.2 Construction of the Backbone Entry Vector and Second Expression Vector that can be Applied in Bipartite Gene-Targeting A backbone entry vector was constructed that was suitable for targeted integration into the RePepA locus. Genomic DNA of *Rasamsonia emersonii* strain CBS393.64 was sequenced and analysed. The gene with translated protein annotated as protease pepA was identified in the genome. Sequences of *Rasamsonia emersonii* pepA (RePepA), comprising the genomic sequence of the ORF and approximately 3000 bp of the 5' region and 2500 bp of the 3' flanking regions, cDNA and protein sequence, are shown in SEQ ID NOs: 126, 127 and 128, respectively.

Figure 14:
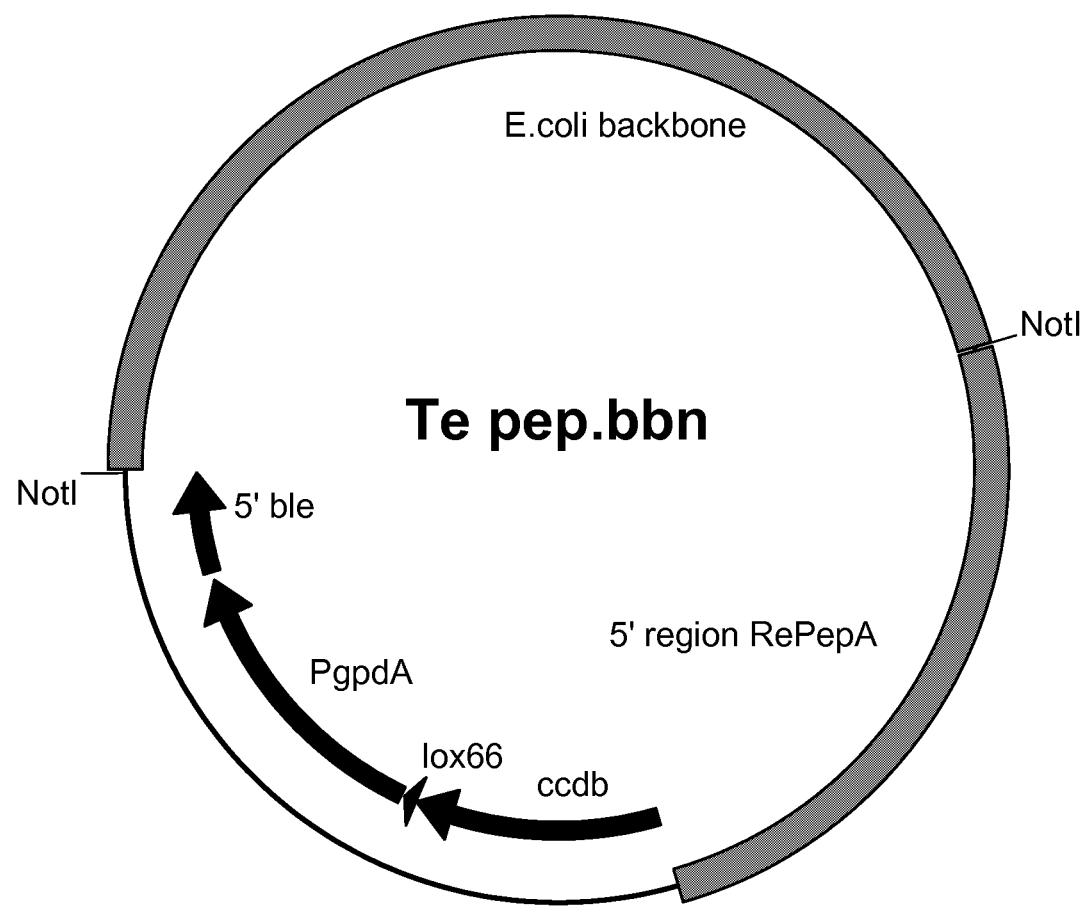
FIG. 14 shows a schematic diagram of plasmid Te pep-.bbn, which was used to assemble the EBA328 and EBA332 expression cassettes. The vector comprises a 1500 bp 5' flanking region 1.5 kb upstream of the RePepA ORF for targeting in the RePepA locus, a lox66 site, the non-functional 5' part of the ble coding region (5'ble) driven by the *A.nidulans* gpdA promoter, and a ccdB gene.

As mentioned above two vectors were constructed according to routine cloning procedures for targeting into the RePepA locus. The first vector Te pep.bbn (General layout as in FIG. 14) comprises a 1500 bp 5' flanking region approximately 1.5 kb upstream of the RePepA ORF for targeting in the RePepA locus (ORF and approximately 1500 bp of the RePepA promoter), a lox66 site, and the non-functional 5' part of the ble coding region driven by the *A. nidulans* gpdA promoter (PgpdA-ble sequence missing the last 104 bases of the coding sequence at the 3' end of ble, SEQ ID NO: 129). To allow efficient cloning of expression cassettes in *E. coli*, a ccdB gene was inserted in between the 5' RePepA flanking region and the lox66 site. The ccdB cassette was flanked by the bridges and BsaI sites that allow ligations of promoter, ORF, terminator cassettes as described in Example 1.

Figure 15:
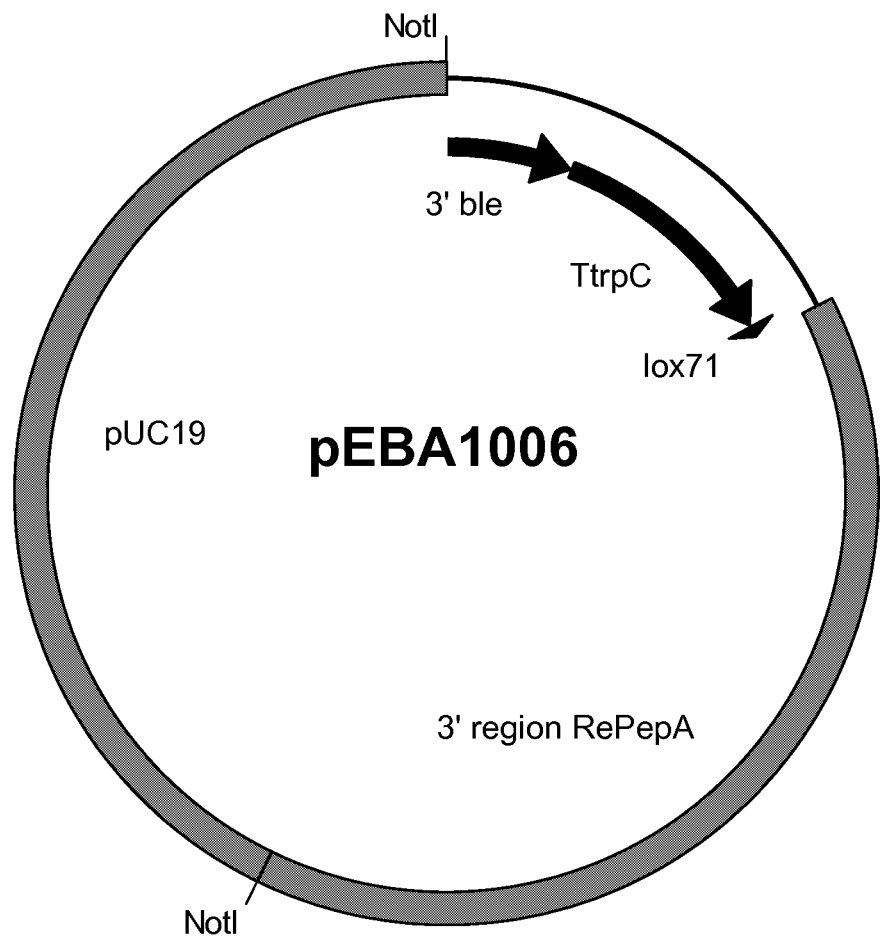
FIG. 15 shows a schematic diagram of plasmid pEBA1006 that was used in bipartite gene-targeting method in combination with pEBA328_EBA332 with the goal to replace the RePepA ORF and approximately 1500 nucleotides upstream of the start ATG codon by two GH61 expression cassettes in *Rasamsonia emersonii*. The vector comprises the 3' part of the ble coding region, the *A.nidulans trpC* terminator, a lox71 site, a 2500 bp 3'flanking region of the RePepA ORF, and the backbone of pUC19 (Invitrogen, Breda, The Netherlands). The *E. coli* DNA was removed by digestion with restriction enzyme NotI, prior to transformation of the *R. emersonii* strains.

The second pEBA1006 vector (General layout as in FIG. 15) comprises the non-functional 3' part of the ble coding region and the *A. nidulans* trpC terminator (ble-TtrpC sequence missing the first 12 bases of the coding sequence at the 5' end of ble, SEQ ID NO: 130), a lox71 site, and a 2500 bp 3' flanking region of the RePepA ORF for targeting in the RePepA locus. Upon homologous recombination, the first and second non-functional fragments become functional producing a functional ble cassette. Both RePepA upstream and downstream gene flanking regions target for homologous recombination of the bipartite fragments at the predestined RePepA genomic locus.

3.3 Assembly of Expression Cassettes with Golden Gate Cloning

The ccdB gene in vector Te pep.bbn was replaced by expression cassettes using

Figure 16:
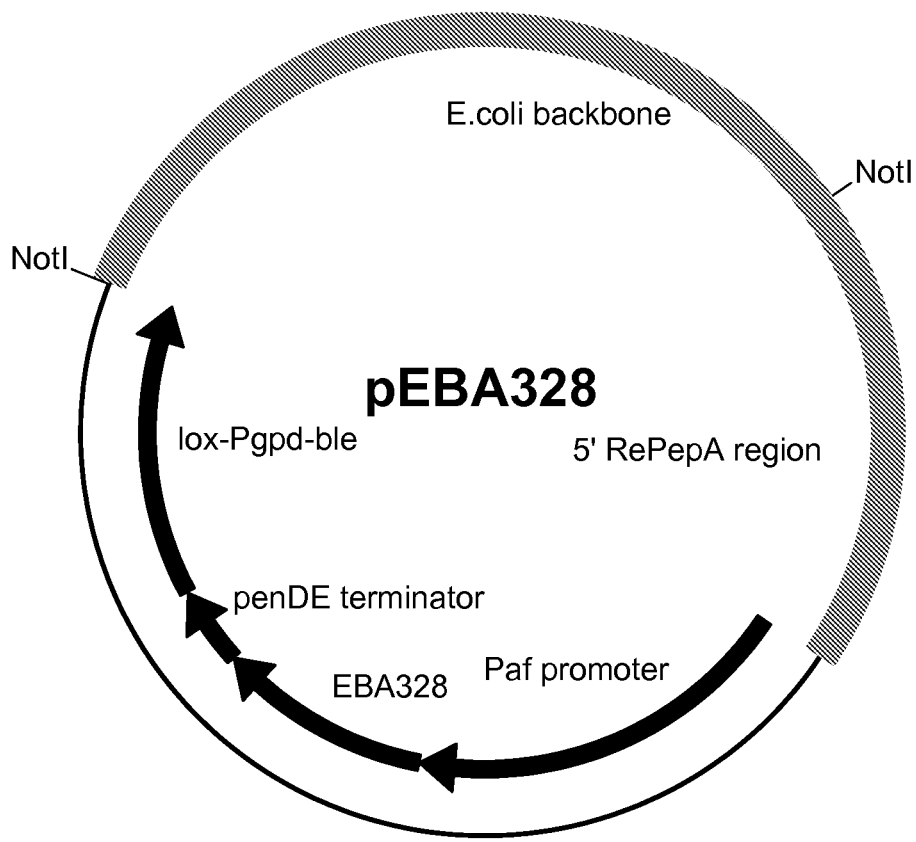
FIG. 16 shows a schematic diagram of plasmid pEBA328 that was used as template for PCR to obtain plasmid pEBA328_EBA332 using Gibson cloning. The vector comprises a 1500 bp 5' flanking region 1.5 kb upstream of the RePepA ORF for targeting in the RePepA locus, the EBA328 expression cassette consisting of *P. chrysogenum* Paf promoter, *Talaromyces thermophilus* GH61 coding region and *P. chrysogenum* penDE terminator, a lox66 site, the non-functional 5' part of the ble coding region (5' ble) driven by the *A.nidulans* gpdA promoter. pEBA328 is representative for pEBA332, which contains the EBA332 expression cassette instead of the EBA328 expression cassette. The EBA332 expression cassette consists of *R. emersonii* promoter 2, *Thermomyces lanuginosa* GH61 coding region and the *A.nidulans* amdS terminator (TamdS)

Golden gate cloning as described in Example 1 resulting in expression plasmids pEBA328 and pEBA332. The expression cassette of pEBA328 consists of the *P. chrysogenum* Paf promoter represented by SEQ ID NO: 131, *Talaromyces thermophilus* GH61 ORF represented by SEQ ID NO: 132 and the *P. chrysogenum* penDE terminator represented by SEQ ID NO: 133. The expression cassette of pEBA332 consists of the *R. emersonii* promoter 2 represented by SEQ ID NO: 134, *Thermomyces lanuginosa* GH61 ORF represented by SEQ ID NO: 135 and the *A. nidulans* AmdS terminator represented by SEQ ID NO: 136. A schematic representation of pEBA328 is shown in FIG. 16, which is representative for pEBA332.

3.4 Preparation and Purification of PCR Fragments for Gibson Cloning

Amplification of expression cassettes from the pEBA328 and pEBA332 expression plasmids was carried out using primers and template as listed in Table 8:

TABLE 8

Overview of primers and templates for amplification of PCR fragments for Gibson cloning

| Gibson fragment | Template | Forward primer | Reverse primer |
|---|---|---|---|
| EBA328 cassette | pEBA328 | 5'pepA-Ppaf (SEQ ID NO: 137) | TpenDE (SEQ ID NO: 138) |
| EBA332 cassette | pEBA332 | TpenDE-Ppra (SEQ ID NO: 139) | Tanid_amds (SEQ ID NO: 140) |
| vector | pEBA328 | Tanid_amds-loxP-gpd-ble (SEQ ID NO: 141) | 5'pepA (SEQ ID NO: 142) |

2.5 Assembly of Multi Cassette Constructs Using Gibson Cloning

Figure 17:
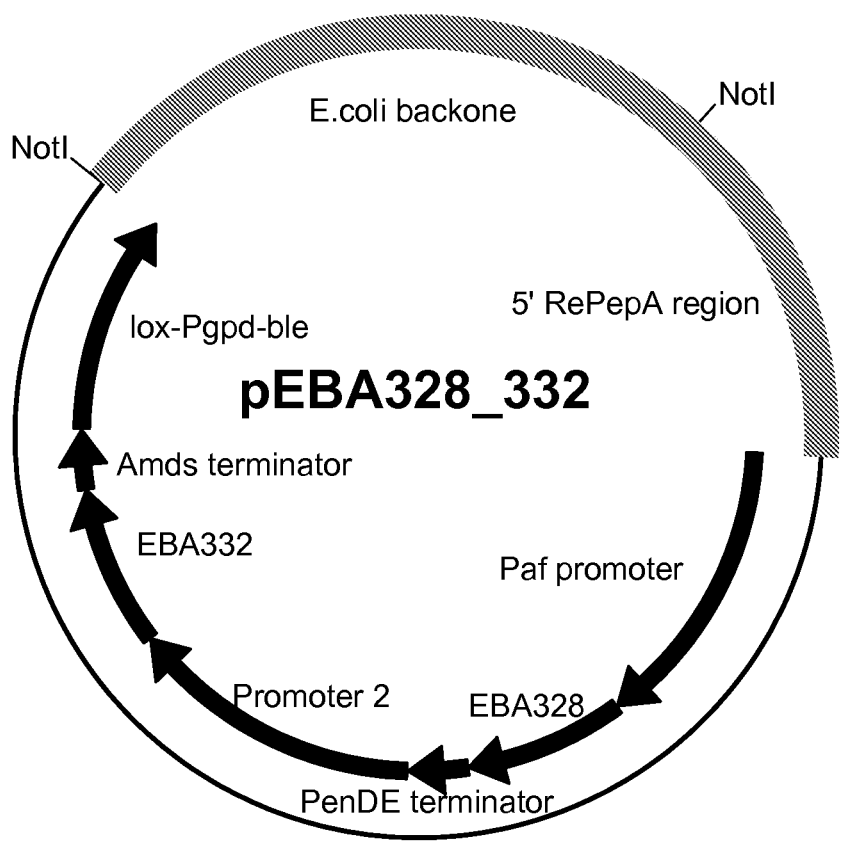
FIG. 17 shows a schematic diagram of plasmid pEBA328_EBA332 that was used in bipartite gene-targeting method in combination with the pEBA1006 vector with the goal to replace the RePepA ORF and approximately 1500 nucleotides upstream of the start ATG codon by two GH61 expression cassettes in *Rasamsonia emersonii*. The vector comprises a 1500 bp 5' flanking region 1.5 kb upstream of the RePepA ORF for targeting in the RePepA locus, GH61 expression cassette EBA328 consisting of *P. chrysogenum* Paf promoter, *Talaromyces thermophilus* GH61 coding region and *P. chrysogenum* penDE terminator, GH61 expression cassette EBA332 consisting of *R. emersonii* promoter 2, *Thermomyces lanuginosa* GH61 coding region and the *A.nidulans* amdS terminator (TamdS), a lox66 site, the non-functional 5' part of the ble coding region (5' ble) driven by the *A.nidulans* gpdA promoter. The *E. coli* DNA was removed by digestion with restriction enzyme NotI, prior to transformation of the *R. emersonii* strains.

Expression vector pEBA328-332 (General layout as in FIG. 17) was obtained by Gibson cloning. Gibson cloning reactions were performed as described in Gibson DG, Young L, Chuang RY, Venter JC, Hutchison CA 3rd, Smith HO. (2009). "Enzymatic assembly of DNA molecules up to several hundred kilobases". Nature Methods 6 (5): 343-345. More specifically, the protocol was used that is described in 2010.igem.org/Team:Newcastle/Gibson_Cloning. In the Gibson reaction 75 ng of vector fragment, 37 ng of EBA328 and 37 ng of EBA332 fragment was used. *E.coli* transformations, DNA isolations and restriction enzyme analysis of constructs were performed according to routine cloning procedures.

Example 4

Inactivation of the ReKu80 Gene in *Rasamsonia emersonii* to Improve Gene Targeting This example describes the cloning and deletion of the *R. emersonii* Ku80 gene, to improve gene targeting.

4.1 Cloning of ReKu80 Deletion Constructs

Genomic DNA of *Rasamsonia emersonii* strain CBS393.64 was sequenced and analysed. The *Rasamsonia emersonii* Ku80 gene (ReKu80) was identified. Sequences of ReKu80, comprising the genomic sequence of the ORF and approximately 2500 bp of the 5' region and 2500 bp of the 3' flanking regions, cDNA and protein sequence, are shown in SEQ ID NOs: 143, 144 and 145, respectively.

Figure 18:
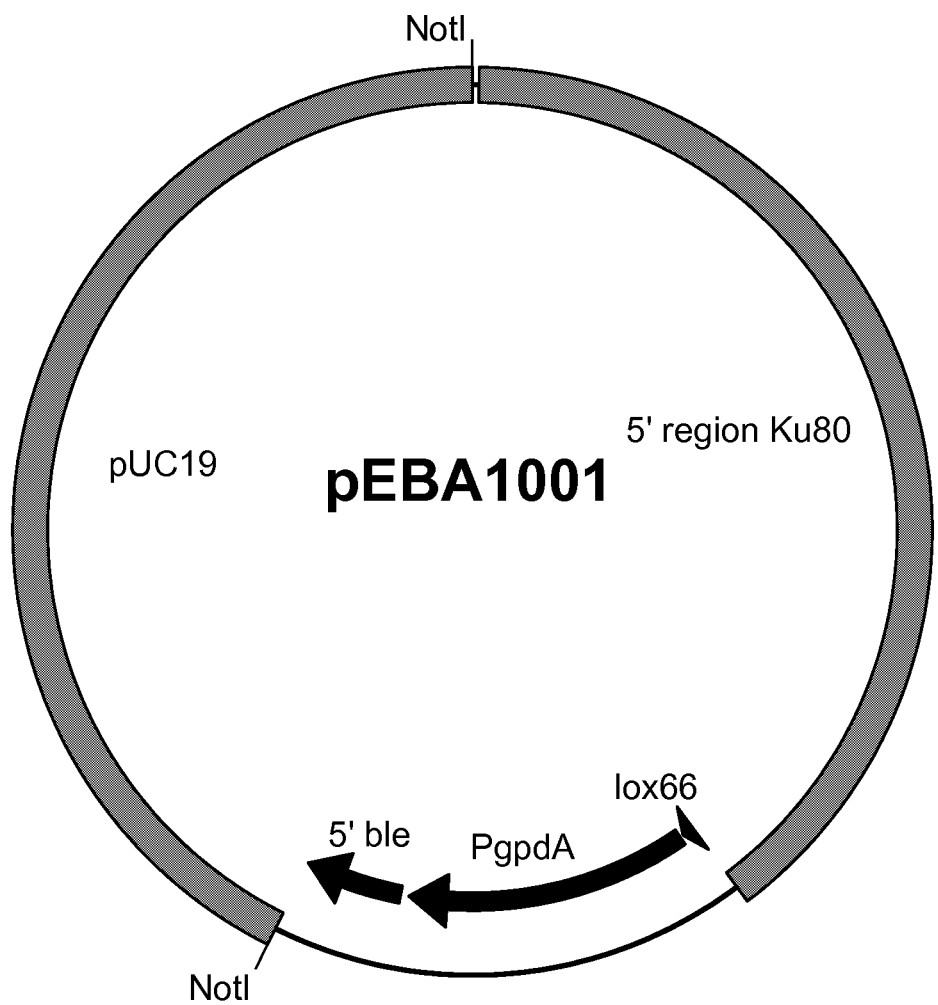
FIG. 18 shows a schematic diagram of plasmid pEBA1001 that was used in bipartite gene-targeting method in combination with the pEBA1002 vector with the goal to delete the ReKu80 ORF in *Rasamsonia emersonii*. The vector comprises a 2500 bp 5' upstream flanking region, a lox66 site, the 5' part of the ble coding sequence driven by the *A.nidulans* gpdA promoter and the backbone of pUC19 (Invitrogen, Breda, The Netherlands). The *E. coli* DNA was removed by digestion with restriction enzyme NotI, prior to transformation of the *R. emersonii* strains.
Figure 19:
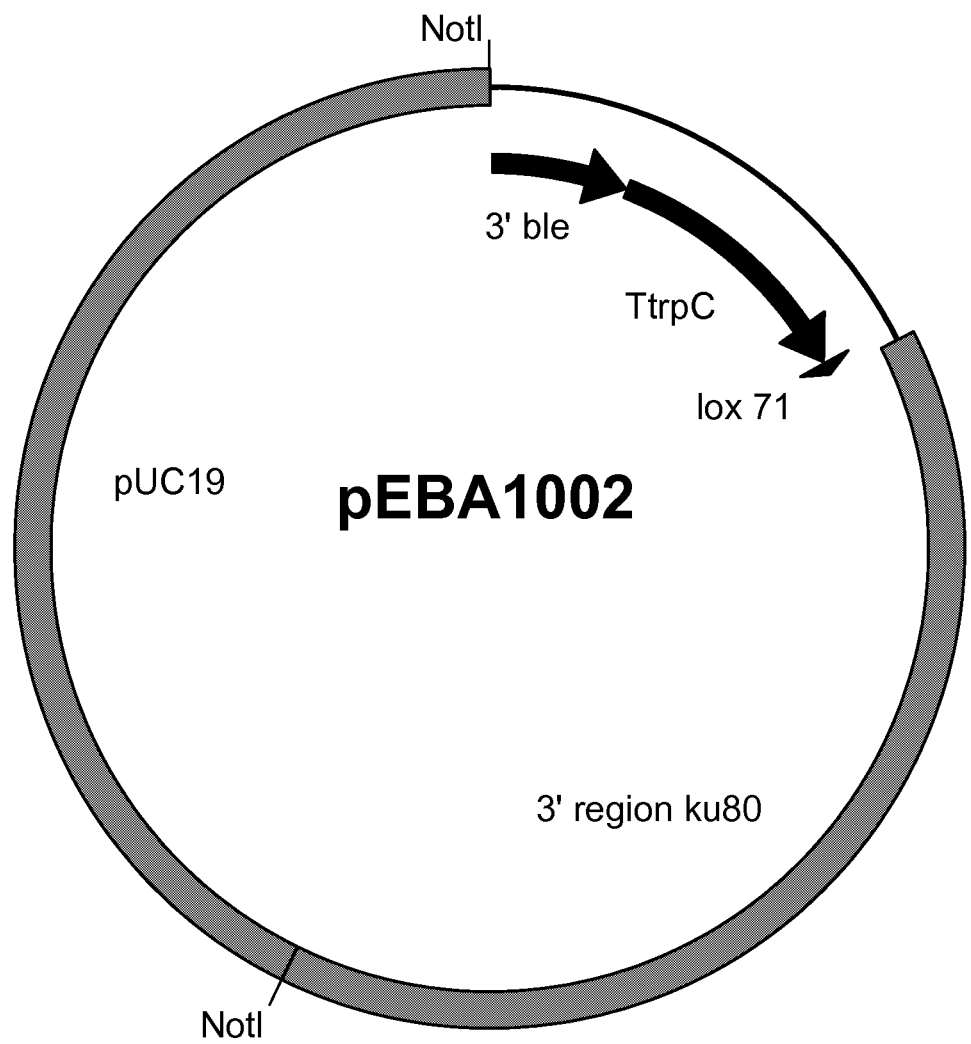
FIG. 19 shows a schematic diagram of plasmid pEBA1002 that was used in bipartite gene-targeting method in combination with the pEBA1001 vector with the goal to delete the ReKu80 ORF in *Rasamsonia emersonii*. The vector comprises the 3' part of the ble coding region, the *A. nidulans* trpC terminator, a lox71 site, a 2500 bp 3' downstream flanking region of the ReKu80 ORF, and the backbone of pUC19 (Invitrogen, Breda, The Netherlands). The *E. coli* DNA was removed by digestion with restriction enzyme NotI, prior to transformation of the *R. emersonii* strains.

Two replacement vectors for ReKu80, pEBA1001 and pEBA1002, were constructed according to routine cloning procedures (see FIGS. 18 and 19). The insert fragments of both vectors together can be applied in the so-called "bipartite gene-targeting" method as described in Example 2. The pEBA1001 vector comprises a 2500 bp 5' flanking region of the ReKu80 ORF for targeting in the ReKu80 locus, a lox66 site, and the 5' part of the ble coding region as described in Example 2 driven by the *A. nidulans* gpdA promoter (FIG. 18). The pEBA1002 vector comprises the 3' part of the ble coding region as described in Example 2, the *A. nidulans* trpC terminator, a lox71 site, and a 2500 bp 3' flanking region of the ReKu80 ORF for targeting in the ReKu80 locus (FIG. 19).

4.2 Deletion of ReKu80 in *Rasamsonia emersonii*

Figure 20:
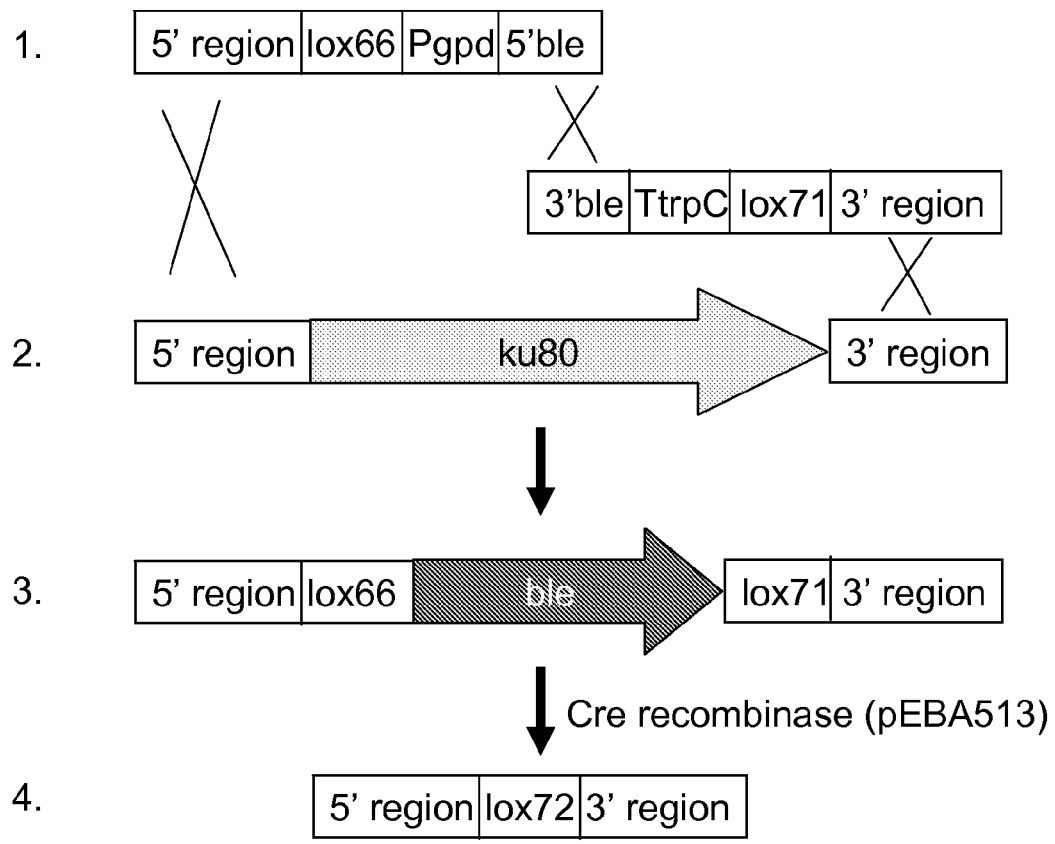
FIG. 20 shows the strategy used to delete the ReKu80 gene of *R. emersonii*. The vectors for deletion of ReKu80 comprise the overlapping non-functional ble selection marker fragments (split marker) flanked by loxP sites and 5' and 3' homologous regions of the ReKu80 gene for targeting (1). The constructs integrate through triple homologous recombination (X) at the genomic ReKu80 locus and at the overlapping homologous non-functional ble selection marker fragment (2) and replaces the genomic ReKu80 gene copy (3). Subsequently, the selection marker is removed by transient expression of cre recombinase leading to recombination between the lox66 and lox71 sites resulting in the deletion of the ble gene with a remainder double-mutant lox72 site left within the genome (4). Using this overall strategy, the ReKu80 ORF is removed from the genome.

Linear DNA of the deletion constructs pEBA1001 and pEBA1002 were isolated and used to transform *Rasamsonia emersonii* using method as described earlier in WO2011/054899. These linear DNAs can integrate into the genome at the ReKu80 locus, thus substituting the ReKu80 gene by the ble gene as depicted in FIG. 20. Transformants were selected on phleomycin media and colony purified and tested according to procedures as described in WO2011/054899. Growing colonies were diagnosed by PCR for integration at the ReKu80 locus using a primer in the gpdA promoter of the deletion cassette and a primer directed against the genomic sequence directly upstream of the 5' targeting region. From a pool of approximately 250 transformants, 4 strains showed a removal of the genomic ReKu80 gene.

Figure 21:
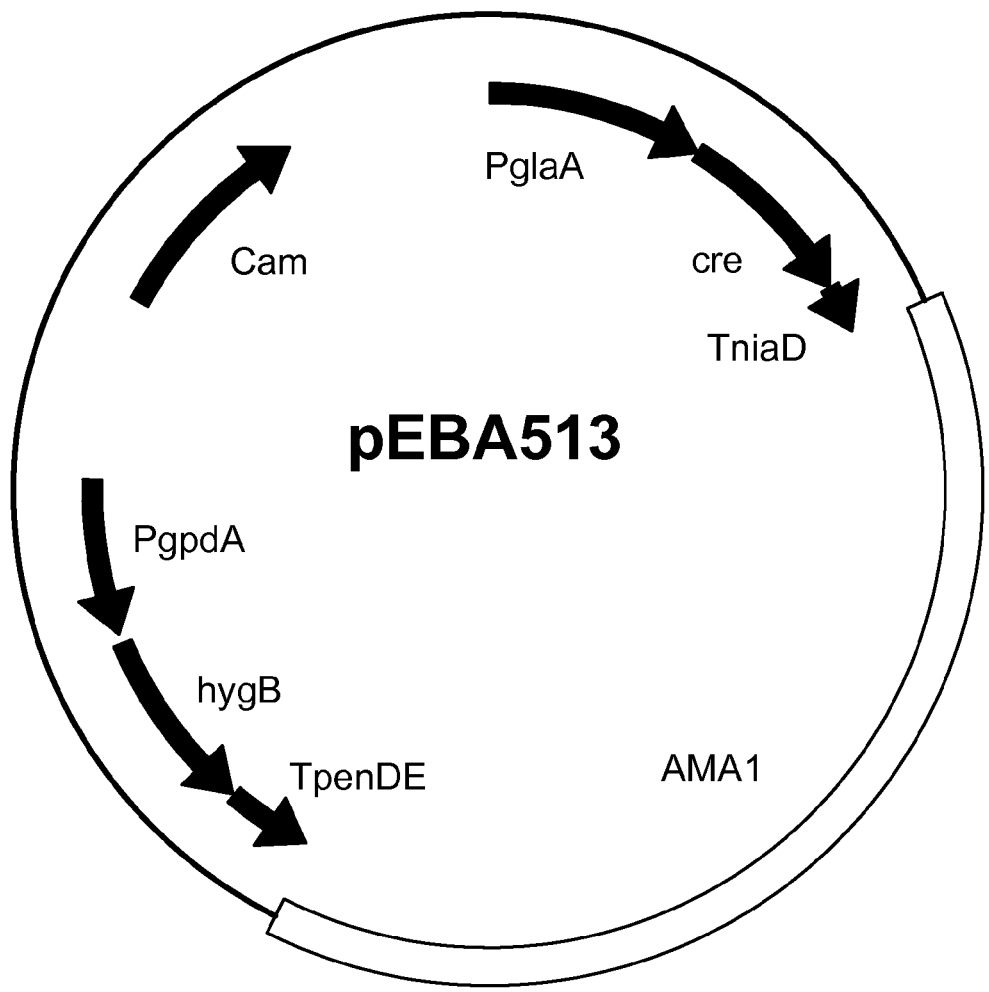
FIG. 21 shows a schematic diagram of plasmid pEBA513 for transient expression of cre recombinase in fungi. pEBA513 is a pAMPF21 derived vector containing the AMA1 region and the CAT chloramphenicol resistance gene. Depicted are the cre recombinase gene (cre) expression cassette, containing the *A.niger* glaA promoter (Pgla), cre recombinase coding region, and niaD terminator. In addition, the hygromycin resistance cassette consisting of the *A. nidulans* gpdA promoter (PgpdA), hygB coding region and the *P. chrysogenum*penDE terminator (TpenDE) is indicated.

4.3 Cloning of Transient Expression Plasmid pEBA513 Encoding Cre Recombinase pEBA513 was constructed by DNA2.0 (Menlo Park, USA) and contains the following components: expression cassette consisting of the *A. niger* glaA promoter, ORF encoding cre-recombinase (AAY56380) and *A. nidulans* niaD terminator; expression cassette consisting of the *A. nidulans* gpdA promoter, ORF encoding hygromycin B resistance protein and *P. chrysogenum* penDE terminator (Genbank: M31454.1, nucleotides 1750-2219); pAMPF21 derived vector containing the AMA1 region and the CAT chloramphenicol resistance gene. FIG. 21 represents a map of pEBA513.

4.4 Marker Removal of Phleomycin Resistant ReKu80 Deletion Strains by Transient Expression of Cre Recombinase Subsequently, 3 candidate ReKu80 knock out strains were transformed with pEBA513 to remove the ble selection marker by transient expression of the cre recombinase. pEBA513 transformants were plated in overlay on regeneration medium containing 50 μg/ml of hygromycin B. Hygromycin-resistant transformants were grown on PDA containing 50 μg/ml of hygromycin B to allow expression of the cre recombinase. Single colonies were plated on non-selective *Rasamsonia* agar medium to obtain purified spore batches. Removal of the ble marker was tested phenotypically by growing the transformants on media with and without 10 μg/ml of phleomycin. The majority (>90%) of the transformants after transformation with pEBA513 (with the cre recombinase) were phleomycin sensitive, indicating removal of the pEBA1001 and pEBA1002-based ble marker. Removal of the pEBA513 construct in ble-negative strains was subsequently diagnosed phenotypically by growing the transformants on media with and without 50 μg/ml of hygromycin. Approximately 50% of the transformants lost hygromycin resistance due to spontaneously loss of the pEBA513 plasmid.

Candidate marker-free knock-out strains were tested by Southern analysis and PCR for deletion of the ReKu80 gene. Marker-free ReKu80 deletion strains were obtained and a representative strain was used for targeted integration of the double GH61 pEB328_EBA332 construct (Example 4)

4.5 Transformation of *Rasamsonia emersonii* with pEBA328_332 and pEBA1006

Linear DNA of pEBA328_332 and pEBA1006 were isolated and used to transform the *Rasamsonia emersonii* ReKu80 knock out strain described in Example 3 using method as described earlier in WO2011/054899. The linear DNAs of pEBA328_332 can integrate together with pEBA1006 into the genome at the RePepA locus, thus substituting the RePepA gene by the pEBA328_332 double expression cassette and ble gene. Transformants are selected on phleomycin media and colony purified and tested according to procedures as described in WO2011/054899. Growing colonies are diagnosed by PCR for integration at the RePepA locus using a primer in the *P. chrysogenum* Paf promoter of the deletion cassette and a primer directed against the genomic sequence directly upstream of the 5' targeting region. Candidate transformants in which RePepA is replaced by EBA328_EBA332/ble cassettes were obtained.

4.6 Cellulase activity in double GH61 overexpressing strains

Figure 22:
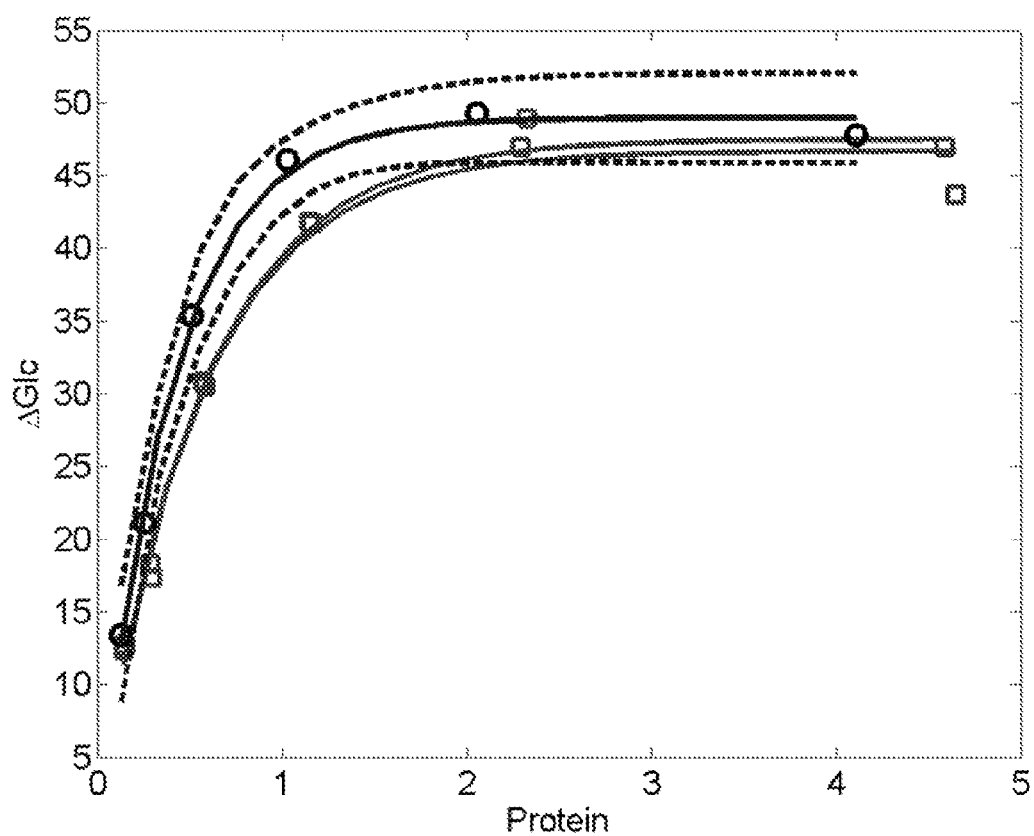
FIG. 22 shows the dose response curves of supernatants tested in a 2% corn stover activity assay. Different dosages of supernatants of shake flask fermentations were incubated with 2% corn stover and inubated for 72 hours at 65° C. Released sugar was quantified using NMR. X-axis: protein concentration of (diluted) supernatants of which 200μl was added to 800 μl of substrate resulting in a final assay volume of 1 ml. Y-axis: relative glucose release (ΔGlc, arbitrary units): the glucose measured in the samples was corrected for the residual sugar present in the enzyme solution (measured from the blank) and the residual sugar present in the acid pretreated corn stover. Open circles: pEBA328_EBA332transformant; open squares: curves of 2 empty reference strains; dashed lines: 95% confidence interval of pEBA328_EBA332 curve fit.

Spores of pEBA328_EBA332 transformants overexpressing two GH61 enzymes were fermented in shake flasks as described in General methods for *Rasamsonia emersonii*. Supernatants were analysed for cellulase activity in an 2% corn stover activity assay. The dose-response curves of the GH61 overexpressing and reference strain are shown in FIG. 22. Lower dosages of supernatants derived from pEBA328_EBA332 transformant fermentations are required to obtain the same corn stover hydrolysis level compared to supernatants derived from the reference strain, indicating that cellulase activity was improved in GH61-overexpressing *R. emersonii* strains.

4.7 Conclusions

Multi cassette constructs were successfully generated by combining promoter, ORF and terminator fragments using Golden gate assembly (Level 1) and subsequent multi cassette assembly using Gibson cloning (Level 2). R. emersonii was transformed with the double expression cassette fragment and the cassettes were successfully integrated into the RePepA locus. Transformants showed improved cellulase activity compared to reference strains, indicating that the multi cassette fragment was functioning well. In conclusion, the method is suitable for the efficient cloning of multicassette constructs and the introduction of multiple genes in one R. emersonii transformation step.

The invention claimed is:

1. A method for recombining two or more standardized expression cassettes in vivo in a host cell at a target locus, which method comprises
   A) preparing two or more standardized expression cassettes according to a method comprising,
      a) providing two or more sets of element sequences, each set of element sequences together comprising at least one functional expression cassette,
         each element sequence being flanked on both sides by a type IIs restriction endonuclease cleavage site followed by the recognition site thereof,
         the type IIs restriction endonuclease recognition sites and cleavage sites being selected so that the sets of element sequences may be assembled into a functional expression cassette;
      b) providing at least two backbone entry vectors,
         each backbone entry vector comprising in this order (i) a restriction enzyme cleavage site with its recognition site and a first connector sequence (LF); (ii) a vector backbone comprising a selectable marker gene; and (iii) a second connector sequence (RF) and a restriction enzyme recognition site with its cleavage sequence, and; (iv) optionally, an insert between the recognition sites of (i) and (iii),
         the connector sequences, RF and LF, on any backbone entry vector being selected so that they can assemble with a LF or RF connector sequence respectively on the same or a different backbone entry vector; and
      c) assembling the two or more sets of element sequences as functional expression cassettes in the at least two backbone entry vectors, using a method based on the use of restriction enzyme digestion and ligation via the cleavage sites,
      thereby to prepare two or more standardized expression cassettes,
   wherein,
      i) the RF and LF connector sequences comprise homologous recombination sequences; and
      ii) the RF and LF connector sequences on any backbone entry vector are selected so that they can assemble by recombination in vivo with a LF or RF connector sequence, respectively, with the same or a different backbone entry vector and/or with a sequence flanking the target locus; and
   B) recovering the expression cassettes from the backbone entry vectors including the LF and RF sequences; and
   C) recombining the recovered expression cassettes in vivo in a host cell with each other at the target locus.

2. A method according to claim 1, wherein at least two backbone entry vectors comprise, in this order (i) a type II restriction enzyme recognition site followed by the cleavage site thereof and a first at least 25-basepair connector sequence (LF); (ii) a vector backbone comprising a selectable marker gene; and (iii) a second at least 25-basepair connector sequence (RF) and a further cleavage site of a type II restriction enzyme followed by the recognition site of said cleavage site, and; (iv) optionally, an insert between the recognition sites of (i) and (iii).

3. A method according to claim 1, wherein the recombination step is carried out in the presence of two integration sequences, one of which recombines with a first expression cassette and a sequence flanking the target locus, and the second of which recombines with a second expression cassette and a sequence flanking the other side of the target locus.

4. A method according to claim 3, wherein the integration sequences mediate integration via homologous recombination or site-specific recombination.

5. A method according to claim 1, wherein, in the recombination step, a first expression cassette comprises an integration sequence which recombines with a sequence flanking the target locus, and a second expression cassette comprises an integration sequence which recombines with a sequence flanking the other side of the target locus.

6. A method according to claim 5, wherein the integration sequences comprise additional sequences for recombination with a second target locus, optionally a locus in a host cell of species different than the first target locus.

7. A method according to claim 6, wherein the integration sequences, connectors or other element sequence comprise site-specific recombination sequences for recombination with the second target locus, said sequences located outside of the assembled expression cassettes and allowing recombination at the second target locus using site-specific recombination, optionally at a target locus in a host cell species different than the host cell species for first target locus.

8. A method according to claim 1, wherein the two or more expression cassettes are assembled and recombined in a predetermined order in series at the target locus.

9. A method according to claim 1, wherein at least one expression cassette is a marker expression cassette.

10. A method according to claim 9, where the marker expression cassette is flanked by at least two site-specific recombination sites.

11. A method according to claim 1, wherein at least two of the sets of element sequences comprise a promoter element, an open reading frame element and a terminator element.

12. A method according to claim 1, wherein assembly of each set of elements into a functional expression cassette in the at least two backbone entry vectors is carried out in a one pot reaction.

13. A method according to claim 1, wherein the elements in each set are defined so that the expression cassette is assembled in a pre-determined order.

14. A method according to claim 1, wherein the host cells are prokaryotic or eukaryotic cells.

15. A method for recombining two or more standardized expression cassettes in vivo in a host cell at a target locus, which method comprises
   A) preparing two or more standardized modular expression cassettes according to a method comprising,
      a) providing two or more sets of element sequences, each set of element sequences together comprising at least one functional expression cassette, each element sequence being flanked on both sides by a type IIs restriction endonuclease cleavage site followed by the recognition site thereof, the type IIs restriction endonuclease recognition sites and cleavage sites being selected so that the sets of element sequences may be assembled into a functional expression cassette;

b) providing at least two backbone entry vectors, each backbone entry vector comprising in this order (i) a restriction enzyme cleavage site with its recognition site and a first connector sequence (LF); (ii) a vector backbone comprising a selectable marker gene; and (iii) a second connector sequence (RF) and a restriction enzyme recognition site with its cleavage sequence, and; (iv) optionally, an insert between the recognition sites of (i) and (iii), the connector sequences, RF and LF, on any backbone entry vector being selected so that they can assemble with a LF or RF connector sequence respectively on the same or a different backbone entry vector; and c) assembling the two or more sets of element sequences as functional expression cassettes in the at least two backbone entry vectors, using a method based on the use of restriction enzyme digestion and ligation via the cleavage sites, thereby to prepare two or more standardized expression cassettes, wherein, i) the RF and LF connector sequences comprise at least 9-base pair homologous sequences; and ii) the RF and LF connector sequences on any backbone entry vector are selected so that they can assemble using these sequences by an in vitro method with a LF or RF connector sequence, respectively, with the same or a different backbone entry vector and/or with a sequence flanking the target locus; and B) recovering the expression cassettes from the backbone entry vectors and assembling them in vitro connected by LF and RF sequences; and C) recombining the assembled and recovered expression cassettes in vivo in a host cell at the target locus.

16. A method for integration of a DNA sequence at a target locus, which method comprises A) preparing two or more standardized modular expression cassettes according to a method comprising:

a) providing two or more sets of element sequences, each set of element sequences together comprising at least one functional expression cassette, each element sequence being flanked on both sides by a type IIs restriction endonuclease cleavage site followed by the recognition site thereof, the type IIs restriction endonuclease recognition sites and cleavage sites being selected so that the sets of element sequences may be assembled into a functional expression cassette;

b) providing at least two backbone entry vectors, each backbone entry vector comprising in this order (i) a restriction enzyme cleavage site with its recognition site and a first connector sequence (LF); (ii) optionally, a left integration (int-L) sequence of at least 200 base pairs homologous to a target locus in a host cell; (iii) a vector backbone comprising a selectable marker gene; (iv) optionally, a right integration (int-R) sequence of at least 200 base pairs homologous to the target locus in a host cell; (v) a second connector sequence (RF) and a restriction enzyme recognition site with its cleavage sequence; and (vi) optionally, an insert between the recognition sites of (i) and (v), the connector sequences, RF and LF, on any backbone entry vector being selected so that they can assemble with a LF or RF connector sequence respectively on the same or a different backbone entry vector; and c) assembling the two or more sets of element sequences as functional expression cassettes in the at least two backbone entry vectors, using a method based on the use of restriction enzyme digestion and ligation via the cleavage sites, thereby to prepare two or more standardized expression cassettes, wherein, i) the RF and LF connector sequences comprise at least 25-base pair homologous recombination sequences; and ii) the RF and LF sequences on any backbone entry vector are selected so that they can assemble by recombination in vivo with a LF or RF connector sequence, respectively, with the same or a different backbone entry vector and/or with a sequence flanking the target locus;

B) recovering the expression cassettes from the backbone entry vectors including the LF and RF sequences, and, optionally, the int-L and int-R sequences; and C) recombining the recovered expression cassettes in vivo in a host cell with each other at the target locus.

17. A method according to claim 16, wherein the at least two backbone entry vectors comprise int-L or int-R.

18. A method according to claim 17, wherein a second functional expression cassette is formed at a second target locus.

19. A method according to claim 16, wherein recombination. at the target locus results in functional knock-out or downregulation of one of more genes at the target locus.

* * * * *